US010064937B2

(12) United States Patent
Cain

(10) Patent No.: US 10,064,937 B2
(45) Date of Patent: *Sep. 4, 2018

(54) TREATMENT OF DERMAL FIBROSIS

(71) Applicant: OncoMed Pharmaceuticals, Inc., Redwood City, CA (US)

(72) Inventor: Jennifer Anne Cain, Moss Beach, CA (US)

(73) Assignee: OncoMed Pharmaceuticals, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/855,053

(22) Filed: Sep. 15, 2015

(65) Prior Publication Data
US 2016/0166684 A1 Jun. 16, 2016

Related U.S. Application Data

(60) Provisional application No. 62/051,026, filed on Sep. 16, 2014.

(51) Int. Cl.
*A61K 39/395* (2006.01)
*A61K 39/00* (2006.01)
*A61K 45/06* (2006.01)
*C07K 16/18* (2006.01)
*C07K 16/28* (2006.01)
*C07K 16/26* (2006.01)
*C07K 16/40* (2006.01)
*C12Q 1/6883* (2018.01)

(52) U.S. Cl.
CPC .......... *A61K 39/3955* (2013.01); *A61K 45/06* (2013.01); *C07K 16/18* (2013.01); *C07K 16/28* (2013.01); *C12Q 1/6883* (2013.01); *A61K 2039/505* (2013.01); *A61K 2039/507* (2013.01); *C07K 2317/52* (2013.01); *C07K 2317/56* (2013.01); *C07K 2317/565* (2013.01); *C07K 2317/76* (2013.01); *C12Q 2600/106* (2013.01); *C12Q 2600/158* (2013.01)

(58) Field of Classification Search
CPC ................ A61K 2300/00; A61K 45/06; A61K 2039/505; A61K 39/3955; A61K 2039/507; C07K 16/18; C07K 16/28; C07K 16/24; C07K 2317/76; C07K 2317/565; C07K 2317/52; C12Q 2600/158; C12Q 2600/106; C12Q 1/6883
See application file for complete search history.

(56) References Cited

U.S. PATENT DOCUMENTS

| 6,004,528 | A | 12/1999 | Bergstein |
|---|---|---|---|
| 6,824,973 | B2 | 11/2004 | Tang |
| 7,193,069 | B2 | 3/2007 | Isogai et al. |
| 7,319,141 | B2 | 1/2008 | Tang et al. |
| 7,320,880 | B2 | 1/2008 | Nishikawa et al. |
| 7,411,052 | B2 | 8/2008 | Tang |
| 7,439,332 | B2 | 10/2008 | Nishikawa |
| 7,498,416 | B2 | 3/2009 | Yayon et al. |
| 7,541,431 | B2 | 6/2009 | Yoon et al. |
| 7,723,112 | B2 | 5/2010 | Clarke et al. |
| 7,951,381 | B2 | 5/2011 | Funk et al. |
| 8,088,374 | B2 | 1/2012 | Niehrs et al. |
| 8,158,757 | B2 | 4/2012 | Gurney et al. |
| 8,158,758 | B2 | 4/2012 | Gurney |
| 8,540,989 | B2 | 9/2013 | Gurney |
| 8,628,774 | B2 | 1/2014 | Gurney et al. |
| 8,802,097 | B2 | 8/2014 | Gurney et al. |
| 8,883,736 | B2 | 11/2014 | Gurney |
| 9,040,044 | B2 | 5/2015 | Gurney et al. |
| 9,109,024 | B2 | 8/2015 | Gurney et al. |
| 9,109,025 | B2 | 8/2015 | Gurney et al. |
| 9,181,333 | B2 | 11/2015 | Gurney et al. |
| 9,598,497 | B2 | 3/2017 | Gurney et al. |
| 9,610,348 | B2 | 4/2017 | Gurney et al. |
| 2002/0065394 | A1 | 5/2002 | Jacobs et al. |
| 2003/0022217 | A1 | 1/2003 | Ceccardi et al. |
| 2003/0100741 | A1 | 5/2003 | Muller et al. |
| 2004/0197778 | A1 | 10/2004 | Morris et al. |
| 2005/0054829 | A1 | 3/2005 | Wiley et al. |
| 2005/0130145 | A1 | 6/2005 | Yue et al. |
| 2005/0142600 | A1 | 6/2005 | Warren et al. |
| 2005/0232927 | A1 | 10/2005 | Clarke et al. |
| 2005/0256036 | A1 | 11/2005 | Boyle et al. |
| 2005/0256044 | A1 | 11/2005 | Boyle et al. |
| 2006/0019256 | A1 | 1/2006 | Clarke et al. |
| 2006/0057149 | A1 | 3/2006 | Johnson et al. |
| 2006/0149049 | A1 | 7/2006 | Tang |
| 2006/0263803 | A1 | 11/2006 | Tang |
| 2006/0275870 | A1 | 12/2006 | Gu |
| 2007/0042359 | A1 | 2/2007 | Throsby et al. |
| 2007/0117751 | A1 | 5/2007 | Gurney et al. |
| 2007/0124581 | A1 | 5/2007 | Khare et al. |
| 2007/0237770 | A1 | 10/2007 | Lai et al. |
| 2007/0244061 | A1 | 10/2007 | Niehrs et al. |
| 2008/0038257 | A1 | 2/2008 | Han et al. |
| 2008/0064049 | A1 | 3/2008 | Clarke et al. |
| 2008/0108565 | A1 | 5/2008 | Winston, Jr. et al. |
| 2008/0286261 | A1 | 11/2008 | Morgan et al. |
| 2008/0306004 | A1 | 12/2008 | Tang |

(Continued)

FOREIGN PATENT DOCUMENTS

CA 2691378 A1 1/2009
DE 10339820 A1 3/2005

(Continued)

OTHER PUBLICATIONS

Beyer, C. et al. Blockade of canonical Wnt signaling ameliorates experimental dermal fibrosis. Annals of Rheumatic Disease, 2013, vol. 72, p. 1255-1258.*

(Continued)

*Primary Examiner* — Robert S Landsman
*Assistant Examiner* — Bruce D. Hissong
(74) *Attorney, Agent, or Firm* — Sterne, Kessler, Goldstein & Fox P.L.L.C.

(57) ABSTRACT

The present invention relates to RSPO and LGR antagonists, and methods of using the RSPO and LGR antagonists for treating or preventing fibrotic diseases.

13 Claims, 5 Drawing Sheets

Specification includes a Sequence Listing.

(56) References Cited

U.S. PATENT DOCUMENTS

| | | |
|---|---|---|
| 2009/0036369 A1 | 2/2009 | Kakitani et al. |
| 2009/0074782 A1 | 3/2009 | Gurney |
| 2009/0118176 A1 | 5/2009 | Emtage et al. |
| 2009/0191205 A1 | 7/2009 | Gurney et al. |
| 2009/0208484 A1 | 8/2009 | Christiano |
| 2009/0220495 A1 | 9/2009 | Fanidi et al. |
| 2010/0003258 A1 | 1/2010 | Weng et al. |
| 2010/0047257 A1 | 2/2010 | Blanc et al. |
| 2010/0071078 A1 | 3/2010 | Niehrs et al. |
| 2010/0278800 A1 | 11/2010 | Boyle et al. |
| 2010/0292155 A1 | 11/2010 | Tang |
| 2010/0330089 A1 | 12/2010 | Damle et al. |
| 2011/0123532 A1 | 5/2011 | Gurney et al. |
| 2011/0176995 A1 | 7/2011 | Funahashi |
| 2011/0287444 A1 | 11/2011 | Kanamori et al. |
| 2012/0039912 A1 | 2/2012 | Rawadi et al. |
| 2012/0082659 A1 | 4/2012 | Land et al. |
| 2012/0088727 A1 | 4/2012 | Niehrs et al. |
| 2012/0114646 A1 | 5/2012 | Tchessalov et al. |
| 2012/0165270 A1 | 6/2012 | Choi et al. |
| 2012/0171226 A1 | 7/2012 | Horwitz |
| 2012/0184616 A9 | 7/2012 | Rabbani et al. |
| 2012/0189639 A1 | 7/2012 | Schebye et al. |
| 2012/0263730 A1 | 10/2012 | Niehrs et al. |
| 2012/0329994 A1 | 12/2012 | Chen et al. |
| 2013/0095116 A1 | 4/2013 | Gurney et al. |
| 2013/0115206 A1 | 5/2013 | Gurney et al. |
| 2013/0121993 A1 | 5/2013 | Gurney |
| 2013/0137130 A1 | 5/2013 | Wells et al. |
| 2013/0209473 A1 | 8/2013 | De Sauvage et al. |
| 2013/0336885 A1 | 12/2013 | Hongo et al. |
| 2013/0337533 A1 | 12/2013 | Niehrs et al. |
| 2014/0017253 A1 | 1/2014 | Gurney et al. |
| 2014/0127223 A1 | 5/2014 | Yamazaki et al. |
| 2014/0134177 A1 | 5/2014 | Gurney et al. |
| 2014/0256041 A1 | 9/2014 | Reyes et al. |
| 2014/0302054 A1 | 10/2014 | Reyes et al. |
| 2014/0328859 A1 | 11/2014 | Cong et al. |
| 2015/0147333 A1 | 5/2015 | Storm et al. |
| 2015/0165024 A1 | 6/2015 | Gurney |
| 2016/0000780 A1 | 1/2016 | An |
| 2016/0152947 A1 | 6/2016 | Pioszak |

FOREIGN PATENT DOCUMENTS

| | | |
|---|---|---|
| EP | 2157192 A1 | 2/2010 |
| EP | 1673475 B1 | 4/2010 |
| EP | 1427747 B1 | 4/2012 |
| EP | 2997975 A1 | 3/2016 |
| JP | 2010532169 A | 10/2010 |
| WO | WO-9849302 A1 | 11/1998 |
| WO | WO-9915660 A1 | 4/1999 |
| WO | WO-9948921 A1 | 9/1999 |
| WO | WO-0021555 A1 | 4/2000 |
| WO | WO-0107611 A2 | 2/2001 |
| WO | WO-0157190 A2 | 8/2001 |
| WO | WO-0177169 A2 | 10/2001 |
| WO | WO-0187338 A1 | 11/2001 |
| WO | WO-0188092 A2 | 11/2001 |
| WO | WO-0192297 A2 | 12/2001 |
| WO | WO-0212447 A2 | 2/2002 |
| WO | WO-02102972 A2 | 12/2002 |
| WO | WO-03029405 A2 | 4/2003 |
| WO | WO-03050502 A2 | 6/2003 |
| WO | WO-03054152 A2 | 7/2003 |
| WO | WO-2004005457 A2 | 1/2004 |
| WO | WO-2004074436 A2 | 9/2004 |
| WO | WO-2004098521 A2 | 11/2004 |
| WO | WO-2005040418 A2 | 5/2005 |
| WO | WO-2005040828 A2 | 5/2005 |
| WO | WO-2006110581 A2 | 10/2006 |
| WO | WO-2007096149 A1 | 8/2007 |
| WO | WO-2007100357 A2 | 9/2007 |
| WO | WO-2008020942 A2 | 2/2008 |
| WO | WO-2008042236 A2 | 4/2008 |
| WO | WO-2008046649 A1 | 4/2008 |
| WO | WO-2008075796 A1 | 6/2008 |
| WO | WO-2008088524 A2 | 7/2008 |
| WO | WO-2009005809 A2 | 1/2009 |
| WO | WO-2009045443 A2 | 4/2009 |
| WO | WO-2010016766 A2 | 2/2010 |
| WO | WO-2010050554 A1 | 5/2010 |
| WO | WO-2010121923 A1 | 10/2010 |
| WO | WO-2011076932 A1 | 6/2011 |
| WO | WO-2012092336 A2 | 7/2012 |
| WO | WO-2012140274 A2 | 10/2012 |
| WO | WO-2012178058 A1 | 12/2012 |
| WO | WO-2013012747 A1 | 1/2013 |
| WO | WO-2013120056 A1 | 8/2013 |
| WO | WO-2013149159 A1 | 10/2013 |
| WO | WO-2014012007 A2 | 1/2014 |
| WO | WO-2014165232 A1 | 10/2014 |
| WO | WO-2014192974 A1 | 12/2014 |
| WO | WO-2015058132 A2 | 4/2015 |
| WO | WO-2016090024 A2 | 6/2016 |

OTHER PUBLICATIONS

Vajdos, F.F. et al. Comprehensive functional mapss of the antigen-binding site of an anti-ErbB2 antibody obtained with shotgun scanning mutagenesis. Journal of Molecular Biology, 2002, vol. 320, p. 415-428.*

Adams, G.P. and Weiner, L.M., "Monoclonal Antibody Therapy of Cancer," Nature Biotechnology 23(9):1147-1157, Nature Publishing Group, United States (2005) (D23 as cited in Opposition of EP 2173379).

Assignment from Austin Gurney to Oncomed Pharmaceuticals, Inc., (D12 as cited in Opposition of EP 2173379).

Assignment of Austin Gurney to Oncomed Pharmaceuticals, Screenshot of USPTO Recordal Database, 2 pages, recorded on Jan. 27, 2009 (D13 as cited in Opposition of EP 2173379).

Baljinnyam, B., et al., "Recombinant R-spondin2 and Wnt3a Up- and Down-regulate Novel Target Genes in C57MG Mouse Mammary Epithelial Cells," PLoS One 7(1):e29455, Public Library of Science, United States (2012).

Barker, N. and Clevers, H., "Mining the Wnt Pathway for Cancer Therapeutics," Nature Reviews/Drug Discovery 5(12):997-1014, Nature Publishing Group, United States (2006) (D5 as cited in Opposition of EP 2173379).

Barker, N., et al., "Identification of Stem Cells in Small Intestine and Colon by Marker Gene Lgr5," Nature 449(7165):1003-1007, Nature Publishing Group, England (2007) (D33 as cited in Opposition of EP 2173379).

Bergmann, C., et al., "Mutations in the Gene Encoding the Wnt-signaling Component R-spondin 4 (RSPO4) Cause Autosomal Recessive Anonychia," American Journal of Human Genetics 79(6):1105-1109, University of Chicago Press, United States (2006) (D21 as cited in Opposition of EP 2173379).

Blaydon, D.C., et al., "R-spondins in Cutaneous Biology: Nails and Cancer," Cell Cycle 6(8):895-897, Taylor & Francis, United States (2007) (D19 as cited in Opposition of EP 2173379).

Chartier, C., et al., "Therapeutic Targeting of Tumor-Derived R-Spondin Attenuates β-Catenin Signaling and Tumorigenesis in Multiple Cancer Types," Cancer Research 76(3):713-723, American Association for Cancer Research, United States (2016).

Crystal Image of LGR5 with Binding Sites Overlaid, 1 page (D35 as cited in Opposition of EP 2173379).

De Lau, W., et al., "Lgr5 Homologues Associate with Wnt Receptors and Mediate R-spondin Signalling," Nature 476(7360):293-297, Macmillan Publishers Limited, England (2011) (D14 as cited in Opposition of EP 2173379).

De Lau, W., et al., "The R-spondin/Lgr5/Rnf43 Module: Regulator of Wnt Signal Strength," Genes and Development 28(4):305-316, Cold Spring Harbor Laboratory Press, United States (2014) (D31 as cited in Opposition of EP 2173379.

Hsu, S.Y., et al., "Characterization of Two LGR Genes Homologous to Gonadotropin and Thyrotropin Receptors with Extracellular Leucine-rich Repeats and a G protein-coupled, Seven-transmembrane Region," Molecular Endocrinology 12(12):1830-1845, Endocrine Society, United States (1998) (D29 as cited in Opposition of EP 2173379).

(56) References Cited

OTHER PUBLICATIONS

International Search Report for Application No. PCT/US2015/063480, ISA/US, Alexandria, Virginia, United States, dated May 3, 2016, 5 pages.

Klaus, A. and Birchmeier, W., "Wnt Signaling and its Impact on Development and Cancer," Nature Reviews/Cancer 8(5):387-398, Nature Publishing Group, United States (2008) (D34 as cited in Opposition of EP 2173379).

Kudryavtseva, E., et al., "Wnt Signaling Genes of Murine Chromosome 15 are Involved in Sex-affected Pathways of Inflammatory Arthritis," Arthritis and Rheumatism 64(4):1057-1068, Wiley-Blackwell, United States (2012).

LifeSpan BioSciences, Inc., Anti-GPR49/LGR5 Antibody (N-Terminus) IHC-plus LS-A1232, Retrieved on May 31, 2016, 2 pages (D38 as cited in Opposition of EP 2173379).

Maeda, K., et al., "Wnt5a-Ror2 Signaling between Osteoblast-lineage Cells and Osteoclast Precursors Enhances Osteoclastogenesis," Nature Medicine 18(3):405-412, Nature Publishing Company, United States (2012).

Peng, W.C., et al., "Structure of Stem Cell Growth Factor R-spondin 1 in Complex with the Ectodomain of its Receptor LGR5," Cell Reports 3(6):1885-1892, Cell Press, United States (2013) (D16 as cited in Opposition of EP 2173379).

Platanias, L.C., "Soluble protein inhibitors of the TGF-β pathway," in Cytokines and Cancer, Platanias, L.C., ed., p. 141, Springer Science+Business Media, Inc., United States (2005) (D30 as cited in Opposition of EP 2173379).

Reya, T., et al., "A Role for Wnt Signalling in Self-renewal of Haematopoietic Stem Cells," Nature 423(6938):409-414, Nature Publishing Group, England (2003).

Sequence Alignment 1: EP2173379 B1 SEQ ID No. 13 (LGR5 PRT, top) vs. WO9915660 SEQ ID No. 2 (HG38 PRT, bottom) (D36 as cited in Opposition of EP 2173379).

Sequence Alignment 2: EP2173379 B1 SEQ ID No. 13 (LGR5 PRT, top) vs. WO2004074436 SEQ ID No. 1 (HG38 PRT, bottom) (D37 as cited in Opposition of EP 2173379).

Statement of Grounds of Appeal by Appellant, Offensive Opposition to European U.S. Pat. No. 2157192, filed Sep. 1, 2016, 64 pages.

Storm, E.E., et al., "Targeting PTPRK-RSPO3 Colon Tumours Promotes Differentiation and Loss of Stem-cell Function," Nature 529(7584):97-100, Nature Publishing Group, England (2016).

Supplementary Information in De Lau, W., et al., "Lgr5 Homologues Associate with Wnt Receptors and Mediate R-spondin Signalling," Nature 476(7360):293-297, Nature Publishing Group, England (2011), 23 pages (D15 as cited in Opposition of EP 2173379).

Unexamined Application for German Patent Application No. 103 39 820.1, filed Aug. 22, 2003 with the Federal Republic of Germany German Patent and Trademark Office, 126 pages (D6 and D6A as cited in Opposition of EP 2173379).

U.S. Appl. No. 60/947,611, filed Jul. 2, 2007, 98 pages (D11 as cited in Opposition of EP 2173379).

Written Opinion for International Application No. PCT/US2015/063480, United States Patent and Trademark Office, United States, dated May 3, 2016, 9 pages.

Yamamoto, Y., et al., "Overexpression of Orphan G-protein-coupled Receptor, Gpr49, in Human Hepatocellular Carcinomas with beta-catenin Mutations," Hepatology 37(3):528-533, Wiley, United States (2003) (D28 as cited in Opposition of EP 2173379).

Yang, Y., et al., "Wnt5a and Wnt5b Exhibit Distinct Activities in Coordinating Chondrocyte Proliferation and Differentiation," Development 130(5):1003-1015, Company of Biologists Limited, England (2003).

Yoon, J.K., and Lee, J.S., "Cellular Signaling and Biological Functions of R-spondins," Cell Signalling 24(2):369-377, Elsevier Science Ltd, England (2012).

Al-Hajj, M., et al., "Prospective Identification of Tumorigenic Breast Cancer Cells," Proceedings of the National Academy of Sciences 100(7):3983-3988, The National Academy of Sciences, United States (2003).

Almagro, J.C. and Fransson, J., "Humanization of Antibodies," Frontiers in Bioscience 13:1619-1633, Frontiers in Bioscience Publications, United States (2008).

Anonymous, "Human R-Spondin 2 Antibody. Antigen Affinity-purified Polyclonal Goat IgG, Catalog No. AF3266," R&D Systems, Tools for Cell Biology Research, accessed at http://www.rndsystems.comjpdf/AF3266.pdf, accessed on Jun. 23, 2010, 1 page.

Aubele, M. and Werner, M., "Heterogeneity in Breast Cancer and the Problem of Relevance of Findings," Analytical Cellular Pathology 19(2):53-58, IOS Press, Netherlands (1999).

Beachy, P.A., et al., "Tissue Repair and Stem Cell Renewal in Carcinogenesis," Nature 432(7015):324-331, Nature Publishing Group, England (2004).

Beerman, H., et al., "Flow Cytometric Analysis of DNA Stemline Heterogeneity in Primary and Metastatic Breast Cancer," Cytometry 12(2):147-154, Wiley-Liss, Inc., United States (1991).

Bienz, M. and Clevers, H., "Linking Colorectal Cancer to Wnt Signaling," Cell 103(2):311-320, Cell Press, United States (2000).

Bonsing, B.A., et al., "Allelotype Analysis of Flow-Sorted Breast Cancer Cells Demonstrates Genetically Related Diploid and Aneuploid Subpopulations in Primary Tumors and Lymph Node Metastases," Genes, Chromosomes and Cancer 28(2):173-183, Wiley-Liss, Inc., United States (2000).

Bonsing, B.A., et al. "High Levels of DNA Index Heterogeneity in Advanced Breast Carcinomas. Evidence for DNA ploidy Differences between Lymphatic and Hematogenous Metastases," Cancer 71(2):382-391, American Cancer Society, United States (1993).

Boyden, L.M., et al., "High Bone Density Due to a Mutation in LDL-Receptor—Related Protein 5," The New England Journal of Medicine 346(20):1513-1521, Massachusetts Medical Society, United States (2002).

Brennan, K.R., and Brown, A.M.C., "Wnt Proteins in Mammary Development and Cancer," Journal of Mammary Gland Biology and Neoplasia 9(2):119-131, Kluwer Academic/Plenum Publishers, United States (2004).

Cabrera, C.V., et al., "Phenocopies Induced with Antisense RNA Identify the Wingless Gene," Cell 50(4):659-663, Cell Press, United States (1987).

Campbell, A.M., "Characterisation of monoclonal antibodies," in Monoclonal Antibody Technology The Production and Characterization of Rodent and Human Hybridomas, Chapter 10, pp. 186-215, Elsevier Science Publishers B.V, The Netherlands (1984).

Campbell, A.M., "General Properties and Application of Monoclonal Antibodies," in Monoclonal Antibody Technology The Production and Characterization of Rodent and Human Hybridomas, Chapter 1, pp. 1-32, Elsevier Science Publishers B.V., Amsterdam (1984).

Carmon, K.S., et al., "R-Spondins Function as Ligands of the Orphan Receptors LGR4 and LGR5 to Regulate Wnt/β-Catenin Signaling," Proceedings of the National Academy of Sciences 108(28):11452-11457, National Academy of Sciences, United States (2011).

Carter, P.J., "Potent Antibody Therapeutics by Design," Nature Reviews, Immunology 6(5):343-357, Nature Pub. Group, England (2006).

Casset, F., et al., "A Peptide Mimetic of an Anti-CD4 Monoclonal Antibody by Rational Design," Biochemical and Biophysical Research Communications 307(1):198-205, Academic Press, United States (2003).

Chen, J.Z., et al., "Cloning and Identification of a cDNA that encodes a Novel Human Protein with Thrombospondin Type I Repeat Domain, hPWTSR," Molecular Biology Reports 29:287-292, Kluwer Academic Publishers, Netherlands (2002).

Chen, Y., et al., "Selection and Analysis of an Optimized Anti-VEGF Antibody: Crystal Structure of an Affinity-matured Fab in Complex with Antigen," Journal of Molecular Biology 293(4):865-881, Academic Press, England (1999).

Chien, A.J., et al., "Activated Wnt/β-Catenin Signaling in Melanoma is Associated with Decreased Proliferation in Patient Tumors and a Murine Melanoma Model," Proceedings of the National Academy of Sciences 106(4):1193-1198, National Academy of Sciences, United States (2009).

(56) References Cited

OTHER PUBLICATIONS

Cho, M., et al. "Cardamonin Suppresses Melanogenesis by Inhibition of Wnt/Beta-catenin Signaling," Biochemical and Biophysical Research Communications 390:500-505, Elsevier Inc., United States (2009).
Clevers, H., "Wnt/beta-Catenin Signaling in Development and Disease," Cell 127(3):469-480, Elsevier Inc., United States (2006).
De Genst, E., et al., "Antibody Repertoire Development in Camelids," Developmental and Comparative Immunology 30(1-2):187-198, Elsevier Science, United States (2006).
De Pascalis, R., et al., "Grafting of 'Abbreviated' Complementarity-Determining Regions Containing Specificity-Determining Residues Essential for Ligand Contact to Engineer a Less Immunogenic Humanized Monoclonal Antibody," Journal of Immunology 169(6):3076-3084, The American Association of Immunologists, United States (2002).
Dermer, G.B., "Another Anniversary for the War on Cancer," Biotechnology 12:320, Nature Publishing Co., United States (1994).
Doring, E. et al., "Identification and Characterization of the TNFalpha Antagonist Derived from a Monoclonal Antibody," Molecular Immunology 31(14):1059-1067, Elsevier Science Ltd., England (1994).
Easwaran, V., et al., "Beta-Catenin Regulates Vascular Endothelial Growth Factor Expression in Colon Cancer," Cancer Research 63(12):3145-3153, American Association for Cancer Research, United States (2003).
English language Abstract of DE10339820A1, espacenet database, Worldwide published Mar. 17, 2005.
English language Abstract of JP2010-532169A, espacenet database, Worldwide published Jan. 8, 2009.
European Opposition Brief for European Patent No. 2157192 filed May 8, 2014, 46 pages.
Extended European Search Report for EP Application No. 12814264, European Patent Office, Germany, dated Jan. 28, 2015, 7 pages.
Fischer, L., et al., "Wnt-3A Enhances Bone Morphogenetic Protein-2-Mediated Chondrogenesis of Murine C3H10T1/2 Mesenchymal Cells," The Journal of Biological Chemistry 277(34):30870-30878, JBC Papers in Press, American Society for Biochemistry and Molecular Biology, United States (2002).
Freshney, R.I., "Culture of Animal Cells," A Manual of Basic Technique 4, Alan R. Liss, Inc., United States (1983).
Fujino, T., et al., "Low-Density Lipoprotein Receptor-Related Protein 5 (LRP5) is Essential for Normal Cholesterol Metabolism and Glucose-Induced Insulin Secretion," Proceedings of the National Academy of Sciences 100(1):229-234, National Academy of Sciences, United States (2003).
Gazit A., et al., "Human Frizzled 1 Interacts with Transforming Wnts to Transduce a TCF Dependent Transcriptional Response," Ocogene 18(44):5959-5966, Nature Publishing Group, England (1999).
Goldblum, S.E., et al., "Thrombospondin-1 Induces Tyrosine Phosphorylation of Adherens Junction Proteins and Regulates an Endothelial Paracellular Pathway," Molecular Biology of the Cell 10(5):1537-1551, The American Society for Cell Biology, United States (1999).
Gong, Y., et al., "LDL Receptor-Related Protein 5 (LRP5) Affects Bone Accrual and Eye Development," Cell 107(4):513-523, Cell Press, United States (2001).
Gradl, D., et al., "The Wnt/Wg Signal Transducer Beta-Catenin Controls Fibronectin Expression," Molecular Cell Biology 19(8):5576-5587, Microbiology, United States (1999).
Gura, T., "Systems for Identifying New Drugs are often Faulty," Science 278(5340):1041-1042, American Association for the Advancement of Science, United States (1997).
Gurney, A., et al., "Inhibition of R-spondin (RSPO) signaling reduces the growth of multiple human tumors," AACR Annual Meeting 2014, Abstract 1764, Apr. 5-9, 1 pages (2014).

Harada, N., et al., "Intestinal Polyposis in Mice with a Dominant Stable Mutation of the β-catenin Gene," European Molecular Biology Organization Journal 18(21):5931-5942, Wiley-Blackwell, Inc., England (1999).
Hartmann, C., "Wnt-Signaling and Skeletogenesis," Journal of Musculoskelet & Neuronal Interactions 2(3):274-276, International Society of Musculoskeletal and Neuronal Interactions, Greece (2002).
Hatsell, S., et al., "Beta-Catenin and Tcfs in Mammary Development and Cancer," Journal of Mammary Gland Biology and Neoplasia 8(2):145-158, Kluwer Academic/Plenum Publishers, United States (2003).
He, T.C., et al., "Identification of c-MYC as a Target of the APC Pathway," Science 281(5382):1509-1512, American Association for the Advancement of Science, United States (1998).
Horesh, Y., et al., "A Rapid Method for Detection of Putative RNAi Target Genes in Genomic Data" Bioinformatics 19(Suppl 2):ii73-ii80, Oxford University Press, England (2003).
Hsu, S.Y., et al., "Activation of Orphan Receptors by the Hormone Relaxin," Science 295:671-674, American Association for the Advancement of Science, United States (2002).
Imbert, A., et al., "Delta N89 Beta-Catenin induces Precocious Development, Differentiation, and Neoplasia in Mammary Gland," The Journal of Cell Biology 153(3):555-568, Rockefeller University Press, United States (2001).
International Preliminary Report on Patentability for International Application No. PCT/US2008/008210, the International Bureau of WIPO, Geneva, Switzerland, dated Jan. 5, 2010, 9 pages.
International Search Report for International Application No. PCT/US15/45210, United States Patent and Trademark Office, United States, dated Jan. 6, 2016, 7 pages.
International Search Report for International Application No. PCT/US2008/008210, European Patent Office, Netherlands, dated Mar. 2, 2009, 6 pages.
International Search Report for International Application No. PCT/US2012/046746, the International Searching Authority, Alexandria, dated Oct. 23, 2012, 3 pages.
International Search Report for International Application No. PCT/US2013/050300, from the International Bureau of WO, Geneva Switzerland, dated Feb. 7, 2014, 7 pages.
Jackson, A.L. and Linsley, P.S., "Noise Amidst The Silence: Off-Target Effects of siRNAs?," Trends in Genetics 20(11):521-524, Elsevier Science Publishers B.V., Netherlands (2004).
Jain, R.K., "Barriers to Drug Delivery in Solid Tumors," Scientific American 271(1):58-65, Scientific American, Inc., United States (1994).
Jemal, A., et al., "Cancer Statistics, 2003," CA—A Cancer Journal for Clinicians 53(1):05-26, American Cancer Society, United States (2003).
Kamata, T., et al., "R-Spondin, A Novel Gene with Thrombospondin Type 1 Domain, was Expressed in the Dorsal Neural Tube and Affected in Wnts Mutants," Biochimica et Biophysica Acta 1676(1):51-62, Elsevier Pub. Co., Netherlands (2004).
Kazanskaya, O., et al., "R-Spondin2 is a Secreted activator of Wnt/.beta.-Catenin Signaling and is required for Xenopus Myogenesis," Developmental Cell 7:525-534, Cell Press, United States (2004).
Kim, K.A., et al., "Mitogenic Influence of Human R-Spondin1 on the Intestinal Epithelium," Science 309(5738):1256-1259, American Association for the Advancement of Science, United States (2005).
Kim, K.A., et al., "R-Spondin Family Members Regulate the Wnt Pathway by a Common Mechanism," Molecular Biology of the Cell 19:2588-2596, The American Society for Cell Biology, United States (2008).
Kim, K.A., et al., "R-Spondin Proteins: A Novel Link to Beta-Catenin Activation," Cell Cycle 5(1):23-26, Landes Bioscience, United States (2006).
Korinek, V., et al., "Constitutive Transcriptional Activation by a Beta-Catenin-Tcf Complex in APC -/- Colon Carcinoma," Science 275(5307):1784-1787, American Association for the Advancement of Science, United States (1997).

(56) References Cited

OTHER PUBLICATIONS

Kumar, K.K., et al., "Structure and Function of LGR5: An Enigmatic G-Protein Coupled Receptor Marking Stem Cells," Protein Science 23:551-565, Wiley-Blackwell, United States (2014).
Kuukasjrvi, P., et al., "Overview of Systematic Reviews on Invasive Treatment of Stable Coronary Artery Disease," The International Journal of Technology Assessment in Health Care 22(2):219-234, Cambridge University Press, England (2006).
Larue, L. and Delmas, V., "The Wnt/Beta-Catenin Pathway in Melanoma," Frontiers in Bioscience 11:733-742, Frontiers in Bioscience Publications, United States (2006).
Li, S.J., et al., "Loss-of-Function Point Mutations and Two-Furin Domain Derivatives Provide Insights about R-Spondin2 Structure and Function," Cellular Signalling 21(6): 916-925, Elsevier Science Ltd, England (2009).
Lonberg, N., "Human Antibodies from Transgenic Animals," Nature Biotechnology 23(9):1117-1125, Nature Publishing Group, United Kingdom (2005).
Luo, C-W., et al., "Genomic Analyses of the Evolution of LGR Genes," Chang Gung Med J 29:2-8, Chau-Xiong Zhang, China (2006).
Luu, H.H., et al., "Wnt/beta-Catenin Signaling Pathway as Novel Cancer Drug Targets," Current Cancer Drug Targets 4:653-671, Bentham Science Publishers, Netherlands (2004).
MacCallum, R.M., et al., "Antibody-Antigen Interactions: Contact Analysis and Binding Site Topography," Journal of Molecular Biology 262(5):732-745, Elsevier, England (1996).
Mazerbourg, S., et al., "Leucine-Rich Repeat-Containing, G Protein-Coupled Receptor 4 Null Mice Exhibit Intrauterine Growth Retardation Associated with Embryonic and Perinatal Lethality," Molecular Endocrinology 18(9):2241-2254, The Endocrine Society, United States (2004).
McClanahan, T., et al., "Identification of Overexpression of Orphan G Protein-Coupled Receptor GPR49 in Human Colon and Ovarian Primary Tumors," Cancer Biology and Therapy 5(4):419-426, Landes Bioscience, United States (2006).
Meniel, V. and Clarke, A.R., "Wnt-Cadherin Connections in Normal and Neoplastic Mammary Epithelium," Journal of Mammary Gland Biology and Neoplasia 8(4):435-447, Kluwer Academic/Plenum Publishers, United States (2003).
Michaelson, J.S, and Leder, P., "Beta-Catenin is a Downstream Effector of Wnt-Mediated Tumorigenesis in the Mammary Gland," Oncogene 20(37):5093-5099, Nature Publishing Group, England (2001).
Miller, J.R., et al., "Mechanism and Function of Signal Transduction by the Wnt/β-catenin and Wnt/Ca2+ Pathways," Oncogene 18(55):7860-7872, Nature Publishing Group, England (1999).
Milovanovic, T., et al., "Expression of Wnt Genes and Frizzled 1 and 2 Receptors in Normal Breast Epithelium and Infiltrating Breast Carcinoma," International Journal of Oncology 25(5):1337-1342, D.A. Spandidos, Greece (2004).
Morita, H., et al., "Neonatal Lethality of LGR5 Null Mice Is Associated with Ankyloglossia and Gastrointestinal Distension," Molecular Cell Biology 24(22):9736-9743, American Society for Microbiology, United States (2004).
Morrison, S.J., et al., "Hematopoietic Stem Cells: Challenges to Expectations," Current Opinion in Immunology 9(2):216-221, Elsevier Science, United States (1997).
Morrison, S.J.,et al., "Regulatory Mechanisms in Stem Cell Biology," Cell 88(3):287-298, Elsevier Science, United States (1997).
Morrison, S.J.,et al., "The Biology of Hematopoietic Stem Cells," Annual Review of Cell and Developmental Biology 11:35-71, Annual Reviews, United States (1995).
Nam, J.S., et al., "Mouse Cristin/R-Spondin Family Proteins are Novel Ligands for The Fizzled 8 and LRP6 Receptors and Activate Beta-Catenin-Dependent Gene Expression," The Journal of Biological Chemistry 281(19):13247-13257, American Society for Biochemistry and Molecular Biology, United States (2006).

Nusse, R. and Varmus, H.E., "Many Tumors Induced by the Mouse Mammary Tumor Virus contain a Provirus Integrated in the Same Region of the Host Genome," Cell 31(1):99-109, Cell Press, United States (1982).
Ohkawara, B., et al., "Rspo3 Binds Syndecan 4 and Induces Wnt/PCP Signaling via Clathrin-Mediated Endocytosis to Promote Morphogenesis," Developmental Cell 20:303-314, Elsevier Inc., United States (2011).
Ohkawara, B., et al., "Rspo3 Binds Syndecan 4 and Induces Wnt/PCP Signaling via Clathrin-Mediated Endocytosis to Promote Morphogenesis," Supplemental Information and Supplemental Figures, Developmental Cell 20:14 pages (2011).
OncoMed Pharmaceuticals Press Release, "OncoMed Presents Data on Clinical and Preclinical Anti-Cancer Stem Cell Programs at American Association for Cancer Research Annual Meeting," Apr. 21, 2015, 3 pages.
OncoMed Pharmaceuticals, Press Release, "OncoMed Presents Data on Multiple Anti-Cancer Stem Cell Programs at American Association for Cancer Research Annual Meeting," Apr. 8, 2014, 4 pages.
OncoMed Pharmaceuticals Press Release, "OncoMed to Present Data on Multiple Anti-Cancer Stem Cell Candidates at the American Association of Cancer Research Meeting," Mar. 19, 2015, 2 pages.
Oshima, H., et al., "Morphological and Molecular Processes of Polyp Formation in ApcΔ716 Knockout Mice," Cancer Research 57(9):1644-1649, The American Association for Cancer Research, United States (1997).
Pandis, N., et al., "Cytogenetic Comparison of Primary Tumors and Lymph Node Metastases in Breast Cancer Patients," Genes, Chromosomes & Cancer 22:122-129, Wiley-Liss, Inc., United States (1998).
Paul, W.E., "Structure and Function of Immunoglobulins," in *Fundamental Immunology*, Third Edition, pp. 292-295, Raven Press, New York, United States (1993).
Perantoni, A.O., "Renal Development: Perspectives on a Wnt-Dependent Process," Seminars in Cells and Development Biology Abstract, 1 page, Academic Press, United Kingdom (2003).
Polakis, P., "Wnt signaling and cancer," Genes & Development 14:1837-1851, Cold Spring Harbor Laboratory Press, United States (2000).
Polesskaya, A., et al., "Wnt Signaling Induces the Myogenic Specification of Resident CD45+ Adult Stem Cells during Muscle Regeneration," Cell Abstract, 1 page, MIT Press, United States (2003).
Reply to European Opposition Brief for European Patent No. 2157192 filed Jan. 8, 2015, 42 pages.
Response to attend Oral Proceedings in Opposition to European Patent 2157192, Opponent OncoMed Pharmaceuticals, Inc., 22 pages, Dec. 18, 2015.
Response to European Opposition Brief Reply for European Patent No. 2157192, filed May 14, 2015, 14 pages.
Reya, T. and Clevers, H., "Wnt Signaling in Stem Cells and Cancer," Nature 434(7035):843- 850, Nature Publishing Group, England (2005).
Rijsewijk, F., et al., "The *Drosophila* Homolog of the Mouse Mammary Oncogene int-1 is Identical to the Segment Polarity Gene wingless," Cell 50(4):649-657, Cell Press, United States (1987).
Rudikoff, S., et al., "Single Amino Acid Substitution Altering Antigen-Binding Specificity," Proceedings of the National Academy of Sciences 79(6):1979-1983, The National Academy of Sciences, United States (1982).
Saadi-Kheddouci, S., et al., "Early Development of Polycystic Kidney Disease in Transgenic Mice Expressing an Activated Mutant of the Beta-Catenin Gene," Oncogene 20(42):5972-5981, Nature Publishing Group, England (2001).
Shen, C.Y., et al., "Genome-Wide Search for Loss of Heterozygosity Using Laser Capture Microdissected Tissue of Breast Carcinoma: An Implication for Mutator Phenotype and Breast Cancer Pathogenesis," Cancer Research 60(14):3884-3892, American Association of Cancer Research, United States (2000).
Smalley, M.J. and Dale, T.C., "Wnt Signalling in Mammalian Development and Cancer," Cancer and Metastasis Reviews 18(2):215-230, Kluwer Academic Publishers, Netherlands (1999).

(56) References Cited

OTHER PUBLICATIONS

Stump, R.J., et al., "A Role for Wnt/Beta-Catenin Signaling in Lens Epithelial Differentiation," Developmental Biology Abstract, 1 page, Elsevier Inc., United States (2003).
Surendran, K., et al, "A Role for Wnt-4 in Renal Fibrosis," American Journal of Physiology. Renal Physiology 282(3):F431-F441, American Physiological Society, United Sates (2002).
Takahashi-Yanaga, F. and Sasaguri, T., "The Wnt/.Beta.-Catenin Signaling Pathway as a Target in Drug Discovery," Journal of Pharmaceutical Sciences 104:293-302, The Japanese Phamacological society, Japan (2007).
Tan, B.T., et al., "The Cancer Stem Cell Hypothesis: A Work in Progress," Laboratory Investigation 86(12):1203-1207, USCAP, United States (2006).
Tepera, S.B., et al., "A Beta-Catenin Survival Signal is required for Normal Lobular Development in the Mammary Gland," Journal of Cell Science 116(Pt 6):1137-1149, Company of Biologists, England (2003).
Tetsu, O. and McCormick, F., "Beta-Catenin Regulates Expression of Cyclin D1 in Colon Carcinoma Cells," Nature 398(6726):422-426, Nature Publishing Group, England (1999).
Theodorou, V., et al., "MMTV Insertional Mutagenesis Identifies Genes, Gene Families and Pathways Involved in Mammary Cancer," Nature Genetics 39(6):759-769, Nature Publishing Group, England (2007).
Transmittal of third party observations sent on Dec. 17, 2014 in European Application No. 08779934.2, 6 pages.
UniProt "Thrombospondin-1," identifying No. P07996-TSP1_HUMAN, accessed at http://www.uniprot.org/uniprot/P07996, accessed on Sep. 25, 2014, 14 pages.
Van Ooyen, A. and Nusse, R., "Structure and Nucelotide Sequence of the Putative Mammary Oncogene Int-1; Proviral Insertions Leave the Protein-Encoding Domain Intact," Cell 39(1):233-240, Cell Press, United States (1984).
Veeman, M.T., et al., "A Second Canon: Functions and Mechanisms of Beta-Catenin-Independent Wnt Signaling," Developmental Cell 5(3):367-377, Cell Press, United States (2003).
Written Opinion for International Application No. PCT/US15/45210, United States Patent and Trademark Office, United States, dated Jan. 6, 2016, 6 pages.
Written Opinion of the International Searching Authority for International Application No. PCT/US2008/008210, European Patent Office, Netherlands, dated Jan. 5, 2010, 8 pages.
Written Opinion of the International Searching Authority for International Application No. PCT/US2012/046746, dated Oct. 4, 2012, 7 pages.
Written Opinion of the International Searching Authority for International Application No. PCT/US2013/050300, dated Feb. 7, 2014, 11 pages.
Written Submission including New Main Request and Auxiliary Request in preparation for Oral Proceedings in Opposition to European Patent 2157192, Opponent OncoMed Pharmaceuticals, Inc., 12 pages, Dec. 18, 2015.
Wu, C-H., and Nusse, R., "Ligand Receptor Interactions in the Wnt Signaling Pathway in Drosophila," The Journal of Biological Chemistry 277(44):41762-41769, American Society for Biochemistry and Molecular Biology, United States (2002).
Wu, H., et al., "Humanization of a Murine Monoclonal Antibody by Simultaneous Optimization of Framework and CDR Residues," Journal of Molecular Biology 294(1):151-162, Elsevier, England (1999).
Wu, W., et al., "Mutual Antagonism between Dickkopf1 and Dickkopf2 Regulates Wnt/Beta-Catenin Signalling," Current Biology 10(24):1611-1614, Elsevier Science Ltd., England (2000).
Zhao, J., et al., "R-spondin1, A Novel Intestinotrophic Mitogen, Ameliorates Experimental Colitis in Mice," Gastroenterology 132(4):1331-1334, W.B. Saunders, United States (2007).
Akhmetshina, A., et al., "Actication of canonical Wnt signaling is required for TGF-β-mediated fibrosis," Nature Communications 3:735, 12 pages, Macmillan Publishers Limited, England (2012).
Chua, A.W.C., et al., "The Role of R-Spondin2 in Keratinocyte Proliferation and Epidermal Thickening in Keloid Scarring," Journal of Investigative Dermatology 131:644-654, The Society for Investigative Dermatology, United States (2011).
Guo, Y., et al., "Wnt/β-Catenin Signaling: a Promising New Target for Fibrosis Diseases," Physiology Research 61:337-346, Institute of Physiology, Czech Republic (2012).
Lam, A.P. and Gottardi, C.J., "β-catenin signaling: a novel mediator of fibrosis and potential therapeutic target," Current Opinion in Rheumatology 23(6):562-567, Lippincott Williams & Wilkins, United States (2011).
Miao, C-g., et al., "Wnt signaling in liver fibrosis: Progress, challenges and potential directions," Biochimie 95:2326-2335, Elsevier Masson SAS, France (2013).
Yin, X., et al., "R-Spondin2 Activates Hepatic Stellate Cells and Promotes Liver Fibrosis," Digestive Diseases and Sciences 59(10):2452-2461, Springer Science + Business Media, United States (2014).
Kazanskaya, O., et al., "The Wnt signaling regulator R-spondin 3 promotes angioblast and vascular development," Development 135:3655-3664, Company of Biologists, England (2008).
Alberts, B., et al., Molecular Biology of the Cell, 4th Edition, Garland Science, Taylor & Francis Group, 2002, pp. 895-896, 1282-1283, 1352 and 1358 (D7 as cited iin Opposition of EP 2081586 B1).
Annex to the Summons to attend Oral Proceedings, EP Application No. 08779934.2, OncoMed Pharmaceuticals Inc., dated Mar. 10, 2017, 28 pages.
Antagonists of R-spondin 3 for Treatment of Bone Disorders (P-881), dkfz, German Cancer Research Center in the Helmholtz Association, Jul. 12, 2 pages.
Aoki, M., et al., "R-spondin3 is Required for Mouse Placental Development," Developmental Biology 301(1):218-226, Elsevier, United States (2007) (D6 as cited in Opposition of EP 2081586 B1).
Armbruster, N., et al., "β-catenin Signaling in Mouse Hepatoma Cells Stabity Transfected with Hairless Gene," Naunyn-Schmiedeberg's Archives of Pharmacology 375(Suppl 1):90, Abstract 448 (2007).
Atwood, B.K., et al., "Expression of G Protein-coupled Receptors and Related Proteins in HEK293, AtT20, BV2, and N18 Cell Lines as Revealed by Microarray Analysis," BMC Genornica 12:14, BioMed Central, England (2011).
Chen, P.H., et al., "The Structural Basis of R-Spondin Recognition by LGR5 and RNF43," Genes & Development 27(12)1345-1350, Cold Spring Harbor Laboratory Press, United States (2013 with Supplementary Information).
Chilosi, M., et al., "Aberrant Wnt/β-Catenin Pathway Activation in Idiopathic Pulmonary Fibrosis," American Journal of Pathology 162(5):1495-1502, Elsevier, United States (2003).
Cruciat, C.M. and Niehrs, C., "Secreted and Transmembrane wnt Inhibitors and Activators,"Cold Springs Harbor perspectives in Biology 5(3):a015081, Cold Spring Harbor Laboratory Press, United States (2013).
De Lau, W.B., et al., "The R-Spondin Protein Family," Genome Biology 13(3):242, BioMed Central Ltd, England (2012).
Dkrz, "R-spondins 2 and 3 as inhibitors of angiogenesis: Potential cancer therapeutics (P-732)," Technology offer, German Cancer Research Center, Jun. 12, 2 pages.
Ellis, L.M., and Hicklin, D.J., "VEGF-targeted Therapy: Mechanisms of Anti-tumour Activity," Nature Reviews, Cancer 6(8):579-591, Nature Publishing Group, England (2008), D11 as cited in Opposition of EP 2081586.
Enzo, M.V., et al., "The Wnt/β-catenin Pathway in Human Fibrotic-like Diseases and its Eligibility as a Therapeutic Target," Molecular and Cellular Therapies 3, 1, 13 pages, Shanghai Institute of Clinical Bioinformatics, China (2015).
Fafilek, B., et al., "Troy, a Tumor Necrosis Factor Receptor Family Member, Interacts with LGR5 to Inhibit Wnt Signaling in Intestinal Stem Cells," Gastroenterology 144(2):381-391, AGA Institute, United States (2013).
Glinka, A., et al., "LGR4 and LGR5 are R-Spondin Receptors Mediating Wnt/β-Catenin and Wnt/PCP Signalling," EMBO Reports 12(10):1055-1061, Wiley Blackwell, England (2011).

(56) References Cited

OTHER PUBLICATIONS

Gong, X., et al., "LGR5-Targeted Antibody-Drug Conjugate Eradicates Gastrointestinal Tumors and Prevents Recurrence," Molecular Cancer Therapeutics 13(7):1580-1590, American Association for Cancer Research, Inc., United States (2016).
Goodwin, A.M., and D'Amore, P.A., "Wnt Signaling in the Vasculature," Angiogenesis 5(1-2):1-9, Springer, Germany (2002) (D10 as cited as Opposition of EP 2081586 B1).
Hao, H.X., et al., "ZNRF3 Promotes Wnt Receptor Turnover in a R-Spondin-Sensitive Manner," Nature 485(7397):195-200, Nature Publishing Group, England (2012), with Supplemental Information.
Hendrickx, M. and Leyns, L., "Non-Conventional Frizzled Ligands and Wnt Receptors," Development, Growth & Differntiation 50(4):229-243, Japanese Society of Developmental Biologists, Japan (2008).
International Preliminary Report on Patentability for Application Serial No. PCT/US2015/045210, dated Feb. 21, 2017, 9 pages.
International Search Report for Application No. PCT/US2016/049697, ISA/US, Alexandria, Virginia, United States, dated Dec. 30, 2016, 4 pages.
International Search Report for International Application No. PCT/US2015/050225, ISA/US, Alexandria, Virginia, dated Dec. 22, 2015, 5 pages.
International Search Report for International Application No. PCT/US2016/064207, ISA/US Alexandria, Virginia, dated Jun. 2, 2017, 8 pages.
Jin, Y.R. and Yoon, J.K., "The R-Spondin Family of Proteins: Emerging Regulators of WNT Signaling," The International Journal of Biochemistry & Cell Biology 44(12):2278-2287, Elsevier, Netherlands (2012).
Junttila, M.R., et al., "Targeting LGR5+Cells with an Antibody-Drug Conjugate for the Treatment of Colon Cancer," Science Translational Medicine 7(314):314ra186, American Association for the Advancement of Science, United States, 12 pages (2015).
Junttila, M.R., et al , "Supplementary Materials lot Targeting LGR5+cells with an antibody-drug conjugate for the treatment of colon canoer," Science Transtational Medicine 7(314):314ra186, American Association for the Advancement of Science, United States: 17 pages (2015).
Katoh, M., "WNT/PCP Signaling Pathway and Human Cancer (review)," Oncology Reports, 14(6);1583-1588, D.A. Spendidos, Greece (2005).
Kobayashi. S., et al., "LGR5-Positive Colon Cancer Stem Cells Interconvert with Drug-Resistant LGR5-Negative Cells and are Capable of Tumor Reconstitution," Stem Cells 30(12)2631-2644, AlphaMed Press, United States (2012).
Kwon, M.S., et al., "Leucine-Rich Repeat-Containing G-Protein Coupled Receptor 5/GPR49 Activates G12/13-Rho GTPase Pathway," Molecules and Cells 36(3)267-272, The Korean Society for Molecular and Cellular Biology, South Korea (2013).
Matsuzaki, S. and Darcha, C. "Involvement of the Wnt/β-Catenin Signaling Pathway in the Cellular and Molecular Mechanisms of Fibrosis in Endometriosis," PLoS One (10):e76806, Public Library of Science, United States (2013).
Niehrs, C., "The Complex World of WNT Receptor Signalling" Nature Reviews Molecular Cell Biology 13(12):767-799, Nature Publishing Group, England (2012).
"Opposition Against EP2173379," by Strewman Limited, cited in the European Opposition, European Patent No. 2173379, filed Jun. 2, 2010, 23 pages.
Patent Owners Response to the Notice of Opposition against European Patent No. 2173379 B, filed on Jun. 2, 2016, Strawman Limited vs OncoMed Pharmaceuticals, Inc., submitted Nov. 15, 2010, 37 pages.
Patentee's Reply to Appeal Brief for European Patent No. EP 2157192, filed Jan. 17, 2017, 42 pages.
Patentee's Response to Notice of Opposition in Opposition of EP 2081586, European Patent Office, filed Mar. 13, 2017, 42 pages.
Priority document of the Patent (EP06022070.4) (D8 as cited in Opposition of EP 2081586 B1).
Rignall, B., et al., "GPR49 is a Target on β-Catenin and NFκB Signalling," Naunyn-Schmiedeberg's Archives of Pharmacology 375(Suppl 1):90, Abstract 449 (2007).
Rossant, J., and Cross, J.C., "Placental Development Lessons from Mouse Mutants," Nature Reviews. Genetics 2(7):538-545, Nature Publishing Group, England (2001), D12 as cited in Opposition of EP 2051586.
Sasaki, Y., et al., "Establishment of a Novel Monoclonal Antibody against LGR5," and Biophysical Research Communications 394(3):498-502, Elsevier Inc., United States (2010).
Schreiber, S., et al., "Transgenic Expression of S33Y Mutated β-Catenin in Mouse Liver Consistutively Activates β-Catenin Singnalling," Naunyn-Schmiedebers's Archives of Pharmacology 375(Suppl 1):90, Abstract 450 (2007).
Schuijers, J. and Clevers, H., "Adult Mammalian Stem Cells: the Role of Wnt, Lgr5 and R-Spondins," The EMBO Journal 31(12):2685-2696, Wiley Blackwell, England (2012).
Seshagiri, S., et al., "Recurrent R-spandln Fusions in Colon Cancer," Nature 488(7413):660-664, Nature Publishing Group, England (2012).
Statement of Facts and Arguments in Opposition of EP 2081586B1, filed Sep. 23, 2016, 39 pages.
Tanese, K., et al., "G-Protein-Coupled Receptor GPR49 is up-Regulated in Basal Cell Carcinoma and Promotes Cell Proliferation and Tumor Formation," The American Journal of Pathology 173(3):835-843, Elsevier, United States (2008).
Tomaselli, S., et al., "Human RSPO1/R-Spondin1 is Expressed During Early Ovary Development and Augments β-Catenin Signalling," PloS one 6(1):e16366, Public Library of Science, United States (2011).
Walker, F., et al., "LGR5 is a Negative Regulator of Tumourigenicity, Antagonizes Wnt Signalling and Regulates Cell Adhesion in Colorectal Cancer Cell Lines," PLoS One 6(7):e22733, Public Library and Science, United States, 20 pages (2011).
Wang, D., et al., "Structural Basis for R-Spondin Recognition by LGR4/4/6 Receptors," Genes & Development 27(12):1339-1344, Cold Spring Harbor Laboratory Press, United States (2013).
Wei, Q., et al., "R-Spondin1 is a High Affinity Ligand for LRP6 and Induces LRP6 Phosphorylation and Beta-Catenin Signaling," The Journal of Biological Chemistry 282(21):15903-15911, American Society for Biochemistry and Molecular Biology, United States (2007).
Written Opinion for International Application No. PCT/US2015/050225, ISA/US, Alexandria, Virginia, dated Dec. 22, 2015, 5 pages.
Written Opinion for International Application No. PCT/US2015/064207, ISA/US Alexandria, Virginia, dated Jun. 2, 2017, 29 pages.
Yang, K., et al:, "The Evolving Roles of Canonical WNT Signaling in Stem Cells and Tumorigenesis: Implications in Targeted Cancer Therapies," Laboratory Investigation 96(2)116-136, Nature Publishing Group, United States (2016).

* cited by examiner

SEQUENCE LISTING

```
<160> NUMBER OF SEQ ID NOS: 80

<210> SEQ ID NO 1
<211> LENGTH: 263
<212> TYPE: PRT
<213> ORGANISM: Artificial Sequence
<220> FEATURE:
<223> OTHER INFORMATION: Human RSPO1 amino acid sequence with signal
      sequence

<400> SEQUENCE: 1

Met Arg Leu Gly Leu Cys Val Val Ala Leu Val Leu Ser Trp Thr His
1               5                   10                  15

Leu Thr Ile Ser Ser Arg Gly Ile Lys Gly Lys Arg Gln Arg Arg Ile
                20                  25                  30

Ser Ala Glu Gly Ser Gln Ala Cys Ala Lys Gly Cys Glu Leu Cys Ser
            35                  40                  45

Glu Val Asn Gly Cys Leu Lys Cys Ser Pro Lys Leu Phe Ile Leu Leu
        50                  55                  60

Glu Arg Asn Asp Ile Arg Gln Val Gly Val Cys Leu Pro Ser Cys Pro
65                  70                  75                  80

Pro Gly Tyr Phe Asp Ala Arg Asn Pro Asp Met Asn Lys Cys Ile Lys
                85                  90                  95

Cys Lys Ile Glu His Cys Glu Ala Cys Phe Ser His Asn Phe Cys Thr
            100                 105                 110

Lys Cys Lys Glu Gly Leu Tyr Leu His Lys Gly Arg Cys Tyr Pro Ala
        115                 120                 125

Cys Pro Glu Gly Ser Ser Ala Ala Asn Gly Thr Met Glu Cys Ser Ser
    130                 135                 140

Pro Ala Gln Cys Glu Met Ser Glu Trp Ser Pro Trp Gly Pro Cys Ser
145                 150                 155                 160

Lys Lys Gln Gln Leu Cys Gly Phe Arg Arg Gly Ser Glu Glu Arg Thr
                165                 170                 175
```

```
Arg Arg Val Leu His Ala Pro Val Gly Asp His Ala Ala Cys Ser Asp
            180                 185                 190

Thr Lys Glu Thr Arg Arg Cys Thr Val Arg Arg Val Pro Cys Pro Glu
            195                 200                 205

Gly Gln Lys Arg Arg Lys Gly Gly Gln Gly Arg Glu Asn Ala Asn
            210                 215                 220

Arg Asn Leu Ala Arg Lys Glu Ser Lys Glu Ala Gly Ala Gly Ser Arg
225                 230                 235                 240

Arg Arg Lys Gly Gln Gln Gln Gln Gln Gln Gly Thr Val Gly Pro
                245                 250                 255

Leu Thr Ser Ala Gly Pro Ala
            260

<210> SEQ ID NO 2
<211> LENGTH: 243
<212> TYPE: PRT
<213> ORGANISM: Artificial Sequence
<220> FEATURE:
<223> OTHER INFORMATION: Human RSPO2 amino acid sequence with signal
      sequence

<400> SEQUENCE: 2

Met Gln Phe Arg Leu Phe Ser Phe Ala Leu Ile Ile Leu Asn Cys Met
1               5                   10                  15

Asp Tyr Ser His Cys Gln Gly Asn Arg Trp Arg Arg Ser Lys Arg Ala
            20                  25                  30

Ser Tyr Val Ser Asn Pro Ile Cys Lys Gly Cys Leu Ser Cys Ser Lys
            35                  40                  45

Asp Asn Gly Cys Ser Arg Cys Gln Gln Lys Leu Phe Phe Phe Leu Arg
        50                  55                  60

Arg Glu Gly Met Arg Gln Tyr Gly Glu Cys Leu His Ser Cys Pro Ser
65                  70                  75                  80

Gly Tyr Tyr Gly His Arg Ala Pro Asp Met Asn Arg Cys Ala Arg Cys
            85                  90                  95

Arg Ile Glu Asn Cys Asp Ser Cys Phe Ser Lys Asp Phe Cys Thr Lys
            100                 105                 110

Cys Lys Val Gly Phe Tyr Leu His Arg Gly Arg Cys Phe Asp Glu Cys
            115                 120                 125

Pro Asp Gly Phe Ala Pro Leu Glu Glu Thr Met Glu Cys Val Glu Gly
        130                 135                 140

Cys Glu Val Gly His Trp Ser Glu Trp Gly Thr Cys Ser Arg Asn Asn
145                 150                 155                 160

Arg Thr Cys Gly Phe Lys Trp Gly Leu Glu Thr Arg Thr Arg Gln Ile
            165                 170                 175

Val Lys Lys Pro Val Lys Asp Thr Ile Pro Cys Pro Thr Ile Ala Glu
            180                 185                 190

Ser Arg Arg Cys Lys Met Thr Met Arg His Cys Pro Gly Gly Lys Arg
            195                 200                 205

Thr Pro Lys Ala Lys Glu Lys Arg Asn Lys Lys Lys Arg Lys Leu
        210                 215                 220

Ile Glu Arg Ala Gln Glu Gln His Ser Val Phe Leu Ala Thr Asp Arg
225                 230                 235                 240

Ala Asn Gln
```

-continued

```
<210> SEQ ID NO 3
<211> LENGTH: 272
<212> TYPE: PRT
<213> ORGANISM: Artificial Sequence
<220> FEATURE:
<223> OTHER INFORMATION: Human RSPO3 amino acid sequence with signal
      sequence

<400> SEQUENCE: 3

Met His Leu Arg Leu Ile Ser Trp Leu Phe Ile Ile Leu Asn Phe Met
1               5                   10                  15

Glu Tyr Ile Gly Ser Gln Asn Ala Ser Arg Gly Arg Arg Gln Arg Arg
            20                  25                  30

Met His Pro Asn Val Ser Gln Gly Cys Gln Gly Gly Cys Ala Thr Cys
        35                  40                  45

Ser Asp Tyr Asn Gly Cys Leu Ser Cys Lys Pro Arg Leu Phe Phe Ala
    50                  55                  60

Leu Glu Arg Ile Gly Met Lys Gln Ile Gly Val Cys Leu Ser Ser Cys
65                  70                  75                  80

Pro Ser Gly Tyr Tyr Gly Thr Arg Tyr Pro Asp Ile Asn Lys Cys Thr
                85                  90                  95

Lys Cys Lys Ala Asp Cys Asp Thr Cys Phe Asn Lys Asn Phe Cys Thr
            100                 105                 110

Lys Cys Lys Ser Gly Phe Tyr Leu His Leu Gly Lys Cys Leu Asp Asn
        115                 120                 125

Cys Pro Glu Gly Leu Glu Ala Asn Asn His Thr Met Glu Cys Val Ser
    130                 135                 140

Ile Val His Cys Glu Val Ser Glu Trp Asn Pro Trp Ser Pro Cys Thr
145                 150                 155                 160

Lys Lys Gly Lys Thr Cys Gly Phe Lys Arg Gly Thr Glu Thr Arg Val
                165                 170                 175

Arg Glu Ile Ile Gln His Pro Ser Ala Lys Gly Asn Leu Cys Pro Pro
            180                 185                 190

Thr Asn Glu Thr Arg Lys Cys Thr Val Gln Arg Lys Lys Cys Gln Lys
        195                 200                 205

Gly Glu Arg Gly Lys Lys Gly Arg Glu Arg Lys Arg Lys Lys Pro Asn
    210                 215                 220

Lys Gly Glu Ser Lys Glu Ala Ile Pro Asp Ser Lys Ser Leu Glu Ser
225                 230                 235                 240

Ser Lys Glu Ile Pro Glu Gln Arg Glu Asn Lys Gln Gln Gln Lys Lys
                245                 250                 255

Arg Lys Val Gln Asp Lys Gln Lys Ser Val Ser Val Ser Thr Val His
            260                 265                 270

<210> SEQ ID NO 4
<211> LENGTH: 234
<212> TYPE: PRT
<213> ORGANISM: Artificial Sequence
<220> FEATURE:
<223> OTHER INFORMATION: Human RSPO4 amino acid sequence with signal
      sequence

<400> SEQUENCE: 4

Met Arg Ala Pro Leu Cys Leu Leu Leu Leu Val Ala His Ala Val Asp
1               5                   10                  15

Met Leu Ala Leu Asn Arg Arg Lys Lys Gln Val Gly Thr Gly Leu Gly
            20                  25                  30
```

-continued

```
Gly Asn Cys Thr Gly Cys Ile Ile Cys Ser Glu Glu Asn Gly Cys Ser
            35                  40                  45

Thr Cys Gln Gln Arg Leu Phe Leu Phe Ile Arg Glu Gly Ile Arg
 50                  55                  60

Gln Tyr Gly Lys Cys Leu His Asp Cys Pro Pro Gly Tyr Phe Gly Ile
 65                  70                  75                  80

Arg Gly Gln Glu Val Asn Arg Cys Lys Lys Cys Gly Ala Thr Cys Glu
                 85                  90                  95

Ser Cys Phe Ser Gln Asp Phe Cys Ile Arg Cys Lys Arg Gln Phe Tyr
                100                 105                 110

Leu Tyr Lys Gly Lys Cys Leu Pro Thr Cys Pro Pro Gly Thr Leu Ala
                115                 120                 125

His Gln Asn Thr Arg Glu Cys Gln Gly Glu Cys Glu Leu Gly Pro Trp
                130                 135                 140

Gly Gly Trp Ser Pro Cys Thr His Asn Gly Lys Thr Cys Gly Ser Ala
145                 150                 155                 160

Trp Gly Leu Glu Ser Arg Val Arg Glu Ala Gly Arg Ala Gly His Glu
                165                 170                 175

Glu Ala Ala Thr Cys Gln Val Leu Ser Glu Ser Arg Lys Cys Pro Ile
                180                 185                 190

Gln Arg Pro Cys Pro Gly Glu Arg Ser Pro Gly Gln Lys Lys Gly Arg
                195                 200                 205

Lys Asp Arg Arg Pro Arg Lys Asp Arg Lys Leu Asp Arg Leu Asp
                210                 215                 220

Val Arg Pro Arg Gln Pro Gly Leu Gln Pro
225                 230

<210> SEQ ID NO 5
<211> LENGTH: 6
<212> TYPE: PRT
<213> ORGANISM: Artificial Sequence
<220> FEATURE:
<223> OTHER INFORMATION: 89M5 Heavy chain CDR1

<400> SEQUENCE: 5

Thr Gly Tyr Thr Met His
1               5

<210> SEQ ID NO 6
<211> LENGTH: 17
<212> TYPE: PRT
<213> ORGANISM: Artificial Sequence
<220> FEATURE:
<223> OTHER INFORMATION: 89M5 Heavy chain CDR2

<400> SEQUENCE: 6

Gly Ile Asn Pro Asn Asn Gly Gly Thr Thr Tyr Asn Gln Asn Phe Lys
1               5                   10                  15

Gly

<210> SEQ ID NO 7
<211> LENGTH: 12
<212> TYPE: PRT
<213> ORGANISM: Artificial Sequence
<220> FEATURE:
<223> OTHER INFORMATION: 89M5 Heavy chain CDR3

<400> SEQUENCE: 7

Lys Glu Phe Ser Asp Gly Tyr Tyr Phe Phe Ala Tyr
1               5                   10
```

```
<210> SEQ ID NO 8
<211> LENGTH: 11
<212> TYPE: PRT
<213> ORGANISM: Artificial Sequence
<220> FEATURE:
<223> OTHER INFORMATION: 89M5 Light chain CDR1

<400> SEQUENCE: 8

Lys Ala Ser Gln Asp Val Ile Phe Ala Val Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: 89M5 Light chain CDR2

<400> SEQUENCE: 9

Trp Ala Ser Thr Arg His Thr
1               5

<210> SEQ ID NO 10
<211> LENGTH: 8
<212> TYPE: PRT
<213> ORGANISM: Artificial Sequence
<220> FEATURE:
<223> OTHER INFORMATION: 89M5 Light chain CDR3

<400> SEQUENCE: 10

Gln Gln His Tyr Ser Thr Pro Trp
1               5

<210> SEQ ID NO 11
<211> LENGTH: 121
<212> TYPE: PRT
<213> ORGANISM: Artificial Sequence
<220> FEATURE:
<223> OTHER INFORMATION: h89M5-H8L5 Heavy chain variable region amino
      acid sequence

<400> SEQUENCE: 11

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Gly Tyr
                20                  25                  30

Thr Met His Trp Val Arg Gln Met Pro Gly Lys Gly Leu Glu Trp Met
            35                  40                  45

Gly Gly Ile Asn Pro Asn Asn Gly Gly Thr Thr Tyr Asn Gln Asn Phe
    50                  55                  60

Lys Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Lys Glu Phe Ser Asp Gly Tyr Tyr Phe Phe Ala Tyr Trp Gly
            100                 105                 110

Gln Gly Thr Leu Val Thr Val Ser Ser
        115                 120

<210> SEQ ID NO 12
<211> LENGTH: 107
<212> TYPE: PRT
<213> ORGANISM: Artificial Sequence
```

```
<220> FEATURE:
<223> OTHER INFORMATION: h89M5-H8L5 Light chain variable region amino
      acid sequence

<400> SEQUENCE: 12

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Val Ile Phe Ala
            20                  25                  30

Val Ala Trp Tyr Gln Gln Lys Pro Gly Gln Pro Pro Lys Leu Leu Ile
        35                  40                  45

Tyr Trp Ala Ser Thr Arg His Thr Gly Val Pro Asp Arg Phe Ser Gly
50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln His Tyr Ser Thr Pro Trp
                85                  90                  95

Thr Phe Gly Gly Gly Thr Lys Val Glu Ile Lys
            100                 105

<210> SEQ ID NO 13
<211> LENGTH: 470
<212> TYPE: PRT
<213> ORGANISM: Artificial Sequence
<220> FEATURE:
<223> OTHER INFORMATION: h89M5-H8L5 Heavy chain amino acid sequence with
      predicted signal sequence
<220> FEATURE:
<221> NAME/KEY: SIGNAL
<222> LOCATION: (1)..(19)

<400> SEQUENCE: 13

Met Asp Trp Thr Trp Arg Ile Leu Phe Leu Val Ala Ala Thr Gly
1               5                   10                  15

Ala His Ser Glu Val Gln Leu Val Gln Ser Gly Ala Glu Val Lys Lys
            20                  25                  30

Pro Gly Glu Ser Leu Arg Ile Ser Cys Lys Gly Ser Gly Tyr Ser Phe
        35                  40                  45

Thr Gly Tyr Thr Met His Trp Val Arg Gln Met Pro Gly Lys Gly Leu
50                  55                  60

Glu Trp Met Gly Gly Ile Asn Pro Asn Asn Gly Gly Thr Thr Tyr Asn
65                  70                  75                  80

Gln Asn Phe Lys Gly His Val Thr Ile Ser Ala Asp Lys Ser Ile Ser
                85                  90                  95

Thr Ala Tyr Leu Gln Trp Ser Ser Leu Lys Ala Ser Asp Thr Ala Met
            100                 105                 110

Tyr Tyr Cys Ala Arg Lys Glu Phe Ser Asp Gly Tyr Tyr Phe Phe Ala
        115                 120                 125

Tyr Trp Gly Gln Gly Thr Leu Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205
```

```
Val Thr Val Pro Ser Ser Leu Gly Thr Gln Thr Tyr Ile Cys Asn
    210             215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
                275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
                355                 360                 365

Pro Gln Val Tyr Thr Leu Pro Pro Ser Arg Glu Glu Met Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
                435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 14
<211> LENGTH: 451
<212> TYPE: PRT
<213> ORGANISM: Artificial Sequence
<220> FEATURE:
<223> OTHER INFORMATION: h89M5-H8L5 Heavy chain amino acid sequence
      without predicted signal sequence

<400> SEQUENCE: 14

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Gly Tyr
                20                  25                  30

Thr Met His Trp Val Arg Gln Met Pro Gly Lys Gly Leu Glu Trp Met
            35                  40                  45

Gly Gly Ile Asn Pro Asn Gly Gly Thr Thr Tyr Asn Gln Asn Phe
        50                  55                  60

Lys Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95
```

```
Ala Arg Lys Glu Phe Ser Asp Gly Tyr Tyr Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
    435                 440                 445

Pro Gly Lys
    450

<210> SEQ ID NO 15
<211> LENGTH: 234
<212> TYPE: PRT
<213> ORGANISM: Artificial Sequence
<220> FEATURE:
<223> OTHER INFORMATION: h89M5-H8L5 Light chain amino acid sequence with
      predicted signal sequence
```

```
<220> FEATURE:
<221> NAME/KEY: SIGNAL
<222> LOCATION: (1)..(20)

<400> SEQUENCE: 15

Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Asp Ser Leu Ala
            20                  25                  30

Val Ser Leu Gly Glu Arg Ala Thr Ile Asn Cys Lys Ala Ser Gln Asp
        35                  40                  45

Val Ile Phe Ala Val Ala Trp Tyr Gln Gln Lys Pro Gly Gln Pro Pro
    50                  55                  60

Lys Leu Leu Ile Tyr Trp Ala Ser Thr Arg His Thr Gly Val Pro Asp
65              70                  75                  80

Arg Phe Ser Gly Ser Gly Ser Gly Thr Asp Phe Thr Leu Thr Ile Ser
                85                  90                  95

Ser Leu Gln Ala Glu Asp Val Ala Val Tyr Tyr Cys Gln Gln His Tyr
            100                 105                 110

Ser Thr Pro Trp Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Asn Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 16
<211> LENGTH: 214
<212> TYPE: PRT
<213> ORGANISM: Artificial Sequence
<220> FEATURE:
<223> OTHER INFORMATION: h89M5-H8L5 Light chain amino acid sequence
      without predicted signal sequence

<400> SEQUENCE: 16

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Val Ile Phe Ala
            20                  25                  30

Val Ala Trp Tyr Gln Gln Lys Pro Gly Gln Pro Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Ala
65              70                  75                  80

Glu Asp Val Ala Val Tyr Tyr Cys Gln Gln His Tyr Ser Thr Pro Trp
                85                  90                  95
```

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Asn Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 17
<211> LENGTH: 363
<212> TYPE: DNA
<213> ORGANISM: Artificial Sequence
<220> FEATURE:
<223> OTHER INFORMATION: h89M5-H8L5 Heavy chain variable region
      nucleotide sequence

<400> SEQUENCE: 17
gaagtgcagc tggtgcagtc tggagcagag gtcaaaaagc ccggggagtc tctgaggatc      60
tcctgcaagg gttctggata cagctttact ggatacacca tgcactgggt gcgccagatg     120
cccgggaaag gactggagtg gatggggggt attaatccta acaatggtgg tactacttac     180
aaccagaact tcaagggcca cgtcaccatc tcagctgaca agtccatcag cactgcctac     240
ctgcaatgga gcagcctgaa ggcttctgac accgccatgt attactgtgc aagaaaggag     300
ttctctgatg gatactactt ttttgcttac tggggccaag ggaccctggt gaccgtcagc     360
tca                                                                   363

<210> SEQ ID NO 18
<211> LENGTH: 321
<212> TYPE: DNA
<213> ORGANISM: Artificial Sequence
<220> FEATURE:
<223> OTHER INFORMATION: h89M5-H8L5 Light chain variable region
      nucleotide sequence

<400> SEQUENCE: 18
gacatcgtga tgacccagtc tccagactcc ctggctgtgt ctctgggcga gagggccacc      60
atcaactgca aggcttccca ggacgtgatt tttgctgttg cctggtatca gcagaaacca     120
ggacagcctc ctaagctgct catttactgg gcatctaccc gccacactgg ggtccctgac     180
cgcttcagtg gcagcgggtc tgggacagat ttcactctca ccatcagcag cctccaggct     240
gaagatgtgg cagtttatta ctgtcagcaa cattatagca ctccttggac tttcggcgga     300
gggaccaagg tggagatcaa a                                               321

<210> SEQ ID NO 19
<211> LENGTH: 1413
<212> TYPE: DNA
<213> ORGANISM: Artificial Sequence
<220> FEATURE:
<223> OTHER INFORMATION: h89M5-H8L5 Heavy chain nucleotide sequence

<400> SEQUENCE: 19

```
atggactgga cctggaggat actctttctc gtggcggcag ccacaggagc ccactccgaa      60
gtgcagctgg tgcagtctgg agcagaggtc aaaaagcccg ggagtctct gaggatctcc     120
tgcaagggtt ctggatacag ctttactgga tacaccatgc actgggtgcg ccagatgccc    180
gggaaaggac tggagtggat ggggggtatt aatcctaaca atggtggtac tacttacaac    240
cagaacttca agggccacgt caccatctca gctgacaagt ccatcagcac tgcctacctg    300
caatggagca gcctgaaggc ttctgacacc gccatgtatt actgtgcaag aaaggagttc    360
tctgatggat actactttt tgcttactgg ggccaaggga ccctggtgac cgtcagctca    420
gccagcacaa agggccctc cgtgttccct ctggcccctt cctccaagtc cacctccggc     480
ggcaccgccg ctctgggctg cctggtgaag gactacttcc ctgagcctgt gaccgtgtcc    540
tggaactctg gcgcactgac ctctggcgtg cacaccttcc cagccgtgct ccagtcctcc    600
ggcctgtact ccctgtcctc cgtcgtcacc gtgccttcct cctccctggg cacccagacc    660
tacatctgca acgtgaacca caagccttcc aacacaaagg tggacaagcg ggtggagcct    720
aagtcctgcg acaagaccca cacctgccct ccctgccctg ccctgagct gctgggcgga    780
ccttccgtgt tcctgttccc tcctaagcct aaggacaccc tgatgatctc ccggaccct    840
gaagtgacat gcgtggtggt ggacgtgtcc cacgaggacc ctgaggtgaa gttcaactgg    900
tatgtggacg gcgtggaggt gcacaacgct aagaccaagc gagggagga gcagtacaac    960
tccacctacc gggtggtgtc tgtgctgacc gtgctgcacc aggactggct gaacggcaaa   1020
gaatacaagt gcaaggtctc caacaaggcc ctgcccgctc ccatcgagaa accatcagc    1080
aaggcaaagg ccagcctcg cgagcctcag gtgtacaccc tgccacccag ccgggaggag   1140
atgaccaaga accaggtgtc cctgacctgt ctggtgaagg gcttttaccc ttccgatatt   1200
gccgtggagt gggagtctaa cggccagccc gagaacaact acaagaccac ccctcctgtg   1260
ctggactccg acggctcctt cttcctgtac tccaagctga ccgtggacaa gtcccggtgg   1320
cagcagggca acgtgttctc ctgctccgtg atgcacgagg ccctgcacaa ccactacacc   1380
cagaagagcc tgtctctgtc tcctggcaag tga                                 1413
```

<210> SEQ ID NO 20
<211> LENGTH: 705
<212> TYPE: DNA
<213> ORGANISM: Artificial Sequence
<220> FEATURE:
<223> OTHER INFORMATION: h89M5-H8L5 Light chain nucleotide sequence

<400> SEQUENCE: 20

```
atggtgctcc agacccaggt cttcatttct ctgctcctct ggatctctgg tgcctacggg      60
gacatcgtga tgacccagtc tccagactcc ctggctgtgt ctctgggcga gagggccacc    120
atcaactgca aggcttccca ggacgtgatt tttgctgttg cctggtatca gcagaaacca    180
ggacagcctc ctaagctgct catttactgg gcatctaccc gccacactgg ggtccctgac    240
cgcttcagtg gcagcgggtc tgggacagat ttcactctca ccatcagcag cctccaggct    300
gaagatgtgg cagtttatta ctgtcagcaa cattatagca ctccttggac tttcggcgga    360
gggaccaagg tggagatcaa acggactgtg gctgcaccat ctgtcttcat cttccctcca    420
tctgatgagc agttgaaatc tggaactgcc tctgttgtgt gcctgctgaa taacttctat    480
cccagagagg ccaaagtcca gtggaaggtg gataacgccc tccaatccgg taactcccag    540
gagagtgtca cagagcagga cagcaaggac agcacctaca gcctcagcaa caccctgaca    600
```

```
ctgagcaaag cagactacga gaaacacaaa gtctatgcct gcgaagtcac ccatcagggc      660
ctgtcttccc ccgtcacaaa gagcttcaac aggggagagt gctaa                     705
```

<210> SEQ ID NO 21
<211> LENGTH: 6
<212> TYPE: PRT
<213> ORGANISM: Artificial Sequence
<220> FEATURE:
<223> OTHER INFORMATION: 130M23 Heavy chain CDR1

<400> SEQUENCE: 21

```
Ser Ser Tyr Ala Met Ser
1               5
```

<210> SEQ ID NO 22
<211> LENGTH: 16
<212> TYPE: PRT
<213> ORGANISM: Artificial Sequence
<220> FEATURE:
<223> OTHER INFORMATION: 130M23 Heavy chain CDR2

<400> SEQUENCE: 22

```
Ser Ile Ser Ser Gly Gly Ser Thr Tyr Tyr Pro Asp Ser Val Lys Gly
1               5                   10                  15
```

<210> SEQ ID NO 23
<211> LENGTH: 18
<212> TYPE: PRT
<213> ORGANISM: Artificial Sequence
<220> FEATURE:
<223> OTHER INFORMATION: 130M23 Heavy chain CDR3

<400> SEQUENCE: 23

```
Arg Gly Gly Asp Pro Gly Val Tyr Asn Gly Asp Tyr Glu Asp Ala Met
1               5                   10                  15

Asp Tyr
```

<210> SEQ ID NO 24
<211> LENGTH: 11
<212> TYPE: PRT
<213> ORGANISM: Artificial Sequence
<220> FEATURE:
<223> OTHER INFORMATION: 130M23 Light chain CDR1

<400> SEQUENCE: 24

```
Lys Ala Ser Gln Asp Val Ser Ser Ala Val Ala
1               5                   10
```

<210> SEQ ID NO 25
<211> LENGTH: 7
<212> TYPE: PRT
<213> ORGANISM: Artificial Sequence
<220> FEATURE:
<223> OTHER INFORMATION: 130M23 Light chain CDR2

<400> SEQUENCE: 25

```
Trp Ala Ser Thr Arg His Thr
1               5
```

<210> SEQ ID NO 26
<211> LENGTH: 7
<212> TYPE: PRT
<213> ORGANISM: Artificial Sequence
<220> FEATURE:
<223> OTHER INFORMATION: 130M23 Light chain CDR3

```
<400> SEQUENCE: 26

Gln Gln His Tyr Ser Thr Pro
1               5

<210> SEQ ID NO 27
<211> LENGTH: 125
<212> TYPE: PRT
<213> ORGANISM: Artificial Sequence
<220> FEATURE:
<223> OTHER INFORMATION: h130M23-H1L6 Heavy chain variable region amino
      acid sequence

<400> SEQUENCE: 27

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Ser Gly Gly Ser Thr Tyr Tyr Pro Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Asp Pro Gly Val Tyr Asn Gly Asp Tyr Glu Asp Ala Met
            100                 105                 110

Asp Tyr Trp Gly Gln Gly Thr Thr Val Thr Val Ser Ser
        115                 120                 125

<210> SEQ ID NO 28
<211> LENGTH: 107
<212> TYPE: PRT
<213> ORGANISM: Artificial Sequence
<220> FEATURE:
<223> OTHER INFORMATION: h130M23-H1L6 Light chain variable region amino
      acid sequence

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ser Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gln Gly Thr Lys Val Glu Ile Lys
            100                 105

<210> SEQ ID NO 29
<211> LENGTH: 470
<212> TYPE: PRT
<213> ORGANISM: Artificial Sequence
```

<220> FEATURE:
<223> OTHER INFORMATION: h130M23-H1L6 Heavy chain amino acid sequence
      with predicted signal sequence
<220> FEATURE:
<221> NAME/KEY: SIGNAL
<222> LOCATION: (1)..(19)

<400> SEQUENCE: 29

Met Glu Leu Gly Leu Arg Trp Val Phe Leu Val Ala Ile Leu Glu Gly
1               5                   10                  15

Val Gln Cys Glu Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Ser Tyr Ala Met Ser Trp Val Arg Gln Ala Pro Gly Lys Gly Leu
    50                  55                  60

Glu Trp Val Ser Ser Ile Ser Ser Gly Gly Ser Thr Tyr Tyr Pro Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Thr Ala Val Tyr
            100                 105                 110

Tyr Cys Ala Arg Gly Gly Asp Pro Gly Val Tyr Asn Gly Asp Tyr Glu
        115                 120                 125

Asp Ala Met Asp Tyr Trp Gly Gln Gly Thr Thr Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
    210                 215                 220

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Gln Phe Asn Trp Tyr Val Asp Gly
    290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val His Gln Asp Trp
                325                 330                 335

Leu Asn Gly Lys Glu Tyr Lys Cys Lys Val Ser Asn Lys Gly Leu Pro
            340                 345                 350

Ala Pro Ile Glu Lys Thr Ile Ser Lys Thr Lys Gly Gln Pro Arg Glu
        355                 360                 365

```
Pro Gln Val Tyr Thr Leu Pro Pro Ser Arg Glu Glu Met Thr Lys Asn
            370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Met Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
                435                 440                 445

Ser Val Met His Glu Ala Leu His Asn His Tyr Thr Gln Lys Ser Leu
450                 455                 460

Ser Leu Ser Pro Gly Lys
465                 470

<210> SEQ ID NO 30
<211> LENGTH: 451
<212> TYPE: PRT
<213> ORGANISM: Artificial Sequence
<220> FEATURE:
<223> OTHER INFORMATION: h130M23-H1L6 Heavy chain amino acid sequence
      without predicted signal sequence

<400> SEQUENCE: 30

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ser Ile Ser Ser Gly Gly Ser Thr Tyr Tyr Pro Asp Ser Val Lys
50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Asp Pro Gly Val Tyr Asn Gly Asp Tyr Glu Asp Ala Met
            100                 105                 110

Asp Tyr Trp Gly Gln Gly Thr Thr Val Thr Val Ser Ser Ala Ser Thr
            115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
            195                 200                 205

Asn Val Asp His Lys Pro Ser Asn Thr Lys Val Asp Lys Thr Val Glu
210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255
```

```
Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
            275                 280                 285

His Asn Ala Lys Thr Lys Pro Arg Glu Glu Gln Phe Asn Ser Thr Phe
    290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
    435                 440                 445

Pro Gly Lys
    450

<210> SEQ ID NO 31
<211> LENGTH: 238
<212> TYPE: PRT
<213> ORGANISM: Artificial Sequence
<220> FEATURE:
<223> OTHER INFORMATION: h130M23-H1L6 Light chain amino acid sequence
      with predicted signal sequence
<220> FEATURE:
<221> NAME/KEY: SIGNAL
<222> LOCATION: (1)..(24)

<400> SEQUENCE: 31

Met Gly Ile Lys Met Glu Ser Gln Ile Gln Ala Phe Val Phe Val Phe
1               5                   10                  15

Leu Trp Leu Ser Gly Val Asp Gly Asp Ile Gln Met Thr Gln Ser Pro
            20                  25                  30

Ser Ser Leu Ser Ala Ser Val Gly Asp Arg Val Thr Ile Thr Cys Lys
        35                  40                  45

Ala Ser Gln Asp Val Ser Ala Val Ala Trp Tyr Gln Gln Lys Pro
    50                  55                  60

Gly Lys Ala Pro Lys Leu Leu Ile Tyr Trp Ala Ser Thr Arg His Thr
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Thr Tyr Tyr Cys
            100                 105                 110

Gln Gln His Tyr Ser Thr Pro Trp Thr Phe Gly Gln Gly Thr Lys Val
        115                 120                 125

Glu Ile Lys Arg Thr Val Ala Ala Pro Ser Val Phe Ile Phe Pro Pro
    130                 135                 140
```

```
Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Asn Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 32
<211> LENGTH: 214
<212> TYPE: PRT
<213> ORGANISM: Artificial Sequence
<220> FEATURE:
<223> OTHER INFORMATION: h130M23-H1L6 Light chain amino acid sequence
      without predicted signal sequence

<400> SEQUENCE: 32

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ser Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Asn Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210
```

<210> SEQ ID NO 33
<211> LENGTH: 375
<212> TYPE: DNA
<213> ORGANISM: Artificial Sequence
<220> FEATURE:
<223> OTHER INFORMATION: h130M23-H1L6 Heavy chain variable region
      nucleotide sequence

<400> SEQUENCE: 33

```
gaggtgcagc tggtggagtc tgggggaggc ctggtcaagc ctggaggatc tctgcggctc      60
tcctgtgcag cctctggatt caccttctcc tcttatgcca tgtcttgggt ccggcaggct     120
ccagggaagg ggctggaatg ggtctcatcc atttctagtg gaggtagcac atattatcct     180
gacagcgtga agggccggtt caccatctcc agagacaacg ccaagaacag cctgtatctg     240
caaatgaaca gcctgagagc cgaggacaca gctgtgtatt actgtgctag aggtggagat     300
cctggggtct acaatggaga ttacgaagat gctatggact actgggggca aggaacaaca     360
gtcacagtca gctca                                                     375
```

<210> SEQ ID NO 34
<211> LENGTH: 321
<212> TYPE: DNA
<213> ORGANISM: Artificial Sequence
<220> FEATURE:
<223> OTHER INFORMATION: h130M23-H1L6 Light chain variable region nucleotide sequence

<400> SEQUENCE: 34

```
gacatccaga tgacccagtc cccttcctcc ctgtctgctt ccgtcggaga cagagtcacc      60
atcacttgca aggcctccca ggatgtgtcc tctgctgtcg cttggtatca gcagaaacca     120
ggaaaagctc ctaagctcct gatctattgg catccacca ggcacacagg agtcccttcc      180
aggttctccg gctctggatc tgggacagat ttcactctca ccatcagctc cctgcaacct     240
gaagattttg caacttacta ctgtcagcaa cattatagca ctccttggac attcggacaa     300
gggaccaagg tggaaatcaa a                                               321
```

<210> SEQ ID NO 35
<211> LENGTH: 1413
<212> TYPE: DNA
<213> ORGANISM: Artificial Sequence
<220> FEATURE:
<223> OTHER INFORMATION: h130M23-H1L6 Heavy chain nucleotide sequence

<400> SEQUENCE: 35

```
atggaactgg gactcagatg gttttcctc gttgctattc tggaaggagt ccagtgtgag       60
gtgcagctgg tggagtctgg gggaggcctg gtcaagcctg aggatctct gcggctctcc      120
tgtgcagcct ctggattcac cttctcctct tatgccatgt cttgggtccg gcaggctcca     180
gggaaggggc tggaatgggt ctcatccatt tctagtggag gtagcacata ttatcctgac     240
agcgtgaagg gccggttcac catctccaga gacaacgcca agaacagcct gtatctgcaa     300
atgaacagcc tgagagccga ggacacagct gtgtattact gtgctagagg tggagatcct     360
ggggtctaca atggagatta cgaagatgct atggactact ggggggcaagg aacaacagtc    420
acagtcagct cagccagcac aaagggccct agcgtcttcc ctctggctcc ctgcagcagg    480
agcaccagcg agagcacagc cgccctgggc tgcctggtca aggactactt ccccgaaccg    540
gtgacggtgt cgtggaactc aggcgctctg accagcggcg tgcacacctt cccagctgtc    600
ctacagtcct caggactcta ctccctcagc agcgtggtga ccgtgccctc agcaacttc     660
ggcacccaga cctacacctg caacgtagat cacaagccca gcaacaccaa ggtggacaag    720
acagttgagc gcaaatgttg tgtcgagtgc ccaccgtgcc cagcaccacc tgtggcagga    780
ccgtcagtct tcctcttccc cccaaaaccc aaggacaccc tcatgatctc ccggaccct    840
gaggtcacgt gcgtggtggt ggacgtgagc cacgaagacc ccgaggtcca gttcaactgg    900
```

```
tacgtggacg gcgtggaggt gcataatgcc aagacaaagc cacgggagga gcagttcaac    960
agcacgttcc gtgtggtcag cgtcctcacc gttgtgcacc aggactggct gaacggcaag   1020
gagtacaagt gcaaggtctc caacaaaggc ctcccagccc ccatcgagaa aaccatctcc   1080
aaaaccaaag ggcagccccg agaaccacag gtgtacaccc tgcccccatc ccgggaggag   1140
atgaccaaga accaggtcag cctgacctgc ctggtcaaag gcttctaccc cagcgacatc   1200
gccgtggagt gggagagcaa tgggcagccg gagaacaact acaagaccac acctcccatg   1260
ctggactccg acggctcctt cttcctctac agcaagctca ccgtggacaa gagcaggtgg   1320
cagcagggga acgtcttctc atgctccgtg atgcatgagg ctctgcacaa ccactacacg   1380
cagaagagcc tctccctgtc tccgggtaaa tga                                1413
```

`<210>` SEQ ID NO 36
`<211>` LENGTH: 717
`<212>` TYPE: DNA
`<213>` ORGANISM: Artificial Sequence
`<220>` FEATURE:
`<223>` OTHER INFORMATION: h130M23-H1L6 Light chain nucleotide sequence

`<400>` SEQUENCE: 36

```
atgggcatca agatggagtc acagattcag gcatttgtat tcgtgtttct ctggttgtct     60
ggtgttgacg gagacatcca gatgacccag tccccttcct ccctgtctgc ttccgtcgga   120
gacagagtca ccatcacttg caaggcctcc caggatgtgt cctctgctgt cgcttggtat   180
cagcagaaac caggaaaagc tcctaagctc ctgatctatt gggcatccac caggcacaca   240
ggagtccctt ccaggttctc cggctctgga tctgggacag atttcactct caccatcagc   300
tccctgcaac ctgaagattt tgcaacttac tactgtcagc aacattatag cactccttgg   360
acattcggac aagggaccaa ggtggaaatc aaaagaactg tggctgcacc ttctgtcttc   420
atcttccctc catctgatga gcagctcaaa tctggaactg cctccgttgt gtgcctgctg   480
aataacttct atcctagaga ggccaaagtc cagtggaagg tggataacgc cctccaatcc   540
ggtaactccc aggagtctgt cacagagcag gactccaagg acagcaccta ctccctcagc   600
aacaccctga cactgtctaa agctgactac gagaaacaca agtctacgc ctgcgaagtc   660 acccatcagg gactgagctc ccccgtcaca aaatccttca cagggagaga gtgctaa     717
```

`<210>` SEQ ID NO 37
`<211>` LENGTH: 5
`<212>` TYPE: PRT
`<213>` ORGANISM: Artificial Sequence
`<220>` FEATURE:
`<223>` OTHER INFORMATION: 131R010 Heavy chain CDR1

`<400>` SEQUENCE: 37

Asp Tyr Ser Ile His
1               5

`<210>` SEQ ID NO 38
`<211>` LENGTH: 16
`<212>` TYPE: PRT
`<213>` ORGANISM: Artificial Sequence
`<220>` FEATURE:
`<223>` OTHER INFORMATION: 131R010 Heavy chain CDR2

`<400>` SEQUENCE: 38

Tyr Ile Tyr Pro Ser Asn Gly Asp Ser Gly Tyr Asn Gln Lys Phe Lys
1               5                   10                  15

```
<210> SEQ ID NO 39
<211> LENGTH: 8
<212> TYPE: PRT
<213> ORGANISM: Artificial Sequence
<220> FEATURE:
<223> OTHER INFORMATION: 131R010 Heavy chain CDR3

<400> SEQUENCE: 39

Thr Tyr Phe Ala Asn Asn Phe Asp
1               5

<210> SEQ ID NO 40
<211> LENGTH: 10
<212> TYPE: PRT
<213> ORGANISM: Artificial Sequence
<220> FEATURE:
<223> OTHER INFORMATION: 131R010 Alternative Heavy chain CDR3

<400> SEQUENCE: 40

Ala Thr Tyr Phe Ala Asn Asn Phe Asp Tyr
1               5                   10

<210> SEQ ID NO 41
<211> LENGTH: 15
<212> TYPE: PRT
<213> ORGANISM: Artificial Sequence
<220> FEATURE:
<223> OTHER INFORMATION: 131R010 Light chain CDR1

<400> SEQUENCE: 41

Lys Ala Ser Gln Ser Val Asp Tyr Asp Gly Asp Ser Tyr Met Asn
1               5                   10                  15

<210> SEQ ID NO 42
<211> LENGTH: 7
<212> TYPE: PRT
<213> ORGANISM: Artificial Sequence
<220> FEATURE:
<223> OTHER INFORMATION: 131R010 Light chain CDR2

<400> SEQUENCE: 42

Ala Ala Ser Asn Leu Glu Ser
1               5

<210> SEQ ID NO 43
<211> LENGTH: 3
<212> TYPE: PRT
<213> ORGANISM: Artificial Sequence
<220> FEATURE:
<223> OTHER INFORMATION: 131R010 Alternative Light chain CDR2

<400> SEQUENCE: 43

Ala Ala Ser
1

<210> SEQ ID NO 44
<211> LENGTH: 9
<212> TYPE: PRT
<213> ORGANISM: Artificial Sequence
<220> FEATURE:
<223> OTHER INFORMATION: 131R010 Light chain CDR3

<400> SEQUENCE: 44

Gln Gln Ser Asn Glu Asp Pro Leu Thr
1               5

<210> SEQ ID NO 45
```

-continued

```
<211> LENGTH: 10
<212> TYPE: PRT
<213> ORGANISM: Artificial Sequence
<220> FEATURE:
<223> OTHER INFORMATION: 131R010 Alternative Light chain CDR3

<400> SEQUENCE: 45

Gln Gln Ser Asn Glu Asp Pro Leu Thr Phe
1               5                   10

<210> SEQ ID NO 46
<211> LENGTH: 117
<212> TYPE: PRT
<213> ORGANISM: Artificial Sequence
<220> FEATURE:
<223> OTHER INFORMATION: 131R010 Heavy chain variable region amino acid
      sequence

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ser Ile His Trp Val Arg Gln Ala Pro Gly Gln Gly Leu Glu Trp Ile
        35                  40                  45

Gly Tyr Ile Tyr Pro Ser Asn Gly Asp Ser Tyr Asn Gln Lys Phe
    50                  55                  60

Lys Asn Arg Val Thr Met Thr Arg Asp Thr Ser Thr Ser Thr Ala Tyr
65                  70                  75                  80

Met Glu Leu Ser Arg Leu Arg Ser Glu Asp Thr Ala Val Tyr Tyr Cys
                85                  90                  95

Ala Thr Tyr Phe Ala Asn Asn Phe Asp Tyr Trp Gly Gln Gly Thr Thr
            100                 105                 110

Leu Thr Val Ser Ser
        115

<210> SEQ ID NO 47
<211> LENGTH: 112
<212> TYPE: PRT
<213> ORGANISM: Artificial Sequence
<220> FEATURE:
<223> OTHER INFORMATION: 131R010 Light chain variable region amino acid
      sequence

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Pro Val Gln Ala Glu Asp Phe Ala Thr Tyr Tyr Cys Gln Gln Ser Asn
                85                  90                  95

Glu Asp Pro Leu Thr Phe Gly Ala Gly Thr Lys Leu Glu Leu Lys Arg
            100                 105                 110
```

```
<210> SEQ ID NO 48
<211> LENGTH: 466
<212> TYPE: PRT
<213> ORGANISM: Artificial Sequence
<220> FEATURE:
<223> OTHER INFORMATION: 131R010 Heavy chain amino acid sequence with
      predicted signal sequence
<220> FEATURE:
<221> NAME/KEY: SIGNAL
<222> LOCATION: (1)..(19)

<400> SEQUENCE: 48

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Ser Ile His Trp Val Arg Gln Ala Pro Gly Gln Gly Leu
    50                  55                  60

Glu Trp Ile Gly Tyr Ile Tyr Pro Ser Asn Gly Asp Ser Gly Tyr Asn
65              70                  75                  80

Gln Lys Phe Lys Asn Arg Val Thr Met Thr Arg Asp Thr Ser Thr Ser
            85                  90                  95

Thr Ala Tyr Met Glu Leu Ser Arg Leu Arg Ser Glu Asp Thr Ala Val
        100                 105                 110

Tyr Tyr Cys Ala Thr Tyr Phe Ala Asn Asn Phe Asp Tyr Trp Gly Gln
    115                 120                 125

Gly Thr Thr Leu Thr Val Ser Ser Ala Ser Thr Lys Gly Pro Ser Val
130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350
```

```
Lys Thr Ile Ser Lys Ala Lys Gly Gln Pro Arg Glu Pro Gln Val Tyr
                355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
450                 455                 460

Gly Lys
465

<210> SEQ ID NO 49
<211> LENGTH: 447
<212> TYPE: PRT
<213> ORGANISM: Artificial Sequence
<220> FEATURE:
<223> OTHER INFORMATION: 131R010 Heavy chain amino acid sequence without
      predicted signal sequence

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Ser Ile His Trp Val Arg Gln Ala Pro Gly Gln Gly Leu Glu Trp Ile
            35                  40                  45

Gly Tyr Ile Tyr Pro Ser Asn Gly Asp Ser Gly Tyr Asn Gln Lys Phe
    50                  55                  60

Lys Asn Arg Val Thr Met Thr Arg Asp Thr Ser Thr Ser Thr Ala Tyr
65                  70                  75                  80

Met Glu Leu Ser Arg Leu Arg Ser Glu Asp Thr Ala Val Tyr Tyr Cys
                85                  90                  95

Ala Thr Tyr Phe Ala Asn Asn Phe Asp Tyr Trp Gly Gln Gly Thr Thr
            100                 105                 110

Leu Thr Val Ser Ser Ala Ser Thr Lys Gly Pro Ser Val Phe Pro Leu
    115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
    195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240
```

```
Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 50
<211> LENGTH: 237
<212> TYPE: PRT
<213> ORGANISM: Artificial Sequence
<220> FEATURE:
<223> OTHER INFORMATION: 131R010 Light chain amino acid sequence with
      predicted signal sequence
<220> FEATURE:
<221> NAME/KEY: SIGNAL
<222> LOCATION: (1)..(19)

<400> SEQUENCE: 50

Met Lys His Leu Trp Phe Phe Leu Leu Leu Val Ala Ala Pro Arg Trp
1               5                   10                  15

Val Leu Ser Asp Ile Gln Met Thr Gln Ser Pro Ser Ser Leu Ser Ala
            20                  25                  30

Ser Val Gly Asp Arg Val Thr Ile Thr Cys Lys Ala Ser Gln Ser Val
        35                  40                  45

Asp Tyr Asp Gly Asp Ser Tyr Met Asn Trp Tyr Gln Gln Lys Pro Gly
    50                  55                  60

Lys Ala Pro Lys Leu Leu Ile Tyr Ala Ala Ser Asn Leu Glu Ser Gly
65                  70                  75                  80

Val Pro Ser Arg Phe Ser Gly Ser Gly Ser Gly Thr Asp Phe Thr Leu
                85                  90                  95

Thr Ile Ser Pro Val Gln Ala Glu Asp Phe Ala Thr Tyr Tyr Cys Gln
            100                 105                 110

Gln Ser Asn Glu Asp Pro Leu Thr Phe Gly Ala Gly Thr Lys Leu Glu
        115                 120                 125

Leu Lys Arg Thr Val Ala Ala Pro Ser Val Phe Ile Phe Pro Pro Ser
```

```
                130              135                 140
Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
                180                 185                 190

Asp Ser Thr Tyr Ser Leu Ser Ser Thr Leu Thr Leu Ser Lys Ala Asp
                195                 200                 205

Tyr Glu Lys His Lys Val Tyr Ala Cys Glu Val Thr His Gln Gly Leu
                210                 215                 220

Ser Ser Pro Val Thr Lys Ser Phe Asn Arg Gly Glu Cys
225                 230                 235
```

<210> SEQ ID NO 51
<211> LENGTH: 218
<212> TYPE: PRT
<213> ORGANISM: Artificial Sequence
<220> FEATURE:
<223> OTHER INFORMATION: 131R010 Light chain amino acid sequence without predicted signal sequence

<400> SEQUENCE: 51

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
                20                  25                  30

Gly Asp Ser Tyr Met Asn Trp Tyr Gln Gln Lys Pro Gly Lys Ala Pro
                35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Pro Val Gln Ala Glu Asp Phe Ala Thr Tyr Tyr Cys Gln Gln Ser Asn
                85                  90                  95

Glu Asp Pro Leu Thr Phe Gly Ala Gly Thr Lys Leu Glu Leu Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
    210                 215
```

<210> SEQ ID NO 52
<211> LENGTH: 350
<212> TYPE: DNA
<213> ORGANISM: Artificial Sequence
<220> FEATURE:

<223> OTHER INFORMATION: 131R010 Heavy chain variable region nucleotide
      sequence

<400> SEQUENCE: 52
caagtgcaat tggtgcagtc cggagcggaa gtgaagaagc ctggtgcctc ggtcaaagtc    60
tcatgcaagg ccagcggata cactttcacc gactactcca tccattgggt gaggcaggct   120
ccgggccagg gcctggagtg gattgggtac atctacccgt cgaacggaga ttcggggtac   180
aatcagaagt tcaagaaccg cgtgaccatg actcgggaca cctcaacttc acacgcttat   240
atggaactga ccgcctgag atccgaggac actgcggtgt actactgtgc cacctacttt   300
gcgaacaatt tcgattactg gggacaagga accacgctca ctgtcagctc              350

<210> SEQ ID NO 53
<211> LENGTH: 336
<212> TYPE: DNA
<213> ORGANISM: Artificial Sequence
<220> FEATURE:
<223> OTHER INFORMATION: 131R010 Light chain variable region nucleotide
      sequence

<400> SEQUENCE: 53
gatatccaga tgactcagtc gcccctcatcg ttgagcgcct cggtcgggga tcgcgtgact    60
attacttgta aagcgtccca gagcgtggac tacgacggag attcctacat gaactggtat   120
cagcaaaaac cggaaaggc tcctaaactt ctcatctacg cagcctcgaa tctggaatca   180
ggagtcccga gccggttcag cggatcaggc tccggtactg attttaccct cacgatctcg   240
ccagtgcaag ccgaggactt cgcgacctac tactgccaac agtccaacga ggacccgctg   300
accttcggcg cagggaccaa gctggaactg aagcgt                            336

<210> SEQ ID NO 54
<211> LENGTH: 1404
<212> TYPE: DNA
<213> ORGANISM: Artificial Sequence
<220> FEATURE:
<223> OTHER INFORMATION: 131R010 Heavy chain nucleotide sequence

<400> SEQUENCE: 54
atgaaacact tgtggttctt tctgctcctt gtcgcagcac cacggtgggt gctgtcgcaa    60
gtgcaattgg tgcagtccgg agcggaagtg aagaagcctg gtgcctcggt caaagtctca   120
tgcaaggcca gcggatacac tttcaccgac tactccatcc attgggtgag gcaggctccg   180
ggccagggcc tggagtggat tgggtacatc tacccgtcga acggagattc ggggtacaat   240
cagaagttca agaaccgcgt gaccatgact cgggacacct caacttccac ggcttatatg   300
gaactgagcc gcctgagatc cgaggacact gcggtgtact actgtgccac ctactttgcg   360
aacaatttcg attactgggg acaaggaacc acgctcactg tcagctcagc cagcaccaag   420
ggcccctccg tgttccctct ggccccttcc tccaagtcca cctccggcgg caccgccgct   480
ctgggctgcc tggtgaagga ctacttccct gagcctgtga ccgtgtcctg gaactctggc   540
gccctgacct ctggcgtgca caccttccca gccgtgctgc agtcctccgg cctgtactcc   600
ctgtcctccg tggtgaccgt gccttcctcc tccctgggca cccagaccta catctgcaac   660
gtgaaccaca agccttccaa caccaaggtg gacaagcggg tggagcctaa gtcctgcgac   720
aagacccaca cctgccctcc ctgccctgcc cctgagctgc tgggcggacc ttccgtgttc   780
ctgttccctc ctaagcctaa ggacaccctg atgatctccc ggacccctga ggtgacctgc   840
gtggtggtgg acgtgtccca cgaggatcct gaggtgaagt tcaattggta cgtggacggc   900

```
gtggaggtgc acaacgctaa gaccaagcca agggaggagc agtacaactc cacctaccgg    960
gtggtgtctg tgctgaccgt gctgcaccag gactggctga acggcaaaga atacaagtgc   1020
aaggtctcca acaaggccct gcccgctccc atcgagaaaa ccatctccaa ggccagggc    1080 cagcctcgcg agcctcaggt gtacaccctg ccacccagcc gggaggagat gaccaagaac   1140
caggtgtccc tgacctgtct ggtgaagggc ttctaccctt ccgatatcgc cgtggagtgg   1200
gagtctaacg gccagcccga gaacaactac aagaccaccc ctcctgtgct ggactccgac   1260
ggctccttct tcctgtactc caagctgacc gtggacaagt cccggtggca gcagggcaac   1320
gtgttctcct gctccgtgat gcacgaggcc ctgcacaacc actacaccca gaagagcctg   1380
tctctgtctc ctggcaagtg ataa                                          1404
```

<210> SEQ ID NO 55
<211> LENGTH: 714
<212> TYPE: DNA
<213> ORGANISM: Artificial Sequence
<220> FEATURE:
<223> OTHER INFORMATION: 131R010 Light chain nucleotide sequence

<400> SEQUENCE: 55

```
atgaaacacc tgtggttctt cctcctgctg gtggcagctc ccagatgggt cctgtccgat     60
atccagatga ctcagtcgcc ctcatcgttg agcgcctcgg tcggggatcg cgtgactatt    120
acttgtaaag cgtcccagag cgtggactac gacggagatt cctacatgaa ctggtatcag    180
caaaaaccgg aaaggctcc taaacttctc atctacgcag cctcgaatct ggaatcagga    240
gtcccgagcc ggttcagcgg atcaggctcc ggtactgatt ttaccctcac gatctcgcca    300
gtgcaagccg aggacttcgc gacctactac tgccaacagt ccaacgagga cccgctgacc    360
ttcggcgcag ggaccaagct ggaactgaag cgtacggtgg ccgctccatc cgtgtttatc    420
tttccgccgt ccgatgagca gctcaagtcg ggcactgcca gcgtggtctg cctgcttaac    480
aatttctacc ctagggaagc caaggtgcag tggaaggtgg ataacgcgct ccaatccggt    540
aactcgcaag agagcgtgac cgaacaggac tcaaaggact cgacgtacag cctgtcatcg    600
accttgactc tctcaaaggc cgactacgaa aagcacaagg tctacgcgtg cgaagtcacc    660
catcagggac tgtcctcgcc tgtgaccaag agcttcaatc gcggagagtg ctga          714
```

<210> SEQ ID NO 56
<211> LENGTH: 121
<212> TYPE: PRT
<213> ORGANISM: Artificial Sequence
<220> FEATURE:
<223> OTHER INFORMATION: h89M5-H2L2 Heavy chain variable region amino
      acid sequence

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Gly Tyr
            20                  25                  30

Thr Met His Trp Val Arg Gln Ala Pro Gly Gln Arg Leu Glu Trp Met
        35                  40                  45

Gly Gly Ile Asn Pro Asn Asn Gly Gly Thr Thr Tyr Asn Gln Asn Phe
    50                  55                  60

Lys Gly Arg Val Thr Ile Thr Arg Asp Thr Ser Ala Ser Thr Ala Tyr
65                  70                  75                  80
```

Met Glu Leu Ser Ser Leu Arg Ser Glu Asp Thr Ala Val Tyr Tyr Cys
                85                  90                  95

Ala Arg Lys Glu Phe Ser Asp Gly Tyr Tyr Phe Phe Ala Tyr Trp Gly
            100                 105                 110

Gln Gly Thr Leu Val Thr Val Ser Ser
        115                 120

<210> SEQ ID NO 57
<211> LENGTH: 107
<212> TYPE: PRT
<213> ORGANISM: Artificial Sequence
<220> FEATURE:
<223> OTHER INFORMATION: h89M5-H2L2 Light chain variable region amino
      acid sequence

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ile Phe Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gly Gly Thr Lys Val Glu Ile Lys
            100                 105

<210> SEQ ID NO 58
<211> LENGTH: 466
<212> TYPE: PRT
<213> ORGANISM: Artificial Sequence
<220> FEATURE:
<223> OTHER INFORMATION: h89M5-H2L2 Heavy chain amino acid sequence with
      predicted signal sequence
<220> FEATURE:
<221> NAME/KEY: SIGNAL
<222> LOCATION: (1)..(19)

<400> SEQUENCE: 58

Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Thr Ser Gly Tyr Thr Phe
        35                  40                  45

Thr Gly Tyr Thr Met His Trp Val Arg Gln Ala Pro Gly Gln Arg Leu
    50                  55                  60

Glu Trp Met Gly Gly Ile Asn Pro Asn Asn Gly Thr Thr Tyr Asn
65                  70                  75                  80

Gln Asn Phe Lys Gly Arg Val Thr Ile Thr Arg Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Lys Glu Phe Ser Asp Gly Tyr Tyr Phe Phe Ala
        115                 120                 125

```
Tyr Trp Gly Gln Gly Thr Leu Val Thr Val Ser Ser Ala Ser Thr Lys
        130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
        355                 360                 365

Thr Leu Pro Pro Ser Arg Glu Glu Met Thr Lys Asn Gln Val Ser Leu
370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
450                 455                 460

Gly Lys
465

<210> SEQ ID NO 59
<211> LENGTH: 447
<212> TYPE: PRT
<213> ORGANISM: Artificial Sequence
<220> FEATURE:
<223> OTHER INFORMATION: h89M5-H2L2 Heavy chain amino acid sequence
      without predicted signal sequence

<400> SEQUENCE: 59

Gln Val Gln Leu Val Gln Ser Gly Ala Glu Val Lys Lys Pro Gly Ala
1               5                   10                  15
```

-continued

```
Ser Val Lys Val Ser Cys Lys Thr Ser Gly Tyr Thr Phe Thr Gly Tyr
             20                  25                  30
Thr Met His Trp Val Arg Gln Ala Pro Gly Gln Arg Leu Glu Trp Met
             35                  40                  45
Gly Gly Ile Asn Pro Asn Asn Gly Gly Thr Thr Tyr Asn Gln Asn Phe
 50                  55                  60
Lys Gly Arg Val Thr Ile Thr Arg Asp Thr Ser Ala Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Lys Glu Phe Ser Asp Gly Tyr Tyr Phe Ala Tyr Trp Gly
                100                 105                 110
Gln Gly Thr Leu Val Thr Val Ser Ser Ala Ser Thr Lys Gly Pro Ser
                115                 120                 125
Val Phe Pro Leu Ala Pro Cys Ser Arg Ser Thr Ser Glu Ser Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Asn Phe Gly Thr Gln Thr Tyr Thr Cys Asn Val Asp His
                195                 200                 205
Lys Pro Ser Asn Thr Lys Val Asp Lys Thr Val Glu Arg Lys Cys Cys
    210                 215                 220
Val Glu Cys Pro Pro Cys Pro Ala Pro Pro Val Ala Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
                260                 265                 270
Val Gln Phe Asn Trp Tyr Val Asp Gly Val Glu Val His Asn Ala Lys
                275                 280                 285
Thr Lys Pro Arg Glu Glu Gln Phe Asn Ser Thr Phe Arg Val Val Ser
    290                 295                 300
Val Leu Thr Val Val His Gln Asp Trp Leu Asn Gly Lys Glu Tyr Lys
305                 310                 315                 320
Cys Lys Val Ser Asn Lys Gly Leu Pro Ala Pro Ile Glu Lys Thr Ile
                325                 330                 335
Ser Lys Thr Lys Gly Gln Pro Arg Glu Pro Gln Val Tyr Thr Leu Pro
                340                 345                 350
Pro Ser Arg Glu Glu Met Thr Lys Asn Gln Val Ser Leu Thr Cys Leu
                355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Met Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
                420                 425                 430
```

His Asn His Tyr Thr Gln Lys Ser Leu Ser Leu Ser Pro Gly Lys
            435                 440                 445

<210> SEQ ID NO 60
<211> LENGTH: 236
<212> TYPE: PRT
<213> ORGANISM: Artificial Sequence
<220> FEATURE:
<223> OTHER INFORMATION: h89M5-H2L2 Light chain amino acid sequence with
      predicted signal sequence
<220> FEATURE:
<221> NAME/KEY: SIGNAL
<222> LOCATION: (1)..(22)

<400> SEQUENCE: 60

Met Asp Met Arg Val Pro Ala Gln Leu Leu Gly Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Lys Ala Ser
            35                  40                  45

Gln Asp Val Ile Phe Ala Val Ala Trp Tyr Gln Gln Lys Pro Gly Lys
    50                  55                  60

Ala Pro Lys Leu Leu Ile Tyr Trp Ala Ser Thr Arg His Thr Gly Val
65                  70                  75                  80

Pro Ser Arg Phe Ser Gly Ser Gly Ser Gly Thr Asp Tyr Thr Leu Thr
                85                  90                  95

Ile Ser Ser Leu Gln Pro Glu Asp Phe Ala Thr Tyr Tyr Cys Gln Gln
            100                 105                 110

His Tyr Ser Thr Pro Trp Thr Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Asn Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 61
<211> LENGTH: 214
<212> TYPE: PRT
<213> ORGANISM: Artificial Sequence
<220> FEATURE:
<223> OTHER INFORMATION: h89M5-H2L2 Light chain amino acid sequence
      without predicted signal sequence

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ile Phe Ala
            20                  25                  30

```
Val Ala Trp Tyr Gln Gln Lys Pro Gly Lys Ala Pro Lys Leu Leu Ile
         35                  40                  45
Tyr Trp Ala Ser Thr Arg His Thr Gly Val Pro Ser Arg Phe Ser Gly
 50                  55                  60
Ser Gly Ser Gly Thr Asp Tyr Thr Leu Thr Ile Ser Ser Leu Gln Pro
 65                  70                  75                  80
Glu Asp Phe Ala Thr Tyr Tyr Cys Gln Gln His Tyr Ser Thr Pro Trp
                 85                  90                  95
Thr Phe Gly Gly Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Asn Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

```
<210> SEQ ID NO 62
<211> LENGTH: 363
<212> TYPE: DNA
<213> ORGANISM: Artificial Sequence
<220> FEATURE:
<223> OTHER INFORMATION: h89M5-H2L2 Heavy chain variable region
      nucleotide sequence

<400> SEQUENCE: 62
caggtccagc tcgtgcagtc tggggctgag gtgaagaagc ctggggcctc tgtgaaggtt    60
tcctgcaaga cttctggata caccttcact ggatacacca tgcactgggt tagacaggcc   120
cccggacaaa ggctggagtg gatgggaggt attaatccta caatggtgg tactacttac   180 aaccagaact tcaagggcag agtcaccatt accaggaca catccgcaag cacagcctac   240
atggagctgt ccagcctgag atctgaagac acagctgtgt attactgtgc aagaaaggag   300
ttctctgatg gatactactt ttttgcttac tggggccaag gaccctggt caccgtcagc   360 tca                                                                 363
```

```
<210> SEQ ID NO 63
<211> LENGTH: 321
<212> TYPE: DNA
<213> ORGANISM: Artificial Sequence
<220> FEATURE:
<223> OTHER INFORMATION: h89M5-H2L2 Light chain variable region
      nucleotide sequence

<400> SEQUENCE: 63
gacatccaga tgacccagtc tccatcctcc ctgtctgcat ctgtcggaga cagagtcacc    60
atcacttgca aggcctccca ggatgtgatt tttgctgttg cctggtatca gcagaaacca   120
gggaaagccc ctaagctcct gatctattgg gcatccaccc ggcacactgg ggtcccatca   180
aggttcagtg gcagtggatc tgggacagat tacactctca ccatcagcag tctgcaacct   240
```

```
gaagattttg caacttacta ctgtcagcaa cattatagca ctccttggac tttcggcgga    300
gggaccaagg tggagatcaa a                                              321
```

<210> SEQ ID NO 64
<211> LENGTH: 1401
<212> TYPE: DNA
<213> ORGANISM: Artificial Sequence
<220> FEATURE:
<223> OTHER INFORMATION: h89M5-H2L2 Heavy chain nucleotide sequence

<400> SEQUENCE: 64

```
atggactgga cctggaggat actctttctc gtggcagcag ccacaggagc ccactcccag    60
gtccagctcg tgcagtctgg ggctgaggtg aagaagcctg ggcctctgt gaaggtttcc    120 tgcaagactt ctggatacac cttcactgga tacaccatgc actgggttag acaggccccc   180
ggacaaaggc tggagtggat gggaggtatt aatcctaaca atggtggtac tacttacaac   240
cagaacttca gggcagagt caccattacc agggacacat ccgcaagcac agcctacatg    300
gagctgtcca gcctgagatc tgaagacaca gctgtgtatt actgtgcaag aaaggagttc    360
tctgatggat actacttttt tgcttactgg ggccaaggga ccctggtcac cgtcagctca    420
gccagcacaa agggcctag cgtcttccct ctggctccct gcagcaggag caccagcgag    480
agcacagccg ccctgggctg cctggtcaag gactacttcc ccgaaccggt gacggtgtcg    540
tggaactcag gcgctctgac cagcggcgtg cacaccttcc cagctgtcct acagtcctca    600
ggactctact ccctcagcag cgtggtgacc gtgccctcca gcaacttcgg cacccagacc    660
tacacctgca acgtagatca caagcccagc aacaccaagg tggacaagac agttgagcgc    720
aaatgttgtg tcgagtgccc accgtgccca gcaccacctg tgcaggacc gtcagtcttc    780 ctcttccccc caaaacccaa ggacaccctc atgatctccc ggacccctga ggtcacgtgc    840
gtggtggtgg acgtgagcca cgaagacccc gaggtccagt tcaactggta cgtggacggc    900
gtggaggtgc ataatgccaa gacaaagcca cgggaggagc agttcaacag cacgttccgt    960
gtggtcagcg tcctcaccgt tgtgcaccag gactggctga acggcaagga gtacaagtgc   1020
aaggtctcca acaaaggcct cccagccccc atcgagaaaa ccatctccaa aaccaaaggg   1080
cagccccgag aaccacaggt gtacaccctg cccccatccc gggaggagat gaccaagaac   1140
caggtcagcc tgacctgcct ggtcaaaggc ttctacccca gcgacatcgc cgtggagtgg   1200
gagagcaatg ggcagccgga gaacaactac aagaccacac ctcccatgct ggactccgac   1260
ggctccttct cctctacag caagctcacc gtggacaaga gcaggtggca gcaggggaac   1320
gtcttctcat gctccgtgat gcatgaggct ctgcacaacc actacacgca gaagagcctc   1380
tccctgtctc cgggtaaatg a                                             1401
```

<210> SEQ ID NO 65
<211> LENGTH: 711
<212> TYPE: DNA
<213> ORGANISM: Artificial Sequence
<220> FEATURE:
<223> OTHER INFORMATION: h89M5-H2L2 Light chain nucleotide sequence

<400> SEQUENCE: 65

```
atggacatga gggtccccgc acagctcctg ggctcctgc tcctctggct ccggggtgcc    60
agatgtgaca tccagatgac ccagtctcca tcctccctgt ctgcatctgt cggagacaga   120
gtcaccatca cttgcaaggc ctcccaggat gtgatttttg ctgttgcctg gtatcagcag   180
```

-continued

```
aaaccaggga aagcccctaa gctcctgatc tattgggcat ccacccggca cactggggtc    240
ccatcaaggt tcagtggcag tggatctggg acagattaca ctctcaccat cagcagtctg    300
caacctgaag attttgcaac ttactactgt cagcaacatt atagcactcc ttggactttc    360
ggcggaggga ccaaggtgga gatcaaacgg actgtggctg caccatctgt cttcatcttc    420
cctccatctg atgagcagtt gaaatctgga actgcctctg ttgtgtgcct gctgaataac    480
ttctatccca gagaggccaa agtccagtgg aaggtggata acgccctcca atccggtaac    540
tcccaggaga gtgtcacaga gcaggacagc aaggacagca cctacagcct cagcaacacc    600
ctgacactga gcaaagcaga ctacgagaaa cacaaagtct acgcctgcga agtcacccat    660
cagggcctga gctcccccgt cacaaagagc ttcaacaggg gagagtgcta a             711
```

<210> SEQ ID NO 66
<211> LENGTH: 107
<212> TYPE: PRT
<213> ORGANISM: Artificial Sequence
<220> FEATURE:
<223> OTHER INFORMATION: h130M23-H1L2 Light chain variable region amino
      acid sequence

<400> SEQUENCE: 66

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ser Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Val Gln Ala
65                  70                  75                  80

Glu Asp Phe Ala Thr Tyr Tyr Cys Gln Gln His Tyr Ser Thr Pro Trp
                85                  90                  95

Thr Phe Gly Gln Gly Thr Lys Val Glu Ile Lys
            100                 105
```

<210> SEQ ID NO 67
<211> LENGTH: 236
<212> TYPE: PRT
<213> ORGANISM: Artificial Sequence
<220> FEATURE:
<223> OTHER INFORMATION: h130M23-H1L2 Light chain amino acid sequence
      with predicted signal sequence
<220> FEATURE:
<221> NAME/KEY: SIGNAL
<222> LOCATION: (1)..(22)

<400> SEQUENCE: 67

```
Met Lys Tyr Leu Leu Pro Thr Ala Ala Ala Gly Leu Leu Leu Leu Ala
1               5                   10                  15

Ala Gln Pro Ala Met Ala Asp Ile Gln Met Thr Gln Ser Pro Ser Ser
            20                  25                  30

Leu Ser Ala Ser Val Gly Asp Arg Val Thr Ile Thr Cys Lys Ala Ser
        35                  40                  45

Gln Asp Val Ser Ser Ala Val Ala Trp Tyr Gln Gln Lys Pro Gly Lys
    50                  55                  60

Ala Pro Lys Leu Leu Ile Tyr Trp Ala Ser Thr Arg His Thr Gly Val
65                  70                  75                  80
```

```
Pro Ser Arg Phe Ser Gly Ser Gly Ser Gly Thr Asp Phe Thr Leu Thr
                85                  90                  95

Ile Ser Ser Val Gln Ala Glu Asp Phe Ala Thr Tyr Tyr Cys Gln Gln
            100                 105                 110

His Tyr Ser Thr Pro Trp Thr Phe Gly Gln Gly Thr Lys Val Glu Ile
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Asn Thr Leu Thr Leu Ser Lys Ala Asp Tyr
        195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 68
<211> LENGTH: 214
<212> TYPE: PRT
<213> ORGANISM: Artificial Sequence
<220> FEATURE:
<223> OTHER INFORMATION: h130M23-H1L2 Light chain amino acid sequence
      without predicted signal sequence

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ser Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Val Gln Ala
65                  70                  75                  80

Glu Asp Phe Ala Thr Tyr Tyr Cys Gln Gln His Tyr Ser Thr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Asn Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
<210> SEQ ID NO 69
<211> LENGTH: 321
<212> TYPE: DNA
<213> ORGANISM: Artificial Sequence
<220> FEATURE:
<223> OTHER INFORMATION: h130M23-H1L2 Light chain variable region
      nucleotide sequence

<400> SEQUENCE: 69
gacatccaga tgacccagtc cccttcctcc ctgtctgctt ccgtcggaga cagagtcacc      60
atcacttgca aggcctccca ggatgtgtcc tctgctgtcg cttggtatca gcagaaacca     120
ggaaaagctc ctaagctcct gatctattgg catccacca ggcacacagg agtcccttcc      180
aggttctccg gctctggatc tgggacagat ttcactctca ccatcagctc cgtgcaagct     240
gaagattttg caacttacta ctgtcagcaa cattatagca ctccttggac attcggacaa     300
gggaccaagg tggaaatcaa a                                                321

<210> SEQ ID NO 70
<211> LENGTH: 711
<212> TYPE: DNA
<213> ORGANISM: Artificial Sequence
<220> FEATURE:
<223> OTHER INFORMATION: h130M23-H1L2 Light chain nucleotide sequence

<400> SEQUENCE: 70
atgaaatacc tcctccctac agctgccgct ggactcctcc tcctcgctgc ccagcctgcc      60
atggccgaca tccagatgac ccagtcccct tcctccctgt ctgcttccgt cggagacaga     120
gtcaccatca cttgcaaggc ctcccaggat gtgtcctctg ctgtcgcttg gtatcagcag     180
aaaccaggaa aagctcctaa gctcctgatc tattgggcat ccaccaggca cacaggagtc     240
ccttccaggt tctccggctc tggatctggg acagatttca ctctcaccat cagctccgtg     300
caagctgaag attttgcaac ttactactgt cagcaacatt atagcactcc ttggacattc     360
ggacaaggga ccaaggtgga aatcaaaaga actgtggctg caccttctgt cttcatcttc     420
cctccatctg atgagcagct caaatctgga actgcctccg ttgtgtgcct gctgaataac     480
ttctatccca gagaggccaa agtccagtgg aaggtggata acgccctcca atccggtaac     540
tcccaggagt ctgtcacaga gcaggactcc aaggacagca cctactccct cagcaacacc     600
ctgacactgt ctaaagctga ctacgagaaa cacaaagtct acgcctgcga agtcacccat     660
cagggactga gctccccgt cacaaaatcc ttcaacaggg gagagtgcta a                711

<210> SEQ ID NO 71
<211> LENGTH: 951
<212> TYPE: PRT
<213> ORGANISM: Artificial Sequence
<220> FEATURE:
<223> OTHER INFORMATION: Human LGR4 protein sequence

<400> SEQUENCE: 71

Met Pro Gly Pro Leu Gly Leu Leu Cys Phe Leu Ala Leu Gly Leu Leu
1               5                   10                  15

Gly Ser Ala Gly Pro Ser Gly Ala Ala Pro Pro Leu Cys Ala Ala Pro
            20                  25                  30

Cys Ser Cys Asp Gly Asp Arg Arg Val Asp Cys Ser Gly Lys Gly Leu
        35                  40                  45
```

Phe Asn Arg Gly Glu Cys
    210

```
Thr Ala Val Pro Glu Gly Leu Ser Ala Phe Thr Gln Ala Leu Asp Ile
    50              55                  60

Ser Met Asn Asn Ile Thr Gln Leu Pro Glu Asp Ala Phe Lys Asn Phe
65                  70                  75                  80

Pro Phe Leu Glu Glu Leu Gln Leu Ala Gly Asn Asp Leu Ser Phe Ile
                85                  90                  95

His Pro Lys Ala Leu Ser Gly Leu Lys Glu Leu Lys Val Leu Thr Leu
            100                 105                 110

Gln Asn Asn Gln Leu Lys Thr Val Pro Ser Glu Ala Ile Arg Gly Leu
            115                 120                 125

Ser Ala Leu Gln Ser Leu Arg Leu Asp Ala Asn His Ile Thr Ser Val
    130                 135                 140

Pro Glu Asp Ser Phe Glu Gly Leu Val Gln Leu Arg His Leu Trp Leu
145                 150                 155                 160

Asp Asp Asn Ser Leu Thr Glu Val Pro Val His Pro Leu Ser Asn Leu
                165                 170                 175

Pro Thr Leu Gln Ala Leu Thr Leu Ala Leu Asn Lys Ile Ser Ser Ile
            180                 185                 190

Pro Asp Phe Ala Phe Thr Asn Leu Ser Ser Leu Val Val Leu His Leu
    195                 200                 205

His Asn Asn Lys Ile Arg Ser Leu Ser Gln His Cys Phe Asp Gly Leu
    210                 215                 220

Asp Asn Leu Glu Thr Leu Asp Leu Asn Tyr Asn Asn Leu Gly Glu Phe
225                 230                 235                 240

Pro Gln Ala Ile Lys Ala Leu Pro Ser Leu Lys Glu Leu Gly Phe His
                245                 250                 255

Ser Asn Ser Ile Ser Val Ile Pro Asp Gly Ala Phe Asp Gly Asn Pro
            260                 265                 270

Leu Leu Arg Thr Ile His Leu Tyr Asp Asn Pro Leu Ser Phe Val Gly
    275                 280                 285

Asn Ser Ala Phe His Asn Leu Ser Asp Leu His Ser Leu Val Ile Arg
290                 295                 300

Gly Ala Ser Met Val Gln Gln Phe Pro Asn Leu Thr Gly Thr Val His
305                 310                 315                 320

Leu Glu Ser Leu Thr Leu Thr Gly Thr Lys Ile Ser Ser Ile Pro Asn
                325                 330                 335

Asn Leu Cys Gln Glu Gln Lys Met Leu Arg Thr Leu Asp Leu Ser Tyr
            340                 345                 350

Asn Asn Ile Arg Asp Leu Pro Ser Phe Asn Gly Cys His Ala Leu Glu
            355                 360                 365

Glu Ile Ser Leu Gln Arg Asn Gln Ile Tyr Gln Ile Lys Glu Gly Thr
    370                 375                 380

Phe Gln Gly Leu Ile Ser Leu Arg Ile Leu Asp Leu Ser Arg Asn Leu
385                 390                 395                 400

Ile His Glu Ile His Ser Arg Ala Phe Ala Thr Leu Gly Pro Ile Thr
                405                 410                 415

Asn Leu Asp Val Ser Phe Asn Glu Leu Thr Ser Phe Pro Thr Glu Gly
            420                 425                 430

Leu Asn Gly Leu Asn Gln Leu Lys Leu Val Gly Asn Phe Lys Leu Lys
            435                 440                 445

Glu Ala Leu Ala Ala Lys Asp Phe Val Asn Leu Arg Ser Leu Ser Val
    450                 455                 460
```

```
Pro Tyr Ala Tyr Gln Cys Cys Ala Phe Trp Gly Cys Asp Ser Tyr Ala
465                 470                 475                 480

Asn Leu Asn Thr Glu Asp Asn Ser Leu Gln Asp His Ser Val Ala Gln
            485                 490                 495

Glu Lys Gly Thr Ala Asp Ala Ala Asn Val Thr Ser Thr Leu Glu Asn
                500                 505                 510

Glu Glu His Ser Gln Ile Ile Ile His Cys Thr Pro Ser Thr Gly Ala
            515                 520                 525

Phe Lys Pro Cys Glu Tyr Leu Leu Gly Ser Trp Met Ile Arg Leu Thr
530                 535                 540

Val Trp Phe Ile Phe Leu Val Ala Leu Phe Phe Asn Leu Leu Val Ile
545                 550                 555                 560

Leu Thr Thr Phe Ala Ser Cys Thr Ser Leu Pro Ser Ser Lys Leu Phe
                565                 570                 575

Ile Gly Leu Ile Ser Val Ser Asn Leu Phe Met Gly Ile Tyr Thr Gly
                580                 585                 590

Ile Leu Thr Phe Leu Asp Ala Val Ser Trp Gly Arg Phe Ala Glu Phe
            595                 600                 605

Gly Ile Trp Trp Glu Thr Gly Ser Gly Cys Lys Val Ala Gly Phe Leu
610                 615                 620

Ala Val Phe Ser Ser Glu Ser Ala Ile Phe Leu Leu Met Leu Ala Thr
625                 630                 635                 640

Val Glu Arg Ser Leu Ser Ala Lys Asp Ile Met Lys Asn Gly Lys Ser
                645                 650                 655

Asn His Leu Lys Gln Phe Arg Val Ala Ala Leu Leu Ala Phe Leu Gly
                660                 665                 670

Ala Thr Val Ala Gly Cys Phe Pro Leu Phe His Arg Gly Glu Tyr Ser
            675                 680                 685

Ala Ser Pro Leu Cys Leu Pro Phe Pro Thr Gly Glu Thr Pro Ser Leu
            690                 695                 700

Gly Phe Thr Val Thr Leu Val Leu Leu Asn Ser Leu Ala Phe Leu Leu
705                 710                 715                 720

Met Ala Val Ile Tyr Thr Lys Leu Tyr Cys Asn Leu Glu Lys Glu Asp
                725                 730                 735

Leu Ser Glu Asn Ser Gln Ser Ser Met Ile Lys His Val Ala Trp Leu
            740                 745                 750

Ile Phe Thr Asn Cys Ile Phe Phe Cys Pro Val Ala Phe Phe Ser Phe
            755                 760                 765

Ala Pro Leu Ile Thr Ala Ile Ser Ile Ser Pro Glu Ile Met Lys Ser
            770                 775                 780

Val Thr Leu Ile Phe Phe Pro Leu Pro Ala Cys Leu Asn Pro Val Leu
785                 790                 795                 800

Tyr Val Phe Phe Asn Pro Lys Phe Lys Glu Asp Trp Lys Leu Leu Lys
                805                 810                 815

Arg Arg Val Thr Lys Lys Ser Gly Ser Val Ser Val Ser Ile Ser Ser
                820                 825                 830

Gln Gly Gly Cys Leu Glu Gln Asp Phe Tyr Tyr Asp Cys Gly Met Tyr
            835                 840                 845

Ser His Leu Gln Gly Asn Leu Thr Val Cys Asp Cys Cys Glu Ser Phe
            850                 855                 860

Leu Leu Thr Lys Pro Val Ser Cys Lys His Leu Ile Lys Ser His Ser
865                 870                 875                 880

Cys Pro Ala Leu Ala Val Ala Ser Cys Gln Arg Pro Glu Gly Tyr Trp
```

```
              885                 890                 895
Ser Asp Cys Gly Thr Gln Ser Ala His Ser Asp Tyr Ala Asp Glu Glu
            900                 905                 910

Asp Ser Phe Val Ser Asp Ser Asp Gln Val Gln Ala Cys Gly Arg
            915                 920                 925

Ala Cys Phe Tyr Gln Ser Arg Gly Phe Pro Leu Val Arg Tyr Ala Tyr
        930                 935                 940

Asn Leu Pro Arg Val Lys Asp
945                 950

<210> SEQ ID NO 72
<211> LENGTH: 907
<212> TYPE: PRT
<213> ORGANISM: Artificial Sequence
<220> FEATURE:
<223> OTHER INFORMATION: Human LGR5 protein sequence

<400> SEQUENCE: 72

Met Asp Thr Ser Arg Leu Gly Val Leu Leu Ser Leu Pro Val Leu Leu
1               5                   10                  15

Gln Leu Ala Thr Gly Gly Ser Ser Pro Arg Ser Gly Val Leu Leu Arg
            20                  25                  30

Gly Cys Pro Thr His Cys His Cys Glu Pro Asp Gly Arg Met Leu Leu
        35                  40                  45

Arg Val Asp Cys Ser Asp Leu Gly Leu Ser Glu Leu Pro Ser Asn Leu
    50                  55                  60

Ser Val Phe Thr Ser Tyr Leu Asp Leu Ser Met Asn Asn Ile Ser Gln
65                  70                  75                  80

Leu Leu Pro Asn Pro Leu Pro Ser Leu Arg Phe Leu Glu Glu Leu Arg
                85                  90                  95

Leu Ala Gly Asn Ala Leu Thr Tyr Ile Pro Lys Gly Ala Phe Thr Gly
            100                 105                 110

Leu Tyr Ser Leu Lys Val Leu Met Leu Gln Asn Asn Gln Leu Arg His
        115                 120                 125

Val Pro Thr Glu Ala Leu Gln Asn Leu Arg Ser Leu Gln Ser Leu Arg
    130                 135                 140

Leu Asp Ala Asn His Ile Ser Tyr Val Pro Pro Ser Cys Phe Ser Gly
145                 150                 155                 160

Leu His Ser Leu Arg His Leu Trp Leu Asp Asp Asn Ala Leu Thr Glu
                165                 170                 175

Ile Pro Val Gln Ala Phe Arg Ser Leu Ser Ala Leu Gln Ala Met Thr
            180                 185                 190

Leu Ala Leu Asn Lys Ile His His Ile Pro Asp Tyr Ala Phe Gly Asn
        195                 200                 205

Leu Ser Ser Leu Val Val Leu His Leu His Asn Asn Arg Ile His Ser
    210                 215                 220

Leu Gly Lys Lys Cys Phe Asp Gly Leu His Ser Leu Glu Thr Leu Asp
225                 230                 235                 240

Leu Asn Tyr Asn Asn Leu Asp Glu Phe Pro Thr Ala Ile Arg Thr Leu
                245                 250                 255

Ser Asn Leu Lys Glu Leu Gly Phe His Ser Asn Asn Ile Arg Ser Ile
            260                 265                 270

Pro Glu Lys Ala Phe Val Gly Asn Pro Ser Leu Ile Thr Ile His Phe
        275                 280                 285

Tyr Asp Asn Pro Ile Gln Phe Val Gly Arg Ser Ala Phe Gln His Leu
```

```
            290                 295                 300
Pro Glu Leu Arg Thr Leu Thr Leu Asn Gly Ala Ser Gln Ile Thr Glu
305                 310                 315                 320

Phe Pro Asp Leu Thr Gly Thr Ala Asn Leu Glu Ser Leu Thr Leu Thr
                325                 330                 335

Gly Ala Gln Ile Ser Ser Leu Pro Gln Thr Val Cys Asn Gln Leu Pro
                340                 345                 350

Asn Leu Gln Val Leu Asp Leu Ser Tyr Asn Leu Leu Glu Asp Leu Pro
                355                 360                 365

Ser Phe Ser Val Cys Gln Lys Leu Gln Lys Ile Asp Leu Arg His Asn
370                 375                 380

Glu Ile Tyr Glu Ile Lys Val Asp Thr Phe Gln Gln Leu Leu Ser Leu
385                 390                 395                 400

Arg Ser Leu Asn Leu Ala Trp Asn Lys Ile Ala Ile His Pro Asn
                405                 410                 415

Ala Phe Ser Thr Leu Pro Ser Leu Ile Lys Leu Asp Leu Ser Ser Asn
                420                 425                 430

Leu Leu Ser Ser Phe Pro Ile Thr Gly Leu His Gly Leu Thr His Leu
                435                 440                 445

Lys Leu Thr Gly Asn His Ala Leu Gln Ser Leu Ile Ser Ser Glu Asn
                450                 455                 460

Phe Pro Glu Leu Lys Val Ile Glu Met Pro Tyr Ala Tyr Gln Cys Cys
465                 470                 475                 480

Ala Phe Gly Val Cys Glu Asn Ala Tyr Lys Ile Ser Asn Gln Trp Asn
                485                 490                 495

Lys Gly Asp Asn Ser Ser Met Asp Asp Leu His Lys Lys Asp Ala Gly
                500                 505                 510

Met Phe Gln Ala Gln Asp Glu Arg Asp Leu Glu Asp Phe Leu Leu Asp
                515                 520                 525

Phe Glu Glu Asp Leu Lys Ala Leu His Ser Val Gln Cys Ser Pro Ser
530                 535                 540

Pro Gly Pro Phe Lys Pro Cys Glu His Leu Leu Asp Gly Trp Leu Ile
545                 550                 555                 560

Arg Ile Gly Val Trp Thr Ile Ala Val Leu Ala Leu Thr Cys Asn Ala
                565                 570                 575

Leu Val Thr Ser Thr Val Phe Arg Ser Pro Leu Tyr Ile Ser Pro Ile
                580                 585                 590

Lys Leu Leu Ile Gly Val Ile Ala Ala Val Asn Met Leu Thr Gly Val
                595                 600                 605

Ser Ser Ala Val Leu Ala Gly Val Asp Ala Phe Thr Phe Gly Ser Phe
610                 615                 620

Ala Arg His Gly Ala Trp Trp Glu Asn Gly Val Gly Cys His Val Ile
625                 630                 635                 640

Gly Phe Leu Ser Ile Phe Ala Ser Glu Ser Ser Val Phe Leu Leu Thr
                645                 650                 655

Leu Ala Ala Leu Glu Arg Gly Phe Ser Val Lys Tyr Ser Ala Lys Phe
                660                 665                 670

Glu Thr Lys Ala Pro Phe Ser Ser Leu Lys Val Ile Ile Leu Leu Cys
                675                 680                 685

Ala Leu Leu Ala Leu Thr Met Ala Ala Val Pro Leu Leu Gly Gly Ser
                690                 695                 700

Lys Tyr Gly Ala Ser Pro Leu Cys Leu Pro Leu Pro Phe Gly Glu Pro
705                 710                 715                 720
```

```
Ser Thr Met Gly Tyr Met Val Ala Leu Ile Leu Leu Asn Ser Leu Cys
            725                 730                 735

Phe Leu Met Met Thr Ile Ala Tyr Thr Lys Leu Tyr Cys Asn Leu Asp
        740                 745                 750

Lys Gly Asp Leu Glu Asn Ile Trp Asp Cys Ser Met Val Lys His Ile
        755                 760                 765

Ala Leu Leu Leu Phe Thr Asn Cys Ile Leu Asn Cys Pro Val Ala Phe
770                 775                 780

Leu Ser Phe Ser Ser Leu Ile Asn Leu Thr Phe Ile Ser Pro Glu Val
785                 790                 795                 800

Ile Lys Phe Ile Leu Leu Val Val Val Pro Leu Pro Ala Cys Leu Asn
            805                 810                 815

Pro Leu Leu Tyr Ile Leu Phe Asn Pro His Phe Lys Glu Asp Leu Val
            820                 825                 830

Ser Leu Arg Lys Gln Thr Tyr Val Trp Thr Arg Ser Lys His Pro Ser
            835                 840                 845

Leu Met Ser Ile Asn Ser Asp Asp Val Glu Lys Gln Ser Cys Asp Ser
        850                 855                 860

Thr Gln Ala Leu Val Thr Phe Thr Ser Ser Ile Thr Tyr Asp Leu
865                 870                 875                 880

Pro Pro Ser Ser Val Pro Ser Pro Ala Tyr Pro Val Thr Glu Ser Cys
                885                 890                 895

His Leu Ser Ser Val Ala Phe Val Pro Cys Leu
            900                 905

<210> SEQ ID NO 73
<211> LENGTH: 915
<212> TYPE: PRT
<213> ORGANISM: Artificial Sequence
<220> FEATURE:
<223> OTHER INFORMATION: Human LGR6 protein sequence

<400> SEQUENCE: 73

Met Gly Arg Pro Arg Leu Thr Leu Val Cys Gln Val Ser Ile Ile Ile
1               5                   10                  15

Ser Ala Arg Asp Leu Ser Met Asn Asn Leu Thr Glu Leu Gln Pro Gly
                20                  25                  30

Leu Phe His His Leu Arg Phe Leu Glu Glu Leu Arg Leu Ser Gly Asn
            35                  40                  45

His Leu Ser His Ile Pro Gly Gln Ala Phe Ser Gly Leu Tyr Ser Leu
        50                  55                  60

Lys Ile Leu Met Leu Gln Asn Asn Gln Leu Gly Gly Ile Pro Ala Glu
65                  70                  75                  80

Ala Leu Trp Glu Leu Pro Ser Leu Gln Ser Leu Arg Leu Asp Ala Asn
                85                  90                  95

Leu Ile Ser Leu Val Pro Glu Arg Ser Phe Glu Gly Leu Ser Ser Leu
            100                 105                 110

Arg His Leu Trp Leu Asp Asp Asn Ala Leu Thr Glu Ile Pro Val Arg
        115                 120                 125

Ala Leu Asn Asn Leu Pro Ala Leu Gln Ala Met Thr Leu Ala Leu Asn
    130                 135                 140

Arg Ile Ser His Ile Pro Asp Tyr Ala Phe Gln Asn Leu Thr Ser Leu
145                 150                 155                 160

Val Val Leu His Leu His Asn Asn Arg Ile Gln His Leu Gly Thr His
                165                 170                 175
```

```
Ser Phe Glu Gly Leu His Asn Leu Glu Thr Leu Asp Leu Asn Tyr Asn
            180                 185                 190

Lys Leu Gln Glu Phe Pro Val Ala Ile Arg Thr Leu Gly Arg Leu Gln
        195                 200                 205

Glu Leu Gly Phe His Asn Asn Asn Ile Lys Ala Ile Pro Glu Lys Ala
    210                 215                 220

Phe Met Gly Asn Pro Leu Leu Gln Thr Ile His Phe Tyr Asp Asn Pro
225                 230                 235                 240

Ile Gln Phe Val Gly Arg Ser Ala Phe Gln Tyr Leu Pro Lys Leu His
                245                 250                 255

Thr Leu Ser Leu Asn Gly Ala Met Asp Ile Gln Glu Phe Pro Asp Leu
            260                 265                 270

Lys Gly Thr Thr Ser Leu Glu Ile Leu Thr Leu Thr Arg Ala Gly Ile
        275                 280                 285

Arg Leu Leu Pro Ser Gly Met Cys Gln Gln Leu Pro Arg Leu Arg Val
    290                 295                 300

Leu Glu Leu Ser His Asn Gln Ile Glu Glu Leu Pro Ser Leu His Arg
305                 310                 315                 320

Cys Gln Lys Leu Glu Glu Ile Gly Leu Gln His Asn Arg Ile Trp Glu
                325                 330                 335

Ile Gly Ala Asp Thr Phe Ser Gln Leu Ser Ser Leu Gln Ala Leu Asp
            340                 345                 350

Leu Ser Trp Asn Ala Ile Arg Ser Ile His Pro Glu Ala Phe Ser Thr
        355                 360                 365

Leu His Ser Leu Val Lys Leu Asp Leu Thr Asp Asn Gln Leu Thr Thr
    370                 375                 380

Leu Pro Leu Ala Gly Leu Gly Gly Leu Met His Leu Lys Leu Lys Gly
385                 390                 395                 400

Asn Leu Ala Leu Ser Gln Ala Phe Ser Lys Asp Ser Phe Pro Lys Leu
                405                 410                 415

Arg Ile Leu Glu Val Pro Tyr Ala Tyr Gln Cys Cys Pro Tyr Gly Met
            420                 425                 430

Cys Ala Ser Phe Phe Lys Ala Ser Gly Gln Trp Glu Ala Glu Asp Leu
        435                 440                 445

His Leu Asp Asp Glu Glu Ser Ser Lys Arg Pro Leu Gly Leu Leu Ala
    450                 455                 460

Arg Gln Ala Glu Asn His Tyr Asp Gln Asp Leu Asp Glu Leu Gln Leu
465                 470                 475                 480

Glu Met Glu Asp Ser Lys Pro His Pro Ser Val Gln Cys Ser Pro Thr
                485                 490                 495

Pro Gly Pro Phe Lys Pro Cys Glu Tyr Leu Phe Glu Ser Trp Gly Ile
            500                 505                 510

Arg Leu Ala Val Trp Ala Ile Val Leu Leu Ser Val Leu Cys Asn Gly
        515                 520                 525

Leu Val Leu Leu Thr Val Phe Ala Gly Gly Pro Val Pro Leu Pro Pro
    530                 535                 540

Val Lys Phe Val Val Gly Ala Ile Ala Gly Ala Asn Thr Leu Thr Gly
545                 550                 555                 560

Ile Ser Cys Gly Leu Leu Ala Ser Val Asp Ala Leu Thr Phe Gly Gln
                565                 570                 575

Phe Ser Glu Tyr Gly Ala Arg Trp Glu Thr Gly Leu Gly Cys Arg Ala
            580                 585                 590
```

Thr Gly Phe Leu Ala Val Leu Gly Ser Glu Ala Ser Val Leu Leu
            595                 600                 605

Thr Leu Ala Ala Val Gln Cys Ser Val Ser Val Ser Cys Val Arg Ala
    610                 615                 620

Tyr Gly Lys Ser Pro Ser Leu Gly Ser Val Arg Ala Gly Val Leu Gly
625                 630                 635                 640

Cys Leu Ala Leu Ala Gly Leu Ala Ala Ala Leu Pro Leu Ala Ser Val
                645                 650                 655

Gly Glu Tyr Gly Ala Ser Pro Leu Cys Leu Pro Tyr Ala Pro Pro Glu
            660                 665                 670

Gly Gln Pro Ala Ala Leu Gly Phe Thr Val Ala Leu Val Met Met Asn
        675                 680                 685

Ser Phe Cys Phe Leu Val Val Ala Gly Ala Tyr Ile Lys Leu Tyr Cys
    690                 695                 700

Asp Leu Pro Arg Gly Asp Phe Glu Ala Val Trp Asp Cys Ala Met Val
705                 710                 715                 720

Arg His Val Ala Trp Leu Ile Phe Ala Asp Gly Leu Leu Tyr Cys Pro
                725                 730                 735

Val Ala Phe Leu Ser Phe Ala Ser Met Leu Gly Leu Phe Pro Val Thr
            740                 745                 750

Pro Glu Ala Val Lys Ser Val Leu Leu Val Val Leu Pro Leu Pro Ala
        755                 760                 765

Cys Leu Asn Pro Leu Leu Tyr Leu Leu Phe Asn Pro His Phe Arg Asp
    770                 775                 780

Asp Leu Arg Arg Leu Arg Pro Arg Ala Gly Asp Ser Gly Pro Leu Ala
785                 790                 795                 800

Tyr Ala Ala Ala Gly Glu Leu Glu Lys Ser Ser Cys Asp Ser Thr Gln
                805                 810                 815

Ala Leu Val Ala Phe Ser Asp Val Asp Leu Ile Leu Glu Ala Ser Glu
            820                 825                 830

Ala Gly Arg Pro Pro Gly Leu Glu Thr Tyr Gly Phe Pro Ser Val Thr
        835                 840                 845

Leu Ile Ser Cys Gln Gln Pro Gly Ala Pro Arg Leu Glu Gly Ser His
    850                 855                 860

Cys Val Glu Pro Glu Gly Asn His Phe Gly Asn Pro Gln Pro Ser Met
865                 870                 875                 880

Asp Gly Glu Leu Leu Leu Arg Ala Glu Gly Ser Thr Pro Ala Gly Gly
                885                 890                 895

Gly Leu Ser Gly Gly Gly Gly Phe Gln Pro Ser Gly Leu Ala Phe Ala
            900                 905                 910

Ser His Val
        915

<210> SEQ ID NO 74
<211> LENGTH: 543
<212> TYPE: PRT
<213> ORGANISM: Artificial Sequence
<220> FEATURE:
<223> OTHER INFORMATION: LGR5 ECD amino acids 22-564

<400> SEQUENCE: 74

Gly Ser Ser Pro Arg Ser Gly Val Leu Leu Arg Gly Cys Pro Thr His
1               5                   10                  15

Cys His Cys Glu Pro Asp Gly Arg Met Leu Leu Arg Val Asp Cys Ser
                20                  25                  30

-continued

```
Asp Leu Gly Leu Ser Glu Leu Pro Ser Asn Leu Ser Val Phe Thr Ser
         35                  40                  45

Tyr Leu Asp Leu Ser Met Asn Asn Ile Ser Gln Leu Leu Pro Asn Pro
 50                  55                  60

Leu Pro Ser Leu Arg Phe Leu Glu Glu Leu Arg Leu Ala Gly Asn Ala
 65                  70                  75                  80

Leu Thr Tyr Ile Pro Lys Gly Ala Phe Thr Gly Leu Tyr Ser Leu Lys
                 85                  90                  95

Val Leu Met Leu Gln Asn Asn Gln Leu Arg His Val Pro Thr Glu Ala
             100                 105                 110

Leu Gln Asn Leu Arg Ser Leu Gln Ser Leu Arg Leu Asp Ala Asn His
         115                 120                 125

Ile Ser Tyr Val Pro Pro Ser Cys Phe Ser Gly Leu His Ser Leu Arg
 130                 135                 140

His Leu Trp Leu Asp Asp Asn Ala Leu Thr Glu Ile Pro Val Gln Ala
 145                 150                 155                 160

Phe Arg Ser Leu Ser Ala Leu Gln Ala Met Thr Leu Ala Leu Asn Lys
                 165                 170                 175

Ile His His Ile Pro Asp Tyr Ala Phe Gly Asn Leu Ser Ser Leu Val
             180                 185                 190

Val Leu His Leu His Asn Asn Arg Ile His Ser Leu Gly Lys Lys Cys
         195                 200                 205

Phe Asp Gly Leu His Ser Leu Glu Thr Leu Asp Leu Asn Tyr Asn Asn
 210                 215                 220

Leu Asp Glu Phe Pro Thr Ala Ile Arg Thr Leu Ser Asn Leu Lys Glu
225                 230                 235                 240

Leu Gly Phe His Ser Asn Asn Ile Arg Ser Ile Pro Glu Lys Ala Phe
                 245                 250                 255

Val Gly Asn Pro Ser Leu Ile Thr Ile His Phe Tyr Asp Asn Pro Ile
             260                 265                 270

Gln Phe Val Gly Arg Ser Ala Phe Gln His Leu Pro Glu Leu Arg Thr
         275                 280                 285

Leu Thr Leu Asn Gly Ala Ser Gln Ile Thr Glu Phe Pro Asp Leu Thr
 290                 295                 300

Gly Thr Ala Asn Leu Glu Ser Leu Thr Leu Thr Gly Ala Gln Ile Ser
305                 310                 315                 320

Ser Leu Pro Gln Thr Val Cys Asn Gln Leu Pro Asn Leu Gln Val Leu
                 325                 330                 335

Asp Leu Ser Tyr Asn Leu Leu Glu Asp Leu Pro Ser Phe Ser Val Cys
             340                 345                 350

Gln Lys Leu Gln Lys Ile Asp Leu Arg His Asn Glu Ile Tyr Glu Ile
         355                 360                 365

Lys Val Asp Thr Phe Gln Gln Leu Leu Ser Leu Arg Ser Leu Asn Leu
 370                 375                 380

Ala Trp Asn Lys Ile Ala Ile Ile His Pro Asn Ala Phe Ser Thr Leu
385                 390                 395                 400

Pro Ser Leu Ile Lys Leu Asp Leu Ser Ser Asn Leu Leu Ser Ser Phe
                 405                 410                 415

Pro Ile Thr Gly Leu His Gly Leu Thr His Leu Lys Leu Thr Gly Asn
             420                 425                 430

His Ala Leu Gln Ser Leu Ile Ser Ser Glu Asn Phe Pro Glu Leu Lys
         435                 440                 445

Val Ile Glu Met Pro Tyr Ala Tyr Gln Cys Cys Ala Phe Gly Val Cys
```

```
            450                 455                 460
Glu Asn Ala Tyr Lys Ile Ser Asn Gln Trp Asn Lys Gly Asp Asn Ser
465                 470                 475                 480

Ser Met Asp Asp Leu His Lys Lys Asp Ala Gly Met Phe Gln Ala Gln
                485                 490                 495

Asp Glu Arg Asp Leu Glu Asp Phe Leu Leu Asp Phe Glu Glu Asp Leu
                500                 505                 510

Lys Ala Leu His Ser Val Gln Cys Ser Pro Ser Pro Gly Pro Phe Lys
            515                 520                 525

Pro Cys Glu His Leu Leu Asp Gly Trp Leu Ile Arg Ile Gly Val
            530                 535                 540

<210> SEQ ID NO 75
<211> LENGTH: 794
<212> TYPE: PRT
<213> ORGANISM: Artificial Sequence
<220> FEATURE:
<223> OTHER INFORMATION: LGR5-Fc protein sequence

<400> SEQUENCE: 75

Met Asp Thr Ser Arg Leu Gly Val Leu Leu Ser Leu Pro Val Leu Leu
1               5                   10                  15

Gln Leu Ala Thr Gly Gly Ser Ser Pro Arg Ser Gly Val Leu Leu Arg
            20                  25                  30

Gly Cys Pro Thr His Cys His Cys Glu Pro Asp Gly Arg Met Leu Leu
            35                  40                  45

Arg Val Asp Cys Ser Asp Leu Gly Leu Ser Glu Leu Pro Ser Asn Leu
50                  55                  60

Ser Val Phe Thr Ser Tyr Leu Asp Leu Ser Met Asn Asn Ile Ser Gln
65                  70                  75                  80

Leu Leu Pro Asn Pro Leu Pro Ser Leu Arg Phe Leu Glu Glu Leu Arg
                85                  90                  95

Leu Ala Gly Asn Ala Leu Thr Tyr Ile Pro Lys Gly Ala Phe Thr Gly
            100                 105                 110

Leu Tyr Ser Leu Lys Val Leu Met Leu Gln Asn Asn Gln Leu Arg His
            115                 120                 125

Val Pro Thr Glu Ala Leu Gln Asn Leu Arg Ser Leu Gln Ser Leu Arg
            130                 135                 140

Leu Asp Ala Asn His Ile Ser Tyr Val Pro Pro Ser Cys Phe Ser Gly
145                 150                 155                 160

Leu His Ser Leu Arg His Leu Trp Leu Asp Asp Asn Ala Leu Thr Glu
                165                 170                 175

Ile Pro Val Gln Ala Phe Arg Ser Leu Ser Ala Leu Gln Ala Met Thr
            180                 185                 190

Leu Ala Leu Asn Lys Ile His His Ile Pro Asp Tyr Ala Phe Gly Asn
            195                 200                 205

Leu Ser Ser Leu Val Val Leu His Leu His Asn Asn Arg Ile His Ser
            210                 215                 220

Leu Gly Lys Lys Cys Phe Asp Gly Leu His Ser Leu Glu Thr Leu Asp
225                 230                 235                 240

Leu Asn Tyr Asn Asn Leu Asp Glu Phe Pro Thr Ala Ile Arg Thr Leu
                245                 250                 255

Ser Asn Leu Lys Glu Leu Gly Phe His Ser Asn Asn Ile Arg Ser Ile
            260                 265                 270

Pro Glu Lys Ala Phe Val Gly Asn Pro Ser Leu Ile Thr Ile His Phe
```

```
            275                 280                 285
Tyr Asp Asn Pro Ile Gln Phe Val Gly Arg Ser Ala Phe Gln His Leu
290                 295                 300

Pro Glu Leu Arg Thr Leu Thr Leu Asn Gly Ala Ser Gln Ile Thr Glu
305                 310                 315                 320

Phe Pro Asp Leu Thr Gly Thr Ala Asn Leu Glu Ser Leu Thr Leu Thr
                    325                 330                 335

Gly Ala Gln Ile Ser Ser Leu Pro Gln Thr Val Cys Asn Gln Leu Pro
                340                 345                 350

Asn Leu Gln Val Leu Asp Leu Ser Tyr Asn Leu Leu Glu Asp Leu Pro
            355                 360                 365

Ser Phe Ser Val Cys Gln Lys Leu Gln Lys Ile Asp Leu Arg His Asn
370                 375                 380

Glu Ile Tyr Glu Ile Lys Val Asp Thr Phe Gln Gln Leu Leu Ser Leu
385                 390                 395                 400

Arg Ser Leu Asn Leu Ala Trp Asn Lys Ile Ala Ile Ile His Pro Asn
                405                 410                 415

Ala Phe Ser Thr Leu Pro Ser Leu Ile Lys Leu Asp Leu Ser Ser Asn
                420                 425                 430

Leu Leu Ser Ser Phe Pro Ile Thr Gly Leu His Gly Leu Thr His Leu
            435                 440                 445

Lys Leu Thr Gly Asn His Ala Leu Gln Ser Leu Ile Ser Ser Glu Asn
450                 455                 460

Phe Pro Glu Leu Lys Val Ile Glu Met Pro Tyr Ala Tyr Gln Cys Cys
465                 470                 475                 480

Ala Phe Gly Val Cys Glu Asn Ala Tyr Lys Ile Ser Asn Gln Trp Asn
                485                 490                 495

Lys Gly Asp Asn Ser Ser Met Asp Asp Leu His Lys Lys Asp Ala Gly
                500                 505                 510

Met Phe Gln Ala Gln Asp Glu Arg Asp Leu Glu Asp Phe Leu Leu Asp
            515                 520                 525

Phe Glu Glu Asp Leu Lys Ala Leu His Ser Val Gln Cys Ser Pro Ser
530                 535                 540

Pro Gly Pro Phe Lys Pro Cys Glu His Leu Leu Asp Gly Trp Leu Ile
545                 550                 555                 560

Arg Ile Gly Val Gly Arg Ala Asp Lys Thr His Thr Cys Pro Pro Cys
                565                 570                 575

Pro Ala Pro Glu Leu Leu Gly Gly Pro Ser Val Phe Leu Phe Pro Pro
                580                 585                 590

Lys Pro Lys Asp Thr Leu Met Ile Ser Arg Thr Pro Glu Val Thr Cys
            595                 600                 605

Val Val Val Asp Val Ser His Glu Asp Pro Glu Val Lys Phe Asn Trp
610                 615                 620

Tyr Val Asp Gly Val Glu Val His Asn Ala Lys Thr Lys Pro Arg Glu
625                 630                 635                 640

Glu Gln Tyr Asn Ser Thr Tyr Arg Val Val Ser Val Leu Thr Val Leu
                645                 650                 655

His Gln Asp Trp Leu Asn Gly Lys Glu Tyr Lys Cys Lys Val Ser Asn
                660                 665                 670

Lys Ala Leu Pro Ala Pro Ile Glu Lys Thr Ile Ser Lys Ala Lys Gly
            675                 680                 685

Gln Pro Arg Glu Pro Gln Val Tyr Thr Leu Pro Pro Ser Arg Asp Glu
690                 695                 700
```

```
Leu Thr Lys Asn Gln Val Ser Leu Thr Cys Leu Val Lys Gly Phe Tyr
705                 710                 715                 720

Pro Ser Asp Ile Ala Val Glu Trp Glu Ser Asn Gly Gln Pro Glu Asn
                725                 730                 735

Asn Tyr Lys Thr Thr Pro Pro Val Leu Asp Ser Asp Gly Ser Phe Phe
            740                 745                 750

Leu Tyr Ser Lys Leu Thr Val Asp Lys Ser Arg Trp Gln Gln Gly Asn
        755                 760                 765

Val Phe Ser Cys Ser Val Met His Glu Ala Leu His Asn His Tyr Thr
    770                 775                 780

Gln Lys Ser Leu Ser Leu Ser Pro Gly Lys
785                 790

<210> SEQ ID NO 76
<211> LENGTH: 227
<212> TYPE: PRT
<213> ORGANISM: Artificial Sequence
<220> FEATURE:
<223> OTHER INFORMATION: Human IgG1 Fc region

<400> SEQUENCE: 76

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 77
<211> LENGTH: 227
<212> TYPE: PRT
<213> ORGANISM: Artificial Sequence
```

<220> FEATURE:
<223> OTHER INFORMATION: Human IgG1 Fc region

<400> SEQUENCE: 77

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 78
<211> LENGTH: 230
<212> TYPE: PRT
<213> ORGANISM: Artificial Sequence
<220> FEATURE:
<223> OTHER INFORMATION: Human IgG1 Fc region

<400> SEQUENCE: 78

Lys Ser Ser Asp Lys Thr His Thr Cys Pro Pro Cys Pro Ala Pro Glu
1               5                   10                  15

Leu Leu Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser His Glu Asp Pro Glu Val Lys Phe Asn Trp Tyr Val Asp Gly
    50                  55                  60

Val Glu Val His Asn Ala Lys Thr Lys Pro Arg Glu Glu Gln Tyr Asn
65                  70                  75                  80

Ser Thr Tyr Arg Val Val Ser Val Leu Thr Val Leu His Gln Asp Trp
                85                  90                  95

-continued

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Gln Pro Arg Glu
            115                 120                 125

Pro Gln Val Tyr Thr Leu Pro Pro Ser Arg Asp Glu Leu Thr Lys Asn
            130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
            165                 170                 175

Thr Pro Pro Val Leu Asp Ser Asp Gly Ser Phe Phe Leu Tyr Ser Lys
            180                 185                 190

Leu Thr Val Asp Lys Ser Arg Trp Gln Gln Gly Asn Val Phe Ser Cys
            195                 200                 205

Ser Val Met His Glu Ala Leu His Asn His Tyr Thr Gln Lys Ser Leu
            210                 215                 220

Ser Leu Ser Pro Gly Lys
225                 230

<210> SEQ ID NO 79
<211> LENGTH: 232
<212> TYPE: PRT
<213> ORGANISM: Artificial Sequence
<220> FEATURE:
<223> OTHER INFORMATION: Human IgG1 Fc region

<400> SEQUENCE: 79

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
            130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
            165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

```
Ser Cys Ser Val Met His Glu Ala Leu His Asn His Tyr Thr Gln Lys
    210             215                 220

Ser Leu Ser Leu Ser Pro Gly Lys
225                 230

<210> SEQ ID NO 80
<211> LENGTH: 224
<212> TYPE: PRT
<213> ORGANISM: Artificial Sequence
<220> FEATURE:
<223> OTHER INFORMATION: Human IgG2 Fc region

<400> SEQUENCE: 80

Cys Val Glu Cys Pro Pro Cys Pro Ala Pro Pro Val Ala Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Asp Val Ser His Glu Asp Pro
        35                  40                  45

Glu Val Gln Phe Asn Trp Tyr Val Asp Gly Val Glu Val His Asn Ala
    50                  55                  60

Lys Thr Lys Pro Arg Glu Glu Gln Phe Asn Ser Thr Phe Arg Val Val
65                  70                  75                  80

Ser Val Leu Thr Val Val His Gln Asp Trp Leu Asn Gly Lys Glu Tyr
                85                  90                  95

Lys Cys Lys Val Ser Asn Lys Gly Leu Pro Ala Pro Ile Glu Lys Thr
            100                 105                 110

Ile Ser Lys Thr Lys Gly Gln Pro Arg Glu Pro Gln Val Tyr Thr Leu
        115                 120                 125

Pro Pro Ser Arg Glu Glu Met Thr Lys Asn Gln Val Ser Leu Thr Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Met Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly Lys
    210                 215                 220
```

TREATMENT OF DERMAL FIBROSIS

CROSS-REFERENCE TO RELATED APPLICATIONS

This application claims the priority benefit of U.S. Provisional Application No. 62/051,026, filed Sep. 16, 2014, which is hereby incorporated by reference herein in its entirety.

REFERENCE TO A SEQUENCE LISTING SUBMITTED ELECTRONICALLY VIA EFS-WEB

The content of the electronically submitted sequence listing (Name: 2293_1270001_SeqListing_ST25.txt, Size: 141,449 bytes; and Date of Creation: Sep. 15, 2015) is herein incorporated by reference in its entirety.

FIELD OF THE INVENTION

The field of this invention generally relates to RSPO and LGR antagonists, including but not limited to, antibodies and other agents that bind RSPO, particularly human RSPO1, RSPO2, and RSPO3, as well as to methods of using the RSPO and/or LGR antagonists for the treatment of fibrotic diseases.

BACKGROUND OF THE INVENTION

Fibrosis is estimated to contribute, either directly or indirectly, to nearly 45% of deaths in the developed world. Fibrotic diseases are characterized by an excessive accumulation of extracellular matrix components, which disrupts the physiological tissue architecture, leading to the dysfunction of the affected organ. In some instances, fibrosis is thought to be a consequence of chronic tissue irritation or chronic inflammation. In some instances, fibrosis is thought to be a consequence of autoimmune reactions within the body. The progressive replacement of parenchymal tissues with extracellular matrix components is observed in fibrotic diseases such as scleroderma, pulmonary fibrosis, and liver cirrhosis. However, the cellular and molecular factors that sustain the fibrotic cascade remain poorly understood.

Wnt-signaling has been implicated in several human fibrotic diseases. Activated Wnt-signaling in some types of fibrotic diseases may be identified by accumulation of β-catenin, up-regulation of Wnt pathway ligands such as Wnt1 and Wnt10B, and down-regulation of Wnt pathway negative regulators such as Dkk1 (Akhmetshina et al., 2012, *Nature Communications*, 3:735; Guo et al., 2012, *Physiol. Res.*, 61:337-346). The Wnt signaling pathway is one of several critical regulators of embryonic pattern formation, post-embryonic tissue maintenance, and stem cell biology. Unregulated activation of the Wnt pathway is associated with many human diseases where pathogenesis may proceed by overtaking homeostatic mechanisms which control normal development and/or tissue repair.

Wnt ligands and R-spondin (RSPO) proteins have been shown to synergize to activate the canonical Wnt pathway. RSPO proteins are known to activate β-catenin signaling similar to Wnt signaling, however the relationship between RSPO proteins and Wnt signaling is still being investigated. It has been reported that RSPO proteins possess a positive modulatory activity on Wnt ligands (Nam et al., 2006, *JBC* 281:13247-57). This study also reported that RSPO proteins could function as Frizzled8 and LRP6 receptor ligands and induce β-catenin signaling (Nam et al., 2006, *JBC* 281: 13247-57). Recent studies have identified an interaction between RSPO proteins and LGR (leucine-rich repeat containing, G protein-coupler receptor) proteins, such as LGR5 (U.S. Patent Publication Nos. 2009/0074782 and 2009/0191205), and these data present an alternative pathway for the activation of β-catenin signaling.

The R-Spondin (RSPO) family of proteins is conserved among vertebrates and comprises four members, RSPO1, RSPO2, RSPO3, and RSPO4. These proteins have been referred to by a variety of names, including roof plate-specific spondins, hPWTSR (hRSPO3), THS2D (RSPO3), Cristin 1-4, and Futrin 1-4. The RSPOs are small secreted proteins that overall share approximately 40-60% sequence homology and domain organization. All RSPO proteins contain two furin-like cysteine-rich domains at the N-terminus followed by a thrombospondin domain and a basic charged C-terminal tail (Kim et al., 2006, *Cell Cycle*, 5:23-26).

Studies have shown that RSPO proteins have a role during vertebrate development (Kamata et al., 2004, *Biochim. Biophys Acta*, 1676:51-62) and in *Xenopus* myogenesis (Kazanskaya et al., 2004, *Dev. Cell*, 7:525-534). RSPO1 has also been shown to function as a potent mitogen for gastrointestinal epithelial cells (Kim et al., 2005, *Science*, 309:1256-1259). It has been reported that RSPO3 is prominently expressed in or close by endothelial cells and their cellular precursors in *Xenopus* and mouse. Furthermore, it has been suggested that RSPO3 may act as an angiogenic factor in embryogenesis (Kazanskaya et al., 2008, *Development*, 135: 3655-3664).

Drug treatment options for patients diagnosed with a fibrotic disease are very limited. There is a need for new agents targeting fibrosis, and signaling pathways involved in fibrosis. Thus, biomolecules such as RSPO-binding agents that disrupt signaling pathways involved in fibrosis are a potential source of new therapeutic agents.

BRIEF SUMMARY OF THE INVENTION

The present invention provides methods for treating a fibrotic disease in a subject, where the methods include administering to a subject a therapeutically effective amount of a RPSO and/or LGR antagonist, such as an anti-RSPO antibody, an anti-LGR antibody, or a soluble LGR receptor.

In some embodiments, a RSPO or LGR antagonist includes, but is not limited to, antibodies and other polypeptides that bind to at least one RSPO or LGR protein, small molecules that bind at least one RSPO or LGR protein, and soluble LGR proteins. The RSPO protein (e.g., human protein) may be one of RSPO1, RSPO2, RSPO3, and RSPO4. The LGR protein may be LGR4, LGR5, or LGR6.

In some embodiments, the RSPO or LGR antagonist is a RSPO-binding agent. In some embodiments, the RSPO or LGR antagonist is a LGR-binding agent. In some embodiments, the RSPO or LGR antagonist is an antibody. In some embodiments, the RSPO or LGR antagonist is an anti-RSPO antibody. In some embodiments, the RSPO or LGR antagonist is an anti-LGR antibody. In some embodiments, the RSPO or LGR antagonist is a soluble receptor. In some embodiments, the RSPO or LGR antagonist is a LGR-Fc soluble receptor. In some embodiments, the RSPO or LGR antagonist is a LGR5-Fc soluble receptor.

In some embodiments, the RSPO or LGR antagonist is an antibody that specifically binds at least one RSPO protein or portion thereof. In some embodiments, the antibody specifically binds at least one human RSPO protein selected from the group consisting of: RSPO1, RSPO2, RSPO3, and RSPO4.

The present invention provides methods of treating or preventing a fibrotic disease in a subject, comprising administering to the subject a therapeutically effective amount of a RSPO-binding agent, including any of those described herein. In some embodiments, the RSPO-binding agent is an antibody that specifically binds a human RSPO protein. In some embodiments, the RSPO-binding agent is an antibody that specifically binds human RSPO1. In some embodiments, the RSPO-binding agent is an antibody that specifically binds human RSPO2. In some embodiments, the RSPO-binding agent is an antibody that specifically binds human RSPO3. In some embodiments, the RSPO-binding agent is an antibody that specifically binds human RSPO4. In some embodiments, a method of treating or preventing a fibrotic disease in a subject comprises administering to the subject a therapeutically effective amount of an antibody that specifically binds human RSPO1. In some embodiments, a method of treating or preventing a fibrotic disease in a subject comprises administering to the subject a therapeutically effective amount of an antibody that specifically binds human RSPO2. In some embodiments, a method of treating or preventing a fibrotic disease in a subject comprises administering to the subject a therapeutically effective amount of an antibody that specifically binds human RSPO3. In some embodiments, a method of treating or preventing a fibrotic disease in a subject comprises administering to the subject a therapeutically effective amount of an antibody that specifically binds human RSPO1 and a therapeutically effective amount of an antibody that specifically binds human RSPO2. In some embodiments, a method of treating or preventing a fibrotic disease in a subject comprises administering to the subject a therapeutically effective amount of an antibody that specifically binds human RSPO1 and a therapeutically effective amount of an antibody that specifically binds human RSPO3. In some embodiments, a method of treating or preventing a fibrotic disease in a subject comprises administering to the subject a therapeutically effective amount of an antibody that specifically binds human RSPO2 and a therapeutically effective amount of an antibody that specifically binds human RSPO3.

In some embodiments, the RSPO-binding agent is a soluble receptor that specifically binds a human RSPO protein. In some embodiments, the RSPO-binding agent is a soluble receptor that specifically binds human RSPO1. In some embodiments, the RSPO-binding agent a soluble receptor that specifically binds human RSPO2. In some embodiments, the RSPO-binding agent a soluble receptor that specifically binds human RSPO3. In some embodiments, the RSPO-binding agent is a soluble receptor that comprises the extracellular domain, or a fragment thereof, of LGR4, LGR5, or LGR6. In some embodiments, the RSPO-binding agent is a soluble receptor that comprises the extracellular domain, or a fragment thereof, of LGR5. In some embodiments, the RSPO-binding agent is a soluble receptor that comprises amino acids 22-564 LGR5. In some embodiments, the RSPO-binding agent is a soluble receptor that comprises a fragment of amino acids 22-264 of LGR5. In some embodiments, the soluble receptor comprises a non-LGR polypeptide. In some embodiments, the non-LGR polypeptide is directly linked to the extracellular domain of the LGR protein. In some embodiments, the non-LGR polypeptide is linked to the extracellular domain of the LGR protein by a linker. In some embodiments, the non-LGR polypeptide is a human Fc region. In some embodiments, the non-LGR polypeptide is a human Fc region, selected from the group consisting of SEQ ID NO:76, SEQ ID NO:77, SEQ ID NO:78, SEQ ID NO:79, and SEQ ID NO:80.

The present invention also provides methods of treating or preventing a fibrotic disease in a subject, comprising administering to the subject a therapeutically effective amount of a LGR-binding agent, including any of those described herein. In some embodiments, the LGR-binding agent is an antibody that specifically binds a human LGR protein. In some embodiments, the LGR-binding agent is an antibody that specifically binds human LGR4. In some embodiments, the LGR-binding agent is an antibody that specifically binds human LGR5. In some embodiments, the LGR-binding agent is an antibody that specifically binds human LGR6. In some embodiments, a method of treating or preventing a fibrotic disease in a subject comprises administering to the subject a therapeutically effective amount of an antibody that specifically binds human LGR4. In some embodiments, a method of treating or preventing a fibrotic disease in a subject comprises administering to the subject a therapeutically effective amount of an antibody that specifically binds human LGR5. In some embodiments, a method of treating or preventing a fibrotic disease in a subject comprises administering to the subject a therapeutically effective amount of an antibody that specifically binds human LGR6.

In some embodiments of the methods, the fibrotic disease is selected from the group consisting of: pulmonary fibrosis, renal fibrosis, liver fibrosis, dermal fibrosis, cardiac fibrosis, and adhesion formation. In some embodiments, the fibrotic disease is dermal fibrosis. In some embodiments, the dermal fibrosis includes, but is not limited to, scleroderma, systemic sclerosis, scleroderma-like disease, sine scleroderma, keloid formation, and hypertrophic scarring. In some embodiments, the fibrotic disease is renal fibrosis. In some embodiments, the renal fibrosis includes, but is not limited to, chronic kidney disease. In some embodiments, the fibrotic disease is pulmonary fibrosis. In some embodiments, the pulmonary fibrosis includes, but is not limited to, idiopathic pulmonary fibrosis, interstitial pulmonary fibrosis, lung fibrosis, mediastinal fibrosis, and pleural fibrosis. In some embodiments, the pulmonary fibrosis is primary pulmonary fibrosis. In some embodiments, the pulmonary fibrosis is secondary pulmonary fibrosis. In some embodiments, the fibrotic disease is liver fibrosis. In some embodiments, the liver fibrosis includes, but is not limited to, cirrhosis of the liver. In some embodiments, the fibrotic disease is cardiac fibrosis. In some embodiments, the cardiac fibrosis includes, but is not limited to, myocardial fibrosis, cardiac valve fibrosis, endomyocardial fibrosis, and atherosclerosis. In some embodiments, the fibrotic disease is not pulmonary fibrosis. In some embodiments, the fibrotic disease is not liver fibrosis. In some embodiments, the cardiac fibrosis is not atherosclerosis.

In some embodiments, the method comprises administration of at least one additional therapeutic agent. In some embodiments, the additional therapeutic agent is a second antibody. In some embodiments, the additional therapeutic agent is an anti-inflammatory agent.

In certain embodiments of the methods described herein, the invention provides methods comprising a RSPO1-binding agent (e.g., an antibody) that specifically binds human RSPO1, wherein the RSPO1-binding agent (e.g., an antibody) comprises one, two, three, four, five, and/or six of the CDRs of antibody 89M5 (see Table 1 herein).

In certain embodiments, the invention provides methods comprising a RSPO1-binding agent (e.g., an antibody) that specifically binds human RSPO1, wherein the RSPO1- binding agent comprises: (a) a heavy chain CDR1 comprising TGYTMH (SEQ ID NO:5), a heavy chain CDR2 comprising GINPNNGGTTYNQNFKG (SEQ ID NO:6), and a heavy chain CDR3 comprising KEFSDGYYFFAY (SEQ ID NO:7); and (b) a light chain CDR1 comprising KASQDVIFAVA (SEQ ID NO:8), a light chain CDR2 comprising WASTRHT (SEQ ID NO:9), and a light chain CDR3 comprising QQHYSTPW (SEQ ID NO:10).

In certain embodiments, the invention provides methods comprising a RSPO1-binding agent (e.g., an antibody) that specifically binds RSPO1, wherein the RSPO1-binding agent comprises a heavy chain variable region having at least about 80%, at least about 85%, at least about 90%, at least about 95%, at least about 97%, or at least about 99% sequence identity to SEQ ID NO:11 or SEQ ID NO:56. In certain embodiments, the RSPO1-binding agent comprises a light chain variable region having at least about 80%, at least about 85%, at least about 90%, at least about 95%, at least about 97%, or at least about 99% sequence identity to SEQ ID NO:12 or SEQ ID NO:57. In certain embodiments, the RSPO1-binding agent comprises a heavy chain variable region comprising SEQ ID NO:11 and/or a light chain variable region comprising SEQ ID NO:12. In certain embodiments, the RSPO1-binding agent comprises a heavy chain variable region comprising SEQ ID NO:56 and/or a light chain variable region comprising SEQ ID NO:57.

In certain embodiments, the invention provides methods comprising a RSPO1-binding agent (e.g., an antibody) that specifically binds RSPO1, wherein the RSPO1-binding agent comprises a heavy chain having at least 90% sequence identity to SEQ ID NO:13 or SEQ ID NO:14, and/or a light chain having at least 90% sequence identity to SEQ ID NO:15 or SEQ ID NO:16. In some embodiments, the RSPO1-binding agent comprises a heavy chain having at least 95% sequence identity to SEQ ID NO:13 or SEQ ID NO:14, and/or a light chain having at least 95% sequence identity to SEQ ID NO:15 or SEQ ID NO:16. In some embodiments, the RSPO1-binding agent comprises a heavy chain comprising SEQ ID NO:14 and/or a light chain comprising SEQ ID NO:16. In some embodiments, the RSPO1-binding agent comprises a heavy chain comprising SEQ ID NO:14 and a light chain comprising SEQ ID NO:16. In some embodiments, the anti-RSPO1 antibody is h89M5-H8L5.

In certain embodiments, the invention provides methods comprising a RSPO1-binding agent (e.g., an antibody) that specifically binds RSPO1, wherein the RSPO1-binding agent comprises a heavy chain having at least 90% sequence identity to SEQ ID NO:58 or SEQ ID NO:59, and/or a light chain having at least 90% sequence identity to SEQ ID NO:60 or SEQ ID NO:61. In some embodiments, the RSPO1-binding agent comprises a heavy chain having at least 95% sequence identity to SEQ ID NO:58 or SEQ ID NO:59, and/or a light chain having at least 95% sequence identity to SEQ ID NO:60 or SEQ ID NO:61. In some embodiments, the RSPO1-binding agent comprises a heavy chain comprising SEQ ID NO:59 and/or a light chain comprising SEQ ID NO:61. In some embodiments, the RSPO1-binding agent comprises a heavy chain comprising SEQ ID NO:59 and a light chain comprising SEQ ID NO:61. In some embodiments, the anti-RSPO1 antibody is h89M5-H2L2.

In certain embodiments of the methods described herein, the invention provides methods comprising a RSPO2-binding agent (e.g., an antibody) that specifically binds human RSPO2, wherein the RSPO2-binding agent (e.g., an antibody) comprises one, two, three, four, five, and/or six of the CDRs of antibody 130M23 (see Table 1 herein).

In certain embodiments, the invention provides methods comprising a RSPO2-binding agent (e.g., an antibody) that specifically binds human RSPO2, wherein the RSPO2-binding agent comprises: (a) a heavy chain CDR1 comprising SSYAMS (SEQ ID NO:21), a heavy chain CDR2 comprising SISSGGSTYYPDSVKG (SEQ ID NO:22), and a heavy chain CDR3 comprising RGGDPGVYNGDYEDAMDY (SEQ ID NO:23); and (b) a light chain CDR1 comprising KASQDVSSAVA (SEQ ID NO:24), a light chain CDR2 comprising WASTRHT (SEQ ID NO:25), and a light chain CDR3 comprising QQHYSTP (SEQ ID NO:26).

In certain embodiments, the invention provides methods comprising a RSPO2-binding agent (e.g., an antibody) that specifically binds RSPO2, wherein the RSPO2-binding agent comprises a heavy chain variable region having at least about 80%, at least about 85%, at least about 90%, at least about 95%, at least about 97%, or at least about 99% sequence identity to SEQ ID NO:27. In certain embodiments, the RSPO2-binding agent comprises a light chain variable region having at least about 80%, at least about 85%, at least about 90%, at least about 95%, at least about 97%, or at least about 99% sequence identity to SEQ ID NO:28 or SEQ ID NO:66. In certain embodiments, the RSPO2-binding agent comprises a heavy chain variable region comprising SEQ ID NO:27 and/or a light chain variable region comprising SEQ ID NO:28. In certain embodiments, the RSPO2-binding agent comprises a heavy chain variable region comprising SEQ ID NO:27 and/or a light chain variable region comprising SEQ ID NO:66.

In certain embodiments, the invention provides methods comprising a RSPO2-binding agent (e.g., an antibody) that specifically binds RSPO2, wherein the RSPO2-binding agent comprises a heavy chain having at least 90% sequence identity to SEQ ID NO:29 or SEQ ID NO:30, and/or a light chain having at least 90% sequence identity to SEQ ID NO:31 or SEQ ID NO:32. In some embodiments, the RSPO2-binding agent comprises a heavy chain having at least 95% sequence identity to SEQ ID NO:29 or SEQ ID NO:30, and/or a light chain having at least 95% sequence identity to SEQ ID NO:31 or SEQ ID NO:32. In some embodiments, the RSPO2-binding agent comprises a heavy chain comprising SEQ ID NO:30 and/or a light chain comprising SEQ ID NO:32. In some embodiments, the RSPO2-binding agent comprises a heavy chain comprising SEQ ID NO:30 and a light chain comprising SEQ ID NO:32. In some embodiments, the anti-RSPO2 antibody is h130M23-H1L6.

In certain embodiments, the invention provides methods comprising a RSPO2-binding agent (e.g., an antibody) that specifically binds RSPO2, wherein the RSPO2-binding agent comprises a heavy chain having at least 90% sequence identity to SEQ ID NO:29 or SEQ ID NO:30, and/or a light chain having at least 90% sequence identity to SEQ ID NO:67 or SEQ ID NO:68. In some embodiments, the RSPO2-binding agent comprises a heavy chain having at least 95% sequence identity to SEQ ID NO:29 or SEQ ID NO:30, and/or a light chain having at least 95% sequence identity to SEQ ID NO:67 or SEQ ID NO:68. In some embodiments, the RSPO2-binding agent comprises a heavy chain comprising SEQ ID NO:30 and/or a light chain comprising SEQ ID NO:68. In some embodiments, the RSPO2-binding agent comprises a heavy chain comprising SEQ ID NO:30 and a light chain comprising SEQ ID NO:68. In some embodiments, the anti-RSPO2 antibody is h130M23-H1L2.

In certain embodiments of the methods described herein, the invention provides methods comprising a RSPO3-binding agent (e.g., an antibody) that specifically binds human RSPO3, wherein the RSPO3-binding agent (e.g., an antibody) comprises one, two, three, four, five, and/or six of the CDRs of antibody 131R011 (see Table 1 herein).

In certain embodiments, the invention provides methods comprising a RSPO3-binding agent (e.g., an antibody) that specifically binds human RSPO3, wherein the RSPO3-binding agent comprises: (a) a heavy chain CDR1 comprising DYSIH (SEQ ID NO:37), a heavy chain CDR2 comprising YIYPSNGDSGYNQKFK (SEQ ID NO:38), and a heavy chain CDR3 comprising TYFANNFD (SEQ ID NO:39) or ATYFANNFDY (SEQ ID NO:40); and (b) a light chain CDR1 comprising KASQSVDYDGDSYMN (SEQ ID NO:41), a light chain CDR2 comprising AASNLES (SEQ ID NO:42) or AAS (SEQ ID NO:43), and a light chain CDR3 comprising QQSNEDPLT (SEQ ID NO:44) or QQSNEDPLTF (SEQ ID NO:45).

In certain embodiments, the invention provides a RSPO3-binding agent (e.g., an antibody) that specifically binds RSPO3, wherein the RSPO3-binding agent comprises a heavy chain variable region having at least about 80%, at least about 85%, at least about 90%, at least about 95%, at least about 97%, or at least about 99% sequence identity to SEQ ID NO:46. In certain embodiments, the RSPO3-binding agent comprises a light chain variable region having at least about 80%, at least about 85%, at least about 90%, at least about 95%, at least about 97%, or at least about 99% sequence identity to SEQ ID NO:47. In certain embodiments, the RSPO3-binding agent comprises a heavy chain variable region comprising SEQ ID NO:46 and/or a light chain variable region comprising SEQ ID NO:47.

In certain embodiments, the invention provides a RSPO3-binding agent (e.g., an antibody) that specifically binds RSPO3, wherein the RSPO3-binding agent comprises a heavy chain having at least 90% sequence identity to SEQ ID NO:48 or SEQ ID NO:49, and/or a light chain having at least 90% sequence identity to SEQ ID NO:50 or SEQ ID NO:51. In some embodiments, the RSPO3-binding agent comprises a heavy chain having at least 95% sequence identity to SEQ ID NO:48 or SEQ ID NO:49, and/or a light chain having at least 95% sequence identity to SEQ ID NO:50 or SEQ ID NO:51. In some embodiments, the RSPO3-binding agent comprises a heavy chain comprising SEQ ID NO:49 and/or a light chain comprising SEQ ID NO:51. In some embodiments, the RSPO3-binding agent comprises a heavy chain comprising SEQ ID NO:49 and a light chain comprising SEQ ID NO:51. In some embodiments, the anti-RSPO3 antibody is 131R010.

In some embodiments, the RSPO-binding agent is a monoclonal antibody. In some embodiments, the RSPO-binding agent is a recombinant antibody. In some embodiments, the RSPO-binding agent is a chimeric antibody. In some embodiments, the RSPO-binding agent is a humanized antibody. In some embodiments, the RSPO-binding agent is a human antibody. In some embodiments, the RSPO-binding agent is an IgG1 antibody. In some embodiments, the RSPO-binding agent is an IgG2 antibody. In some embodiments, the RSPO-binding agent is a bispecific antibody. In some embodiments, the RSPO-binding agent is a monovalent antibody.

In some embodiments of the methods described herein, a method comprises a RSPO1-binding agent that competes for specific binding to human RSPO1 with an anti-RSPO1 antibody of the invention. In some embodiments, the RSPO1-binding agent competes for specific binding to human RSPO1 with an antibody that comprises a heavy chain variable region comprising SEQ ID NO:11 and a light chain variable region comprising SEQ ID NO:12. In some embodiments, the RSPO1-binding agent competes for specific binding to human RSPO1 with an antibody that comprises a heavy chain variable region comprising SEQ ID NO:56 and a light chain variable region comprising SEQ ID NO:57. In some embodiments, the antibody with which the RSPO1-binding agent competes is an antibody comprising the CDRs of antibody 89M5. In some embodiments, the RSPO1-binding agent competes for specific binding to RSPO1 with an anti-RSPO1 antibody of the invention in an in vitro competitive binding assay.

In certain embodiments, the RSPO1-binding agent is an antibody that binds the same epitope, or essentially the same epitope, on RSPO1 as an anti-RSPO1 antibody of the invention (e.g., 89M5, h89M5-H8L5, or h89M5-H2L2). In some embodiments, the RSPO1-binding agent is an antibody that binds an epitope on RSPO1 that overlaps with the epitope on RSPO1 bound by an anti-RSPO1 antibody of the invention (e.g., 89M5, h89M5-H8L5, or h89M5-H2L2).

In some embodiments of the methods described herein, a method comprises a RSPO2-binding agent that competes for specific binding to human RSPO2 with an anti-RSPO2 antibody of the invention. In some embodiments, the RSPO2-binding agent competes for specific binding to human RSPO2 with an antibody that comprises a heavy chain variable region comprising SEQ ID NO:27 and a light chain variable region comprising SEQ ID NO:28. In some embodiments, the RSPO2-binding agent competes for specific binding to human RSPO2 with an antibody that comprises a heavy chain variable region comprising SEQ ID NO:27 and a light chain variable region comprising SEQ ID NO:66. In some embodiments, the antibody with which the RSPO2-binding agent competes is an antibody comprising the CDRs of antibody 130M23. In some embodiments, the RSPO2-binding agent competes for specific binding to RSPO2 with an anti-RSPO2 antibody of the invention in an in vitro competitive binding assay.

In certain embodiments, the RSPO2-binding agent is an antibody that binds the same epitope, or essentially the same epitope, on RSPO2 as an anti-RSPO2 antibody of the invention (e.g., 130M23, h130M23-H1L6, or h130M23-H1L2). In some embodiments, the RSPO2-binding agent is an antibody that binds an epitope on RSPO2 that overlaps with the epitope on RSPO2 bound by an anti-RSPO2 antibody of the invention (e.g., 130M23, h130M23-H1L6, h130M23-H1L2).

In some embodiments of the methods described herein, a method comprises a RSPO3-binding agent that competes for specific binding to human RSPO3 with an anti-RSPO3 antibody of the invention. In some embodiments, the RSPO3-binding agent competes for specific binding to human RSPO3 with an antibody that comprises a heavy chain variable region comprising SEQ ID NO:46 and a light chain variable region comprising SEQ ID NO:47. In some embodiments, the antibody with which the RSPO3-binding agent competes is an antibody comprising the CDRs of antibody 131R010. In some embodiments, the RSPO3-binding agent competes for specific binding to RSPO3 with an anti-RSPO3 antibody of the invention in an in vitro competitive binding assay.

In certain embodiments, the RSPO3-binding agent is an antibody that binds the same epitope, or essentially the same epitope, on RSPO3 as an anti-RSPO3 antibody of the invention (e.g., 131R010). In some embodiments, the RSPO3-binding agent is an antibody that binds an epitope on RSPO3 that overlaps with the epitope on RSPO3 bound by an anti-RSPO3 antibody of the invention (e.g., 131R010).

In certain embodiments of any of the methods described herein, the RSPO-binding agent or antibody is isolated. In some embodiments, the RSPO-binding agent or antibody is substantially pure.

In some embodiments, the RSPO or LGR antagonist is an antibody that specifically binds at least one human LGR protein or a portion thereof. In some embodiments, the antibody specifically binds at least one human LGR protein selected from the group consisting of LGR4, LGR5, and LGR6. In some embodiments, the antibody specifically binds human LGR5. In certain embodiments, the antibody comprises (a) the heavy chain CDR1, CDR2, and CDR3 sequences of the monoclonal antibody produced by the 88M1 hybridoma having the ATCC deposit number PTA-9342; and (b) the light chain CDR1, CDR2, and CDR3 sequences of the monoclonal antibody produced by the 88M1 hybridoma having the ATCC deposit number PTA-9342. In some embodiments, the antibody comprises the heavy chain variable region and light chain variable region of the monoclonal antibody produced by the 88M1 hybridoma having the ATCC deposit number PTA-9342.

In some embodiments, the RSPO or LGR antagonist is a soluble receptor including an extracellular domain of a human LGR protein (e.g., LGR5) or a fragment thereof, where the extracellular domain is capable of binding a human RSPO protein. In some embodiments, the extracellular domain of a human LGR protein comprises amino acids 22-564 of human LGR5 (SEQ ID NO:74). In some embodiments, a soluble receptor comprises a non-LGR polypeptide. In some embodiments, the non-LGR polypeptide is directly linked to the extracellular domain of the human LGR protein or is connected to the extracellular domain of the human LGR protein by a linker. In some embodiments, the non-LGR polypeptide comprises a human Fc region (e.g., comprises SEQ ID NO:76, SEQ ID NO:77, SEQ ID NO:78, SEQ ID NO:79, or SEQ ID NO:80, or an amino acid sequence at least 80%, 85%, 90%, 95%, or 99% identical to SEQ ID NO:76, SEQ ID NO:77, SEQ ID NO:78, SEQ ID NO:79, or SEQ ID NO:80).

In another aspect, the invention provides a method of inhibiting Wnt signaling in a cell, comprising contacting the cell with an effective amount of a RSPO-binding agent or a LGR-binding agent, including each of those described herein. In some embodiments, the cell expresses elevated levels of at least one RSPO protein. In some embodiments, the cell expresses elevated levels of RSPO1. In some embodiments, the cell expresses elevated levels of RSPO2. In some embodiments, the cell expresses elevated levels of RSPO3. In some embodiments, the cell expresses a high level of at least one RSPO protein. In some embodiments, the cell expresses a high level of RSPO1. In some embodiments, the cell expresses a high level of RSPO2. In some embodiments, the cell expresses a high level of RSPO3. In certain embodiments, the RSPO-binding agent inhibits formation of fibrotic tissue. In certain embodiments, the LGR-binding agent inhibits formation of fibrotic tissue.

In certain embodiments of any of the methods described herein, the method further comprises a step of determining the expression level of at least one RSPO protein in a cell. In some embodiments, the cell is from a fibrotic tissue.

In certain embodiments of any of the methods described herein, the method comprises administering to the subject a RSPO-binding agent and at least one additional therapeutic agent. In certain embodiments of any of the methods described herein, the method comprises administering to the subject a LGR-binding agent and at least one additional therapeutic agent.

Compositions comprising a RSPO-binding agent (e.g., antibody or soluble receptor) or a LGR-binding agent described herein are provided. Pharmaceutical compositions comprising a RSPO-binding agent (e.g., antibody or soluble receptor) or a LGR-binding agent described herein and a pharmaceutically acceptable carrier are provided. Methods of treating fibrotic diseases in a subject (e.g., a human) comprising administering to the subject an effective amount of a pharmaceutical composition comprising a RSPO-binding agent or LGR-binding agent are also provided. Use of a RSPO-binding agent and/or a LGR-binding agent for treatment of a fibrotic disease is also provided.

Where aspects or embodiments of the invention are described in terms of a Markush group or other grouping of alternatives, the present invention encompasses not only the entire group listed as a whole, but also each member of the group individually and all possible subgroups of the main group, and also the main group absent one or more of the group members. The present invention also envisages the explicit exclusion of one or more of any of the group members in the claimed invention.

DETAILED DESCRIPTION OF THE INVENTION

Figure 1:
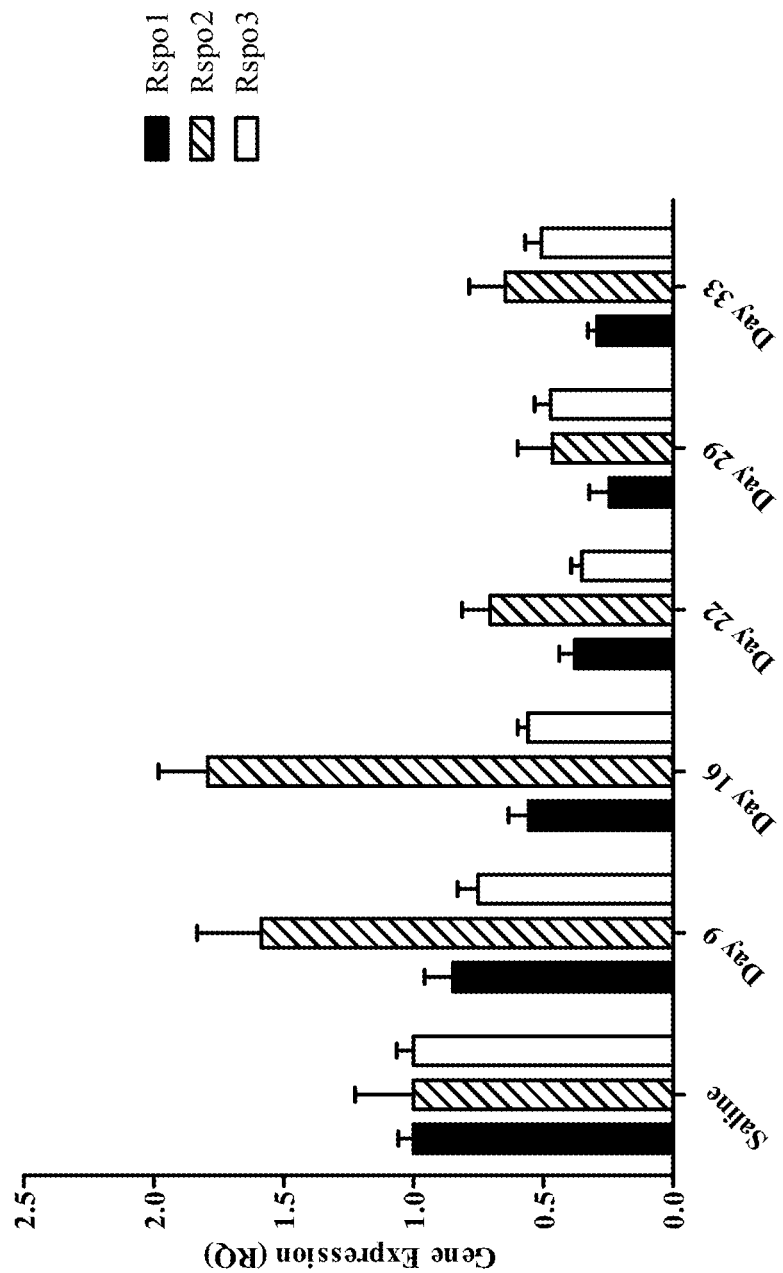
FIG. 1. RSPO expression in bleomycin-induced lung fibrosis model.

The present invention provides novel methods from treating fibrotic diseases and for reducing scarring resulting from wound healing. The invention provides methods of treating or preventing a fibrotic disease in a subject, comprising administering to the subject a therapeutically effective amount of a human RSPO or LGR antagonist. The methods comprise administering RSPO-binding agents and/or LGR-binding agents, particularly anti-RSPO1 antibodies, anti-RSPO2 antibodies, anti-RSPO3 antibodies, anti-LGR5 antibodies, or a LGR5-Fc soluble receptor, to a subject in need thereof. The RSPO-binding agents and LGR-binding agents include, but are not limited to, inhibitors of RSPO and LGR protein interactions.

I. Definitions

To facilitate an understanding of the present invention, a number of terms and phrases are defined below.

The term "fibrotic diseases" as used herein includes but is not limited to connective tissue diseases. Those of skill in the art generally believe fibrosis to be the formation or development of excess fibrous connective tissue in an organ or tissue. In some embodiments, fibrosis occurs as a reparative or reactive process. In some embodiments, fibrosis occurs in response to damage or injury. The term "fibrosis" is to be understood as the formation or development of excess fibrous connective tissue in an organ or tissue as a reparative or reactive process, as opposed to a formation of fibrous tissue as a normal constituent of an organ or tissue.

The terms "antagonist" and "antagonistic" as used herein refer to any molecule that partially or fully blocks, inhibits, reduces, or neutralizes a biological activity of a target and/or signaling pathway. The term "antagonist" is used herein to include any molecule that partially or fully blocks, inhibits, reduces, or neutralizes the activity of a protein (e.g., a RSPO protein or LGR protein). Suitable antagonist molecules specifically include, but are not limited to, antagonist antibodies or antibody fragments.

The terms "modulation" and "modulate" as used herein refer to a change or an alteration in a biological activity. Modulation includes, but is not limited to, stimulating or inhibiting an activity. Modulation may be an increase or a decrease in activity, a change in binding characteristics, or any other change in the biological, functional, or immunological properties associated with the activity of a protein, pathway, or other biological point of interest.

The term "antibody" as used herein refers to an immunoglobulin molecule that recognizes and specifically binds a target, such as a protein, polypeptide, peptide, carbohydrate, polynucleotide, lipid, or combinations of the foregoing, through at least one antigen-binding site within the variable region(s) of the immunoglobulin molecule. As used herein, the term encompasses intact polyclonal antibodies, intact monoclonal antibodies, single chain antibodies, antibody fragments (such as Fab, Fab', F(ab')2, and Fv fragments), single chain Fv (scFv) antibodies, multispecific antibodies such as bispecific antibodies, monospecific antibodies, monovalent antibodies, chimeric antibodies, humanized antibodies, human antibodies, fusion proteins comprising an antigen-binding site of an antibody, and any other modified immunoglobulin molecule comprising an antigen recognition site (i.e., antigen-binding site) as long as the antibodies exhibit the desired biological activity. An antibody can be any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy chain constant domains referred to as alpha, delta, epsilon, gamma, and mu, respectively. The different classes of immunoglobulins have different and well-known subunit structures and three-dimensional configurations. Antibodies can be naked or conjugated to other molecules, including but not limited to, toxins and radioisotopes.

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, single chain antibodies, and multispecific antibodies formed from antibody fragments. "Antibody fragment" as used herein comprises an antigen-binding site or epitope-binding site.

The term "variable region" of an antibody refers to the variable region of an antibody light chain or the variable region of an antibody heavy chain, either alone or in combination. The variable region of each heavy and light chain consists of four framework regions (FR) connected by three complementarity determining regions (CDRs), also known as "hypervariable regions". The CDRs in each chain are held together in close proximity by the framework regions and, with the CDRs from the other chain, contribute to the formation of the antigen-binding site of the antibody. There are at least two techniques for determining CDRs: (1) an approach based on cross-species sequence variability (i.e., Kabat et al., 1991, *Sequences of Proteins of Immunological Interest*, 5th Edition, National Institutes of Health, Bethesda, Md.), and (2) an approach based on crystallographic studies of antigen-antibody complexes (Al-Lazikani et al., 1997, *J. Mol. Biol.*, 273:927-948). In addition, combinations of these two approaches may be used in the art to determine CDRs.

The term "monoclonal antibody" as used herein refers to a homogeneous antibody population involved in the highly specific recognition and binding of a single antigenic determinant or epitope. This is in contrast to polyclonal antibodies that typically include a mixture of different antibodies directed against a variety of different antigenic determinants. The term "monoclonal antibody" encompasses both intact and full-length monoclonal antibodies as well as antibody fragments (e.g., Fab, Fab', F(ab')2, Fv), single chain (scFv) antibodies, bispecific antibodies, fusion proteins comprising an antibody portion, and any other modified immunoglobulin molecule comprising an antigen recognition site (antigen-binding site). Furthermore, "monoclonal antibody" refers to such antibodies made by any number of techniques, including but not limited to, hybridoma production, phage selection, recombinant expression, and transgenic animals.

The term "humanized antibody" as used herein refers to forms of antibodies that are specific immunoglobulin chains, chimeric immunoglobulins, or fragments thereof that contain minimal non-human sequences. Typically, humanized antibodies are human immunoglobulins in which amino acid residues of the CDRs are replaced by amino acid residues from the CDRs of a non-human species (e.g., mouse, rat, rabbit, or hamster) that have the desired specificity, affinity, and/or binding capability. In some instances, the framework region amino acid residues of a human immunoglobulin are replaced with the corresponding amino acid residues in an antibody from a non-human species. The humanized antibody can be further modified by the substitution of additional amino acid residues either in the framework region and/or within the replaced non-human amino acid residues to refine and optimize antibody specificity, affinity, structural, and/or binding capability. In general, a humanized antibody will comprise substantially all of at least one, and typically two or three of the CDRs that correspond to the non-human immunoglobulin whereas all or substantially all of the framework regions are those of a human immunoglobulin sequence. A humanized antibody can also comprise at least a portion of an immunoglobulin constant region or domain (Fc), typically that of a human immunoglobulin.

The term "human antibody" as used herein refers to an antibody produced by a human or an antibody having an amino acid sequence corresponding to an antibody produced by a human. A human antibody may be made using any of the techniques known in the art.

The term "chimeric antibody" as used herein refers to an antibody wherein the amino acid sequence of the immunoglobulin molecule is derived from two or more species. Typically, the variable region of both the light chain and heavy chain corresponds to the variable region of an antibody derived from one species of mammal (e.g., mouse, rat, rabbit, etc.) with the desired specificity, affinity, and/or binding capability, while the constant region corresponds to sequences in antibodies derived from another species (usually human).

The phrase "affinity-matured antibody" as used herein refers to an antibody with one or more alterations in one or more CDRs thereof that result in an improvement in the affinity of the antibody for an antigen, compared to a parent antibody that does not possess those alterations(s). The definition also includes alterations in non-CDR amino acid residues made in conjunction with alterations to CDR amino acid residues. Preferred affinity-matured antibodies generally have nanomolar or even picomolar affinities for the target antigen. Affinity-matured antibodies are produced by procedures known in the art including, but not limited to, heavy chain and light chain variable domain shuffling, random mutagenesis of CDR and/or framework amino acid residues, or site-directed mutagenesis of CDR and/or framework amino acid residues.

The terms "epitope" and "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids (also referred to as linear epitopes) are typically retained upon protein denaturing, whereas epitopes formed by tertiary folding (also referred to as conformational epitopes) are typically lost upon protein denaturing. An epitope typically includes at least 3, and more usually, at least 5 or 8-10 amino acids in a unique spatial conformation.

The terms "selectively binds" or "specifically binds" mean that a binding agent or an antibody reacts or associates more frequently, more rapidly, with greater duration, with greater affinity, or with some combination of the above to the epitope, protein, or target molecule than with alternative substances, including unrelated or related proteins. In certain embodiments "specifically binds" means, for instance, that an antibody binds a protein with a $K_D$ of about 0.1 mM or less, but more usually less than about 1 µM. In certain embodiments, "specifically binds" means that an antibody binds a target at times with a $K_D$ of at least about 0.1 µM or less, at other times at least about 0.01 µM or less, and at other times at least about 1 µM or less. Because of the sequence identity between homologous proteins in different species, specific binding can include an antibody that recognizes a protein in more than one species (e.g., human RSPO3 and mouse RSPO3). Likewise, because of homology within certain regions of polypeptide sequences of different proteins, specific binding can include an antibody (or other polypeptide or binding agent) that recognizes more than one protein (e.g., human RSPO3 and human RSPO1). It is understood that, in certain embodiments, an antibody or binding moiety that specifically binds a first target may or may not specifically bind a second target. As such, "specific binding" does not necessarily require (although it can include) exclusive binding, i.e. binding to a single target. Thus, an antibody may, in certain embodiments, specifically bind more than one target. In certain embodiments, multiple targets may be bound by the same antigen-binding site on the antibody. For example, an antibody may, in certain instances, comprise two identical antigen-binding sites, each of which specifically binds the same epitope on two or more proteins (e.g., RSPO3 and RSPO1). In certain alternative embodiments, an antibody may be multispecific and comprise at least two antigen-binding sites with differing specificities. By way of non-limiting example, a bispecific antibody may comprise one antigen-binding site that recognizes an epitope on one protein (e.g., human RSPO3) and further comprise a second, different antigen-binding site that recognizes a different epitope on a second protein. Generally, but not necessarily, reference to binding means specific binding.

The terms "polypeptide" and "peptide" and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids), as well as other modifications known in the art. It is understood that, because the polypeptides of this invention may be based upon antibodies, in certain embodiments, the polypeptides can occur as single chains or associated chains.

The terms "polynucleotide" and "nucleic acid" are used interchangeably herein and refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase.

"Conditions of high stringency" may be identified by those that: (1) employ low ionic strength and high temperature for washing, for example 15 mM NaCl/1.5 mM sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 in 5×SSC (0.75M NaCl, 75 mM sodium citrate) at 42° C.; or (3) employ during hybridization 50% formamide in 5×SSC, 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC and 50% formamide, followed by a high-stringency wash consisting of 0.1×SSC containing EDTA at 55° C.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software that may be used to obtain alignments of amino acid or nucleotide sequences are well-known in the art. These include, but are not limited to, BLAST, ALIGN, Megalin, BestFit, GCG Wisconsin Package, and variations thereof. In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the sequences that is at least about 10, at least about 20, at least about 40-60 residues, at least about 60-80 residues in length or any integral value therebetween. In some embodiments, identity exists over a longer region than 60-80 residues, such as at least about 80-100 residues, and in some embodiments the sequences are substantially identical over the full length of the sequences being compared, such as the coding region of a nucleotide sequence.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Preferably, conservative substitutions in the sequences of the polypeptides and antibodies of the invention do not abrogate the binding of the polypeptide or antibody containing the amino acid sequence, to the antigen(s), i.e., the one or more RSPO protein(s) to which the polypeptide or antibody binds. Methods of identifying nucleotide and amino acid conservative substitutions which do not eliminate antigen binding are well-known in the art.

The term "vector" as used herein means a construct, which is capable of delivering, and usually expressing, one or more gene(s) or sequence(s) of interest in a host cell. Examples of vectors include, but are not limited to, viral vectors, naked DNA or RNA expression vectors, plasmid, cosmid, or phage vectors, DNA or RNA expression vectors associated with cationic condensing agents, and DNA or RNA expression vectors encapsulated in liposomes.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cells, or compositions include those which have been purified to a degree that they are no longer in a form in which they are found in nature. In some embodiments, a polypeptide, antibody, polynucleotide, vector, cell, or composition which is isolated is substantially pure.

The term "substantially pure" as used herein refers to material which is at least 50% pure (i.e., free from contaminants), at least 90% pure, at least 95% pure, at least 98% pure, or at least 99% pure.

The term "subject" refers to any animal (e.g., a mammal), including, but not limited to, humans, non-human primates, canines, felines, rodents, and the like, which is to be the recipient of a particular treatment. Typically, the terms "subject" and "patient" are used interchangeably herein in reference to a human subject.

The term "pharmaceutically acceptable" refers to a product or compound approved (or approvable) by a regulatory agency of the Federal government or a state government or listed in the U.S. Pharmacopeia or other generally recognized pharmacopeia for use in animals, including humans.

The terms "pharmaceutically acceptable excipient, carrier or adjuvant" or "acceptable pharmaceutical carrier" refer to an excipient, carrier or adjuvant that can be administered to a subject, together with at least one binding agent (e.g., an antibody) of the present disclosure, and which does not destroy the activity of the binding agent. The excipient, carrier, or adjuvant should be non-toxic when administered with a binding agent in doses sufficient to deliver a therapeutic effect. In general, those of skill in the art and the U.S. FDA consider a pharmaceutically acceptable excipient, carrier, or adjuvant to be an inactive ingredient of any formulation.

The terms "effective amount" or "therapeutically effective amount" or "therapeutic effect" refer to an amount of a binding agent, an antibody, polypeptide, polynucleotide, small organic molecule, or other drug effective to "treat" a disease or disorder in a subject or mammal. In the case of fibrotic disease, the therapeutically effective amount of an agent (e.g., an antibody) has a therapeutic effect and as such can prevent the development of a fibrotic disease; slow down the development of a fibrotic disease; slow down the progression of a fibrotic disease; reduce the amount of fibrosis in a disease; reduce pathological deposits of fibrotic material in an organ; reduce pathological deposits of connective tissue or extracellular matrix in an organ; relieve to some extent one or more of the symptoms associated with a fibrotic disease; reduce morbidity and mortality; improve quality of life; or a combination of such effects.

The terms "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent or slow the development of a targeted pathologic condition or disorder. Thus those in need of treatment include those already with the disorder; those prone to have the disorder; and those in whom the disorder is to be prevented. In some embodiments, a subject is successfully "treated" according to the methods of the present invention if the patient shows one or more of the following: prevention of the development of a fibrotic disease; the slowing of development of a fibrotic disease; the slowing of progression of a fibrotic disease; reduction in the amount of fibrosis in a disease; reduction of pathological deposits of fibrotic material in an organ; reduction of pathological deposits of connective tissue or extracellular matrix in an organ; the relief to some extent of one or more symptoms associated with a fibrotic disease; reduction of morbidity and mortality; improvement of quality of life; or some combination of such effects.

As used in the present disclosure and claims, the singular forms "a", "an" and "the" include plural forms unless the context clearly dictates otherwise.

It is understood that wherever embodiments are described herein with the language "comprising" otherwise analogous embodiments described in terms of "consisting of" and/or "consisting essentially of" are also provided. It is also understood that wherever embodiments are described herein with the language "consisting essentially of" otherwise analogous embodiments described in terms of "consisting of" are also provided.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. Methods of Use and Pharmaceutical Compositions

The invention provides methods for the prevention and/or treatment of fibrotic diseases. In some embodiments, a method comprises using RSPO-binding agents and/or LGR-binding agents (e.g., antibodies or soluble receptors) as described herein. In certain embodiments, a RSPO-binding agent is an antagonist of human RSPO1, RSPO2, RSPO3, and/or RSPO4. In certain embodiments, a LGR-binding agent is an antagonist of human LGR4, LGR5, and/or LGR6. The methods may be in vitro, ex vivo, or in vivo methods. The invention also provides the use of a RSPO-binding agent or a LGR-binding agent (e.g., an antibody or a soluble receptor) described herein for the manufacture of a medicament for the treatment of a fibrotic disease.

The present invention provides methods for treating or preventing a fibrotic disease using the RSPO-binding agents or LGR-binding agents (e.g., antibodies or soluble receptors) described herein. In certain embodiments, a method of treating a fibrotic disease comprises contacting a cell or a tissue with a RSPO-binding agent or a LGR-binding agent (e.g., an antibody or a soluble receptor) in vitro. For example, fibroblasts, either a cell line or primary cells from an organ of interest, are contacted with an agent of interest (e.g., a RSPO-binding agent or LGR-binding agent). Affects from the agent of the interest can be observed by evaluating myofibroblast/mesenchymal differentiation, including but not limited to up-regulation of alpha-smooth muscle actin, transforming growth factor best 1, and/or fibronectin; extra-cellular matrix deposition; and collagen/hydroxyproline content.

In certain embodiments, a method of treating a fibrotic disease comprises contacting a cell or a tissue with a RSPO-binding agent or a LGR-binding agent (e.g., an antibody or a soluble receptor) in vivo. In certain embodiments, contacting a cell or a tissue with a RSPO-binding agent or LGR-binding agent is undertaken in an animal model. For example, a RSPO-binding agent may be administered to mice which have a fibrotic disease. In some embodiments, a RSPO-binding agent may be administered to a transgenic mouse. In some embodiments, a RSPO-binding agent is administered to the animal. In some embodiments, the RSPO-binding agent is administered at the same time or shortly after administration of a fibrosis-inducing agent in the animal to prevent development of fibrosis ("preventative model"). In some embodiments, the RSPO-binding agent is administered as a therapeutic after fibrosis has been induced ("therapeutic model"). In some embodiments, the RSPO-binding agent is an antibody. In some embodiments, the RSPO-binding agent is an anti-RSPO1 antibody. In some embodiments, the RSPO-binding agent is an anti-RSPO2 antibody. In some embodiments, the RSPO-binding agent is an anti-RSPO3 antibody. In some embodiments, the RSPO-binding agent is a soluble receptor. In some embodiments, the RSPO-binding agent is a LGR5 soluble receptor. In some embodiments, the RSPO-binding is a LGR5-Fc fusion protein.

Models for inducing fibrosis in animals are known to those of skill in the art. For example, pulmonary fibrosis can be induced in mice by intraperitoneal injection with bleomycin. Pulmonary fibrosis can also be induced by intratracheal instillation of bleomycin, fluorescein isothiocyanate or particulate matter, such as silica and asbestos. Liver fibrosis can be induced in mice by intraperitoneal injection with carbon tetrachloride. Dermal fibrosis can be induced in mice by local injection of bleomycin.

In certain embodiments, a method of treating or preventing a fibrotic disease comprises administering to a subject a therapeutically effective amount of a RSPO-binding agent. In certain embodiments, a method of treating or preventing a fibrotic disease comprises administering to a subject a therapeutically effective amount of an anti-RSPO antibody. In certain embodiments, a method of treating or preventing a fibrotic disease comprises administering to a subject a therapeutically effective amount of a LGR soluble receptor. In certain embodiments, a method of treating or preventing a fibrotic disease comprises administering to a subject a therapeutically effective amount of a LGR-binding agent. In certain embodiments, a method of treating or preventing a fibrotic disease comprises administering to a subject a therapeutically effective amount of an anti-LGR antibody.

In certain embodiments, a method of treating or preventing a fibrotic disease comprises administering to a subject a therapeutically effective amount of an anti-RSPO1 antibody. In certain embodiments, a method of treating or preventing a fibrotic disease comprises administering to a subject a therapeutically effective amount of an anti-RSPO1 antibody, wherein the anti-RSPO1 antibody comprises a heavy chain CDR1 comprising TGYTMH (SEQ ID NO:5), a heavy chain CDR2 comprising GINPNNGGTTYNQNFKG (SEQ ID NO:6), and a heavy chain CDR3 comprising KEFSDGYYF-FAY (SEQ ID NO:7); and a light chain CDR1 comprising KASQDVIFAVA (SEQ ID NO:8), a light chain CDR2 comprising WASTRHT (SEQ ID NO:9), and a light chain CDR3 comprising QQHYSTPW (SEQ ID NO:10). In some embodiments, a method of treating or preventing a fibrotic disease comprises administering to a subject a therapeutically effective amount of an anti-RSPO1 antibody, wherein the anti-RSPO1 antibody comprises a heavy chain variable region having at least 90% sequence identity to SEQ ID NO:11 and a light chain variable region having at least 90% sequence identity to SEQ ID NO:12. In some embodiments, a method of treating or preventing a fibrotic disease comprises administering to a subject a therapeutically effective amount of an anti-RSPO1 antibody, wherein the anti-RSPO1 antibody comprises a heavy chain variable region having at least 90% sequence identity to SEQ ID NO:56 and a light chain variable region having at least 90% sequence identity to SEQ ID NO:57. In some embodiments, a method of treating or preventing a fibrotic disease comprises administering to a subject a therapeutically effective amount of an anti-RSPO1 antibody, wherein the anti-RSPO1 antibody comprises a heavy chain variable region of SEQ ID NO:11 and a light chain variable region of SEQ ID NO:12. In some embodiments, a method of treating or preventing a fibrotic disease comprises administering to a subject a therapeutically effective amount of an anti-RSPO1 antibody, wherein the anti-RSPO1 antibody comprises a heavy chain variable region of SEQ ID NO:56 and a light chain variable region of SEQ ID NO:57. In some embodiments, the anti-RSPO1 antibody is a humanized version of antibody 89M5. In some embodiments, the anti-RSPO1 antibody is antibody h89M5-H8L5. In some embodiments, the anti-RSPO1 antibody is antibody h89M5-H2L2.

In certain embodiments, a method of treating or preventing a fibrotic disease comprises administering to a subject a therapeutically effective amount of an anti-RSPO2 antibody. In certain embodiments, a method of treating or preventing a fibrotic disease comprises administering to a subject a therapeutically effective amount of an anti-RSPO2 antibody, wherein the anti-RSPO2 antibody comprises a heavy chain CDR1 comprising SSYAMS (SEQ ID NO:21), a heavy chain CDR2 comprising SISSGGSTYYPDSVKG (SEQ ID NO:22), and a heavy chain CDR3 comprising RGGD-PGVYNGDYEDAMDY (SEQ ID NO:23); and a light chain CDR1 comprising KASQDVSSAVA (SEQ ID NO:24), a light chain CDR2 comprising WASTRHT (SEQ ID NO:25), and a light chain CDR3 comprising QQHYSTP (SEQ ID NO:26). In some embodiments, a method of treating or preventing a fibrotic disease comprises administering to a subject a therapeutically effective amount of an anti-RSPO2 antibody, wherein the anti-RSPO2 antibody comprises a heavy chain variable region having at least 90% sequence identity to SEQ ID NO:27 and a light chain variable region having at least 90% sequence identity to SEQ ID NO:28 or SEQ ID NO:66. In some embodiments, a method of treating or preventing a fibrotic disease comprises administering to a subject a therapeutically effective amount of an anti-RSPO2 antibody, wherein the anti-RSPO2 antibody comprises a heavy chain variable region of SEQ ID NO:27 and a light chain variable region of SEQ ID NO:28 or SEQ ID NO:66. In some embodiments, the anti-RSPO2 antibody is a humanized version of antibody 130M23. In some embodiments, the anti-RSPO2 antibody is antibody h130M23-H1L6. In some embodiments, the anti-RSPO2 antibody is antibody h130M23-H1L2.

In certain embodiments, a method of treating or preventing a fibrotic disease comprises administering to a subject a therapeutically effective amount of an anti-RSPO3 antibody. In certain embodiments, a method of treating or preventing a fibrotic disease comprises administering to a subject a therapeutically effective amount of an anti-RSPO3 antibody, wherein the anti-RSPO3 antibody comprises a heavy chain CDR1 comprising DYSIH (SEQ ID NO:37), a heavy chain CDR2 comprising YIYPSNGDSGYNQKFK (SQ ID NO:38), and a heavy chain CDR3 comprising TYFANNFD (SEQ ID NO:39) or ATYFANNFDY (SEQ ID NO:40); and a light chain CDR1 comprising KASQSVDYDGDSYMN (SEQ ID NO:41), a light chain CDR2 comprising AASNLES (SEQ ID NO:42) or AAS (SEQ ID NO:43), and a light chain CDR3 comprising QQSNEDPLT (SEQ ID NO:44) or QQSNEDPLTF (SEQ ID NO:45). In some embodiments, a method of treating or preventing a fibrotic disease comprises administering to a subject a therapeutically effective amount of an anti-RSPO3 antibody, wherein the anti-RSPO3 antibody comprises a heavy chain variable region having at least 90% sequence identity to SEQ ID NO:46 and a light chain variable region having at least 90% sequence identity to SEQ ID NO:47. In some embodiments, a method of treating or preventing a fibrotic disease comprises administering to a subject a therapeutically effective amount of an anti-RSPO3 antibody, wherein the anti-RSPO3 antibody comprises a heavy chain variable region of SEQ ID NO:46 and a light chain variable region of SEQ ID NO:47. In some embodiments, the anti-RSPO3 antibody is antibody 131R010.

In certain embodiments, a method of treating or preventing a fibrotic disease comprises administering to a subject a therapeutically effective amount of an anti-LGR antibody. In certain embodiments, a method of treating or preventing a fibrotic disease comprises administering to a subject a therapeutically effective amount of an anti-LGR5 antibody, wherein the anti-LGR5 antibody comprises the heavy chain CDR1, CDR2, and CDR3 sequences of the monoclonal antibody produced by the 88M1 hybridoma having the ATCC deposit number PTA-9342, and the light chain CDR1, CDR2, and CDR3 sequences of the monoclonal antibody produced by the 88M1 hybridoma having the ATCC deposit number PTA-9342. In certain embodiments, a method of treating or preventing a fibrotic disease comprises administering to a subject a therapeutically effective amount of an anti-LGR5 antibody, wherein the anti-LGR5 antibody comprises the heavy chain variable region and light chain variable region of the monoclonal antibody produced by the 88M1 hybridoma having the ATCC deposit number PTA-9342.

In certain embodiments, a method of treating or preventing a fibrotic disease comprises administering to a subject a therapeutically effective amount of a LGR soluble receptor. In certain embodiments, a method of treating or preventing a fibrotic disease comprises administering to a subject a therapeutically effective amount of a LGR5 soluble receptor, wherein the LGR5 soluble receptor comprises the extracellular domain, or a fragment thereof, of LGR5. In some embodiments, a method of treating or preventing a fibrotic disease comprises administering to a subject a therapeutically effective amount of a LGR5 soluble receptor, wherein the LGR5 soluble receptor comprises amino acids 22-564 of human LGR5. In certain embodiments, a method of treating or preventing a fibrotic disease comprises administering to a subject a therapeutically effective amount of a LGR5 soluble receptor, wherein the LGR5 soluble receptor comprises SEQ ID NO:74. In certain embodiments, a method of treating or preventing a fibrotic disease comprises administering to a subject a therapeutically effective amount of a LGR5 soluble receptor, wherein the LGR5 soluble receptor comprises SEQ ID NO:75.

In some embodiments of the methods described herein, the RSPO-binding agent binds RSPO1 and prevents the development of a fibrotic disease. In some embodiments, the RSPO-binding agent binds RSPO1 and slows down the development of a fibrotic disease. In some embodiments, the RSPO-binding agent binds RSPO1 and slows down the progression of a fibrotic disease. In some embodiments, the RSPO-binding agent binds RSPO1 and reduces the amount of fibrosis in a disease. In some embodiments, the RSPO-binding agent binds RSPO1 and reduces pathological deposits of fibrotic material in an organ. In some embodiments, the RSPO-binding agent binds RSPO1 and reduces the pathological deposits of connective tissue and/or extracellular matrix in an organ. In some embodiments, the RSPO-binding agent is an anti-RSPO1 antibody. In some embodiments, the anti-RSPO1 antibody is a humanized version of antibody 89M5. In some embodiments, the anti-RSPO1 antibody is h89M5-H8L5. In some embodiments, the anti-RSPO1 antibody is h89M5-H2L2.

In some embodiments of the methods described herein, the RSPO-binding agent binds RSPO2 and prevents the development of a fibrotic disease. In some embodiments, the RSPO-binding agent binds RSPO2 and slows down the development of a fibrotic disease. In some embodiments, the RSPO-binding agent binds RSPO2 and slows down the progression of a fibrotic disease. In some embodiments, the RSPO-binding agent binds RSPO2 and reduces the amount of fibrosis in a disease. In some embodiments, the RSPO-binding agent binds RSPO2 and reduces pathological deposits of fibrotic material in an organ. In some embodiments, the RSPO-binding agent binds RSPO2 and reduces the pathological deposits of connective tissue and/or extracellular matrix in an organ. In some embodiments, the RSPO-binding agent is an anti-RSPO2 antibody. In some embodiments, the anti-RSPO2 antibody is a humanized version of antibody 130M23. In some embodiments, the anti-RSPO2 antibody is h130M23-H1L6. In some embodiments, the anti-RSPO2 antibody is h130M23-H1L2.

In some embodiments of the methods described herein, the RSPO-binding agent binds RSPO3 and prevents the development of a fibrotic disease. In some embodiments, the RSPO-binding agent binds RSPO3 and slows down the development of a fibrotic disease. In some embodiments, the RSPO-binding agent binds RSPO3 and slows down the progression of a fibrotic disease. In some embodiments, the RSPO-binding agent binds RSPO3 and reduces the amount of fibrosis in a disease. In some embodiments, the RSPO-binding agent binds RSPO3 and reduces pathological deposits of fibrotic material in an organ. In some embodiments, the RSPO-binding agent binds RSPO3 and reduces the pathological deposits of connective tissue and/or extracellular matrix in an organ. In some embodiments, the RSPO-binding agent is an anti-RSPO3 antibody. In some embodiments, the anti-RSPO3 antibody is 131R010.

In some embodiments of the methods described herein, the RSPO-binding agent binds RSPO1, RSPO2, RSPO3, and/or RSPO4 and prevents the development of a fibrotic disease. In some embodiments, the RSPO-binding agent binds RSPO1, RSPO2, RSPO3, and/or RSPO4 and slows down the development of a fibrotic disease. In some embodiments, the RSPO-binding agent binds RSPO1, RSPO2, RSPO3, and/or RSPO4 and slows down the progression of a fibrotic disease. In some embodiments, the RSPO-binding agent binds RSPO1, RSPO2, RSPO3, and/or RSPO4 and reduces the amount of fibrosis in a disease. In some embodiments, the RSPO-binding agent binds RSPO1, RSPO2, RSPO3, and/or RSPO4 and reduces pathological deposits of fibrotic material in an organ. In some embodiments, the RSPO-binding agent binds RSPO1, RSPO2, RSPO3, and/or RSPO4 and reduces the pathological deposits of connective tissue and/or extracellular matrix in an organ. In some embodiments, the RSPO-binding agent is a LGR soluble receptor. In some embodiments, the LGR soluble receptor is a LGR5 soluble receptor. In some embodiments, the LGR5 soluble receptor comprises a Fc region. In some embodiments, the LGR soluble receptor is the LGR5-Fc fusion protein comprising SEQ ID NO:72.

In some embodiments of the methods, the fibrotic disease is selected from the group consisting of: pulmonary fibrosis, renal fibrosis, liver fibrosis, dermal fibrosis, cardiac fibrosis, and adhesion formation. In some embodiments, the fibrotic disease is dermal fibrosis. In some embodiments, the dermal fibrosis includes, but is not limited to, scleroderma, systemic sclerosis, scleroderma-like disease, sine scleroderma, keloid formation, and hypertrophic scarring. In some embodiments, the fibrotic disease is renal fibrosis. In some embodiments, the renal fibrosis includes, but is not limited to, chronic kidney disease. In some embodiments, the fibrotic disease is pulmonary fibrosis. In some embodiments, the pulmonary fibrosis includes, but is not limited to, idiopathic pulmonary fibrosis, interstitial pulmonary fibrosis, lung fibrosis, mediastinal fibrosis, and pleural fibrosis. In some embodiments, the pulmonary fibrosis is primary pulmonary fibrosis. In some embodiments, the pulmonary fibrosis is secondary pulmonary fibrosis. In some embodiments, the fibrotic disease is liver fibrosis. In some embodiments, the liver fibrosis includes, but is not limited to, cirrhosis of the liver. In some embodiments, the fibrotic disease is cardiac fibrosis. In some embodiments, the cardiac fibrosis includes, but is not limited to, myocardial fibrosis, cardiac valve fibrosis, endomyocardial fibrosis, and atherosclerosis. In some embodiments, the fibrotic disease is not pulmonary fibrosis. In some embodiments, the fibrotic disease is not liver fibrosis. In some embodiments, the cardiac fibrosis is not atherosclerosis.

In certain embodiments, a method further comprises a step of determining the expression level of at least one RSPO (i.e., protein or nucleic acid) in a tissue. In some embodiments, the step of determining the expression level of a RSPO in a tissue comprises determining the expression level of RSPO1, RSPO2, RSPO3, and/or RSPO4. In some embodiments, the expression level of RSPO1, RSPO2, RSPO3, and/or RSPO4 in a tissue sample (e.g., fibrotic tissue) is compared to the expression level of RSPO1, RSPO2, RSPO3, and/or RSPO4 in a reference sample. In some embodiments, the expression level of RSPO1, RSPO2, RSPO3, and/or RSPO4 in a tissue sample is compared to the expression level of RSPO1, RSPO2, RSPO3, and/or RSPO4 in normal tissue. In some embodiments, the level of expression of RSPO1, RSPO2, RSPO3, and/or RSPO4 in a tissue sample is compared to a pre-determined level of expression of RSPO1, RSPO2, RSPO3, and/or RSPO4. In some embodiments, the level of expression of RSPO1, RSPO2, RSPO3, and/or RSPO4 in a tissue sample is compared to a pre-determined level of expression of RSPO1, RSPO2, RSPO3, and/or RSPO4 in normal tissue. In some embodiments, the tissue has a high expression level of RSPO1. In some embodiments, the tissue has a high expression level of RSPO2. In some embodiments, the tissue has a high expression level of RSPO3. In general, the expression level of a RSPO (i.e., protein or nucleic acid) in a tissue sample is compared to the expression level of the RSPO (i.e., protein or nucleic acid) in normal tissue of the same tissue type. However, in some embodiments, the expression level of a RSPO (i.e., protein or nucleic acid) is compared to the average expression level of the RSPO (i.e., protein or nucleic acid) within a group of tissue types. In some embodiments, the expression level of a RSPO (i.e., protein or nucleic acid) in a tissue sample is compared to the expression level of the RSPO (i.e., protein or nucleic acid) in other sample of tissue of the same tissue type or a different tissue type.

In some embodiments, determining the level of RSPO expression is done prior to treatment. In some embodiments, the subject is administered a RSPO-binding agent or LGR-binding agent (e.g., an antibody or soluble receptor) describe herein if the tissue sample has an elevated expression level of RSPO as compared to the expression level of the same RSPO in a reference sample (e.g., normal tissue) or a pre-determined level. For example, in some embodiments, the subject is administered a RSPO3-binding agent (e.g., anti-RSPO3 antibody) if the tissue sample has an elevated expression level of RSPO3 (i.e., protein or nucleic acid) as compared to the expression level of RSPO3 in normal or control tissue.

In addition, the present invention provides methods of identifying a human subject for treatment with a RSPO-binding agent or LGR-binding agent, comprising determining if the subject has tissue sample (e.g., fibrotic tissue) that has an elevated expression level of RSPO (i.e., protein or nucleic acid) as compared to expression of the same RSPO (i.e., protein or nucleic acid) in normal tissue, in a reference sample, or to a pre-determined level of the RSPO protein.

In some embodiments, a method of identifying a human subject for treatment with a RSPO1-binding agent comprises determining if the subject has fibrotic tissue that has an elevated expression level of RSPO1 as compared to a reference sample or a pre-determined level of RSPO1. In some embodiments, a method of identifying a human subject for treatment with a RSPO1-binding agent comprises obtaining a sample of fibrotic tissue from the subject, and determining if the fibrotic tissue has an elevated expression level of RSPO1 as compared to a reference sample or a pre-determined level of RSPO1. In some embodiments, if the fibrotic tissue has an elevated expression level of RSPO1, the subject is selected for treatment with an antibody that specifically binds RSPO1. In some embodiments, if selected for treatment, the subject is administered an anti-RSPO1 antibody described herein. In some embodiments, if the fibrotic tissue has an elevated expression level of RSPO1, the subject is selected for treatment with a LGR soluble receptor that specifically binds RSPO1. In some embodiments, if selected for treatment, the subject is administered a LGR soluble receptor described herein.

In some embodiments, a method of identifying a human subject for treatment with a RSPO2-binding agent comprises determining if the subject has fibrotic tissue that has an elevated expression level of RSPO2 as compared to a reference sample or a pre-determined level of RSPO2. In some embodiments, a method of identifying a human subject for treatment with a RSPO2-binding agent comprises obtaining a sample of fibrotic tissue from the subject, and determining if the fibrotic tissue has an elevated expression level of RSPO2 as compared to a reference sample or a pre-determined level of RSPO2. In some embodiments, if the fibrotic tissue has an elevated expression level of RSPO2, the subject is selected for treatment with an antibody that specifically binds RSPO2. In some embodiments, if selected for treatment, the subject is administered an anti-RSPO2 antibody described herein. In some embodiments, if the fibrotic tissue has an elevated expression level of RSPO2, the subject is selected for treatment with a LGR soluble receptor that specifically binds RSPO2. In some embodiments, if selected for treatment, the subject is administered a LGR soluble receptor described herein.

In some embodiments, a method of identifying a human subject for treatment with a RSPO3-binding agent comprises determining if the subject has fibrotic tissue that has an elevated expression level of RSPO3 as compared to a reference sample or a pre-determined level of RSPO3. In some embodiments, a method of identifying a human subject for treatment with a RSPO3-binding agent comprises obtaining a sample of fibrotic tissue from the subject, and determining if the fibrotic tissue has an elevated expression level of RSPO3 as compared to a reference sample or a pre-determined level of RSPO3. In some embodiments, if the fibrotic tissue has an elevated expression level of RSPO3, the subject is selected for treatment with an antibody that specifically binds RSPO3. In some embodiments, if selected for treatment, the subject is administered an anti-RSPO3 antibody described herein. In some embodiments, if the fibrotic tissue has an elevated expression level of RSPO3, the subject is selected for treatment with a LGR soluble receptor that specifically binds RSPO3. In some embodiments, if selected for treatment, the subject is administered a LGR soluble receptor described herein.

In some embodiments, if the fibrotic tissue has an elevated expression level of more than one RSPO (i.e., protein or nucleic acid), the subject is administered a RSPO-binding agent that binds the RSPO with the highest level of expression. In some embodiments, the expression level of RSPO1, RSPO2, RSPO3, and/or RSPO4 in the fibrotic tissue is determined, if the fibrotic tissue has an elevated level of RSPO1 expression as compared to the level of RSPO1 in normal tissue, the subject is selected for treatment with an antibody that specifically binds RSPO1. If selected for treatment, the subject is administered an anti-RSPO1 antibody describe herein. In some embodiments, the RSPO1-binding agent is a humanized version of antibody 89M5. In some embodiments, the RSPO1-binding agent is antibody h89M5-H8L5. In some embodiments, the RSPO1-binding agent is antibody h89M5-H2L3. In some embodiments, the expression level of RSPO1, RSPO2, RSPO3, and/or RSPO4 in fibrotic tissue is determined, if the fibrotic tissue has an elevated level of RSPO2 expression as compared to the level of RSPO2 in normal tissue, the subject is selected for treatment with an antibody that specifically binds RSPO2. If selected for treatment, the subject is administered an anti-RSPO2 antibody describe herein. In some embodiments, the RSPO2-binding agent is a humanized version of antibody 130M23. In some embodiments, the RSPO2-binding agent is antibody h130M23-H1L6. In some embodiments, the RSPO2-binding agent is antibody h130M23-H1L2. In some embodiments, the expression level of RSPO1, RSPO2, RSPO3, and/or RSPO4 in fibrotic tissue is determined, if the fibrotic tissue has an elevated level of RSPO3 expression as compared to the level of RSPO3 in normal tissue, the subject is selected for treatment with an antibody that specifically binds RSPO3. If selected for treatment, the subject is administered an anti-RSPO3 antibody describe herein. In some embodiments, the RSPO3-binding agent is antibody 131R011.

The present invention also provides methods of treating a fibrotic disease in a human subject, comprising: (a) selecting a subject for treatment based, at least in part, on the subject having a tissue sample that has an elevated level of RSPO1, and (b) administering to the subject a therapeutically effective amount of a RSPO1-binding agent described herein. In some embodiments, the RSPO1-binding agent is a humanized version of antibody 89M5. In some embodiments, the RSPO1-binding agent is antibody h89M5-H8L5. In some embodiments, the RSPO1-binding agent is antibody h89M5-H2L2. In some embodiments, the RSPO1-binding agent is a LGR soluble receptor.

The present invention also provides methods of treating a fibrotic disease in a human subject, comprising: (a) selecting a subject for treatment based, at least in part, on the subject having a tissue sample that has an elevated level of RSPO2, and (b) administering to the subject a therapeutically effective amount of a RSPO2-binding agent described herein. In some embodiments, the RSPO2-binding agent is a humanized version of antibody 130M23. In some embodiments, the RSPO2-binding agent is antibody h130M23-H1L6. In some embodiments, the RSPO2-binding agent is antibody h130M23-H1L2. In some embodiments, the RSPO2-binding agent is a LGR soluble receptor.

The present invention also provides methods of treating a fibrotic disease in a human subject, comprising: (a) selecting a subject for treatment based, at least in part, on the subject having a tissue sample that has an elevated level of RSPO3, and (b) administering to the subject a therapeutically effective amount of a RSPO3-binding agent described herein. In some embodiments, the RSPO3-binding agent is antibody 131R010. In some embodiments, the RSPO3-binding agent is a LGR soluble receptor.

Methods for determining the level of RSPO expression in a cell or tissue are known by those of skill in the art. For nucleic acid expression these methods include, but are not limited to, PCR-based assays, microarray analyses and nucleotide sequencing (e.g., NextGen sequencing). For protein expression these methods include, but are not limited to, Western blot analyses, protein arrays, ELISAs, immunohistochemistry (IHC) assays, and FACS.

Methods for determining whether fibrotic tissue has an elevated level of RSPO expression can use a variety of samples. In some embodiments, the sample is taken from a subject having a fibrotic disease. In some embodiments, the sample is a fresh sample. In some embodiments, the sample is a frozen sample. In some embodiments, the sample is a formalin-fixed paraffin-embedded sample. In some embodiments, the sample is processed to a cell lysate. In some embodiments, the sample is processed to DNA or RNA.

The present invention further provides compositions comprising the RSPO-binding agents or LGR-binding agents described herein. In certain embodiments, the compositions are pharmaceutical compositions which comprise a pharmaceutically acceptable vehicle. In some embodiments, the pharmaceutical compositions find use in treating or preventing a fibrotic disease in a subject (e.g., a human patient).

Formulations are prepared for storage and use by combining a purified antibody or agent of the present invention with a pharmaceutically acceptable vehicle (e.g., a carrier or excipient). Those of skill in the art generally consider pharmaceutically acceptable carriers, excipients, and/or stabilizers to be inactive ingredients of a formulation or pharmaceutical composition.

Suitable pharmaceutically acceptable vehicles include, but are not limited to, nontoxic buffers such as phosphate, citrate, and other organic acids; salts such as sodium chloride; antioxidants including ascorbic acid and methionine; preservatives such as octadecyldimethylbenzyl ammonium chloride, hexamethonium chloride, benzalkonium chloride, benzethonium chloride, phenol, butyl or benzyl alcohol, alkyl parabens, such as methyl or propyl paraben, catechol, resorcinol, cyclohexanol, 3-pentanol, and m-cresol; low molecular weight polypeptides (e.g., less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes such as Zn-protein complexes; and non-ionic surfactants such as TWEEN or polyethylene glycol (PEG). (*Remington: The Science and Practice of Pharmacy, 22$^{nd}$ Edition*, 2012, Pharmaceutical Press, London.)

The pharmaceutical compositions of the present invention can be administered in any number of ways for either local or systemic treatment. Administration can be topical by epidermal or transdermal patches, ointments, lotions, creams, gels, drops, suppositories, sprays, liquids and powders; pulmonary by inhalation or insufflation of powders or aerosols, including by nebulizer, intratracheal, and intranasal; oral; or parenteral including intravenous, intraarterial, subcutaneous, intraperitoneal, intramuscular (e.g., injection or infusion), or intracranial (e.g., intrathecal or intraventricular). In some embodiments of the methods described herein, the RSPO-binding agent or LGR-binding agent is administered locally. In some embodiments, the RSPO-binding agent or LGR-binding agent is administered subcutaneously. In some embodiments, the RSPO-binding agent or LGR-binding agent is administered intramuscularly. In some embodiments, the RSPO-binding agent or LGR-binding agent is administered topically. In some embodiments, the RSPO-binding agent or LGR-binding agent is administered intravenously. In some embodiments, the RSPO-binding agent or LGR-binding agent is administered by inhalation.

The therapeutic formulation can be in unit dosage form. Such formulations include tablets, pills, capsules, powders, granules, solutions or suspensions in water or non-aqueous media, or suppositories. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and diluents (e.g., water). These can be used to form a solid pre-formulation composition containing a homogeneous mixture of a compound of the present invention, or a non-toxic pharmaceutically acceptable salt thereof. The solid pre-formulation composition is then subdivided into unit dosage forms of a type described above. The tablets, pills, etc. of the formulation or composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials include a number of polymeric acids and mixtures of polymeric acids with such materials as shellac, cetyl alcohol and cellulose acetate.

The RSPO-binding agents or LGR-binding agents (e.g., antibodies or soluble receptors) described herein can also be entrapped in microcapsules. Such microcapsules are prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nanoparticles and nanocapsules) or in macroemulsions as described in *Remington: The Science and Practice of Pharmacy, 22$^{nd}$ Edition*, 2012, Pharmaceutical Press, London.

In certain embodiments, pharmaceutical formulations include a RSPO-binding agent or LGR-binding agent (e.g., an antibody or a soluble receptor) of the present invention complexed with liposomes. Methods to produce liposomes are known to those of skill in the art. For example, some liposomes can be generated by reverse phase evaporation with a lipid composition comprising phosphatidylcholine, cholesterol, and PEG-derivatized phosphatidylethanolamine (PEG-PE). Liposomes can be extruded through filters of defined pore size to yield liposomes with the desired diameter.

In certain embodiments, sustained-release preparations comprising the RSPO-binding agents or LGR-binding agents described herein can be produced. Suitable examples of sustained-release preparations include semi-permeable matrices of solid hydrophobic polymers containing a RSPO-binding agent or LGR-binding agent (e.g., an antibody or a soluble receptor), where the matrices are in the form of shaped articles (e.g., films or microcapsules). Examples of sustained-release matrices include polyesters, hydrogels such as poly(2-hydroxyethyl-methacrylate) or poly(vinyl alcohol), polylactides, copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

In certain embodiments, in addition to administering a RSPO-binding agent or LGR-binding agent (e.g., an antibody or a soluble receptor), the method or treatment further comprises administering at least one additional therapeutic agent. An additional therapeutic agent can be administered prior to, concurrently with, and/or subsequently to, administration of the RSPO-binding agent or the LGR-binding agent. Pharmaceutical compositions comprising the additional therapeutic agent(s) are also provided. In some embodiments, the at least one additional therapeutic agent comprises 1, 2, 3, or more additional therapeutic agents.

Combination therapy with two or more therapeutic agents often uses agents that work by different mechanisms of action, although this is not required. Combination therapy using agents with different mechanisms of action may result in additive or synergetic effects. Combination therapy may allow for a lower dose of each agent than is used in monotherapy, thereby reducing toxic side effects and/or increasing the therapeutic index of the agent(s).

In some embodiments, the combination of a RSPO-binding agent or LGR-binding agent and at least one additional therapeutic agent results in additive or synergistic results. In some embodiments, the combination therapy results in an increase in the therapeutic index of the RSPO-binding agent or the LGR-binding agent. In some embodiments, the combination therapy results in an increase in the therapeutic index of the additional agent(s). In some embodiments, the combination therapy results in a decrease in the toxicity and/or side effects of the RSPO-binding agent or the LGR-binding agent. In some embodiments, the combination therapy results in a decrease in the toxicity and/or side effects of the additional agent(s).

In some embodiments, an additional therapeutic agent is an anti-inflammatory agent. In some embodiments, an anti-inflammatory agent is a steroid, a glucocorticosteroid, or a corticosteroid. Steroids may include, but are not limited to, beclometasone, budesonide, flunisolide, fluticasone propionate, triamcinolone, methylprednisolone, prednisolone, and prednisone.

In some embodiments, an anti-inflammatory agent is a non-steroid anti-inflammatory (NSAID). NSAIDs may include, but are not limited to, naproxen sodium, celecoxib, sulindac, oxaprozin, salsalate, diflunisal, piroxicam, indomethacin, etodolac, meloxicam, naproxen, nabumetone, ketorolac tromethamine, naproxen/exomeprazole, diclofenac, and aspirin.

In some embodiments, an anti-inflammatory agent is a small molecule. In some embodiments, an anti-inflammatory agent is a tyrosine kinase inhibitor, such as imatinib (GLEEVEC).

In some embodiments, an anti-inflammatory agent is an inhibitor of pro-inflammatory cytokines, interleukins, lymphokines, and/or chemokines. In some embodiments, an anti-inflammatory agent is an antibody that inhibits the activity of a pro-inflammatory cytokine. In some embodiments, an anti-inflammatory agent is antibody which binds and/or inhibits IL-1, IL-18, IL-33, IL36, IL-37, IL-6, IL-11, IL-31, IL-17, IL-25, tumor necrosis factor (TNF), interferon alpha, interferon gamma, and/or interferon beta.

In some embodiments, an additional therapeutic agent is a Wnt pathway inhibitor. In some embodiments, the Wnt pathway inhibitors are frizzled (FZD) protein binding agents, "FZD-binding agents". Non-limiting examples of FZD-binding agents can be found in U.S. Pat. No. 7,982,013. FZD-binding agents may include, but are not limited to, anti-FZD antibodies. In some embodiments, a method comprises administering a RSPO-binding agent in combination with an anti-FZD antibody. In some embodiments, a method comprises administering a RSPO-binding agent in combination with the anti-FZD antibody 18R5. In some embodiments, the Wnt pathway inhibitors are Wnt protein binding agents, "Wnt-binding agents". Non-limiting examples of Wnt-binding agents can be found in U.S. Pat. Nos. 7,723,477 and 7,947,277; and International Publications WO 2011/088127 and WO 2011/088123. Wnt-binding agents may include, but are not limited to, anti-Wnt antibodies and FZD-Fc soluble receptors. In some embodiments, a method comprises administering a RSPO-binding agent or a LGR-binding agent in combination with a FZD-Fc soluble receptor. In some embodiments, a method comprises administering a RSPO-binding agent or a LGR-binding agent in combination with a FZD8-Fc soluble receptor. In some embodiments, a method comprises administering a RSPO-binding agent or a LGR-binding agent in combination with an anti-FZD antibody.

In some embodiments, the methods described herein comprise administering a therapeutically effective amount of a RSPO-binding agent or a LGR-binding agent in combination with more than one additional therapeutic agent.

Combined administration can include co-administration, either in a single pharmaceutical formulation or using separate formulations, or consecutive administration in either order but generally within a time period such that all active agents can exert their biological activities simultaneously.

It will be appreciated that the combination of a RSPO-binding agent or a LGR-binding agent and at least one additional therapeutic agent may be administered in any order or concurrently. In some embodiments, the RSPO-binding agent or the LGR-binding agent will be administered to patients that have previously undergone treatment with a second therapeutic agent. In certain other embodiments, the RSPO-binding agent or the LGR-binding agent and a second therapeutic agent will be administered substantially simultaneously or concurrently. For example, a subject may be given a RSPO-binding agent (e.g., an antibody) while undergoing a course of treatment with a second therapeutic agent (e.g., chemotherapy). In certain embodiments, a RSPO-binding agent or a LGR-binding agent will be administered within 1 year of the treatment with a second therapeutic agent. In certain alternative embodiments, a RSPO-binding agent or a LGR-binding agent will be administered within 10, 8, 6, 4, or 2 months of any treatment with a second therapeutic agent. In certain other embodiments, a RSPO-binding agent or a LGR-binding agent will be administered within 4, 3, 2, or 1 weeks of any treatment with a second therapeutic agent. In some embodiments, a RSPO-binding agent or a LGR-binding agent will be administered within 5, 4, 3, 2, or 1 days of any treatment with a second therapeutic agent. It will further be appreciated that the two (or more) agents or treatments may be administered to the subject within a matter of hours or minutes (i.e., substantially simultaneously).

For the treatment of a disease, the appropriate dosage of an RSPO-binding agent or a LGR-binding agent (e.g., an antibody or a soluble receptor) of the present invention depends on the type of disease to be treated, the severity and course of the disease, the responsiveness of the disease, whether the RSPO-binding agent or LGR-binding agent is administered for therapeutic or preventative purposes, previous therapy, the patient's clinical history, and so on, all at the discretion of the treating physician. The RSPO-binding agent or LGR-binding agent can be administered one time or over a series of treatments lasting from several days to several months, or until a cure is effected or a diminution of the disease state is achieved. Optimal dosing schedules can be calculated from measurements of drug accumulation in the body of the patient and will vary depending on the relative potency of an individual antibody or agent. The administering physician can easily determine optimum dosages, dosing methodologies, and repetition rates. In certain embodiments, dosage is from 0.01 µg to 100 mg/kg of body weight, from 0.1 µg to 100 mg/kg of body weight, from 1 µg to 100 mg/kg of body weight, from 1 mg to 100 mg/kg of body weight, 1 mg to 80 mg/kg of body weight from 10 mg to 100 mg/kg of body weight, from 10 mg to 75 mg/kg of body weight, or from 10 mg to 50 mg/kg of body weight. In certain embodiments, the dosage of the RSPO-binding agent is from about 0.1 mg to about 20 mg/kg of body weight. In certain embodiments, dosage can be given once or more daily, weekly, monthly, or yearly. In certain embodiments, the RSPO-binding agent or LGR-binding agent is given once every week, once every two weeks or once every three weeks.

As is known to those of skill in the art, administration of any therapeutic agent may lead to side effects and/or toxicities. In some cases, the side effects and/or toxicities are so severe as to preclude administration of the particular agent at a therapeutically effective dose. In some cases, drug therapy must be discontinued, and other agents may be tried. However, many agents in the same therapeutic class often display similar side effects and/or toxicities, meaning that the patient either has to stop therapy, or if possible, suffer from the unpleasant side effects associated with the therapeutic agent.

Thus, the present invention provides methods of treating fibrotic diseases in a subject comprising using an intermittent dosing strategy for administering one or more agents, which may reduce side effects and/or toxicities associated with administration of a RSPO-binding agent, a LGR-binding agent, a second agent, etc.

III. RSPO and LGR Antagonists

The present invention provides methods comprising agents that specifically bind human RSPO proteins or human LGR proteins. These agents are referred to herein as "RSPO-binding agents" and "LGR-binding agents", respectively. Non-limiting examples of RSPO-binding agents and LGR-binding agents can be found in U.S. Patent Publication Nos. 2006/0275870, 2009/0074782, 2009/0191205, 2009/0220495, 2010/0071078, 2012/0039912, 2012/0263730, 2013/0095116, 2013/0336885, 2013/0337533, 2014/0017253, 2014/0302054, 2015/0147333, and International Publication No. WO 2010/016766, WO 2014/012007, WO 2014/192974. In some embodiments, the RSPO-binding agent is an antibody. In some embodiments, the RSPO-binding agent is a polypeptide. In certain embodiments, the RSPO-binding agent binds RSPO1 ("RSPO1-binding agents"). In certain embodiments, the RSPO-binding agent binds RSPO2 ("RSPO2-binding agents"). In certain embodiments, the RSPO-binding agent binds RSPO3 ("RSPO3-binding agents"). In certain embodiments, the RSPO-binding agent specifically binds one or more human RSPO proteins. The full-length amino acid (aa) sequences for human RSPO1, RSPO2, RSPO3, and RSPO4 are known in the art and are provided herein as SEQ ID NO:1 (RSPO1), SEQ ID NO:2 (RSPO2), SEQ ID NO:3 (RSPO3), and SEQ ID NO:4 (RSPO4). In some embodiments, the RSPO-binding agent is a soluble receptor. In some embodiments, the RSPO-binding agent is a soluble receptor comprising the extracellular domain, or a fragment thereof, of a human LGR protein. In some embodiments, the human LGR protein is LGR4, LGR5, or LGR6. The full-length amino acid (aa) sequences for human LGR4, LGR5, and LGR6 are known in the art and are provided herein as SEQ ID NO:71 (LGR4), SEQ ID NO:72 (LGR5), and SEQ ID NO:73 (LGR6).

In some embodiments, the LGR-binding agent is an antibody. In some embodiments, the LGR-binding agent is a polypeptide. In certain embodiments, the LGR-binding agent binds LGR4 ("LGR4-binding agents"). In certain embodiments, the LGR-binding agent binds LGR5 ("LGR5-binding agents"). In certain embodiments, the LGR-binding agent binds LGR6 ("LGR6-binding agents"). In certain embodiments, the LGR-binding agent specifically binds one or more human LGR proteins.

In certain embodiments, the antigen-binding site of a RSPO-binding agent (e.g., an antibody or a bispecific antibody) described herein is capable of binding (or binds) one, two, three, or four RSPOs. In certain embodiments, the antigen-binding site of a RSPO-binding agent (e.g., an antibody or a bispecific antibody) described herein is capable of binding (or binds) a first RSPO protein (e.g., RSPO1) as well as one, two, or three other RSPOs (e.g., RSPO2, RSPO3, and/or RSPO4). In some embodiments, the RSPO-binding agent (e.g., antibody) specifically binds both human RSPO and mouse RSPO.

In certain embodiments of the methods described herein, the RSPO-binding agent is an antibody that specifically binds within amino acids 21-263 of human RSPO1 (SEQ ID NO:1). In certain embodiments, the RSPO-binding agent is an antibody that specifically binds within amino acids 31-263 of human RSPO1 (SEQ ID NO:1). In certain embodiments, the RSPO-binding agent is an antibody that specifically binds within amino acids 34-135 of human RSPO1 (SEQ ID NO:1). In certain embodiments, the RSPO-binding agent is an antibody that specifically binds within amino acids 34-85 of human RSPO1 (SEQ ID NO:1). In certain embodiments, the RSPO-binding agent is an antibody that specifically binds within amino acids 91-135 of human RSPO1 (SEQ ID NO:1). In certain embodiments, the RSPO-binding agent is an antibody that specifically binds within amino acids 147-207 of human RSPO1 (SEQ ID NO:1). In certain embodiments, the RSPO-binding agent binds a furin-like cysteine-rich domain of RSPO1. In some embodiments, the RSPO-binding agent binds at least one amino acid within a furin-like cysteine-rich domain of RSPO1. In some embodiments, the RSPO-binding agent binds the thrombospondin domain of RSPO1. In some embodiments, the RSPO-binding agent binds at least one amino acid within the thrombospondin domain of RSPO1.

In certain embodiments, the RSPO-binding agent is an antibody that specifically binds within amino acids 22-243 of human RSPO2 (SEQ ID NO:2). In certain embodiments, the RSPO-binding agent is an antibody that specifically binds within amino acids 22-205 of human RSPO2 (SEQ ID NO:2). In certain embodiments, the RSPO-binding agent is an antibody that specifically binds within amino acids 35-134 of human RSPO2 (SEQ ID NO:2). In certain embodiments, the RSPO-binding agent is an antibody that specifically binds within amino acids 34-84 of human RSPO2 (SEQ ID NO:2). In certain embodiments, the RSPO-binding agent is an antibody that specifically binds within amino acids 90-134 of human RSPO2 (SEQ ID NO:2). In certain embodiments, the RSPO-binding agent binds a furin-like cysteine-rich domain of RSPO2. In some embodiments, the RSPO-binding agent binds at least one amino acid within a furin-like cysteine-rich domain of RSPO2. In some embodiments, the RSPO-binding agent binds the thrombospondin domain of RSPO2. In some embodiments, the RSPO-binding agent binds at least one amino acid within the thrombospondin domain of RSPO2.

In certain embodiments, the RSPO-binding agent is an antibody that specifically binds within amino acids 22-272 of human RSPO3 (SEQ ID NO:3). In certain embodiments, the RSPO-binding agent is an antibody that specifically binds within amino acids 22-207 of human RSPO3 (SEQ ID NO:3). In certain embodiments, the RSPO-binding agent is an antibody that specifically binds within amino acids 35-135 of human RSPO3 (SEQ ID NO:3). In certain embodiments, the RSPO-binding agent is an antibody that specifically binds within amino acids 35-86 of human RSPO3 (SEQ ID NO:3). In certain embodiments, the RSPO-binding agent is an antibody that specifically binds within amino acids 92-135 of human RSPO3 (SEQ ID NO:3). In certain embodiments, the RSPO-binding agent binds a furin-like cysteine-rich domain of RSPO3. In some embodiments, the RSPO-binding agent binds at least one amino acid within a furin-like cysteine-rich domain of RSPO3. In some embodiments, the RSPO-binding agent binds the thrombospondin domain of RSPO3. In some embodiments, the RSPO-binding agent binds at least one amino acid within the thrombospondin domain of RSPO3.

In certain embodiments, the RSPO-binding agent (e.g., an antibody or a soluble receptor) binds at least one RSPO protein with a dissociation constant ($K_D$) of about 1 µM or less, about 100 nM or less, about 40 nM or less, about 20 nM or less, about 10 nM or less, about 1 nM or less, or about 0.1 nM or less. In certain embodiments, a RSPO-binding agent (e.g., an antibody or a soluble receptor) binds at least one RSPO protein with a dissociation constant ($K_D$) of about 1 µM or less, about 100 nM or less, about 40 nM or less, about 20 nM or less, about 10 nM or less, about 1 nM or less, or about 0.1 nM or less. In some embodiments, a RSPO-binding agent (e.g., an antibody or a soluble receptor) binds at least one RSPO protein with a $K_D$ of about 20 nM or less. In some embodiments, a RSPO-binding agent (e.g., an antibody or a soluble receptor) binds at least one RSPO protein with a $K_D$ of about 10 nM or less. In some embodiments, a RSPO-binding agent (e.g., an antibody or a soluble receptor) binds at least one RSPO protein with a $K_D$ of about 1 nM or less. In some embodiments, a RSPO-binding agent (e.g., an antibody or a soluble receptor) binds at least one RSPO protein with a $K_D$ of about 0.5 nM or less. In some embodiments, a RSPO-binding agent (e.g., an antibody or a soluble receptor) binds at least one RSPO protein with a $K_D$ of about 0.1 nM or less. In certain embodiments, a RSPO-binding agent (e.g., an antibody or a soluble receptor) described herein binds at least two RSPO proteins. In some embodiments, the RSPO-binding agent binds both human RSPO and mouse RSPO with a $K_D$ of about 10 nM or less. In some embodiments, a RSPO-binding agent binds both human RSPO and mouse RSPO with a $K_D$ of about 1 nM or less. In some embodiments, a RSPO-binding agent binds both human RSPO and mouse RSPO with a $K_D$ of about 0.1 nM or less. In some embodiments, the dissociation constant of a binding agent (e.g., an antibody or a soluble receptor) to a RSPO protein is the dissociation constant determined using a RSPO fusion protein comprising at least a portion of the RSPO protein immobilized on a Biacore chip. In some embodiments, the dissociation constant of a binding agent (e.g., an antibody or a soluble receptor) to a RSPO protein is the dissociation constant determined using the binding agent captured by an anti-human IgG antibody on a Biacore chip and a RSPO protein.

In certain embodiments, the RSPO-binding agent (e.g., an antibody or a soluble receptor) binds to at least one human RSPO protein with a half maximal effective concentration ($EC_{50}$) of about 1 µM or less, about 100 nM or less, about 40 nM or less, about 20 nM or less, about 10 nM or less, about 1 nM or less, or about 0.1 nM or less. In certain embodiments, a RSPO-binding agent (e.g., an antibody or a soluble receptor) binds to at least one human RSPO with a half maximal effective concentration ($EC_{50}$) of about 1 µM or less, about 100 nM or less, about 40 nM or less, about 20 nM or less, about 10 nM or less, about 1 nM or less, or about 0.1 nM or less.

In certain embodiments, the LGR-binding agent (e.g., an antibody) binds at least one LGR protein with a dissociation constant ($K_D$) of about 1 µM or less, about 100 nM or less, about 40 nM or less, about 20 nM or less, about 10 nM or less, about 1 nM or less, or about 0.1 nM or less. In certain embodiments, a LGR-binding agent (e.g., an antibody) binds at least one LGR protein with a dissociation constant ($K_D$) of about 1 µM or less, about 100 nM or less, about 40 nM or less, about 20 nM or less, about 10 nM or less, about 1 nM or less, or about 0.1 nM or less. In some embodiments, a LGR-binding agent (e.g., an antibody) binds at least one LGR protein with a $K_D$ of about 20 nM or less. In some embodiments, a LGR-binding agent (e.g., an antibody) binds at least one LGR protein with a $K_D$ of about 10 nM or less. In some embodiments, a LGR-binding agent (e.g., an antibody) binds at least one LGR protein with a $K_D$ of about 1 nM or less. In some embodiments, a LGR-binding agent (e.g., an antibody) binds at least one LGR protein with a $K_D$ of about 0.5 nM or less. In some embodiments, a LGR-binding agent (e.g., an antibody) binds at least one LGR protein with a $K_D$ of about 0.1 nM or less. In certain embodiments, a LGR-binding agent (e.g., an antibody) described herein binds at least two LGR proteins. In some embodiments, the dissociation constant of a binding agent (e.g., an antibody) to a LGR protein is the dissociation constant determined using a LGR fusion protein comprising at least a portion of the LGR protein immobilized on a Biacore chip. In some embodiments, the dissociation constant of a binding agent (e.g., an antibody) to a LGR protein is the dissociation constant determined using the binding agent captured by an anti-human IgG antibody on a Biacore chip and a LGR protein.

In certain embodiments, the LGR-binding agent (e.g., an antibody) binds to at least one human LGR protein with a half maximal effective concentration ($EC_{50}$) of about 1 µM or less, about 100 nM or less, about 40 nM or less, about 20 nM or less, about 10 nM or less, about 1 nM or less, or about 0.1 nM or less. In certain embodiments, a LGR-binding agent (e.g., an antibody) binds to at least one human LGR with a half maximal effective concentration ($EC_{50}$) of about 1 µM or less, about 100 nM or less, about 40 nM or less, about 20 nM or less, about 10 nM or less, about 1 nM or less, or about 0.1 nM or less.

In certain embodiments, the RSPO-binding agent or LGR-binding agent is an antibody. In some embodiments, the antibody is a recombinant antibody. In some embodiments, the antibody is a monoclonal antibody. In some embodiments, the antibody is a chimeric antibody. In some embodiments, the antibody is a humanized antibody. In some embodiments, the antibody is a human antibody. In some embodiments, the antibody is an IgA, IgD, IgE, IgG, or IgM antibody. In certain embodiments, the antibody is an IgG1 antibody. In certain embodiments, the antibody is an IgG2 antibody. In some embodiments, the antibody is an IgG4 antibody. In certain embodiments, the antibody is an antibody fragment comprising an antigen-binding site. In some embodiments, the antibody is a bispecific antibody or a multispecific antibody. In some embodiments, the antibody is a monovalent antibody. In some embodiments, the antibody is a monospecific antibody. In some embodiments, the antibody is a bivalent antibody. In some embodiments, the antibody is conjugated to a cytotoxic moiety. In some embodiments, the antibody is isolated. In some embodiments, the antibody is substantially pure.

The RSPO-binding agents (e.g., antibodies) of the present invention can be assayed for specific binding by any method known in the art. The immunoassays which can be used include, but are not limited to, competitive and non-competitive assay systems using techniques such as Biacore analysis, FACS analysis, immunofluorescence, immunocytochemistry, Western blot analysis, radioimmunoassay, ELISA, "sandwich" immunoassay, immunoprecipitation assay, precipitation reaction, gel diffusion precipitin reaction, immunodiffusion assay, agglutination assay, complement-fixation assay, immunoradiometric assay, fluorescent immunoassay, and protein A immunoassay. Such assays are routine and well-known in the art (see, e.g., Ausubel et al., Editors, 1994-present, *Current Protocols in Molecular Biology*, John Wiley & Sons, Inc., New York, N.Y.).

For example, the specific binding of an agent to a human RSPO protein may be determined using ELISA. An ELISA assay comprises preparing antigen, coating wells of a 96 well microtiter plate with antigen, adding the RSPO-binding agent conjugated to a detectable compound such as an enzymatic substrate (e.g. horseradish peroxidase or alkaline phosphatase) to the well, incubating for a period of time, and detecting the presence of the agent bound to the antigen. In some embodiments, the RSPO-binding agent is not conjugated to a detectable compound, but instead a second antibody that recognizes the RSPO-binding agent (e.g., an anti-Fc antibody) and is conjugated to a detectable compound is added to the well. In some embodiments, instead of coating the well with the antigen, the RSPO-binding agent can be coated to the well and a second antibody conjugated to a detectable compound can be added following the addition of the antigen to the coated well. One of skill in the art would be knowledgeable as to the parameters that can be modified to increase the signal detected as well as other variations of ELISAs known in the art.

In another example, the specific binding of an agent to a human RSPO protein may be determined using FACS. A FACS screening assay may comprise generating a cDNA construct that expresses an antigen as a fusion protein (e.g., RSPO-CD4TM), transfecting the construct into cells, expressing the antigen on the surface of the cells, mixing the RSPO-binding agent with the transfected cells, and incubating for a period of time. The cells bound by the RSPO-binding agent may be identified using a secondary antibody conjugated to a detectable compound (e.g., PE-conjugated anti-Fc antibody) and a flow cytometer. One of skill in the art would be knowledgeable as to the parameters that can be modified to optimize the signal detected as well as other variations of FACS that may enhance screening (e.g., screening for blocking antibodies).

The binding affinity of an agent to an antigen and the off-rate of an agent-antigen interaction can be determined by competitive binding assays. One example of a competitive binding assay is a radioimmunoassay comprising the incubation of labeled antigen (e.g., labeled with $^3$H or $^{125}$I), or fragment or variant thereof, with a binding agent of interest in the presence of increasing amounts of unlabeled antigen followed by the detection of the agent bound to the labeled antigen. The affinity of the agent for the antigen and the binding off-rates can be determined from the data by Scatchard plot analysis. In some embodiments, Biacore kinetic analysis is used to determine the binding on and off rates of agents that bind an antigen. In some embodiments, Biacore kinetic analysis comprises analyzing the binding and dissociation of antibodies from chips with immobilized antigen on their surface. In some embodiments, Biacore kinetic analysis comprises analyzing the binding and dissociation of antigen from chips with immobilized binding agent on their surface.

In certain embodiments of the methods described herein, the invention provides methods comprising a RSPO1-binding agent (e.g., an antibody) that specifically binds human RSPO1, wherein the RSPO1-binding agent (e.g., an antibody) comprises one, two, three, four, five, and/or six of the CDRs of antibody 89M5 (see Table 1).

TABLE 1

|  | 89M5 | 130M23 | 131R010 |
|---|---|---|---|
|  | Heavy Chain | | |
| CDR1 | TGYTMH (SEQ ID NO: 5) | SSYAMS (SEQ ID NO: 21) | DYSIH (SEQ ID NO: 37) |
| CDR2 | GINPNNGGTTYNQNFKG (SEQ ID NO: 6) | SISSGGSTYYPDSVKG (SEQ ID NO: 22) | YIYPSNGDSGYNQKFK (SEQ ID NO: 38) |
| CDR3 | KEFSDGYYFFAY (SEQ ID NO: 7) | RGGDPGVYNGDYEDAMDY (SEQ ID NO: 23) | TYFANNFD (SEQ ID NO: 39) or ATYFANNTDY (SEQ ID NO: 40) |
|  | Light Chain | | |
| CDR1 | KASQDVIFAVA (SEQ ID NO: 8) | KASQDVSSAVA (SEQ ID NO: 24) | KASQSVDYDGDSYMN (SEQ ID NO: 41) |
| CDR2 | WASTRHT (SEQ ID NO: 9) | WASTRHT (SEQ ID NO: 25) | AASNLES (SEQ ID NO: 42) or AAS (SEQ ID NO: 43) |
| CDR3 | QQHYSTPW (SEQ ID NO: 10) | QQHYSTP (SEQ ID NO: 26) | QQSNEDPLT (SEQ ID NO: 44) or QQSNEDPLTF (SEQ ID NO: 45) |

In certain embodiments, the invention provides methods comprising a RSPO1-binding agent (e.g., an antibody) that specifically binds human RSPO1, wherein the RSPO1-binding agent comprises a heavy chain CDR1 comprising TGYTMH (SEQ ID NO:5), a heavy chain CDR2 comprising GINPNNGGTTYNQNFKG (SEQ ID NO:6), and a heavy chain CDR3 comprising KEFSDGYYFFAY (SEQ ID NO:7). In some embodiments, the RSPO1-binding agent further comprises a light chain CDR1 comprising KASQD-VIFAVA (SEQ ID NO:8), a light chain CDR2 comprising WASTRHT (SEQ ID NO:9), and a light chain CDR3 comprising QQHYSTPW (SEQ ID NO:10). In some embodiments, the RSPO1-binding agent comprises a light chain CDR1 comprising KASQDVIFAVA (SEQ ID NO:8), a light chain CDR2 comprising WASTRHT (SEQ ID NO:9), and a light chain CDR3 comprising QQHYSTPW (SEQ ID NO:10). In certain embodiments, the RSPO1-binding agent comprises: (a) a heavy chain CDR1 comprising TGYTMH (SEQ ID NO:5), a heavy chain CDR2 comprising GIN-PNNGGTTYNQNFKG (SEQ ID NO:6), and a heavy chain CDR3 comprising KEFSDGYYFFAY (SEQ ID NO:7); and (b) a light chain CDR1 comprising KASQDVIFAVA (SEQ ID NO:8), a light chain CDR2 comprising WASTRHT (SEQ ID NO:9), and a light chain CDR3 comprising QQHYSTPW (SEQ ID NO:10).

In certain embodiments, the invention provides methods comprising a RSPO1-binding agent (e.g., an antibody or bispecific antibody) that specifically binds human RSPO1, wherein the RSPO1-binding agent comprises: (a) a heavy chain CDR1 comprising TGYTMH (SEQ ID NO:5) or a variant thereof comprising 1, 2, 3, or 4 amino acid substitutions; (b) a heavy chain CDR2 comprising GINPNNG-GTTYNQNFKG (SEQ ID NO:6) or a variant thereof comprising 1, 2, 3, or 4 amino acid substitutions; (c) a heavy chain CDR3 comprising KEFSDGYYFFAY (SEQ ID NO:7) or a variant thereof comprising 1, 2, 3, or 4 amino acid substitutions; (d) a light chain CDR1 comprising KASQD-VIFAVA (SEQ ID NO:8) or a variant thereof comprising 1, 2, 3, or 4 amino acid substitutions; (e) a light chain CDR2 comprising WASTRHT (SEQ ID NO:9) or a variant thereof comprising 1, 2, 3, or 4 amino acid substitutions; and (f) a light chain CDR3 comprising QQHYSTPW (SEQ ID NO:10) or a variant thereof comprising 1, 2, 3, or 4 amino acid substitutions. In certain embodiments, the amino acid substitutions are conservative substitutions. In some embodiments, the substitutions are made as part of a germline humanization process.

In certain embodiments, the invention provides methods comprising a RSPO1-binding agent (e.g., an antibody) that specifically binds RSPO1, wherein the RSPO1-binding agent comprises a heavy chain variable region having at least about 80% sequence identity to SEQ ID NO:11 and/or a light chain variable region having at least 80% sequence identity to SEQ ID NO:12. In certain embodiments, the RSPO1-binding agent comprises a heavy chain variable region having at least about 85%, at least about 90%, at least about 95%, at least about 97%, or at least about 99% sequence identity to SEQ ID NO:11. In certain embodiments, the RSPO1-binding agent comprises a light chain variable region having at least about 85%, at least about 90%, at least about 95%, at least about 97%, or at least about 99% sequence identity to SEQ ID NO:12. In certain embodiments, the RSPO1-binding agent comprises a heavy chain variable region having at least about 95% sequence identity to SEQ ID NO:11 and/or a light chain variable region having at least about 95% sequence identity to SEQ ID NO:12. In certain embodiments, the RSPO1-binding agent comprises a heavy chain variable region comprising SEQ ID NO:11, and/or a light chain variable region comprising SEQ ID NO:12. In certain embodiments, the RSPO1-binding agent comprises a heavy chain variable region comprising SEQ ID NO:11 and a light chain variable region comprising SEQ ID NO:12. In certain embodiments, the RSPO1-binding agent comprises a heavy chain variable region consisting of SEQ ID NO:11 and a light chain variable region consisting of SEQ ID NO:12.

In certain embodiments, the invention provides methods comprising a RSPO1-binding agent (e.g., an antibody) that specifically binds RSPO1, wherein the RSPO1-binding agent comprises a heavy chain variable region having at least about 80% sequence identity to SEQ ID NO:56 and/or a light chain variable region having at least 80% sequence identity to SEQ ID NO:57. In certain embodiments, the RSPO1-binding agent comprises a heavy chain variable region having at least about 85%, at least about 90%, at least about 95%, at least about 97%, or at least about 99% sequence identity to SEQ ID NO:56. In certain embodiments, the RSPO1-binding agent comprises a light chain variable region having at least about 85%, at least about 90%, at least about 95%, at least about 97%, or at least about 99% sequence identity to SEQ ID NO:57. In certain embodiments, the RSPO1-binding agent comprises a heavy chain variable region having at least about 95% sequence identity to SEQ ID NO:56 and/or a light chain variable region having at least about 95% sequence identity to SEQ ID NO:57. In certain embodiments, the RSPO1-binding agent comprises a heavy chain variable region comprising SEQ ID NO:56 and/or a light chain variable region comprising SEQ ID NO:57. In certain embodiments, the RSPO1-binding agent comprises a heavy chain variable region comprising SEQ ID NO:56 and a light chain variable region comprising SEQ ID NO:57. In certain embodiments, the RSPO1-binding agent comprises a heavy chain variable region consisting of SEQ ID NO:56 and a light chain variable region consisting of SEQ ID NO:57.

In certain embodiments, the invention provides methods comprising a RSPO1-binding agent (e.g., an antibody) that specifically binds RSPO1, wherein the RSPO1-binding agent comprises: (a) a heavy chain having at least 90% sequence identity to SEQ ID NO:13 or SEQ ID NO:14; and/or (b) a light chain having at least 90% sequence identity to SEQ ID NO:15 or SEQ ID NO:16. In some embodiments, the RSPO1-binding agent comprises: (a) a heavy chain having at least 95% sequence identity to SEQ ID NO:13 or SEQ ID NO:14; and/or (b) a light chain having at least 95% sequence identity to SEQ ID NO:15 or SEQ ID NO:16. In some embodiments, the RSPO1-binding agent comprises a heavy chain comprising SEQ ID NO:14 and/or a light chain comprising SEQ ID NO:16. In some embodiments, the RSPO1-binding agent comprises a heavy chain comprising SEQ ID NO:14 and a light chain comprising SEQ ID NO:16.

In certain embodiments, the invention provides methods comprising a RSPO1-binding agent (e.g., an antibody) that specifically binds RSPO1, wherein the RSPO1-binding agent comprises: (a) a heavy chain having at least 90% sequence identity to SEQ ID NO:58 or SEQ ID NO:59; and/or (b) a light chain having at least 90% sequence identity to SEQ ID NO:60 or SEQ ID NO:61. In some embodiments, the RSPO1-binding agent comprises: (a) a heavy chain having at least 95% sequence identity to SEQ ID NO:58 or SEQ ID NO:59; and/or (b) a light chain having at least 95% sequence identity to SEQ ID NO:60 or SEQ ID NO:61. In some embodiments, the RSPO1-binding agent comprises a heavy chain comprising SEQ ID NO:59 and/or a light chain comprising SEQ ID NO:61. In some embodiments, the RSPO1-binding agent comprises a heavy chain comprising SEQ ID NO:59 and a light chain comprising SEQ ID NO:61.

In certain embodiments, a RSPO1-binding agent comprises the heavy chain variable region and light chain variable region of antibody h89M5-H8L5. In certain embodiments, a RSPO1-binding agent comprises the heavy chain and light chain of antibody h89M5-H8L5 (with or without the leader sequence). In certain embodiments, a RSPO1-binding agent is antibody h89M5-H8L5. In certain embodiments, a RSPO1-binding agent comprises the heavy chain variable region and/or light chain variable region of antibody h89M5-H8L5 in a chimeric form of the antibody. In some embodiments, the anti-RSPO1 antibody is h89M5-H8L5.

In certain embodiments, a RSPO1-binding agent comprises the heavy chain variable region and light chain variable region of antibody h89M5-H2L2. In certain embodiments, a RSPO1-binding agent comprises the heavy chain and light chain of antibody h89M5-H2L2 (with or without the leader sequence). In certain embodiments, a RSPO1-binding agent is antibody h89M5-H2L2. In certain embodiments, a RSPO1-binding agent comprises the heavy chain variable region and/or light chain variable region of antibody h89M5-H2L2 in a chimeric form of the antibody. In some embodiments, the anti-RSPO1 antibody is h89M5-H2L2.

In certain embodiments of the methods described herein, a RSPO1-binding agent comprises the heavy chain CDRs and/or light chain CDRs of antibody 89M5. The hybridoma cell line producing the 89M5 antibody was deposited with American Type Culture Collection (ATCC), 10801 University Boulevard, Manassas, Va., USA, under the conditions of the Budapest Treaty on Jun. 30, 2011 and assigned ATCC deposit designation number PTA-11970.

Plasmids encoding the heavy chain and light chain of antibody h89M5-H8L5 were deposited with ATCC, 10801 University Boulevard, Manassas, Va., USA, under the conditions of the Budapest Treaty on Aug. 15, 2014 and assigned ATCC deposit designation number PTA-121494 and PTA-121495. In some embodiments, the RSPO1-binding agent comprises a heavy chain variable region encoded by the plasmid deposited with ATCC and designated PTA-121494. In some embodiments, the RSPO1-binding agent comprises a light chain variable region encoded by the plasmid deposited with ATCC and designated PTA-121495. In some embodiments, the RSPO1-binding agent comprises a heavy chain variable region encoded by the plasmid deposited with ATCC and designated PTA-121494 and a light chain variable region encoded by the plasmid deposited with ATCC and designated PTA-121495. In some embodiments, the RSPO1-binding agent comprises a heavy chain encoded by the plasmid deposited with ATCC and designated PTA-121494. In some embodiments, the RSPO1-binding agent comprises a light chain encoded by the plasmid deposited with ATCC and designated PTA-121495. In some embodiments, the RSPO1-binding agent comprises a heavy chain encoded by the plasmid deposited with ATCC and designated PTA-121494 and a light chain encoded by the plasmid deposited with ATCC and designated PTA-121495.

In certain embodiments, a RSPO1-binding agent comprises, consists essentially of, or consists of, antibody h89M5-H8L5. In certain embodiments, a RSPO1-binding agent comprises, consists essentially of, or consists of, a variant of antibody 89M5. In certain embodiments, a RSPO1-binding agent comprises, consists essentially of, or consists of, a variant of antibody h89M5-H8L5.

In certain embodiments, a RSPO1-binding agent comprises, consists essentially of, or consists of, antibody h89M5-H2L2. In certain embodiments, a RSPO1-binding agent comprises, consists essentially of, or consists of, a variant of antibody 89M5. In certain embodiments, a RSPO1-binding agent comprises, consists essentially of, or consists of, a variant of antibody h89M5-H2L2.

In certain embodiments of the methods described herein, the invention provides methods comprising a RSPO2-binding agent (e.g., an antibody) that specifically binds human RSPO2, wherein the RSPO2-binding agent (e.g., an antibody) comprises one, two, three, four, five, and/or six of the CDRs of antibody 130M23 (see Table 1).

In certain embodiments, the invention provides methods comprising a RSPO2-binding agent (e.g., an antibody) that specifically binds human RSPO2, wherein the RSPO2-binding agent comprises a heavy chain CDR1 comprising SSYAMS (SEQ ID NO:21), a heavy chain CDR2 comprising SISSGGSTYYPDSVKG (SEQ ID NO:22), and a heavy chain CDR3 comprising RGGDPGVYNGDYEDAMDY (SEQ ID NO:23). In some embodiments, the RSPO2-binding agent further comprises a light chain CDR1 comprising KASQDVSSAVA (SEQ ID NO:24), a light chain CDR2 comprising WASTRHT (SEQ ID NO:25), and a light chain CDR3 comprising QQHYSTP (SEQ ID NO:26). In some embodiments, the RSPO2-binding agent comprises a light chain CDR1 comprising KASQDVSSAVA (SEQ ID NO:24), a light chain CDR2 comprising WASTRHT (SEQ ID NO:25), and a light chain CDR3 comprising QQHYSTP (SEQ ID NO:26). In certain embodiments, the RSPO2-binding agent comprises: (a) a heavy chain CDR1 comprising SSYAMS (SEQ ID NO:21), a heavy chain CDR2 comprising SISSGGSTYYPDSVKG (SEQ ID NO:22), and a heavy chain CDR3 comprising RGGDPGVYNGDYEDAMDY (SEQ ID NO:23); and (b) a light chain CDR1 comprising KASQDVSSAVA (SEQ ID NO:24), a light chain CDR2 comprising WASTRHT (SEQ ID NO:25), and a light chain CDR3 comprising QQHYSTP (SEQ ID NO:26).

In certain embodiments, the invention provides methods comprising a RSPO2-binding agent (e.g., an antibody or bispecific antibody) that specifically binds human RSPO2, wherein the RSPO2-binding agent comprises: (a) a heavy chain CDR1 comprising SSYAMS (SEQ ID NO:21) or a variant thereof comprising 1, 2, 3, or 4 amino acid substitutions; (b) a heavy chain CDR2 comprising SISSGGSTYYPDSVKG (SEQ ID NO:22) or a variant thereof comprising 1, 2, 3, or 4 amino acid substitutions; (c) a heavy chain CDR3 comprising RGGDPGVYNGDYEDAMDY (SEQ ID NO:23) or a variant thereof comprising 1, 2, 3, or 4 amino acid substitutions; (d) a light chain CDR1 comprising KASQDVSSAVA (SEQ ID NO:24) or a variant thereof comprising 1, 2, 3, or 4 amino acid substitutions; (e) a light chain CDR2 comprising WASTRHT (SEQ ID NO:25) or a variant thereof comprising 1, 2, 3, or 4 amino acid substitutions; and (f) a light chain CDR3 comprising QQHYSTP (SEQ ID NO:26) or a variant thereof comprising 1, 2, 3, or 4 amino acid substitutions. In certain embodiments, the amino acid substitutions are conservative substitutions. In some embodiments, the substitutions are made as part of a germline humanization process.

In certain embodiments, the invention provides methods comprising a RSPO2-binding agent (e.g., an antibody) that specifically binds RSPO2, wherein the RSPO2-binding agent comprises a heavy chain variable region having at least about 80% sequence identity to SEQ ID NO:27 and/or a light chain variable region having at least 80% sequence identity to SEQ ID NO:28 or SEQ ID NO:66. In certain embodiments, the RSPO2-binding agent comprises a heavy chain variable region having at least about 85%, at least about 90%, at least about 95%, at least about 97%, or at least about 99% sequence identity to SEQ ID NO:27. In certain embodiments, the RSPO2-binding agent comprises a light chain variable region having at least about 85%, at least about 90%, at least about 95%, at least about 97%, or at least about 99% sequence identity to SEQ ID NO:28. In certain embodiments, the RSPO2-binding agent comprises a light chain variable region having at least about 85%, at least about 90%, at least about 95%, at least about 97%, or at least about 99% sequence identity to SEQ ID NO:66. In certain embodiments, the RSPO2-binding agent comprises a heavy chain variable region having at least about 95% sequence identity to SEQ ID NO:27 and/or a light chain variable region having at least about 95% sequence identity to SEQ ID NO:28 or SEQ ID NO:66. In certain embodiments, the RSPO2-binding agent comprises a heavy chain variable region comprising SEQ ID NO:27 and/or a light chain variable region comprising SEQ ID NO:28 or SEQ ID NO:66. In certain embodiments, the RSPO2-binding agent comprises a heavy chain variable region comprising SEQ ID NO:27 and a light chain variable region comprising SEQ ID NO:28. In certain embodiments, the RSPO2-binding agent comprises a heavy chain variable region comprising SEQ ID NO:27 and a light chain variable region comprising SEQ ID NO:66. In certain embodiments, the RSPO2-binding agent comprises a heavy chain variable region consisting of SEQ ID NO:27 and a light chain variable region consisting of SEQ ID NO:28. In certain embodiments, the RSPO2-binding agent comprises a heavy chain variable region consisting of SEQ ID NO:27 and a light chain variable region consisting of SEQ ID NO:66.

In certain embodiments, the invention provides methods comprising a RSPO2-binding agent (e.g., an antibody) that specifically binds RSPO2, wherein the RSPO2-binding agent comprises: (a) a heavy chain having at least 90% sequence identity to SEQ ID NO:29 or SEQ ID NO:30; and/or (b) a light chain having at least 90% sequence identity to SEQ ID NO:31 or SEQ ID NO:32. In some embodiments, the RSPO2-binding agent comprises: (a) a heavy chain having at least 95% sequence identity to SEQ ID NO:29 or SEQ ID NO:30; and/or (b) a light chain having at least 95% sequence identity to SEQ ID NO:31 or SEQ ID NO:32. In some embodiments, the RSPO2-binding agent comprises a heavy chain comprising SEQ ID NO:30 and/or a light chain comprising SEQ ID NO:32. In some embodiments, the RSPO2-binding agent comprises a heavy chain comprising SEQ ID NO:30 and a light chain comprising SEQ ID NO:32.

In certain embodiments, the invention provides methods comprising a RSPO2-binding agent (e.g., an antibody) that specifically binds RSPO2, wherein the RSPO2-binding agent comprises: (a) a heavy chain having at least 90% sequence identity to SEQ ID NO:29 or SEQ ID NO:30; and/or (b) a light chain having at least 90% sequence identity to SEQ ID NO:67 or SEQ ID NO:68. In some embodiments, the RSPO2-binding agent comprises: (a) a heavy chain having at least 95% sequence identity to SEQ ID NO:29 or SEQ ID NO:30; and/or (b) a light chain having at least 95% sequence identity to SEQ ID NO:67 or SEQ ID NO:68. In some embodiments, the RSPO2-binding agent comprises a heavy chain comprising SEQ ID NO:30 and/or a light chain comprising SEQ ID NO:68. In some embodiments, the RSPO2-binding agent comprises a heavy chain comprising SEQ ID NO:30 and a light chain comprising SEQ ID NO:68.

In certain embodiments, a RSPO2-binding agent comprises the heavy chain variable region and light chain variable region of antibody h130M23-H1L6. In certain embodiments, a RSPO2-binding agent comprises the heavy chain and light chain of antibody h130M23-H1L6 (with or without the leader sequence). In certain embodiments, a RSPO2-binding agent is antibody h130M23-H1L6. In certain embodiments, a RSPO2-binding agent comprises the heavy chain variable region and/or light chain variable region of antibody h130M23-H1L6 in a chimeric form of the antibody. In some embodiments, the anti-RSPO2 antibody is h130M23-H1L6.

In certain embodiments, a RSPO2-binding agent comprises the heavy chain variable region and light chain variable region of antibody h130M23-H1L2. In certain embodiments, a RSPO2-binding agent comprises the heavy chain and light chain of antibody h130M23-H1L2 (with or without the leader sequence). In certain embodiments, a RSPO2-binding agent is antibody h130M23-H1L2. In certain embodiments, a RSPO2-binding agent comprises the heavy chain variable region and/or light chain variable region of antibody h130M23-H1L2 in a chimeric form of the antibody. In some embodiments, the anti-RSPO2 antibody is h130M23-H1L2.

In certain embodiments of the methods described herein, a RSPO2-binding agent comprises the heavy chain CDRs and/or light chain CDRs of antibody 130M23. The hybridoma cell line producing the 130M23 antibody was deposited with ATCC, 10801 University Boulevard, Manassas, Va., USA, under the conditions of the Budapest Treaty on Aug. 10, 2011 and assigned ATCC deposit designation number PTA-12021.

In certain embodiments, a RSPO2-binding agent comprises, consists essentially of, or consists of, antibody h130M23-H1L6. In certain embodiments, a RSPO2-binding agent comprises, consists essentially of, or consists of, a variant of antibody 130M23. In certain embodiments, a RSPO2-binding agent comprises, consists essentially of, or consists of, a variant of antibody h130M23-H1L6.

In certain embodiments, a RSPO2-binding agent comprises, consists essentially of, or consists of, antibody h130M23-H1L2. In certain embodiments, a RSPO2-binding agent comprises, consists essentially of, or consists of, a variant of antibody 130M23. In certain embodiments, a RSPO2-binding agent comprises, consists essentially of, or consists of, a variant of antibody h130M23-H1L2.

In certain embodiments of the methods described herein, the invention provides methods comprising a RSPO3-binding agent (e.g., an antibody) that specifically binds human RSPO3, wherein the RSPO3-binding agent (e.g., an antibody) comprises one, two, three, four, five, and/or six of the CDRs of antibody 131R011 (see Table 1 herein).

In certain embodiments, the invention provides methods comprising a RSPO3-binding agent (e.g., an antibody) that specifically binds human RSPO3, wherein the RSPO3-binding agent comprises a heavy chain CDR1 comprising DYSIH (SEQ ID NO:37), a heavy chain CDR2 comprising YIYPSNGDSGYNQKFK (SEQ ID NO:38), and a heavy chain CDR3 comprising TYFANNFD (SEQ ID NO:39) or ATYFANNFDY (SEQ ID NO:40). In some embodiments, the RSPO3-binding agent further comprises a light chain CDR1 comprising KASQSVDYDGDSYMN (SEQ ID NO:41), a light chain CDR2 comprising AASNLES (SEQ ID NO:42) or AAS (SEQ ID NO:43), and a light chain CDR3 comprising QQSNEDPLT (SEQ ID NO:44) or QQSNEDPLTF (SEQ ID NO:45). In some embodiments, the RSPO3-binding agent comprises a light chain CDR1 comprising KASQSVDYDGDSYMN (SEQ ID NO:41), a light chain CDR2 comprising AASNLES (SEQ ID NO:42) or AAS (SEQ ID NO:43), and a light chain CDR3 comprising QQSNEDPLT (SEQ ID NO:44) or QQSNEDPLTF (SEQ ID NO:45). In certain embodiments, the RSPO3- binding agent comprises: (a) a heavy chain CDR1 comprising DYSIH (SEQ ID NO:37), a heavy chain CDR2 comprising YIYPSNGDSGYNQKFK (SEQ ID NO:38), and a heavy chain CDR3 comprising TYFANNFD (SEQ ID NO:39); and (b) a light chain CDR1 comprising KASQSVDYDGDSYMN (SEQ ID NO:41), a light chain CDR2 comprising AASNLES (SEQ ID NO:42), and a light chain CDR3 comprising QQSNEDPLT (SEQ ID NO:44).

In certain embodiments, the invention provides methods comprising a RSPO3-binding agent (e.g., an antibody or bispecific antibody) that specifically binds human RSPO3, wherein the RSPO3-binding agent comprises: (a) a heavy chain CDR1 comprising DYSIH (SEQ ID NO:37) or a variant thereof comprising 1, 2, 3, or 4 amino acid substitutions; (b) a heavy chain CDR2 comprising YIYPSNGDSGYNQKFK (SEQ ID NO:38) or a variant thereof comprising 1, 2, 3, or 4 amino acid substitutions; (c) a heavy chain CDR3 comprising TYFANNFD (SEQ ID NO:39), ATYFANNFDY (SEQ ID NO:40), or a variant thereof comprising 1, 2, 3, or 4 amino acid substitutions; (d) a light chain CDR1 comprising KASQSVDYDGDSYMN (SEQ ID NO:41) or a variant thereof comprising 1, 2, 3, or 4 amino acid substitutions; (e) a light chain CDR2 comprising AASNLES (SEQ ID NO:42), AAS (SEQ ID NO:43), or a variant thereof comprising 1, 2, 3, or 4 amino acid substitutions; and (f) a light chain CDR3 comprising QQSNEDPLT (SEQ ID NO:44), QQSNEDPLTF (SEQ ID NO:45), or a variant thereof comprising 1, 2, 3, or 4 amino acid substitutions. In certain embodiments, the amino acid substitutions are conservative substitutions. In some embodiments, the substitutions are made as part of a germline humanization process.

In certain embodiments, the invention provides a RSPO3-binding agent (e.g., an antibody) that specifically binds RSPO3, wherein the RSPO3-binding agent comprises a heavy chain variable region having at least about 80% sequence identity to SEQ ID NO:46 and/or a light chain variable region having at least 80% sequence identity to SEQ ID NO:47. In certain embodiments, the RSPO3-binding agent comprises a heavy chain variable region having at least about 85%, at least about 90%, at least about 95%, at least about 97%, or at least about 99% sequence identity to SEQ ID NO:46. In certain embodiments, the RSPO3-binding agent comprises a light chain variable region having at least about 85%, at least about 90%, at least about 95%, at least about 97%, or at least about 99% sequence identity to SEQ ID NO:47. In certain embodiments, the RSPO3-binding agent comprises a heavy chain variable region having at least about 95% sequence identity to SEQ ID NO:46 and/or a light chain variable region having at least about 95% sequence identity to SEQ ID NO:47. In certain embodiments, the RSPO3-binding agent comprises a heavy chain variable region comprising SEQ ID NO:46, and/or a light chain variable region comprising SEQ ID NO:47. In certain embodiments, the RSPO3-binding agent comprises a heavy chain variable region comprising SEQ ID NO:46 and a light chain variable region comprising SEQ ID NO:47. In certain embodiments, the RSPO3-binding agent comprises a heavy chain variable region consisting of SEQ ID NO:46 and a light chain variable region consisting of SEQ ID NO:47.

In certain embodiments, the invention provides a RSPO3-binding agent (e.g., an antibody) that specifically binds RSPO3, wherein the RSPO3-binding agent comprises: (a) a heavy chain having at least 90% sequence identity to SEQ ID NO:48 or SEQ ID NO:49; and/or (b) a light chain having at least 90% sequence identity to SEQ ID NO:50 or SEQ ID NO:51. In some embodiments, the RSPO3-binding agent comprises: (a) a heavy chain having at least 95% sequence identity to SEQ ID NO:48 or SEQ ID NO:49; and/or (b) a light chain having at least 95% sequence identity to SEQ ID NO:50 or SEQ ID NO:51. In some embodiments, the RSPO3-binding agent comprises a heavy chain comprising SEQ ID NO:49 and/or a light chain comprising SEQ ID NO:51. In some embodiments, the RSPO3-binding agent comprises a heavy chain comprising SEQ ID NO:49 and a light chain comprising SEQ ID NO:51.

In certain embodiments, a RSPO3-binding agent comprises the heavy chain variable region and light chain variable region of antibody 131R010. In certain embodiments, a RSPO3-binding agent comprises the heavy chain and light chain of antibody 131R010 (with or without the leader sequence). In certain embodiments, a RSPO3-binding agent is antibody 131R010. In certain embodiments, a RSPO3-binding agent comprises the heavy chain variable region and/or light chain variable region of antibody 131R010 in a chimeric form of the antibody. In certain embodiments, a RSPO3-binding agent comprises the heavy chain CDRs and/or light chain CDRs of antibody 131R010. In some embodiments, the anti-RSPO3 antibody is 131R010.

Plasmids encoding the heavy chain and light chain of antibody 131R010 were deposited with the American Type Culture Collection (ATCC), 10801 University Boulevard, Manassas, Va., USA, under the conditions of the Budapest Treaty on Jun. 18, 2013 and assigned ATCC deposit designation number PTA-120420 and PTA-120421. In some embodiments, the RSPO3-binding agent comprises a heavy chain variable region encoded by the plasmid deposited with ATCC and designated PTA-120420. In some embodiments, the RSPO3-binding agent comprises a light chain variable region encoded by the plasmid deposited with ATCC and designated PTA-120421. In some embodiments, the RSPO3-binding agent comprises a heavy chain variable region encoded by the plasmid deposited with ATCC and designated PTA-120420 and a light chain variable region encoded by the plasmid deposited with ATCC and designated PTA-120421. In some embodiments, the RSPO3-binding agent comprises a heavy chain encoded by the plasmid deposited with ATCC and designated PTA-120420. In some embodiments, the RSPO3-binding agent comprises a light chain encoded by the plasmid deposited with ATCC and designated PTA-120421. In some embodiments, the RSPO3-binding agent comprises a heavy chain encoded by the plasmid deposited with ATCC and designated PTA-120420 and a light chain encoded by the plasmid deposited with ATCC and designated PTA-120421.

In certain embodiments, a RSPO3-binding agent comprises, consists essentially of, or consists of, antibody 131R010. In certain embodiments, a RSPO3-binding agent comprises, consists essentially of, or consists of, a variant of antibody 131R010.

The invention provides methods comprising polypeptides, including, but not limited to, antibodies that specifically bind at least one human RSPO protein or antibodies that specifically bind at least one human LGR protein. In some embodiments, a polypeptide binds human RSPO1. In some embodiments, a polypeptide binds human RSPO2. In some embodiments, a polypeptide binds human RSPO3. In some embodiments, a polypeptide binds human LGR4. In some embodiments, a polypeptide binds human LGR5. In some embodiments, a polypeptide binds human LGR6. The invention also provides methods comprising polypeptides, wherein the polypeptide comprises a soluble receptor that specifically binds at least one human RSPO protein.

In certain embodiments, the polypeptide comprises one, two, three, four, five, and/or six of the CDRs of antibody 89M5 (see Table 1 herein). In certain embodiments, the polypeptide comprises one, two, three, four, five, and/or six of the CDRs of antibody 130M23 (see Table 1 herein). In certain embodiments, the polypeptide comprises one, two, three, four, five, and/or six of the CDRs of antibody 131R010 (see Table 1 herein). In some embodiments, the polypeptide comprises CDRs with up to four (i.e., 0, 1, 2, 3, or 4) amino acid substitutions per CDR. In certain embodiments, the heavy chain CDR(s) are contained within a heavy chain variable region. In certain embodiments, the light chain CDR(s) are contained within a light chain variable region.

In some embodiments, the invention provides methods comprising a polypeptide that specifically binds a human RSPO1, wherein the polypeptide comprises an amino acid sequence having at least about 80% sequence identity to SEQ ID NO:11 and/or SEQ ID NO:12. In some embodiments, the polypeptide comprises an amino acid sequence having at least about 80% sequence identity to SEQ ID NO:13 and/or an amino acid sequence having at least about 80% sequence identity to SEQ ID NO:15. In some embodiments, the polypeptide comprises an amino acid sequence having at least about 80% sequence identity to SEQ ID NO:14 and/or an amino acid sequence having at least about 80% sequence identity to SEQ ID NO:16. In certain embodiments, the polypeptide comprises an amino acid sequence having at least about 85%, at least about 90%, at least about 95%, at least about 97%, or at least about 99% sequence identity to SEQ ID NO:11, SEQ ID NO:12, SEQ ID NO:13, SEQ ID NO:14, SEQ ID NO:15, or SEQ ID NO:16. In certain embodiments, the polypeptide comprises an amino acid sequence having at least about 95% sequence identity to SEQ ID NO:11 and/or an amino acid sequence having at least about 95% sequence identity to SEQ ID NO:12. In certain embodiments, the polypeptide comprises an amino acid sequence having at least about 95% sequence identity to SEQ ID NO:13 and/or an amino acid sequence having at least about 95% sequence identity to SEQ ID NO:15. In certain embodiments, the polypeptide comprises an amino acid sequence having at least about 95% sequence identity to SEQ ID NO:14 and/or an amino acid sequence having at least about 95% sequence identity to SEQ ID NO:16. In certain embodiments, the polypeptide comprises an amino acid sequence of SEQ ID NO:11 and/or an amino acid sequence of SEQ ID NO:12. In certain embodiments, the polypeptide comprises an amino acid sequence of SEQ ID NO:13 and/or an amino acid sequence of SEQ ID NO:15. In certain embodiments, the polypeptide comprises an amino acid sequence of SEQ ID NO:14 and/or an amino acid sequence of SEQ ID NO:16.

In some embodiments, the invention provides methods comprising a polypeptide that specifically binds a human RSPO1, wherein the polypeptide comprises an amino acid sequence having at least about 80% sequence identity to SEQ ID NO:56 and/or SEQ ID NO:57. In some embodiments, the polypeptide comprises an amino acid sequence having at least about 80% sequence identity to SEQ ID NO:58 and/or an amino acid sequence having at least about 80% sequence identity to SEQ ID NO:60. In some embodiments, the polypeptide comprises an amino acid sequence having at least about 80% sequence identity to SEQ ID NO:59 and/or an amino acid sequence having at least about 80% sequence identity to SEQ ID NO:61. In certain embodiments, the polypeptide comprises an amino acid sequence having at least about 85%, at least about 90%, at least about 95%, at least about 97%, or at least about 99% sequence identity to SEQ ID NO:56, SEQ ID NO:57, SEQ ID NO:58, SEQ ID NO:59, SEQ ID NO:60, or SEQ ID NO:61. In certain embodiments, the polypeptide comprises an amino acid sequence having at least about 95% sequence identity to SEQ ID NO:56 and/or an amino acid sequence having at least about 95% sequence identity to SEQ ID NO:57. In certain embodiments, the polypeptide comprises an amino acid sequence having at least about 95% sequence identity to SEQ ID NO:58 and/or an amino acid sequence having at least about 95% sequence identity to SEQ ID NO:60. In certain embodiments, the polypeptide comprises an amino acid sequence having at least about 95% sequence identity to SEQ ID NO:59 and/or an amino acid sequence having at least about 95% sequence identity to SEQ ID NO:61. In certain embodiments, the polypeptide comprises an amino acid sequence of SEQ ID NO:56 and/or an amino acid sequence of SEQ ID NO:57. In certain embodiments, the polypeptide comprises an amino acid sequence of SEQ ID NO:58 and/or an amino acid sequence of SEQ ID NO:60. In certain embodiments, the polypeptide comprises an amino acid sequence of SEQ ID NO:59 and/or an amino acid sequence of SEQ ID NO:61.

In some embodiments, the invention provides methods comprising a polypeptide that specifically binds a human RSPO2, wherein the polypeptide comprises an amino acid sequence having at least about 80% sequence identity to SEQ ID NO:27 and/or SEQ ID NO:28. In some embodiments, the invention provides methods comprising a polypeptide that specifically binds a human RSPO2, wherein the polypeptide comprises an amino acid sequence having at least about 80% sequence identity to SEQ ID NO:27 and/or SEQ ID NO:66. In some embodiments, the polypeptide comprises an amino acid sequence having at least about 80% sequence identity to SEQ ID NO:29 and/or an amino acid sequence having at least about 80% sequence identity to SEQ ID NO:31 or SEQ ID NO:67. In some embodiments, the polypeptide comprises an amino acid sequence having at least about 80% sequence identity to SEQ ID NO:30 and/or an amino acid sequence having at least about 80% sequence identity to SEQ ID NO:32 or SEQ ID NO:68. In certain embodiments, the polypeptide comprises an amino acid sequence having at least about 85%, at least about 90%, at least about 95%, at least about 97%, or at least about 99% sequence identity to SEQ ID NO:27, SEQ ID NO:28, SEQ ID NO:29, SEQ ID NO:30, SEQ ID NO:31, SEQ ID NO:32, SEQ ID NO:66, SEQ ID NO:67, or SEQ ID NO:68. In certain embodiments, the polypeptide comprises an amino acid sequence having at least about 95% sequence identity to SEQ ID NO:27 and/or an amino acid sequence having at least about 95% sequence identity to SEQ ID NO:28 or SEQ ID NO:66. In certain embodiments, the polypeptide comprises an amino acid sequence having at least about 95% sequence identity to SEQ ID NO:29 and/or an amino acid sequence having at least about 95% sequence identity to SEQ ID NO:31 or SEQ ID NO:67. In certain embodiments, the polypeptide comprises an amino acid sequence having at least about 95% sequence identity to SEQ ID NO:30 and/or an amino acid sequence having at least about 95% sequence identity to SEQ ID NO:32 or SEQ ID NO:68. In certain embodiments, the polypeptide comprises an amino acid sequence of SEQ ID NO:27 and/or an amino acid sequence of SEQ ID NO:28. In certain embodiments, the polypeptide comprises an amino acid sequence of SEQ ID NO:27 and/or an amino acid sequence of SEQ ID NO:66. In certain embodiments, the polypeptide comprises an amino acid sequence of SEQ ID NO:29 and/or an amino acid sequence of SEQ ID NO:31. In certain embodiments, the polypeptide comprises an amino acid sequence of SEQ ID NO:29 and/or an amino acid sequence of SEQ ID NO:67. In certain embodiments, the polypeptide comprises an amino acid sequence of SEQ ID NO:30 and/or an amino acid sequence of SEQ ID NO:32. In certain embodiments, the polypeptide comprises an amino acid sequence of SEQ ID NO:30 and/or an amino acid sequence of SEQ ID NO:68.

In some embodiments, the invention provides methods comprising a polypeptide that specifically binds a human RSPO3, wherein the polypeptide comprises an amino acid sequence having at least about 80% sequence identity to SEQ ID NO:46 and/or SEQ ID NO:47. In some embodiments, the polypeptide comprises an amino acid sequence having at least about 80% sequence identity to SEQ ID NO:48 and/or an amino acid sequence having at least about 80% sequence identity to SEQ ID NO:50. In some embodiments, the polypeptide comprises an amino acid sequence having at least about 80% sequence identity to SEQ ID NO:49 and/or an amino acid sequence having at least about 80% sequence identity to SEQ ID NO:51. In certain embodiments, the polypeptide comprises an amino acid sequence having at least about 85%, at least about 90%, at least about 95%, at least about 97%, or at least about 99% sequence identity to SEQ ID NO:46, SEQ ID NO:47, SEQ ID NO:48, SEQ ID NO:49, SEQ ID NO:50, or SEQ ID NO:51. In certain embodiments, the polypeptide comprises an amino acid sequence having at least about 95% sequence identity to SEQ ID NO:46 and/or an amino acid sequence having at least about 95% sequence identity to SEQ ID NO:47. In certain embodiments, the polypeptide comprises an amino acid sequence having at least about 95% sequence identity to SEQ ID NO:48 and/or an amino acid sequence having at least about 95% sequence identity to SEQ ID NO:50. In certain embodiments, the polypeptide comprises an amino acid sequence having at least about 95% sequence identity to SEQ ID NO:49 and/or an amino acid sequence having at least about 95% sequence identity to SEQ ID NO:51. In certain embodiments, the polypeptide comprises an amino acid sequence of SEQ ID NO:46 and/or an amino acid sequence of SEQ ID NO:47. In certain embodiments, the polypeptide comprises an amino acid sequence of SEQ ID NO:48 and/or an amino acid sequence of SEQ ID NO:50. In certain embodiments, the polypeptide comprises an amino acid sequence of SEQ ID NO:49 and/or an amino acid sequence of SEQ ID NO:51.

Many proteins, including antibodies, contain a signal sequence that directs the transport of the proteins to various locations. Signal sequences (also referred to as signal peptides or leader sequences) are located at the N-terminus of nascent polypeptides. They target the polypeptide to the endoplasmic reticulum and the proteins are sorted to their destinations, for example, to the inner space of an organelle, to an interior membrane, to the cell's outer membrane, or to the cell exterior via secretion. Most signal sequences are cleaved from the protein by a signal peptidase after the proteins are transported to the endoplasmic reticulum. The cleavage of the signal sequence from the polypeptide usually occurs at a specific site in the amino acid sequence and is dependent upon amino acid residues within the signal sequence. Although there is usually one specific cleavage site, more than one cleavage site may be recognized and/or may be used by a signal peptidase resulting in a non-homogenous N-terminus of the polypeptide. For example, the use of different cleavage sites within a signal sequence can result in a polypeptide expressed with different N-terminal amino acids. Accordingly, in some embodiments, the polypeptides as described herein may comprise a mixture of polypeptides with different N-termini. In some embodiments, the N-termini differ in length by 1, 2, 3, 4, or 5 amino acids. In some embodiments, the polypeptide is substantially homogeneous, i.e., the polypeptides have the same N-terminus. In some embodiments, the signal sequence of the polypeptide comprises one or more (e.g., one, two, three, four, five, six, seven, eight, nine, ten, etc.) amino acid substitutions and/or deletions as compared to a "native" or "parental" signal sequence. In some embodiments, the signal sequence of the polypeptide comprises amino acid substitutions and/or deletions that allow one cleavage site to be dominant, thereby resulting in a substantially homogeneous polypeptide with one N-terminus. In some embodiments, a signal sequence of the polypeptide affects the expression level of the polypeptide, e.g., increased expression or decreased expression.

In certain embodiments, the invention provides methods comprising a RSPO1-binding agent (e.g., antibody) that competes for specific binding to RSPO1 with an antibody that comprises the CDRs of antibody 89M5. In certain embodiments, the invention provides methods comprising a RSPO2-binding agent (e.g., antibody) that competes for specific binding to RSPO2 with an antibody that comprises the CDRs of antibody 130M23. In certain embodiments, the invention provides methods comprising a RSPO3-binding agent (e.g., antibody) that competes for specific binding to RSPO3 with an antibody that comprises the CDRs of antibody 131R010.

In certain embodiments, the invention provides methods comprising a RSPO1-binding agent (e.g., an antibody) that binds the same epitope, or essentially the same epitope on RSPO1, as an antibody that comprises the CDRs of antibody 89M5. In certain embodiments, the invention provides methods comprising a RSPO2-binding agent (e.g., an antibody) that binds the same epitope, or essentially the same epitope on RSPO2, as an antibody that comprises the CDRs of antibody 89M5. In certain embodiments, the invention provides methods comprising a RSPO3-binding agent (e.g., an antibody) that binds the same epitope, or essentially the same epitope on RSPO3, as an antibody that comprises the CDRs of antibody 131R010.

In certain embodiments, the invention provides methods comprising a RSPO1-binding agent (e.g., an antibody) that binds an epitope on RSPO1 that overlaps with the epitope on RSPO1 bound by an antibody comprising the CDRs of antibody 89M5. In certain embodiments, the invention provides methods comprising a RSPO2-binding agent (e.g., an antibody) that binds an epitope on RSPO2 that overlaps with the epitope on RSPO2 bound by an antibody comprising the CDRs of antibody 130M23. In certain embodiments, the invention provides methods comprising a RSPO3-binding agent (e.g., an antibody) that binds an epitope on RSPO3 that overlaps with the epitope on RSPO3 bound by an antibody comprising the CDRs of antibody 131R010.

In certain embodiments of the methods described herein, a RSPO-binding agent (e.g., an antibody or soluble receptor) described herein binds at least one human RSPO protein and modulates RSPO activity. In some embodiments, the RSPO-binding agent is a RSPO antagonist and decreases RSPO activity. In some embodiments, the RSPO-binding agent is a RSPO antagonist and decreases β-catenin activity.

In certain embodiments, a RSPO1-binding agent (e.g., an antibody or soluble receptor) described herein binds human RSPO1 and modulates RSPO1 activity. In some embodiments, a RSPO1-binding agent is a RSPO1 antagonist and decreases RSPO1 activity. In some embodiments, a RSPO1- binding agent is a RSPO1 antagonist and decreases β-catenin activity. In certain embodiments, a RSPO2-binding agent (e.g., an antibody or soluble receptor) described herein binds human RSPO2 and modulates RSPO2 activity. In some embodiments, a RSPO2-binding agent is a RSPO2 antagonist and decreases RSPO2 activity. In some embodiments, a RSPO2-binding agent is a RSPO2 antagonist and decreases β-catenin activity. In certain embodiments, a RSPO3-binding agent (e.g., an antibody or soluble receptor) described herein binds human RSPO3 and modulates RSPO3 activity. In some embodiments, a RSPO3-binding agent is a RSPO3 antagonist and decreases RSPO3 activity. In some embodiments, a RSPO3-binding agent is a RSPO3 antagonist and decreases β-catenin activity.

In certain embodiments, the RSPO-binding agent (e.g., an antibody or soluble receptor) is an antagonist of at least one human RSPO protein. In some embodiments, the RSPO-binding agent is an antagonist of at least one RSPO and inhibits RSPO activity. In certain embodiments, the RSPO-binding agent inhibits RSPO activity by at least about 10%, at least about 20%, at least about 30%, at least about 50%, at least about 75%, at least about 90%, or about 100%. In some embodiments, the RSPO-binding agent inhibits activity of one, two, three, or four RSPO proteins. In some embodiments, the RSPO-binding agent inhibits activity of human RSPO1, RSPO2, RSPO3, and/or RSPO4.

In certain embodiments, the RSPO-binding agent (e.g., antibody or soluble receptor) is an antagonist of at least one human RSPO protein. In certain embodiments, the RSPO-binding agent inhibits RSPO signaling by at least about 10%, at least about 20%, at least about 30%, at least about 50%, at least about 75%, at least about 90%, or about 100%. In some embodiments, the RSPO-binding agent inhibits signaling by one, two, three, or four RSPO proteins. In some embodiments, the RSPO-binding agent inhibits signaling of human RSPO1, RSPO2, RSPO3, and/or RSPO4.

In certain embodiments, the RSPO-binding agent (e.g., antibody or soluble receptor) is an antagonist of β-catenin signaling. In certain embodiments, the RSPO-binding agent inhibits β-catenin signaling by at least about 10%, at least about 20%, at least about 30%, at least about 50%, at least about 75%, at least about 90%, or about 100%.

In certain embodiments, the RSPO-binding agent (e.g., antibody or soluble receptor) inhibits binding of at least one RSPO protein to a receptor. In certain embodiments, the RSPO-binding agent inhibits binding of a human RSPO protein to one or more of its receptors. In some embodiments, the RSPO-binding agent inhibits binding of a RSPO protein to at least one LGR protein. In some embodiments, the RSPO-binding agent inhibits binding of a RSPO protein to LGR4, LGR5, and/or LGR6. In certain embodiments, the inhibition of binding of a RSPO-binding agent to at least one LGR protein is at least about 10%, at least about 25%, at least about 50%, at least about 75%, at least about 90%, or at least about 95%. In certain embodiments, a RSPO-binding agent that inhibits binding of at least one RSPO to at least one LGR protein further inhibits β-catenin signaling.

In certain embodiments, the RSPO-binding agent (e.g., antibody or soluble receptor) blocks binding of at least one RSPO to a receptor. In certain embodiments, the RSPO-binding agent blocks binding of a human RSPO protein to one or more of its receptors. In some embodiments, the RSPO-binding agent blocks binding of a RSPO to at least one LGR protein. In some embodiments, the RSPO-binding agent blocks binding of at least one RSPO protein to LGR4, LGR5, and/or LGR6. In certain embodiments, the blocking of binding of a RSPO-binding agent to at least one LGR protein is at least about 10%, at least about 25%, at least about 50%, at least about 75%, at least about 90%, or at least about 95%. In certain embodiments, a RSPO-binding agent that blocks binding of at least one RSPO protein to at least one LGR protein further inhibits β-catenin signaling.

In certain embodiments, the RSPO-binding agent (e.g., an antibody or soluble receptor) inhibits β-catenin signaling. It is understood that a RSPO-binding agent that inhibits β-catenin signaling may, in certain embodiments, inhibit signaling by one or more receptors in the β-catenin signaling pathway but not necessarily inhibit signaling by all receptors. In certain alternative embodiments, β-catenin signaling by all human receptors may be inhibited. In certain embodiments, β-catenin signaling by one or more receptors selected from the group consisting of LGR4, LGR5, and LGR6 is inhibited. In certain embodiments, the inhibition of β-catenin signaling by a RSPO-binding agent is a reduction in the level of β-catenin signaling of at least about 10%, at least about 25%, at least about 50%, at least about 75%, at least about 90%, or at least about 95%.

In certain embodiments, the RSPO-binding agent (e.g., an antibody or soluble receptor) inhibits activation of β-catenin. It is understood that a RSPO-binding agent that inhibits activation of β-catenin may, in certain embodiments, inhibit activation of β-catenin by one or more receptors, but not necessarily inhibit activation of β-catenin by all receptors. In certain alternative embodiments, activation of β-catenin by all human receptors may be inhibited. In certain embodiments, activation of β-catenin by one or more receptors selected from the group consisting of LGR4, LGR5, and LGR6 is inhibited. In certain embodiments, the inhibition of activation of β-catenin by a RSPO-binding agent is a reduction in the level of activation of β-catenin of at least about 10%, at least about 25%, at least about 50%, at least about 75%, at least about 90%, or at least about 95%.

In vivo and in vitro assays for determining whether a RSPO-binding agent or a LGR-binding agent (or candidate binding agent) inhibits β-catenin signaling are known in the art. For example, cell-based, luciferase reporter assays utilizing a TCF/Luc reporter vector containing multiple copies of the TCF-binding domain upstream of a firefly luciferase reporter gene may be used to measure β-catenin signaling levels in vitro (Gazit et al., 1999, Oncogene, 18; 5959-66; TOPflash, Millipore, Billerica Mass.). The level of β-catenin signaling in the presence of one or more Wnts (e.g., Wnt(s) expressed by transfected cells or provided by Wnt-conditioned media) with or without a RSPO protein or RSPO-conditioned media in the presence of a RSPO-binding agent is compared to the level of signaling without the RSPO-binding agent present. In addition to the TCF/Luc reporter assay, the effect of a RSPO-binding agent or LGR-binding agent (or a candidate agent) on β-catenin signaling may be measured in vitro or in vivo by measuring the effect of the agent on the level of expression of β-catenin-regulated genes, such as c-myc (He et al., 1998, Science, 281:1509-12), cyclin D1 (Tetsu et al., 1999, Nature, 398:422-6) and/or fibronectin (Gradl et al. 1999, Mol. Cell Biol., 19:5576-87). In certain embodiments, the effect of a RSPO-binding agent or LGR-binding agent on β-catenin signaling may also be assessed by measuring the effect of the agent on the phosphorylation state of Disheveled-1, Disheveled-2, Disheveled-3, LRP5, LRP6, and/or β-catenin.

In certain embodiments, the RSPO-binding agents or LGR-binding agents described herein have a circulating half-life in mice, cynomolgus monkeys, or humans of at least about 2 hours, at least about 5 hours, at least about 10 hours, at least about 24 hours, at least about 3 days, at least about 1 week, or at least about 2 weeks. In certain embodiments, the RSPO-binding agent or LGR-binding is an IgG (e.g., IgG1 or IgG2) antibody that has a circulating half-life in mice, cynomolgus monkeys, or humans of at least about 2 hours, at least about 5 hours, at least about 10 hours, at least about 24 hours, at least about 3 days, at least about 1 week, or at least about 2 weeks. Methods of increasing (or decreasing) the half-life of agents such as polypeptides and antibodies are known in the art. For example, known methods of increasing the circulating half-life of IgG antibodies include the introduction of mutations in the Fc region which increase the pH-dependent binding of the antibody to the neonatal Fc receptor (FcRn) at pH 6.0. Known methods of increasing the circulating half-life of antibody fragments lacking the Fc region include such techniques as PEGylation.

In some embodiments, the RSPO-binding agents or LGR-binding agents are polyclonal antibodies. Polyclonal antibodies can be prepared by any known method. In some embodiments, polyclonal antibodies are produced by immunizing an animal (e.g., a rabbit, rat, mouse, goat, donkey) with an antigen of interest (e.g., a purified peptide fragment, full-length recombinant protein, or fusion protein) using multiple subcutaneous or intraperitoneal injections. The antigen can be optionally conjugated to a carrier such as keyhole limpet hemocyanin (KLH) or serum albumin. The antigen (with or without a carrier protein) is diluted in sterile saline and usually combined with an adjuvant (e.g., Complete or Incomplete Freund's Adjuvant) to form a stable emulsion. After a sufficient period of time, polyclonal antibodies are recovered from the immunized animal, usually from blood or ascites. The polyclonal antibodies can be purified from serum or ascites according to standard methods in the art including, but not limited to, affinity chromatography, ion-exchange chromatography, gel electrophoresis, and dialysis.

In some embodiments, the RSPO-binding agents or LGR-binding agents are monoclonal antibodies. Monoclonal antibodies can be prepared using hybridoma methods known to one of skill in the art. In some embodiments, using the hybridoma method, a mouse, hamster, or other appropriate host animal, is immunized as described above to elicit from lymphocytes the production of antibodies that specifically bind the immunizing antigen. In some embodiments, lymphocytes can be immunized in vitro. In some embodiments, the immunizing antigen can be a human protein or a portion thereof. In some embodiments, the immunizing antigen can be a mouse protein or a portion thereof.

Following immunization, lymphocytes are isolated and fused with a suitable myeloma cell line using, for example, polyethylene glycol. The hybridoma cells are selected using specialized media as known in the art and unfused lymphocytes and myeloma cells do not survive the selection process. Hybridomas that produce monoclonal antibodies directed specifically against a chosen antigen may be identified by a variety of methods including, but not limited to, immunoprecipitation, immunoblotting, and in vitro binding assays (e.g., flow cytometry, FACS, ELISA, and radioimmunoassay). The hybridomas can be propagated either in in vitro culture using standard methods or in vivo as ascites tumors in an animal. The monoclonal antibodies can be purified from the culture medium or ascites fluid according to standard methods in the art including, but not limited to, affinity chromatography, ion-exchange chromatography, gel electrophoresis, and dialysis.

In certain embodiments, monoclonal antibodies can be made using recombinant DNA techniques as known to one skilled in the art. The polynucleotides encoding a monoclonal antibody are isolated from mature B-cells or hybridoma cells, such as by RT-PCR using oligonucleotide primers that specifically amplify the genes encoding the heavy and light chains of the antibody, and their sequence is determined using standard techniques. The isolated polynucleotides encoding the heavy and light chains are then cloned into suitable expression vectors which produce the monoclonal antibodies when transfected into host cells such as E. coli, simian COS cells, Chinese hamster ovary (CHO) cells, or myeloma cells that do not otherwise produce immunoglobulin proteins.

In certain other embodiments, recombinant monoclonal antibodies, or fragments thereof, can be isolated from phage display libraries expressing variable domains or CDRs of a desired species.

The polynucleotide(s) encoding a monoclonal antibody can be modified, for example, by using recombinant DNA technology to generate alternative antibodies. In some embodiments, the constant domains of the light and heavy chains of, for example, a mouse monoclonal antibody can be substituted for those regions of, for example, a human antibody to generate a chimeric antibody, or for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In some embodiments of the methods described herein, a monoclonal antibody against a human RSPO protein or a LGR protein is a humanized antibody. Typically, humanized antibodies are human immunoglobulins in which residues from the CDRs are replaced by residues from a CDR of a non-human species (e.g., mouse, rat, rabbit, hamster, etc.) that have the desired specificity, affinity, and/or binding capability using methods known to one skilled in the art. In some embodiments, the Fv framework region residues of a human immunoglobulin are replaced with the corresponding residues in an antibody from a non-human species. In some embodiments, a humanized antibody can be further modified by the substitution of additional residues either in the Fv framework region and/or within the replaced non-human residues to refine and optimize antibody specificity, affinity, and/or capability. In general, a humanized antibody will comprise variable domain regions containing all, or substantially all, of the CDRs that correspond to the non-human immunoglobulin whereas all, or substantially all, of the framework regions are those of a human immunoglobulin sequence. In some embodiments, a humanized antibody can also comprise at least a portion of an immunoglobulin constant region or domain (Fc), typically that of a human immunoglobulin. In certain embodiments, such humanized antibodies are used therapeutically because they may reduce antigenicity and HAMA (human anti-mouse antibody) responses when administered to a human subject.

In certain embodiments of the methods described herein, the RSPO-binding agent or LGR-binding agent is a human antibody. Human antibodies can be directly prepared using various techniques known in the art. In some embodiments, human antibodies may be generated from immortalized human B lymphocytes immunized in vitro or from lymphocytes isolated from an immunized individual. In either case, cells that produce an antibody directed against a target antigen can be generated and isolated. In some embodiments, the human antibody can be selected from a phage library, where that phage library expresses human antibodies. Alternatively, phage display technology can be used to produce human antibodies and antibody fragments in vitro, from immunoglobulin variable domain gene repertoires from unimmunized donors. Techniques for the generation and use of antibody phage libraries are well known and phage libraries are commercially available. Once antibodies are identified, affinity maturation strategies known in the art, including but not limited to, chain shuffling, domain shuffling, and site-directed mutagenesis, may be employed to generate high affinity human antibodies.

In some embodiments, human antibodies can be made in transgenic mice that contain human immunoglobulin loci. Upon immunization these mice are capable of producing the full repertoire of human antibodies in the absence of endogenous immunoglobulin production.

This invention also encompasses bispecific antibodies that specifically recognize at least one human RSPO protein and/or at least one human LGR protein. Bispecific antibodies are capable of specifically recognizing and binding at least two different antigens or epitopes. The different epitopes can either be within the same molecule (e.g., two epitopes on human RSPO1) or on different molecules (e.g., one epitope on RSPO1 and one epitope on LGR5). In some embodiments, a bispecific antibody has enhanced potency as compared to an individual antibody or to a combination of more than one antibody. In some embodiments, a bispecific antibody has reduced toxicity as compared to an individual antibody or to a combination of more than one antibody. It is known to those of skill in the art that any binding agent (e.g., antibody) may have unique pharmacokinetics (PK) (e.g., circulating half-life). In some embodiments, a bispecific antibody has the ability to synchronize the PK of two active binding agents wherein the two individual binding agents have different PK profiles. In some embodiments, a bispecific antibody has the ability to concentrate the actions of two binding agents (e.g., antibodies) in a common area (e.g., a specific tissue). In some embodiments, a bispecific antibody has the ability to concentrate the actions of two binding agents (e.g., antibodies) to a common target (e.g., a specific tissue). In some embodiments, a bispecific antibody has the ability to target the actions of two binding agents (e.g., antibodies) to more than one biological pathway or function.

In some embodiments, the bispecific antibody is a monoclonal antibody. In some embodiments, the bispecific antibody is a humanized antibody. In some embodiments, the bispecific antibody is a human antibody. In some embodiments, the bispecific antibody is an IgG1 antibody. In some embodiments, the bispecific antibody is an IgG2 antibody. In some embodiments, the bispecific antibody has decreased toxicity and/or side effects. In some embodiments, the bispecific antibody has decreased toxicity and/or side effects as compared to a mixture of the two individual antibodies or the antibodies as single agents. In some embodiments, the bispecific antibody has an increased therapeutic index. In some embodiments, the bispecific antibody has an increased therapeutic index as compared to a mixture of the two individual antibodies or the antibodies as single agents.

In some embodiments, the antibodies can specifically recognize and bind a first antigen target, (e.g., RSPO2) as well as a second antigen target, such as an effector molecule on a leukocyte (e.g., CD2, CD3, CD28, CTLA-4, CD80, or CD86) or a Fc receptor (e.g., CD64, CD32, or CD16) so as to focus cellular defense mechanisms to the cell expressing and/or producing the first antigen target. In some embodiments, the antibodies can be used to direct cytotoxic agents to cells which express a particular target antigen. These antibodies possess an antigen-binding arm and an arm which binds a cytotoxic agent or a radionuclide chelator, such as EOTUBE, DPTA, DOTA, or TETA.

Techniques for making bispecific antibodies are known by those skilled in the art. In some embodiments, the bispecific antibodies comprise heavy chain constant regions with modifications in the amino acids which are part of the interface between the two heavy chains. In some embodiments, the bispecific antibodies can be generated using a "knobs-into-holes" strategy. In some cases, the "knobs" and "holes" terminology is replaced with the terms "protuberances" and "cavities". In some embodiments, the bispecific antibodies may comprise variant hinge regions incapable of forming disulfide linkages between the heavy chains. In some embodiments, the modifications may comprise changes in amino acids that result in altered electrostatic interactions. In some embodiments, the modifications may comprise changes in amino acids that result in altered hydrophobic/hydrophilic interactions.

Bispecific antibodies can be intact antibodies or antibody fragments comprising antigen-binding sites. Antibodies with more than two valencies are also contemplated. Thus, in certain embodiments the antibodies to RSPO proteins are multispecific.

In certain embodiments, the antibodies (or other polypeptides) described herein may be monospecific. In certain embodiments, each of the one or more antigen-binding sites that an antibody contains is capable of binding (or binds) a homologous epitope on RSPO proteins or a homologous epitope on LGR proteins. In certain embodiments, an antigen-binding site of a monospecific antibody described herein is capable of binding (or binds), for example, RSPO2 and RSPO3 (i.e., the same epitope is found on both RSPO2 and RSPO3 proteins).

In certain embodiments of the methods described herein, a RSPO-binding agent or LGR-binding agent is an antibody fragment. Antibody fragments may have different functions or capabilities than intact antibodies; for example, antibody fragments can have increased tissue penetration. Various techniques are known for the production of antibody fragments including, but not limited to, proteolytic digestion of intact antibodies. In some embodiments, antibody fragments include a F(ab')2 fragment produced by pepsin digestion of an antibody molecule. In some embodiments, antibody fragments include a Fab fragment generated by reducing the disulfide bridges of an F(ab')2 fragment. In other embodiments, antibody fragments include a Fab fragment generated by the treatment of the antibody molecule with papain and a reducing agent. In certain embodiments, antibody fragments are produced recombinantly. In some embodiments, antibody fragments include Fv or single chain Fv (scFv) fragments. Fab, Fv, and scFv antibody fragments can be expressed in and secreted from E. coli or other host cells, allowing for the production of large amounts of these fragments. In some embodiments, antibody fragments are isolated from antibody phage libraries as discussed herein. For example, methods can be used for the construction of Fab expression libraries to allow rapid and effective identification of monoclonal Fab fragments with the desired specificity for a RSPO protein or derivatives, fragments, analogs or homologs thereof. In some embodiments, antibody fragments are linear antibody fragments. In certain embodiments, antibody fragments are monospecific or bispecific. In certain embodiments, the RSPO-binding agent is a scFv. Various techniques can be used for the production of single-chain antibodies specific to one or more human RSPO proteins or one or more human LGR proteins.

It can further be desirable, especially in the case of antibody fragments, to modify an antibody in order to alter (e.g., increase or decrease) its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

Heteroconjugate antibodies are also within the scope of the present invention. Heteroconjugate antibodies are composed of two covalently joined antibodies. Such antibodies have, for example, been proposed to target immune cells to unwanted cells. It is also contemplated that the heteroconjugate antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

For the purposes of the present invention, it should be appreciated that modified antibodies can comprise any type of variable region that provides for the association of the antibody with the target (i.e., human RSPO). In this regard, the variable region may comprise or be derived from any type of mammal that can be induced to mount a humoral response and generate immunoglobulins against the desired antigen. As such, the variable region of the modified antibodies can be, for example, of human, murine, non-human primate (e.g. cynomolgus monkeys, macaques, etc.) or rabbit origin. In some embodiments, both the variable and constant regions of the modified immunoglobulins are human. In other embodiments, the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

In certain embodiments, the variable domains in both the heavy and light chains are altered by at least partial replacement of one or more CDRs and, if necessary, by partial framework region replacement and sequence modification and/or alteration. Although the CDRs may be derived from an antibody of the same class or even subclass as the antibody from which the framework regions are derived, it is envisaged that the CDRs may be derived from an antibody of different class and often from an antibody from a different species. It may not be necessary to replace all of the CDRs with all of the CDRs from the donor variable region to transfer the antigen binding capacity of one variable domain to another. Rather, it may only be necessary to transfer those residues that are required to maintain the activity of the antigen-binding site.

Alterations to the variable region notwithstanding, those skilled in the art will appreciate that the modified antibodies of this invention will comprise antibodies (e.g., full-length antibodies or immunoreactive fragments thereof) in which at least a fraction of one or more of the constant region domains has been deleted or otherwise altered so as to provide desired biochemical characteristics such as increased tissue localization or increased serum half-life when compared with an antibody of approximately the same immunogenicity comprising a native or unaltered constant region. In some embodiments, the constant region of the modified antibodies will comprise a human constant region.

Modifications to the constant region compatible with this invention comprise additions, deletions or substitutions of one or more amino acids in one or more domains. The modified antibodies disclosed herein may comprise alterations or modifications to one or more of the three heavy chain constant domains (CH1, CH2 or CH3) and/or to the light chain constant domain (CL). In some embodiments, one or more domains are partially or entirely deleted from the constant regions of the modified antibodies. In some embodiments, the modified antibodies will comprise domain deleted constructs or variants wherein the entire CH2 domain has been removed (ΔCH2 constructs). In some embodiments, the omitted constant region domain is replaced by a short amino acid spacer (e.g., 10 amino acid residues) that provides some of the molecular flexibility typically imparted by the absent constant region.

In some embodiments, the modified antibodies are engineered to fuse the CH3 domain directly to the hinge region of the antibody. In other embodiments, a peptide spacer is inserted between the hinge region and the modified CH2 and/or CH3 domains. For example, constructs may be expressed wherein the CH2 domain has been deleted and the remaining CH3 domain (modified or unmodified) is joined to the hinge region with a 5-20 amino acid spacer. Such a spacer may be added to ensure that the regulatory elements of the constant domain remain free and accessible or that the hinge region remains flexible. However, it should be noted that amino acid spacers may, in some cases, prove to be immunogenic and elicit an unwanted immune response against the construct. Accordingly, in certain embodiments, any spacer added to the construct will be relatively non-immunogenic so as to maintain the desired biological qualities of the modified antibodies.

In some embodiments, the modified antibodies may have only a partial deletion of a constant domain or substitution of a few or even a single amino acid. For example, the mutation of a single amino acid in selected areas of the CH2 domain may be enough to substantially reduce Fc binding and thereby increase cell localization and/or tissue penetration. Similarly, it may be desirable to simply delete the part of one or more constant region domains that control a specific effector function (e.g. complement C1q binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be modified through the mutation or substitution of one or more amino acids that enhances the profile of the resulting construct. In this respect it may be possible to disrupt the activity provided by a conserved binding site (e.g., Fc binding) while substantially maintaining the configuration and immunogenic profile of the modified antibody. In certain embodiments, the modified antibodies comprise the addition of one or more amino acids to the constant region to enhance desirable characteristics such as decreasing or increasing effector function or provide for more cytotoxin or carbohydrate attachment sites.

It is known in the art that the constant region mediates several effector functions. For example, binding of the C1 component of complement to the Fc region of IgG or IgM antibodies (bound to antigen) activates the complement system. Activation of complement is important in the opsonization and lysis of cell pathogens. The activation of complement also stimulates the inflammatory response and can also be involved in autoimmune hypersensitivity. In addition, the Fc region of an antibody can bind a cell expressing a Fc receptor (FcR). There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell cytotoxicity or ADCC), release of inflammatory mediators, placental transfer, and control of immunoglobulin production.

In certain embodiments, the modified antibodies provide for altered effector functions that, in turn, affect the biological profile of the administered antibody. For example, in some embodiments, the deletion or inactivation (through point mutations or other means) of a constant region domain may reduce Fc receptor binding of the circulating modified antibody thereby increasing cell localization and/or tissue penetration. In other embodiments, the constant region modifications increase the serum half-life of the antibody. In other embodiments, the constant region modifications reduce the serum half-life of the antibody. In some embodiments, the constant region is modified to eliminate disulfide linkages or oligosaccharide moieties. Modifications to the constant region in accordance with this invention may easily be made using well known biochemical or molecular engineering techniques.

In certain embodiments, a RSPO-binding agent or LGR-binding agent that is an antibody does not have one or more effector functions. For instance, in some embodiments, the antibody has no ADCC activity, and/or no complement-dependent cytotoxicity (CDC) activity. In certain embodiments, the antibody does not bind an Fc receptor, and/or complement factors. In certain embodiments, the antibody has no effector function.

The present invention further embraces variants and equivalents which are substantially homologous to the chimeric, humanized, and human antibodies, or antibody fragments thereof, set forth herein. These can contain, for example, conservative substitution mutations, i.e. the substitution of one or more amino acids by similar amino acids.

In certain embodiments, the antibodies described herein are isolated. In certain embodiments, the antibodies described herein are substantially pure.

In some embodiments of the present invention, the RSPO-binding agents or LGR-binding agents are polypeptides. The polypeptides can be recombinant polypeptides, natural polypeptides, or synthetic polypeptides comprising an antibody, or fragment thereof, that bind at least one RSPO protein and/or at least one LGR protein. It will be recognized in the art that some amino acid sequences of the invention can be varied without significant effect of the structure or function of the protein. Thus, the invention further includes variations of the polypeptides which show substantial activity or which include regions of an antibody, or fragment thereof, against a human RSPO protein or a human LGR protein. In some embodiments, amino acid sequence variations of RSPO-binding polypeptides or LGR-binding polypeptides include deletions, insertions, inversions, repeats, and/or other types of substitutions.

In certain embodiments, the polypeptides described herein are isolated. In certain embodiments, the polypeptides described herein are substantially pure.

The polypeptides, analogs and variants thereof, can be further modified to contain additional chemical moieties not normally part of the polypeptide. The derivatized moieties can improve or otherwise modulate the solubility, the biological half-life, and/or absorption of the polypeptide. The moieties can also reduce or eliminate undesirable side effects of the polypeptides and variants. An overview for chemical moieties can be found in Remington: The Science and Practice of Pharmacy, $22^{nd}$ Edition, 2012, Pharmaceutical Press, London.

The polypeptides described herein can be produced by any suitable method known in the art. Such methods range from direct protein synthesis methods to constructing a DNA sequence encoding polypeptide sequences and expressing those sequences in a suitable host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof.

In some embodiments, a DNA sequence encoding a polypeptide of interest may be constructed by chemical synthesis using an oligonucleotide synthesizer. Oligonucleotides can be designed based on the amino acid sequence of the desired polypeptide and selecting those codons that are favored in the host cell in which the recombinant polypeptide of interest will be produced. Standard methods can be applied to synthesize a polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis, or another method), the polynucleotide sequences encoding a particular polypeptide of interest can be inserted into an expression vector and operatively linked to an expression control sequence appropriate for expression of the protein in a desired host. Proper assembly can be confirmed by nucleotide sequencing, restriction enzyme mapping, and/or expression of a biologically active polypeptide in a suitable host. As is well-known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express DNA encoding antibodies, or fragments thereof, against a human RSPO protein or a human LGR protein. For example, recombinant expression vectors can be replicable DNA constructs which have synthetic or cDNA-derived DNA fragments encoding a polypeptide chain of a RSPO-binding agent, such as an anti-RSPO antibody, or fragment thereof, operatively linked to suitable transcriptional and/or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences. Regulatory elements can include an operator sequence to control transcription. The ability to replicate in a host, usually conferred by an origin of replication, and a selection gene to facilitate recognition of transformants can additionally be incorporated. DNA regions are "operatively linked" when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. In some embodiments, structural elements intended for use in yeast expression systems include a leader sequence enabling extracellular secretion of translated protein by a host cell. In other embodiments, in situations where recombinant protein is expressed without a leader or transport sequence, it can include an N-terminal methionine residue. This residue can optionally be subsequently cleaved from the expressed recombinant protein to provide a final product.

The choice of an expression control sequence and an expression vector depends upon the choice of host. A wide variety of expression host/vector combinations can be employed. Useful expression vectors for eukaryotic hosts include, for example, vectors comprising expression control sequences from SV40, bovine papilloma virus, adenovirus, and cytomegalovirus. Useful expression vectors for bacterial hosts include known bacterial plasmids, such as plasmids from *E. coli*, including pCR1, pBR322, pMB9 and their derivatives, and wider host range plasmids, such as M13 and other filamentous single-stranded DNA phages.

The RSPO-binding agents or the LGR-binding agents (e.g., polypeptides or antibodies) of the present invention can be expressed from one or more vectors. For example, in some embodiments, one heavy chain polypeptide is expressed by one vector, a second heavy chain polypeptide is expressed by a second vector and a light chain polypeptide is expressed by a third vector. In some embodiments, a first heavy chain polypeptide and a light chain polypeptide is expressed by one vector and a second heavy chain polypeptide is expressed by a second vector. In some embodiments, two heavy chain polypeptides are expressed by one vector and a light chain polypeptide is expressed by a second vector. In some embodiments, three polypeptides are expressed from one vector. Thus, in some embodiments, a first heavy chain polypeptide, a second heavy chain polypeptide, and a light chain polypeptide are expressed by a single vector.

Suitable host cells for expression of a RSPO-binding agent or LGR-binding agent (or a RSPO or LGR protein to use as an antigen) include prokaryotes, yeast cells, insect cells, or higher eukaryotic cells under the control of appropriate promoters. Prokaryotes include gram-negative or gram-positive organisms, for example *E. coli* or *Bacillus*. Higher eukaryotic cells include established cell lines of mammalian origin as described below. Cell-free translation systems may also be employed. Appropriate cloning and expression vectors for use with bacterial, fungal, yeast, and mammalian cellular hosts are known to one of skill in the art.

Various mammalian culture systems may be used to express recombinant polypeptides. Expression of recombinant proteins in mammalian cells may be desirable because these proteins are generally correctly folded, appropriately modified, and biologically functional. Examples of suitable mammalian host cell lines include, but are not limited to, COS-7 (monkey kidney-derived), L-929 (murine fibroblast-derived), C127 (murine mammary tumor-derived), 3T3 (murine fibroblast-derived), CHO (Chinese hamster ovary-derived), HeLa (human cervical cancer-derived), BHK (hamster kidney fibroblast-derived), HEK-293 (human embryonic kidney-derived) cell lines and variants thereof. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences.

Expression of recombinant proteins in insect cell culture systems (e.g., baculovirus) also offers a robust method for producing correctly folded and biologically functional proteins. Baculovirus systems for production of heterologous proteins in insect cells are well-known to those of skill in the art.

The proteins produced by a transformed host can be purified according to any suitable method. Standard methods include chromatography (e.g., ion exchange, affinity, and sizing column chromatography), centrifugation, differential solubility, or by any other standard technique for protein purification. Affinity tags such as hexa-histidine, maltose binding domain, influenza coat sequence, and glutathione-S-transferase can be attached to the protein to allow easy purification by passage over an appropriate affinity column. Affinity chromatography used for purifying immunoglobulins can include Protein A, Protein G, and Protein L chromatography. Isolated proteins can be physically characterized using such techniques as proteolysis, size exclusion chromatography (SEC), mass spectrometry (MS), nuclear magnetic resonance (NMR), isoelectric focusing (IEF), high performance liquid chromatography (HPLC), and x-ray crystallography. The purity of isolated proteins can be determined using techniques known to those of skill in the art, including but not limited to, SDS-PAGE, SEC, capillary gel electrophoresis, IEF, and capillary isoelectric focusing (cIEF).

In some embodiments, supernatants from expression systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. In some embodiments, an anion exchange resin can be employed, for example, a matrix or substrate having pendant diethylaminoethyl (DEAE) groups. The matrices can be acrylamide, agarose, dextran, cellulose, or other types commonly employed in protein purification. In some embodiments, a cation exchange step can be employed. Suitable cation exchangers include various insoluble matrices comprising sulfopropyl or carboxymethyl groups. In some embodiments, a hydroxyapatite media can be employed, including but not limited to, ceramic hydroxyapatite (CHT). In certain embodiments, one or more reverse-phase HPLC steps employing hydrophobic RP-HPLC media, e.g., silica gel having pendant methyl or other aliphatic groups, can be employed to further purify a recombinant protein (e.g., a RSPO-binding agent). Some or all of the foregoing purification steps, in various combinations, can be employed to provide a homogeneous recombinant protein.

In some embodiments, heterodimeric proteins such as bispecific antibodies are purified according the any of the methods described herein. In some embodiments, anti-RSPO or anti-LGR bispecific antibodies are isolated and/or purified using at least one chromatography step. In some embodiments, the at least one chromatography step comprises affinity chromatography. In some embodiments, the at least one chromatography step further comprises anion exchange chromatography. In some embodiments, the isolated and/or purified antibody product comprises at least 90% heterodimeric antibody. In some embodiments, the isolated and/or purified antibody product comprises at least 95%, 96%, 97%, 98% or 99% heterodimeric antibody. In some embodiments, the isolated and/or purified antibody product comprises about 100% heterodimeric antibody.

In some embodiments, recombinant protein produced in bacterial culture can be isolated, for example, by initial extraction from cell pellets, followed by one or more concentration, salting-out, aqueous ion exchange, or size exclusion chromatography steps. HPLC can be employed for final purification steps. Microbial cells employed in expression of a recombinant protein can be disrupted by any convenient method, including freeze-thaw cycling, sonication, mechanical disruption, or use of cell lysing agents.

In certain embodiments, the RSPO-binding agents or LGR-binding agents can be used in any one of a number of conjugated (i.e. an immunoconjugate or radioconjugate) or non-conjugated forms. In certain embodiments, the antibodies can be used in a non-conjugated form to harness the subject's natural defense mechanisms including complement-dependent cytotoxicity and antibody dependent cellular toxicity to eliminate hyperproliferative cells.

In some embodiments, the RSPO-binding agent or LGR-binding agent is conjugated to a cytotoxic agent. In some embodiments, the cytotoxic agent is a chemotherapeutic agent including, but not limited to, methotrexate, adriamicin, doxorubicin, melphalan, mitomycin C, chlorambucil, daunorubicin or other intercalating agents. In some embodiments, the cytotoxic agent is an enzymatically active toxin of bacterial, fungal, plant, or animal origin, or fragments thereof, including, but not limited to, diphtheria A chain, non-binding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. In some embodiments, the cytotoxic agent is a radioisotope to produce a radioconjugate or a radioconjugated antibody. A variety of radionuclides are available for the production of radioconjugated antibodies including, but not limited to $^{90}$Y, $^{125}$I, $^{131}$I, $^{123}$I, $^{111}$In, $^{131}$In, $^{105}$Rh, $^{153}$Sm, $^{67}$Cu, $^{67}$Ga, $^{166}$Ho, $^{177}$Lu, $^{186}$Re, $^{188}$Re and $^{212}$Bi. Conjugates of an antibody and one or more small molecule toxins, such as calicheamicins, maytansinoids, trichothenes, and CC 1065, and the derivatives of these toxins that have toxin activity, can also be used. Conjugates of an antibody and cytotoxic agent may be made using a variety of bifunctional protein-coupling agents such as N-succinimidyl-3-(2-pyridyidithiol) propionate (SPDP), iminothiolane (IT), bifunctional derivatives of imidoesters (such as dimethyl adipimidate HCl), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

IV. Polynucleotides

In certain embodiments, the invention encompasses polynucleotides comprising polynucleotides that encode a polypeptide (or a fragment of a polypeptide) that specifically binds at least one human RSPO protein or at least one human LGR protein. The term "polynucleotides that encode a polypeptide" encompasses a polynucleotide which includes only coding sequences for the polypeptide as well as a polynucleotide which includes additional coding and/or non-coding sequences. For example, in some embodiments, the invention provides a polynucleotide comprising a polynucleotide sequence that encodes an antibody to a human RSPO protein or encodes a fragment of such an antibody (e.g., a fragment comprising the antigen-binding site). In some embodiments, the invention provides a polynucleotide comprising a polynucleotide sequence that encodes an antibody to a human LGR protein or encodes a fragment of such an antibody (e.g., a fragment comprising the antigen-binding site). The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand.

In certain embodiments, the polynucleotide comprises a polynucleotide encoding a polypeptide comprising an amino acid sequence selected from the group consisting of: SEQ ID NO:11, SEQ ID NO:12, SEQ ID NO:13, SEQ ID NO:14, SEQ ID NO:15, SEQ ID NO:16, SEQ ID NO:27, SEQ ID NO:28, SEQ ID NO:29, SEQ ID NO:30, SEQ ID NO:31, SEQ ID NO:32, SEQ ID NO:46, SEQ ID NO:47, SEQ ID NO:48, SEQ ID NO:49, SEQ ID NO:50, SEQ ID NO:51, SEQ ID NO:56, SEQ ID NO:57, SEQ ID NO:58, SEQ ID NO:59, SEQ ID NO:60, SEQ ID NO:61, SEQ ID NO:66, SEQ ID NO:67, and SEQ ID NO:68. In some embodiments, the polynucleotide comprises a polynucleotide sequence selected from the group consisting of: SEQ ID NO:17, SEQ ID NO:18, SEQ ID NO:19, SEQ ID NO:20, SEQ ID NO:33, SEQ ID NO:34, SEQ ID NO:35, SEQ ID NO:36, SEQ ID NO:52, SEQ ID NO:53, SEQ ID NO:54, SEQ ID NO:55, SEQ ID NO:69, and SEQ ID NO:70.

In certain embodiments, the polynucleotide comprises a polynucleotide having a nucleotide sequence at least about 80% identical, at least about 85% identical, at least about 90% identical, at least about 95% identical, and in some embodiments, at least about 96%, 97%, 98% or 99% identical to a polynucleotide comprising a sequence selected from the group consisting of SEQ ID NO:17, SEQ ID NO:18, SEQ ID NO:19, SEQ ID NO:20, SEQ ID NO:33, SEQ ID NO:34, SEQ ID NO:35, SEQ ID NO:36, SEQ ID NO:52, SEQ ID NO:53, SEQ ID NO:54, and SEQ ID NO:55. Also provided is a polynucleotide that comprises a polynucleotide that hybridizes to SEQ ID NO:17, SEQ ID NO:18, SEQ ID NO:19, SEQ ID NO:20, SEQ ID NO:33, SEQ ID NO:34, SEQ ID NO:35, SEQ ID NO:36, SEQ ID NO:52, SEQ ID NO:53, SEQ ID NO:54, SEQ ID NO:55, SEQ ID NO:69, and SEQ ID NO:70. Also provided is a polynucleotide that comprises a polynucleotide that hybridizes to the complement of SEQ ID NO:17, SEQ ID NO:18, SEQ ID NO:19, SEQ ID NO:20, SEQ ID NO:33, SEQ ID NO:34, SEQ ID NO:35, SEQ ID NO:36, SEQ ID NO:52, SEQ ID NO:53, SEQ ID NO:54, SEQ ID NO:55, SEQ ID NO:69, and SEQ ID NO:70. In certain embodiments, the hybridization is under conditions of high stringency.

In certain embodiments, the polynucleotides comprise the coding sequence for the mature polypeptide fused in the same reading frame to a polynucleotide which aids, for example, in expression and secretion of a polypeptide from a host cell (e.g., a leader sequence which functions as a secretory sequence for controlling transport of a polypeptide from the cell). The polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains.

In certain embodiments, the polynucleotides comprise the coding sequence for the mature polypeptide fused in the same reading frame to a marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used. In some embodiments, the marker sequence is a FLAG-tag which can be used in conjunction with other affinity tags.

The present invention further relates to variants of the hereinabove described polynucleotides encoding, for example, fragments, analogs, and/or derivatives.

In certain embodiments, the present invention provides polynucleotides comprising polynucleotides having a nucleotide sequence at least about 80% identical, at least about 85% identical, at least about 90% identical, at least about 95% identical, and in some embodiments, at least about 96%, 97%, 98% or 99% identical to a polynucleotide encoding a polypeptide comprising a RSPO-binding agent (e.g., an antibody), or fragment thereof, described herein.

As used herein, the phrase a polynucleotide having a nucleotide sequence at least, for example, 95% "identical" to a reference nucleotide sequence is intended to mean that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

The polynucleotide variants can contain alterations in the coding regions, non-coding regions, or both. In some embodiments, a polynucleotide variant contains alterations which produce silent substitutions, additions, or deletions, but does not alter the properties or activities of the encoded polypeptide. In some embodiments, a polynucleotide variant comprises silent substitutions that result in no change to the amino acid sequence of the polypeptide (due to the degeneracy of the genetic code). In some embodiments, nucleotide variants comprise nucleotide sequences which result in expression differences (e.g., increased or decreased expression) at the transcript level. Polynucleotide variants can be produced for a variety of reasons, for example, to optimize codon expression for a particular host (i.e., change codons in the human mRNA to those preferred by a bacterial host such as E. coli). In some embodiments, a polynucleotide variant comprises at least one silent mutation in a non-coding or a coding region of the sequence.

In some embodiments, a polynucleotide variant is produced to modulate or alter expression (or expression levels) of the encoded polypeptide. In some embodiments, a polynucleotide variant is produced to increase expression of the encoded polypeptide. In some embodiments, a polynucleotide variant is produced to decrease expression of the encoded polypeptide. In some embodiments, a polynucleotide variant has increased expression of the encoded polypeptide as compared to a parental polynucleotide sequence. In some embodiments, a polynucleotide variant has decreased expression of the encoded polypeptide as compared to a parental polynucleotide sequence.

In some embodiments, at least one polynucleotide variant is produced (without changing the amino acid sequence of the encoded polypeptide) to increase production of a heteromultimeric molecule. In some embodiments, at least one polynucleotide variant is produced (without changing the amino acid sequence of the encoded polypeptide) to increase production of a bispecific antibody.

In certain embodiments, the polynucleotides are isolated. In certain embodiments, the polynucleotides are substantially pure.

Vectors comprising the polynucleotides described herein are also provided. Cells comprising the polynucleotides described herein are also provided. In some embodiments, an expression vector comprises a polynucleotide molecule. In some embodiments, a host cell comprises an expression vector comprising the polynucleotide molecule. In some embodiments, a host cell comprises a polynucleotide molecule.

V. Kits Comprising RSPO-Binding Agents

The present invention provides kits that comprise the RSPO-binding agents or LGR-binding agents (e.g., antibodies or soluble receptors) described herein and that can be used to perform the methods described herein. In certain embodiments, a kit comprises at least one purified antibody against at least one human RSPO protein in one or more containers. In certain embodiments, a kit comprises at least one purified antibody against at least one human LGR protein in one or more containers. In certain embodiments, a kit comprises at least one purified soluble receptor that binds at least one human RSPO protein in one or more containers. In some embodiments, the kits contain all of the components necessary and/or sufficient to perform a detection assay, including all controls, directions for performing assays, and any necessary software for analysis and presentation of results. One skilled in the art will readily recognize that the disclosed RSPO-binding agents and/or LGR-binding proteins of the present invention can be readily incorporated into one of the established kit formats which are well known in the art.

Further provided are kits comprising a RSPO-binding agent or a LGR-binding agent (e.g., an antibody or a soluble receptor), as well as at least one additional therapeutic agent. In certain embodiments, the second (or more) therapeutic agent is an anti-inflammatory agent. In certain embodiments, the second (or more) therapeutic agent is a Wnt pathway inhibitor.

Embodiments of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, may be practiced without departing from the scope of the present disclosure.

EXAMPLES

Example 1

Lung Fibrosis Model

Induction of lung fibrosis in a mouse model is described in Baran et al., 2011, *Am. J. Respir. Cell Mol. Biol.*, 45:999-1006 and Dakhlallah et al., 2013, *Am J. Respir. Crit. Care Med.*, 187:397-405 and this model was generally followed. Briefly, 6 to 8-week-old C57BL/6N mice were injected intraperitoneally with 0.035 U/g bleomycin or vehicle (saline). 100 µl of bleomycin dissolved in 0.9% NaCl at a concentration of 7 U/ml was administered to mice on Day 1, 4, 9, 12, 15, 18, 22, 25, 29, and 32. On Day 9, 16, 22, 29, and 33 five representative mice were euthanized. Tissue fragments from the lungs were harvested for gene expression analysis. The remaining lung tissue was perfused with formalin and stored for histological analysis.

Histological analysis of the lung tissue from mice injected with bleomycin showed evidence of fibrosis at Day 16, with maximum fibrosis observed at Day 29. Gene expression of Rspo1, Rspo2, and Rspo3 in lung tissue from mice injected with bleomycin was assessed by quantitative RT-PCR. Gene expression in lung tissue from mice injected with bleomycin at a given timepoint is relative to gene expression in lung tissue from mice injected with saline. For analysis, glucoronidase beta (Gusb) was used for normalization.

As shown in FIG. 1, Rspo2 expression in lung tissue from mice injected with bleomycin was up-regulated at Day 9 and Day 16, followed by down-regulation on Day 22, 26, and 33. In contrast, gene expression of Rspo1 and Rspo3 was down-regulated at Day 9 and continued to be down-regulated through Day 33.

The elevation of Rspo2 gene expression detected at Day 9 and Day 16 coincided with the presence of infiltrating inflammatory cells into the lung tissue and the onset of lung fibrosis, suggesting that RSPO proteins, particularly RSPO2, may be involved in the fibrotic process.

Example 2

Skin Fibrosis Model

Induction of dermal fibrosis in a mouse model using bleomycin is described in Distler et al., 2007, *Arthritis & Rheumatism*, 56(1):311-322 and this model was generally followed. Briefly, 6 to 8-week-old mice were injected with bleomycin by subcutaneous injection into defined regions of the upper back. Injection site regions were approximately 1 cm² in size and located on the dorsolateral region of the mouse's back (approximately 2 cm laterally from the spinal cord). There were two injection sites per mouse. 1041 of bleomycin dissolved in 0.9% NaCl at a concentration of 0.5 mg/ml was administered on Day 1, 3, 5, 8, and 10. On Day 2, 5, 8, and 12, four representative mice were euthanized. Tissue fragments from the injection sites were harvested for gene expression analysis and formalin-fixed for histological analysis.

Gene expression in skin tissue from mice injected with bleomycin at a given timepoint is relative to gene expression in skin tissue from naïve mice. For analysis, glucuronidase beta was used for normalization.

Figure 2:
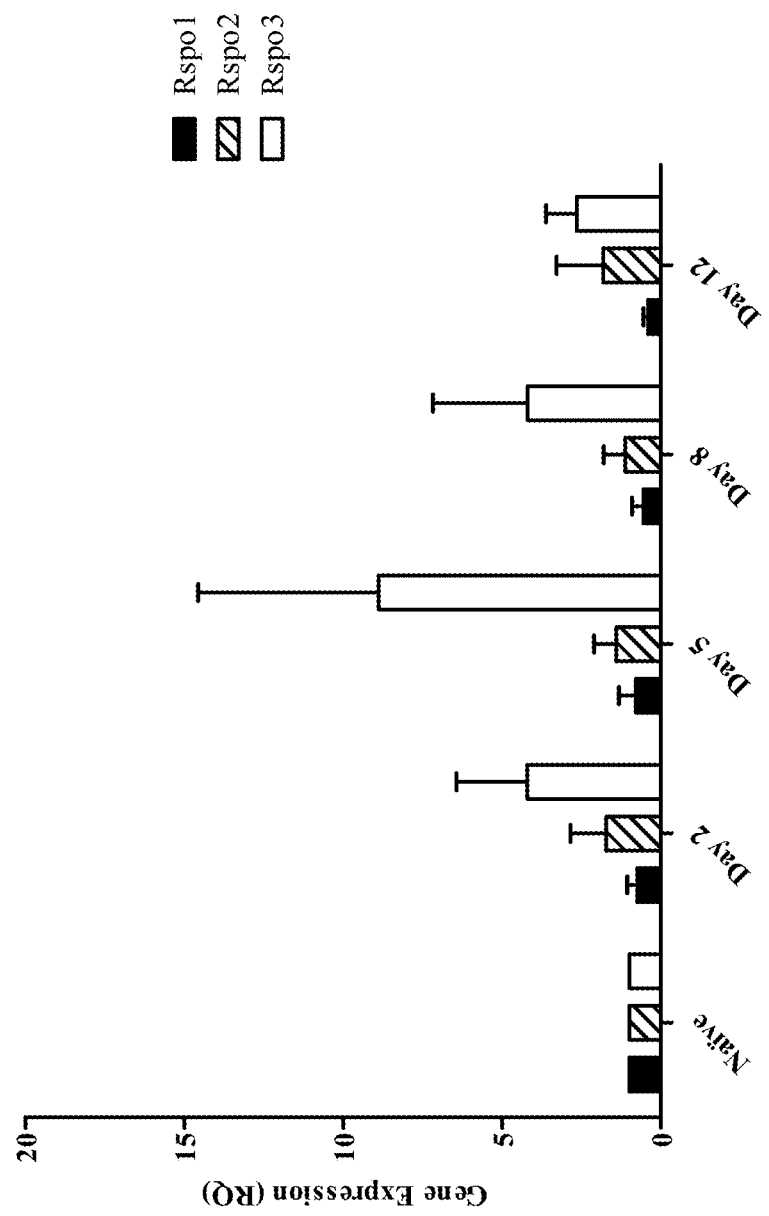
FIG. 2. RSPO expression in bleomycin-induced dermal fibrosis model.

As shown in FIG. 2, Rspo3 expression in skin tissue at the bleomycin injection site was up-regulated 24 hours after the first injection (Day 2) and peaked at Day 5. Rspo3 was still up-regulated on Day 8 and Day 12, but expression levels had decreased from Day 5. Expression levels of Rspo1 did not appear to be affected at the bleomycin injection site in this model, while Rspo2 appeared to be slightly up-regulated.

The observed elevation of Rspo3 gene expression as early as 24 hours after the first injection of bleomycin suggests that RSPO proteins may be involved in the early events of fibrosis. The strong up-regulation of Rspo3 gene expression in the dermal fibrosis model contrasts with the induction of Rspo2 gene expression in the lung fibrosis model. These results suggest that there may be tissue-specific roles for RSPO proteins in the onset and progression of different types of fibrosis.

Example 3

Effect of Anti-RSPO Antibodies on Induction of Skin Lesions by Bleomycin

Dermal fibrosis was induced in mice as described above in Example 2. Six to 8-week-old mice were injected with bleomycin by subcutaneous injection into two defined regions of the upper back. 100 µl of bleomycin dissolved in 0.9% NaCl at a concentration of 0.5 mg/ml was administered on Day 1, 3, 5, 8, and 10. Control antibody 1B7.11, anti-RSPO2 antibody 130M23, anti-RSPO3 antibody 131R010, or a combination of anti-RSPO2 antibody 130M23 and anti-RSPO3 antibody 131R010 were administered at a dose of 25 mg/kg on Day 1 and 8. Four mice were treated in the control antibody group and eight mice were treated in each anti-RSPO antibody group.

Figure 3:
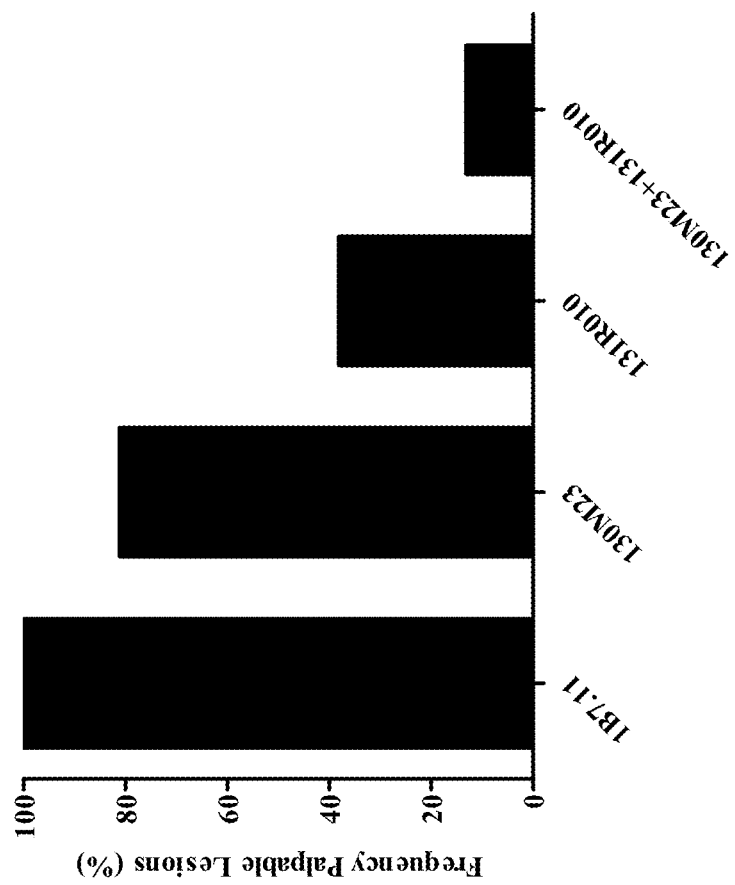
FIG. 3. Inhibition of bleomycin-induced dermal lesions by RSPO antibodies.

On Day 12, palpable skin lesions were present at injection sites on each of the control antibody mice, 8 of 8 injection sites, for a frequency of 100%. In mice treated with anti-RSPO2 antibody 130M23 there were palpable skin lesions at 13 of 16 injection sites, for a frequency of 81%. In mice treated with anti-RSPO3 antibody 131R010, there were palpable lesions at 6 of 16 injection sites for a frequency of 38%. In mice treated with a combination of anti-RSPO2 antibody 130M23 and anti-RSPO3 antibody 131R010, there were palpable lesions at only 2 of 16 injection sites for a frequency of 13%. These results are represented in FIG. 3.

Tissue from the injection site regions was harvested on Day 12 and the tissue was used for gene expression analysis and for histological analysis. Gene expression of several genes was assessed by quantitative RT-PCR. Genes included chemokine (C-X-C motif) ligand 1 (Cxcl1), endoglin (Eng), interferon gamma (Ifng), interleukin 16 (Il16), tumor necrosis factor (Tnf), axin2 (Axin2), leucine-rich repeat containing G protein-coupled receptor 5 (Lgr5), R-spondin 1 (Rspo1), R-spondin 3 (Rspo3), and smooth muscle actin (Acta2).

Figure 4:
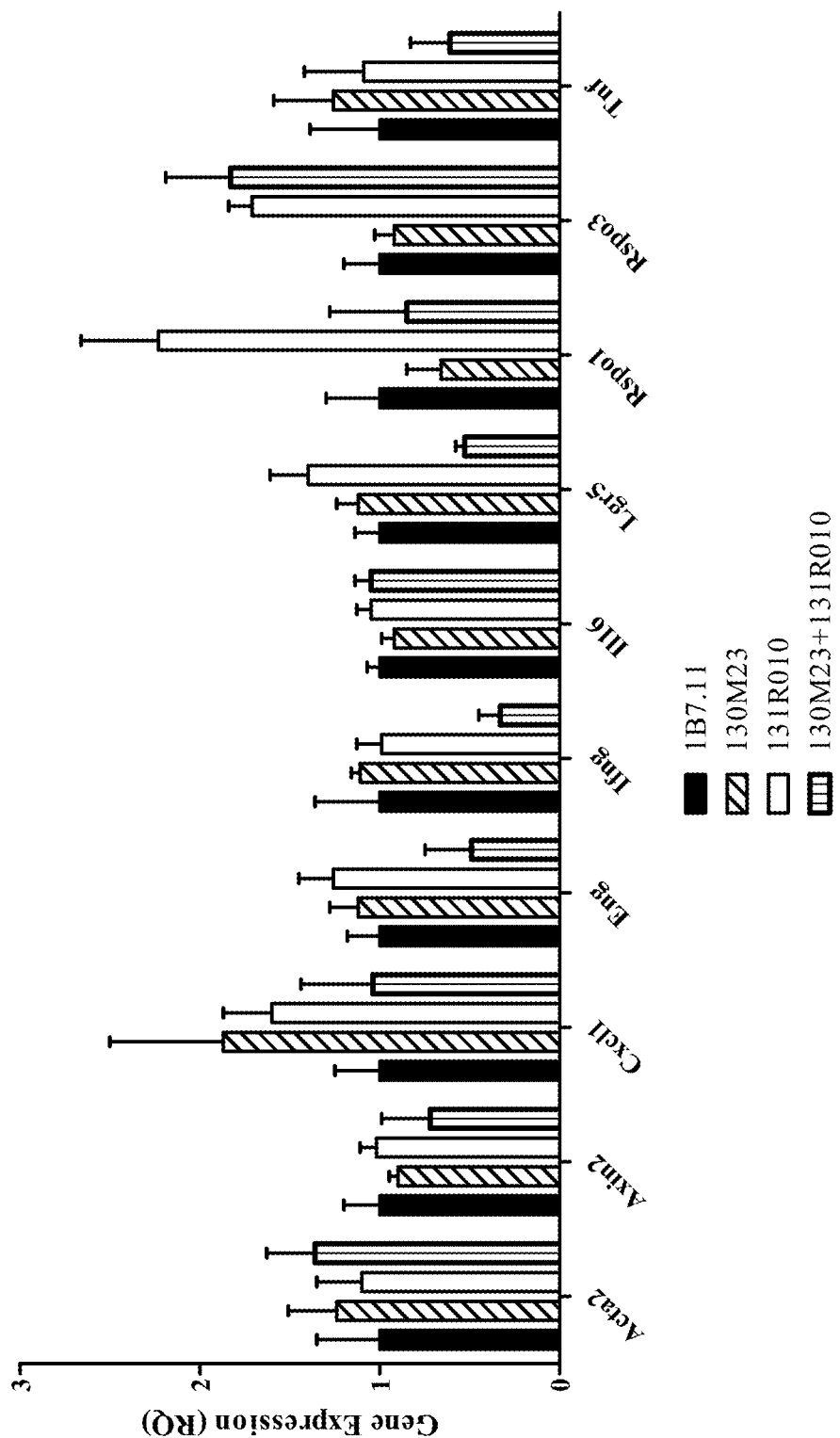
FIG. 4. Gene expression in tissue from bleomycin-induced dermal lesions. Tissue samples were taken from Day 12.
Figure 5:
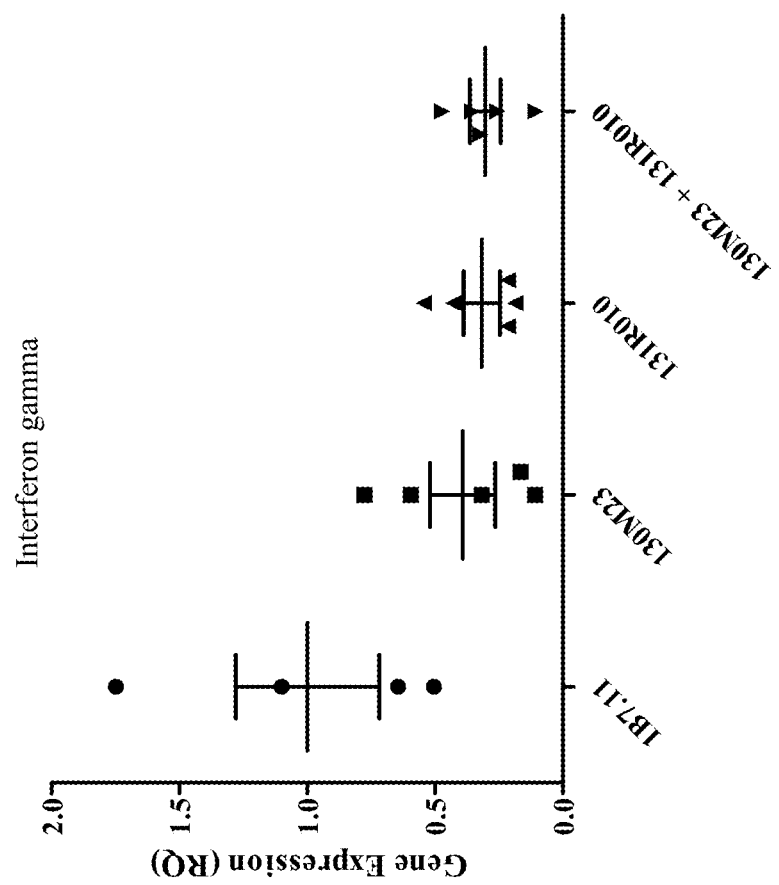
FIG. 5. Gene expression of interferon gamma from bleomycin-induced dermal lesions. Tissue samples were taken 24 hours after administration of a single dose of bleomycin and a single dose of anti-RSPO antibodies.

As shown in FIG. 4, treatment with a combination of anti-RSPO2 antibody 130M23 and anti-RSPO3 131R010 reduced expression of genes involved in inflammation including interferon gamma, tumor necrosis factor, and endoglin (as assessed on Day 12). This treatment also reduced gene expression of Wnt-pathway related gene Lgr5 and to a lesser extent Axin2. At Day 12, treatment with anti-RSPO2 antibody 130M23 and anti-RSPO3 antibody 131R010 as single agents did not reduce expression of these genes. Interestingly, 24 hours after administration of a single dose of bleomycin and a single dose of anti-RSPO antibodies, gene expression of interferon gamma was significantly reduced by the anti-RSPO antibodies as single agents as well as in combination (FIG. 5).

These results show that treatment with an anti-RSPO3 antibody either alone, or in combination with an anti-RSPO2 antibody has the ability to strongly inhibit formation of dermal lesions induced by bleomycin. The reduction in the incidence of palpable dermal lesions and the down-regulation of genes associated with Wnt signaling and inflammation by administration with anti-RSPO2 antibody 130M23 in combination with anti-RSPO3 antibody 131R010 suggests that multiple RSPO proteins may be involved in the onset and development of fibrosis. These results support the hypothesis that anti-RSPO antagonists, such as anti-RSPO antibodies, may be efficacious in treating fibrotic diseases.

It is understood that the examples and embodiments described herein are for illustrative purposes only and that various modifications or changes in light thereof will be suggested to person skilled in the art and are to be included within the spirit and purview of this application.

All publications, patents, patent applications, internet sites, and accession numbers/database sequences including both polynucleotide and polypeptide sequences cited herein are hereby incorporated by reference herein in their entirety for all purposes to the same extent as if each individual publication, patent, patent application, internet site, or accession number/database sequence were specifically and individually indicated to be so incorporated by reference.

The sequences disclosed in the application are:

```
Human RSPO1 amino acid sequence with signal
sequence
                                       (SEQ ID NO: 1)
MRLGLCVVALVLSWTHLTISSRGIKGKRQRRISAEGSQACAKGCELCSEV

NGCLKCSPKLFILLERNDIRQVGVCLPSCPPGYFDARNPDMNKCIKCKIE

HCEACFSHNFCTKCKEGLYLHKGRCYPACPEGSSAANGTMECSSPAQCEM

SEWSPWGPCSKKQQLCGFRRGSEERTRRVLHAPVGDHAACSDTKETRRCT

VRRVPCPEGQKRRKGGQGRRENANRNLARKESKEAGAGSRRRKGQQQQQQ

QGTVGPLTSAGPA

Human RSPO2 amino acid sequence with signal
sequence
                                       (SEQ ID NO: 2)
MQFRLFSFALIILNCMDYSHCQGNRWRRSKRASYVSNPICKGCLSCSKDN

GCSRCQQKLFFFLRREGMRQYGECLHSCPSGYYGHRAPDMNRCARCRIEN

CDSCFSKDFCTKCKVGFYLHRGRCFDECPDGFAPLEETMECVEGCEVGHW

SEWGTCSRNNRTCGFKWGLETRTRQIVKKPVKDTIPCPTIAESRRCKMTM

RHCPGGKRTPKAKEKRNKKKKRKLIERAQEQHSVFLATDRANQ

Human RSPO3 amino acid sequence with signal
sequence
                                       (SEQ ID NO: 3)
MHLRLISWLFIILNFMEYIGSQNASRGRRQRRMHPNVSQGCQGGCATCSD

YNGCLSCKPRLFFALERIGMKQIGVCLSSCPSGYYGTRYPDINKCTKCKA

DCDTCFNKNFCTKCKSGFYLHLGKCLDNCPEGLEANNHTMECVSIVHCEV

SEWNPWSPCTKKGKTCGFKRGTETRVREIIQHPSAKGNLCPPTNETRKCT

VQRKKCQKGERGKKGRERKRKKPNKGESKEAIPDSKSLESSKEIPEQREN

KQQQKKRKVQDKQKSVSVSTVH

Human RSPO4 amino acid sequence with signal
sequence
                                       (SEQ ID NO: 4)
MRAPLCLLLLVAHAVDMLALNRRKKQVGTGLGGNCTGCIICSEENGCSTC

QQRLFLFIRREGIRQYGKCLHDCPPGYFGIRGQEVNRCKKCGATCESCFS

QDFCIRCKRQFYLYKGKCLPTCPPGTLAHQNTRECQGECELGPWGGWSPC

THNGKTCGSAWGLESRVREAGRAGHEEAATCQVLSESRKCPIQRPCPGER

SPGQKKGRKDRRPRKDRKLDRRLDVRPRQPGLQP

89M5 Heavy chain CDR1
                                       (SEQ ID NO: 5)
TGYTMH 89M5 Heavy chain CDR2
                                       (SEQ ID NO: 6)
GINPNNGGTTYNQNFKG 89M5 Heavy chain CDR3
                                       (SEQ ID NO: 7)
KEFSDGYYFFAY 89M5 Light chain CDR1
                                       (SEQ ID NO: 8)
KASQDVIFAVA 89M5 Light chain CDR2
                                       (SEQ ID NO: 9)
WASTRHT 89M5 Light chain CDR3
                                       (SEQ ID NO: 10)
QQHYSTPW h89M5-H8L5 Heavy chain variable region amino acid
sequence
                                       (SEQ ID NO: 11)
EVQLVQSGAEVKKPGESLRISCKGSGYSFTGYTMHWVRQMPGKGLEWMGG

INPNNGGTTYNQNFKGHVTISADKSISTAYLQWSSLKASDTAMYYCARKE

FSDGYYFFAYWGQGTLVTVSS h89M5-H8L5 Light chain variable region amino acid
sequence
                                       (SEQ ID NO: 12)
DIVMTQSPDSLAVSLGERATINCKASQDVIFAVAWYQQKPGQPPKLLIYW

ASTRHTGVPDRFSGSGSGTDFTLTISSLQAEDVAVYYCQQHYSTPWTFGG

GTKVEIK h89M5-H8L5 Heavy chain amino acid sequence with
predicted signal sequence underlined
                                       (SEQ ID NO: 13)
MDWTWRILFLVAAATGAHSEVQLVQSGAEVKKPGESLRISCKGSGYSFTG

YTMHWVRQMPGKGLEWMGGINPNNGGTTYNQNFKGHVTISADKSISTAYL

QWSSLKASDTAMYYCARKEFSDGYYFFAYWGQGTLVTVSSASTKGPSVFP

LAPSSKSTSGGTAALGCLVKDYFPEPVTVSWNSGALTSGVHTFPAVLQSS

GLYSLSSVVTVPSSSLGTQTYICNVNHKPSNTKVDKRVEPKSCDKTHTCP

PCPAPELLGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKA

LPAPIEKTISKAKGQPREPQVYTLPPSREEMTKNQVSLTCLVKGFYPSDI

AVEWESNGQPENNYKTTPPVLDSDGSFFLYSKLTVDKSRWQQGNVFSCSV

MHEALHNHYTQKSLSLSPGK h89M5-H8L5 Heavy chain amino acid sequence without
predicted signal sequence
                                       (SEQ ID NO: 14)
EVQLVQSGAEVKKPGESLRISCKGSGYSFTGYTMHWVRQMPGKGLEWMGG

INPNNGGTTYNQNFKGHVTISADKSISTAYLQWSSLKASDTAMYYCARKE

FSDGYYFFAYWGQGTLVTVSSASTKGPSVFPLAPSSKSTSGGTAALGCLV

KDYFPEPVTVSWNSGALTSGVHTFPAVLQSSGLYSLSSVVTVPSSSLGTQ
```

-continued

TYICNVNHKPSNTKVDKRVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSREEMTKNQVSLTCLVKGFYPSDIAVEWESNGQPENNYKTTPP

VLDSDGSFFLYSKLTVDKSRWQQGNVFSCSVMHEALHNHYTQKSLSLSPG

K h89M5-H8L5 Light chain amino acid sequence with
predicted signal sequence underlined
(SEQ ID NO: 15)
<u>MVLQTQVFISLLLWISGAYG</u>DIVMTQSPDSLAVSLGERATINCKASQDVI

FAVAWYQQKPGQPPKLLIYWASTRHTGVPDRFSGSGSGTDFTLTISSLQA

EDVAVYYCQQHYSTPWTFGGGTKVEIKRTVAAPSVFIFPPSDEQLKSGTA

SVVCLLNNFYPREAKVQWKVDNALQSGNSQESVTEQDSKDSTYSLSNTLT

LSKADYEKHKVYACEVTHQGLSSPVTKSFNRGEC h89M5-H8L5 Light chain amino acid sequence without
predicted signal sequence
(SEQ ID NO: 16)
DIVMTQSPDSLAVSLGERATINCKASQDVIFAVAWYQQKPGQPPKLLIYW

ASTRHTGVPDRFSGSGSGTDFTLTISSLQAEDVAVYYCQQHYSTPWTFGG

GTKVEIKRTVAAPSVFIFPPSDEQLKSGTASVVCLLNNFYPREAKVQWKV

DNALQSGNSQESVTEQDSKDSTYSLSNTLTLSKADYEKHKVYACEVTHQG

LSSPVTKSFNRGEC h89M5-H8L5 Heavy chain variable region nucleotide
sequence
(SEQ ID NO: 17)
GAAGTGCAGCTGGTGCAGTCTGGAGCAGAGGTCAAAAAGCCCGGGGAGTC

TCTGAGGATCTCCTGCAAGGGTTCTGGATACAGCTTTACTGGATACACCA

TGCACTGGGTGCGCCAGATGCCCGGGAAAGGACTGGAGTGGATGGGGGGT

ATTAATCCTAACAATGGTGGTACTACTTACAACCAGAACTTCAAGGGCCA

CGTCACCATCTCAGCTGACAAGTCCATCAGCACTGCCTACCTGCAATGGA

GCAGCCTGAAGGCTTCTGACACCGCCATGTATTACTGTGCAAGAAAGGAG

TTCTCTGATGGATACTACTTTTTTGCTTACTGGGGCCAAGGGACCCTGGT

GACCGTCAGCTCA h89M5-H8L5 Light chain variable region nucleotide
sequence
(SEQ ID NO: 18)
GACATCGTGATGACCCAGTCTCCAGACTCCCTGGCTGTGTCTCTGGGCGA

GAGGGCCACCATCAACTGCAAGGCTTCCCAGGACGTGATTTTTGCTGTTG

CCTGGTATCAGCAGAAACCAGGACAGCCTCCTAAGCTGCTCATTTACTGG

GCATCTACCCGCCACACTGGGGTCCCTGACCGCTTCAGTGGCAGCGGGTC

TGGGACAGATTTCACTCTCACCATCAGCAGCCTCCAGGCTGAAGATGTGG

CAGTTTATTACTGTCAGCAACATTATAGCACTCCTTGGACTTTCGGCGGA

GGGACCAAGGTGGAGATCAAA h89M5-H8L5 Heavy chain nucleotide sequence
(SEQ ID NO: 19)
ATGGACTGGACCTGGAGGATACTCTTTCTCGTGGCGGCAGCCACAGGAGC

CCACTCCGAAGTGCAGCTGGTGCAGTCTGGAGCAGAGGTCAAAAAGCCCG

GGGAGTCTCTGAGGATCTCCTGCAAGGGTTCTGGATACAGCTTTACTGGA

TACACCATGCACTGGGTGCGCCAGATGCCCGGGAAAGGACTGGAGTGGAT

GGGGGGTATTAATCCTAACAATGGTGGTACTACTTACAACCAGAACTTCA

AGGGCCACGTCACCATCTCAGCTGACAAGTCCATCAGCACTGCCTACCTG

CAATGGAGCAGCCTGAAGGCTTCTGACACCGCCATGTATTACTGTGCAAG

AAAGGAGTTCTCTGATGGATACTACTTTTTTGCTTACTGGGGCCAAGGGA

CCCTGGTGACCGTCAGCTCAGCCAGCACAAAGGGCCCCTCCGTGTTCCCT

CTGGCCCCTTCCTCCAAGTCCACCTCCGGCGGCACCGCCGCTCTGGGCTG

CCTGGTGAAGGACTACTTCCCTGAGCCTGTGACCGTGTCCTGGAACTCTG

GCGCACTGACCTCTGGCGTGCACACCTTCCCAGCCGTGCTCCAGTCCTCC

GGCCTGTACTCCCTGTCCTCCGTCGTCACCGTGCCTTCCTCCTCCCTGGG

CACCCAGACCTACATCTGCAACGTGAACCACAAGCCTTCCAACACAAAGG

TGGACAAGCGGGTGGAGCCTAAGTCCTGCGACAAGACCCACACCTGCCCT

CCCTGCCCTGCCCCTGAGCTGCTGGGCGGACCTTCCGTGTTCCTGTTCCC

TCCTAAGCCTAAGGACACCCTGATGATCTCCCGGACCCCTGAAGTGACAT

GCGTGGTGGTGGACGTGTCCCACGAGGACCCTGAGGTGAAGTTCAACTGG

TATGTGGACGGCGTGGAGGTGCACAACGCTAAGACCAAGCCGAGGGAGGA

GCAGTACAACTCCACCTACCGGGTGGTGTCTGTGCTGACCGTGCTGCACC

AGGACTGGCTGAACGGCAAAGAATACAAGTGCAAGGTCTCCAACAAGGCC

CTGCCCGCTCCCATCGAGAAACCATCAGCAAGGCAAAGGGCCAGCCTCG

CGAGCCTCAGGTGTACACCCTGCCACCCAGCCGGGAGGAGATGACCAAGA

ACCAGGTGTCCCTGACCTGTCTGGTGAAGGGCTTTTACCCTTCCGATATT

GCCGTGGAGTGGGAGTCTAACGGCCAGCCCGAGAACAACTACAAGACCAC

CCCTCCTGTGCTGGACTCCGACGGCTCCTTCTTCCTGTACTCCAAGCTGA

CCGTGGACAAGTCCCGGTGGCAGCAGGGCAACGTGTTCTCCTGCTCCGTG

ATGCACGAGGCCCTGCACAACCACTACACCCAGAAGAGCCTGTCTCTGTC

TCCTGGCAAGTGA h89M5-H8L5 Light chain nucleotide sequence
(SEQ ID NO: 20)
ATGGTGCTCCAGACCCAGGTCTTCATTTCTCTGCTCCTCTGGATCTCTGG

TGCCTACGGGGACATCGTGATGACCCAGTCTCCAGACTCCCTGGCTGTGT

CTCTGGGCGAGAGGGCCACCATCAACTGCAAGGCTTCCCAGGACGTGATT

TTTGCTGTTGCCTGGTATCAGCAGAAACCAGGACAGCCTCCTAAGCTGCT

CATTTACTGGGCATCTACCCGCCACACTGGGGTCCCTGACCGCTTCAGTG

GCAGCGGGTCTGGGACAGATTTCACTCTCACCATCAGCAGCCTCCAGGCT

GAAGATGTGGCAGTTTATTACTGTCAGCAACATTATAGCACTCCTTGGAC

TTTCGGCGGAGGGACCAAGGTGGAGATCAAACGGACTGTGGCTGCACCAT

CTGTCTTCATCTTCCCTCCATCTGATGAGCAGTTGAAATCTGGAACTGCC

TCTGTTGTGTGCCTGCTGAATAACTTCTATCCCAGAGAGGCCAAAGTCCA

GTGGAAGGTGGATAACGCCCTCCAATCCGGTAACTCCCAGGAGAGTGTCA

CAGAGCAGGACAGCAAGGACAGCACCTACAGCCTCAGCAACACCCTGACA

CTGAGCAAAGCAGACTACGAGAAACACAAAGTCTATGCCTGCGAAGTCAC

-continued
CCATCAGGGCCTGTCTTCCCCCGTCACAAAGAGCTTCAACAGGGGAGAGT

GCTAA

130M23 Heavy chain CDR1
(SEQ ID NO: 21)
SSYAMS

130M23 Heavy chain CDR2
(SEQ ID NO: 22)
SISSGGSTYYPDSVKG

130M23 Heavy chain CDR3
(SEQ ID NO: 23)
RGGDPGVYNGDYEDAMDY

130M23 Light chain CDR1
(SEQ ID NO: 24)
KASQDVSSAVA

130M23 Light chain CDR2
(SEQ ID NO: 25)
WASTRHT

130M23 Light chain CDR3
(SEQ ID NO: 26)
QQHYSTP h130M23-H1L6 Heavy chain variable region amino
acid sequence
(SEQ ID NO: 27)
EVQLVESGGGLVKPGGSLRLSCAASGFTFSSYAMSWVRQAPGKGLEWVSS

ISSGGSTYYPDSVKGRFTISRDNAKNSLYLQMNSLRAEDTAVYYCARGGD

PGVYNGDYEDAMDYWGQGTTVTVSS h130M23-H1L6 Light chain variable region amino
acid sequence
(SEQ ID NO: 28)
DIQMTQSPSSLSASVGDRVTITCKASQDVSSAVAWYQQKPGKAPKLLIYW

ASTRHTGVPSRFSGSGSGTDFTLTISSLQPEDFATYYCQQHYSTPWTFGQ

GTKVEIK h130M23-H1L6 Heavy chain amino acid sequence with
predicted signal sequence underlined
(SEQ ID NO: 29)
<u>MELGLRWVFLVAILEGVQC</u>EVQLVESGGGLVKPGGSLRLSCAASGFTFSS

YAMSWVRQAPGKGLEWVSSISSGGSTYYPDSVKGRFTISRDNAKNSLYLQ

MNSLRAEDTAVYYCARGGDPGVYNGDYEDAMDYWGQGTTVTVSSASTKGP

SVFPLAPCSRSTSESTAALGCLVKDYFPEPVTVSWNSGALTSGVHTFPAV

LQSSGLYSLSSVVTVPSSNFGTQTYTCNVDHKPSNTKVDKTVERKCCVEC

PPCPAPPVAGPSVFLFPPKPKDTLMISRTPEVTCVVVDVSHEDPEVQFNW

YVDGVEVHNAKTKPREEQFNSTFRVVSVLTVVHQDWLNGKEYKCKVSNKG

LPAPIEKTISKTKGQPREPQVYTLPPSREEMTKNQVSLTCLVKGFYPSDI

AVEWESNGQPENNYKTTPPMLDSDGSFFLYSKLTVDKSRWQQGNVFSCSV

MHEALHNHYTQKSLSLSPGK h130M23-H1L6 Heavy chain amino acid sequence
without predicted signal sequence
(SEQ ID NO: 30)
EVQLVESGGGLVKPGGSLRLSCAASGFTFSSYAMSWVRQAPGKGLEWVSS

ISSGGSTYYPDSVKGRFTISRDNAKNSLYLQMNSLRAEDTAVYYCARGGD

PGVYNGDYEDAMDYWGQGTTVTVSSASTKGPSVFPLAPCSRSTSESTAAL

GCLVKDYFPEPVTVSWNSGALTSGVHTFPAVLQSSGLYSLSSVVTVPSSN

FGTQTYTCNVDHKPSNTKVDKTVERKCCVECPPCPAPPVAGPSVFLFPPK

PKDTLMISRTPEVTCVVVDVSHEDPEVQFNWYVDGVEVHNAKTKPREEQF

NSTFRVVSVLTVVHQDWLNGKEYKCKVSNKGLPAPIEKTISKTKGQPREP

QVYTLPPSREEMTKNQVSLTCLVKGFYPSDIAVEWESNGQPENNYKTTPP

MLDSDGSFFLYSKLTVDKSRWQQGNVFSCSVMHEALHNHYTQKSLSLSPG

K h130M23-H1L6 Light chain amino acid sequence with
predicted signal sequence underlined
(SEQ ID NO: 31)
<u>MGIKMESQIQAFVFVFLWLSGVDG</u>DIQMTQSPSSLSASVGDRVTITCKAS

QDVSSAVAWYQQKPGKAPKLLIYWASTRHTGVPSRFSGSGSGTDFTLTIS

SLQPEDFATYYCQQHYSTPWTFGQGTKVEIKRTVAAPSVFIFPPSDEQLK

SGTASVVCLLNNFYPREAKVQWKVDNALQSGNSQESVTEQDSKDSTYSLS

NTLTLSKADYEKHKVYACEVTHQGLSSPVTKSFNRGEC h130M23-H1L6 Light chain amino acid sequence
without predicted signal sequence
(SEQ ID NO: 32)
DIQMTQSPSSLSASVGDRVTITCKASQDVSSAVAWYQQKPGKAPKLLIYW

ASTRHTGVPSRFSGSGSGTDFTLTISSLQPEDFATYYCQQHYSTPWTFGQ

GTKVEIKRTVAAPSVFIFPPSDEQLKSGTASVVCLLNNFYPREAKVQWKV

DNALQSGNSQESVTEQDSKDSTYSLSNTLTLSKADYEKHKVYACEVTHQG

LSSPVTKSFNRGEC h130M23-H1L6 Heavy chain variable region nucleo-
tide sequence
(SEQ ID NO: 33)
GAGGTGCAGCTGGTGGAGTCTGGGGGAGGCCTGGTCAAGCCTGGAGGATC

TCTGCGGCTCTCCTGTGCAGCCTCTGGATTCACCTTCTCCTCTTATGCCA

TGTCTTGGGTCCGGCAGGCTCCAGGGAAGGGGCTGGAATGGGTCTCATCC

ATTTCTAGTGGAGGTAGCACATATTATCCTGACAGCGTGAAGGGCCGGTT

CACCATCTCCAGAGACAACGCCAAGAACAGCCTGTATCTGCAAATGAACA

GCCTGAGAGCCGAGGACACAGCTGTGTATTACTGTGCTAGAGGTGGAGAT

CCTGGGGTCTACAATGGAGATTACGAAGATGCTATGGACTACTGGGGCCA

AGGAACAACAGTCACAGTCAGCTCA h130M23-H1L6 Light chain variable region nucleo-
tide sequence
(SEQ ID NO: 34)
GACATCCAGATGACCCAGTCCCCTTCCTCCCTGTCTGCTTCCGTCGGAGA

CAGAGTCACCATCACTTGCAAGGCCTCCCAGGATGTGTCCTCTGCTGTCG

CTTGGTATCAGCAGAAACCAGGAAAAGCTCCTAAGCTCCTGATCTATTGG

GCATCCACCAGGCACACAGGAGTCCCTTCCAGGTTCTCCGGCTCTGGATC

TGGGACAGATTTCACTCTCACCATCAGCTCCCTGCAACCTGAAGATTTTG

CAACTTACTACTGTCAGCAACATTATAGCACTCCTTGGACATTCGGACAA

GGGACCAAGGTGGAAATCAAA h130M23-H1L6 Heavy chain nucleotide sequence
(SEQ ID NO: 35)
ATGGAACTGGGACTCAGATGGGTTTTCCTCGTTGCTATTCTGGAAGGAGT

CCAGTGTGAGGTGCAGCTGGTGGAGTCTGGGGGAGGCCTGGTCAAGCCTG

GAGGATCTCTGCGGCTCTCCTGTGCAGCCTCTGGATTCACCTTCTCCTCT

TATGCCATGTCTTGGGTCCGGCAGGCTCCAGGGAAGGGGCTGGAATGGGT

```
CTCATCCATTTCTAGTGGAGGTAGCACATATTATCCTGACAGCGTGAAGG
GCCGGTTCACCATCTCCAGAGACAACGCCAAGAACAGCCTGTATCTGCAA
ATGAACAGCCTGAGAGCCGAGGACACAGCTGTGTATTACTGTGCTAGAGG
TGGAGATCCTGGGGTCTACAATGGAGATTACGAAGATGCTATGGACTACT
GGGGGCAAGGAACAACAGTCACAGTCAGCTCAGCCAGCACAAAGGGCCCT
AGCGTCTTCCCTCTGGCTCCCTGCAGCAGGAGCACCAGCGAGAGCACAGC
CGCCCTGGGCTGCCTGGTCAAGGACTACTTCCCCGAACCGGTGACGGTGT
CGTGGAACTCAGGCGCTCTGACCAGCGGCGTGCACACCTTCCCAGCTGTC
CTACAGTCCTCAGGACTCTACTCCCTCAGCAGCGTGGTGACCGTGCCCTC
CAGCAACTTCGGCACCCAGACCTACACCTGCAACGTAGATCACAAGCCCA
GCAACACCAAGGTGGACAAGACAGTTGAGCGCAAATGTTGTGTCGAGTGC
CCACCGTGCCCAGCACCACCTGTGGCAGGACCGTCAGTCTTCCTCTTCCC
CCCAAAACCCAAGGACACCCTCATGATCTCCCGGACCCCTGAGGTCACGT
GCGTGGTGGTGGACGTGAGCCACGAAGACCCCGAGGTCCAGTTCAACTGG
TACGTGGACGGCGTGGAGGTGCATAATGCCAAGACAAAGCCACGGGAGGA
GCAGTTCAACAGCACGTTCCGTGTGGTCAGCGTCCTCACCGTTGTGCACC
AGGACTGGCTGAACGGCAAGGAGTACAAGTGCAAGGTCTCCAACAAAGGC
CTCCCAGCCCCCATCGAGAAAACCATCTCCAAAACCAAAGGGCAGCCCCG
AGAACCACAGGTGTACACCCTGCCCCCATCCCGGGAGGAGATGACCAAGA
ACCAGGTCAGCCTGACCTGCCTGGTCAAAGGCTTCTACCCCAGCGACATC
GCCGTGGAGTGGGAGAGCAATGGGCAGCCGGAGAACAACTACAAGACCAC
ACCTCCCATGCTGGACTCCGACGGCTCCTTCTTCCTCTACAGCAAGCTCA
CCGTGGACAAGAGCAGGTGGCAGCAGGGGAACGTCTTCTCATGCTCCGTG
ATGCATGAGGCTCTGCACAACCACTACACGCAGAAGAGCCTCTCCCTGTC
TCCGGGTAAATGA
h130M23-H1L6 Light chain nucleotide sequence
                                           (SEQ ID NO: 36)
ATGGGCATCAAGATGGAGTCACAGATTCAGGCATTTGTATTCGTGTTTCT
CTGGTTGTCTGGTGTTGACGGAGACATCCAGATGACCCAGTCCCCTTCCT
CCCTGTCTGCTTCCGTCGGAGACAGAGTCACCATCACTTGCAAGGCCTCC
CAGGATGTGTCCTCTGCTGTCGCTTGGTATCAGCAGAAACCAGGAAAAGC
TCCTAAGCTCCTGATCTATTGGGCATCCACCAGGCACACAGGAGTCCCTT
CCAGGTTCTCCGGCTCTGGATCTGGGACAGATTTCACTCTCACCATCAGC
TCCCTGCAACCTGAAGATTTTGCAACTTACTACTGTCAGCAACATTATAG
CACTCCTTGGACATTCGGACAAGGGACCAAGGTGGAAATCAAAAGAACTG
TGGCTGCACCTTCTGTCTTCATCTTCCCTCCATCTGATGAGCAGCTCAAA
TCTGGAACTGCCTCCGTTGTGTGCCTGCTGAATAACTTCTATCCTAGAGA
GGCCAAAGTCCAGTGGAAGGTGGATAACGCCCTCCAATCCGGTAACTCCC
AGGAGTCTGTCACAGAGCAGGACTCCAAGGACAGCACCTACTCCCTCAGC
AACACCCTGACACTGTCTAAAGCTGACTACGAGAAACACAAAGTCTACGC
CTGCGAAGTCACCCATCAGGGACTGAGCTCCCCCGTCACAAAATCCTTCA
ACAGGGGAGAGTGCTAA
```

131R010 Heavy chain CDR1
                                           (SEQ ID NO: 37)
DYSIH 131R010 Heavy chain CDR2
                                           (SEQ ID NO: 38)
YIYPSNGDSYNQKFK 131R010 Heavy chain CDR3
                                           (SEQ ID NO: 39)
TYFANNFD 131R010 Alternative Heavy chain CDR3
                                           (SEQ ID NO: 40)
ATYFANNFDY 131R010 Light chain CDR1
                                           (SEQ ID NO: 41)
KASQSVDYDGDSYMN 131R010 Light chain CDR2
                                           (SEQ ID NO: 42)
AASNLES 131R010 Alternative Light chain CDR2
                                           (SEQ ID NO: 43)
AAS 131R010 Light chain CDR3
                                           (SEQ ID NO: 44)
QQSNEDPLT 131R010 Alternative Light chain CDR3
                                           (SEQ ID NO: 45)
QQSNEDPLTF 131R010 Heavy chain variable region amino acid
sequence
                                           (SEQ ID NO: 46)
QVQLVQSGAEVKKPGASVKVSCKASGYTFTDYSIHWVRQAPGQGLEWIGY
IYPSNGDSYNQKFKNRVTMTRDTSTSTAYMELSRLRSEDTAVYYCATYF
ANNFDYWGQGTTLTVSS 131R010 Light chain variable region amino acid
sequence
                                           (SEQ ID NO: 47)
DIQMTQSPSSLSASVGDRVTITCKASQSVDYDGDSYMNWYQQKPGKAPKL
LIYAASNLESGVPSRFSGSGSGTDFTLTISPVQAEDFATYYCQQSNEDPL
TFGAGTKLELKR 131R010 Heavy chain amino acid sequence with
predicted signal sequence underlined
                                           (SEQ ID NO: 48)
<u>MKHLWFFLLLVAAPRW</u>VLSQVQLVQSGAEVKKPGASVKVSCKASGYTFTD
YSIHWVRQAPGQGLEWIGYIYPSNGDSYNQKFKNRVTMTRDTSTSTAYM
ELSRLRSEDTAVYYCATYFANNFDYWGQGTTLTVSSASTKGPSVFPLAPS
SKSTSGGTAALGCLVKDYFPEPVTVSWNSGALTSGVHTFPAVLQSSGLYS
LSSVVTVPSSSLGTQTYICNVNHKPSNTKVDKRVEPKSCDKTHTCPPCPA
PELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAP
IEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEA
LHNHYTQKSLSLSPGK 131R010 Heavy chain amino acid sequence without
predicted signal sequence
(SEQ ID NO: 49)
QVQLVQSGAEVKKPGASVKVSCKASGYTFTDYSIHWVRQAPGQGLEWIGY
IYPSNGDSGYNQKFKNRVTMTRDTSTSTAYMELSRLRSEDTAVYYCATYF
ANNFDYWGQGTTLTVSSASTKGPSVFPLAPSSKSTSGGTAALGCLVKDYF
PEPVTVSWNSGALTSGVHTFPAVLQSSGLYSLSSVVTVPSSSLGTQTYIC
NVNHKPSNTKVDKRVEPKSCDKTHTCPPCPAPELLGGPSVFLFPPKPKDT
LMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYT
LPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGK 131R010 Light chain amino acid sequence with
predicted signal sequence underlined
(SEQ ID NO: 50)
<u>MKHLWFFLLLVAAPRWVLS</u>DIQMTQSPSSLSASVGDRVTITCKASQSVDY
DGDSYMNWYQQKPGKAPKLLIYAASNLESGVPSRFSGSGSGTDFTLTISP
VQAEDFATYYCQQSNEDPLTFGAGTKLELKRTVAAPSVFIFPPSDEQLKS
GTASVVCLLNNFYPREAKVQWKVDNALQSGNSQESVTEQDSKDSTYSLSS
TLTLSKADYEKHKVYACEVTHQGLSSPVTKSFNRGEC 131R010 Light chain amino acid sequence without
predicted signal sequence
(SEQ ID NO: 51)
DIQMTQSPSSLSASVGDRVTITCKASQSVDYDGDSYMNWYQQKPGKAPKL
LIYAASNLESGVPSRFSGSGSGTDFTLTISPVQAEDFATYYCQQSNEDPL
TFGAGTKLELKRTVAAPSVFIFPPSDEQLKSGTASVVCLLNNFYPREAKV
QWKVDNALQSGNSQESVTEQDSKDSTYSLSSTLTLSKADYEKHKVYACEV
THQGLSSPVTKSFNRGEC 131R010 Heavy chain variable region nucleotide
sequence
(SEQ ID NO: 52)
CAAGTGCAATTGGTGCAGTCCGGAGCGGAAGTGAAGAAGCCTGGTGCCTC
GGTCAAAGTCTCATGCAAGGCCAGCGGATACACTTTCACCGACTACTCCA
TCCATTGGGTGAGGCAGGCTCCGGGCCAGGGCCTGGAGTGGATTGGGTAC
ATCTACCCGTCGAACGGAGATTCGGGGTACAATCAGAAGTTCAAGAACCG
CGTGACCATGACTCGGGACACCTCAACTTCCACGGCTTATATGGAACTGA
GCCGCCTGAGATCCGAGGACACTGCGGTGTACTACTGTGCCACCTACTTT
GCGAACAATTTCGATTACTGGGGACAAGGAACCACGCTCACTGTCAGCTC 131R010 Light chain variable region nucleotide
sequence
(SEQ ID NO: 53)
GATATCCAGATGACTCAGTCGCCCTCATCGTTGAGCGCCTCGGTCGGGGA
TCGCGTGACTATTACTTGTAAAGCGTCCCAGAGCGTGGACTACGACGGAG
ATTCCTACATGAACTGGTATCAGCAAAAACCGGGAAAGGCTCCTAAACTT
CTCATCTACGCAGCCTCGAATCTGGAATCAGGAGTCCCGAGCCGGTTCAG
CGGATCAGGCTCCGGTACTGATTTTACCCTCACGATCTCGCCAGTGCAAG
CCGAGGACTTCGCGACCTACTACTGCCAACAGTCCAACGAGGACCCGCTG
ACCTTCGGCGCAGGGACCAAGCTGGAACTGAAGCGT 131R010 Heavy chain nucleotide sequence
(SEQ ID NO: 54)
ATGAAACACTTGTGGTTCTTTCTGCTCCTTGTCGCAGCACCACGGTGGGT
GCTGTCGCAAGTGCAATTGGTGCAGTCCGGAGCGGAAGTGAAGAAGCCTG
GTGCCTCGGTCAAAGTCTCATGCAAGGCCAGCGGATACACTTTCACCGAC
TACTCCATCCATTGGGTGAGGCAGGCTCCGGGCCAGGGCCTGGAGTGGAT
TGGGTACATCTACCCGTCGAACGGAGATTCGGGGTACAATCAGAAGTTCA
AGAACCGCGTGACCATGACTCGGGACACCTCAACTTCCACGGCTTATATG
GAACTGAGCCGCCTGAGATCCGAGGACACTGCGGTGTACTACTGTGCCAC
CTACTTTGCGAACAATTTCGATTACTGGGGACAAGGAACCACGCTCACTG
TCAGCTCAGCCAGCACCAAGGGCCCCTCCGTGTTCCCTCTGGCCCCTTCC
TCCAAGTCCACCTCCGGCGGCACCGCCGCTCTGGGCTGCCTGGTGAAGGA
CTACTTCCCTGAGCCTGTGACCGTGTCCTGGAACTCTGGCGCCCTGACCT
CTGGCGTGCACACCTTCCCAGCCGTGCTGCAGTCCTCCGGCCTGTACTCC
CTGTCCTCCGTGGTGACCGTGCCTTCCTCCTCCCTGGGCACCCAGACCTA
CATCTGCAACGTGAACCACAAGCCTTCCAACACCAAGGTGGACAAGCGGG
TGGAGCCTAAGTCCTGCGACAAGACCCACACCTGCCCTCCTGCCCTGCC
CCTGAGCTGCTGGGCGGACCTTCCGTGTTCCTGTTCCCTCCTAAGCCTAA
GGACACCCTGATGATCTCCCGGACCCCTGAGGTGACCTGCGTGGTGGTGG
ACGTGTCCCACGAGGATCCTGAGGTGAAGTTCAATTGGTACGTGGACGGC
GTGGAGGTGCACAACGCTAAGACCAAGCCAAGGGAGGAGCAGTACAACTC
CACCTACCGGGTGGTGTCTGTGCTGACCGTGCTGCACCAGGACTGGCTGA
ACGGCAAGAATAAGTGCAAGGTCTCCAACAAGGCCCTGCCCGCTCCC
ATCGAGAAAACCATCTCCAAGGCCAAGGGCCAGCCTCGCGAGCCTCAGGT
GTACACCCTGCCACCCAGCCGGGAGGAGATGACCAAGAACCAGGTGTCCC
TGACCTGTCTGGTGAAGGGCTTCTACCCTTCCGATATCGCCGTGGAGTGG
GAGTCTAACGGCCAGCCCGAGAACAACTACAAGACCACCCCTCCTGTGCT
GGACTCCGACGGCTCCTTCTTCCTGTACTCCAAGCTGACCGTGGACAAGT
CCCGGTGGCAGCAGGGCAACGTGTTCTCCTGCTCCGTGATGCACGAGGCC
CTGCACAACCACTACACCCAGAAGAGCCTGTCTCTGTCTCCTGGCAAGTG
ATAA 131R010 Light chain nucleotide sequence
(SEQ ID NO: 55)
ATGAAACACCTGTGGTTCTTCCTCCTGCTGGTGGCAGCTCCCAGATGGGT
CCTGTCCGATATCCAGATGACTCAGTCGCCCTCATCGTTGAGCGCCTCGG
TCGGGGATCGCGTGACTATTACTTGTAAAGCGTCCCAGAGCGTGGACTAC
GACGGAGATTCCTACATGAACTGGTATCAGCAAAAACCGGGAAAGGCTCC
TAAACTTCTCATCTACGCAGCCTCGAATCTGGAATCAGGAGTCCCGAGCC
GGTTCAGCGGATCAGGCTCCGGTACTGATTTTACCCTCACGATCTCGCCA
GTGCAAGCCGAGGACTTCGCGACCTACTACTGCCAACAGTCCAACGAGGA
CCCGCTGACCTTCGGCGCAGGGACCAAGCTGGAACTGAAGCGTACGGTGG
CCGCTCCATCCGTGTTTATCTTTCCGCCGTCCGATGAGCAGCTCAAGTCG
GGCACTGCCAGCGTGGTCTGCCTGCTTAACAATTTCTACCCTAGGGAAGC -continued
CAAGGTGCAGTGGAAGGTGGATAACGCGCTCCAATCCGGTAACTCGCAAG

AGAGCGTGACCGAACAGGACTCAAAGGACTCGACGTACAGCCTGTCATCG

ACCTTGACTCTCTCAAAGGCCGACTACGAAAAGCACAAGGTCTACGCGTG

CGAAGTCACCCATCAGGGACTGTCCTCGCCTGTGACCAAGAGCTTCAATC

GCGGAGAGTGCTGA h89M5-H2L2 Heavy chain variable region amino acid sequence
(SEQ ID NO: 56)
QVQLVQSGAEVKKPGASVKVSCKTSGYTFTGYTMHWVRQAPGQRLEWMGG

INPNNGGTTYNQNFKGRVTITRDTSASTAYMELSSLRSEDTAVYYCARKE

FSDGYYFFAYWGQGTLVTVSS h89M5-H2L2 Light chain variable region amino acid sequence
(SEQ ID NO: 57)
DIQMTQSPSSLSASVGDRVTITCKASQDVIFAVAWYQQKPGKAPKLLIYW

ASTRHTGVPSRFSGSGSGTDYTLTISSLQPEDFATYYCQQHYSTPWTFGG

GTKVEIK h89M5-H2L2 Heavy chain amino acid sequence with predicted signal sequence underlined
(SEQ ID NO: 58)
<u>MDWTWRILFLVAAATGAHS</u>QVQLVQSGAEVKKPGASVKVSCKTSGYTFTG

YTMHWVRQAPGQRLEWMGGINPNNGGTTYNQNFKGRVTITRDTSASTAYM

ELSSLRSEDTAVYYCARKEFSDGYYFFAYWGQGTLVTVSSASTKGPSVFP

LAPCSRSTSESTAALGCLVKDYFPEPVTVSWNSGALTSGVHTFPAVLQSS

GLYSLSSVVTVPSSNFGTQTYTCNVDHKPSNTKVDKTVERKCCVECPPCP

APPVAGPSVFLFPPKPKDTLMISRTPEVTCVVVDVSHEDPEVQFNWYVDG

VEVHNAKTKPREEQFNSTFRVVSVLTVVHQDWLNGKEYKCKVSNKGLPAP

IEKTISKTKGQPREPQVYTLPPSREEMTKNQVSLTCLVKGFYPSDIAVEW

ESNGQPENNYKTTPPMLDSDGSFFLYSKLTVDKSRWQQGNVFSCSVMHEA

LHNHYTQKSLSLSPGK h89M5-H2L2 Heavy chain amino acid sequence without predicted signal sequence
(SEQ ID NO: 59)
QVQLVQSGAEVKKPGASVKVSCKTSGYTFTGYTMHWVRQAPGQRLEWMGG

INPNNGGTTYNQNFKGRVTITRDTSASTAYMELSSLRSEDTAVYYCARKE

FSDGYYFFAYWGQGTLVTVSSASTKGPSVFPLAPCSRSTSESTAALGCLV

KDYFPEPVTVSWNSGALTSGVHTFPAVLQSSGLYSLSSVVTVPSSNFGTQ

TYTCNVDHKPSNTKVDKTVERKCCVECPPCPAPPVAGPSVFLFPPKPKDT

LMISRTPEVTCVVVDVSHEDPEVQFNWYVDGVEVHNAKTKPREEQFNSTF

RVVSVLTVVHQDWLNGKEYKCKVSNKGLPAPIEKTISKTKGQPREPQVYT

LPPSREEMTKNQVSLTCLVKGFYPSDIAVEWESNGQPENNYKTTPPMLDS

DGSFFLYSKLTVDKSRWQQGNVFSCSVMHEALHNHYTQKSLSLSPGK h89M5-H2L2 Light chain amino acid sequence with predicted signal sequence underlined
(SEQ ID NO: 60)
<u>MDMRVPAQLLGLLLLWLRGARC</u>DIQMTQSPSSLSASVGDRVTITCKASQD

VIFAVAWYQQKPGKAPKLLIYWASTRHTGVPSRFSGSGSGTDYTLTISSL

QPEDFATYYCQQHYSTPWTFGGGTKVEIKRTVAAPSVFIFPPSDEQLKSG

TASVVCLLNNFYPREAKVQWKVDNALQSGNSQESVTEQDSKDSTYSLSNT

LTLSKADYEKHKVYACEVTHQGLSSPVTKSFNRGEC h89M5-H2L2 Light chain amino acid sequence without predicted signal sequence
(SEQ ID NO: 61)
DIQMTQSPSSLSASVGDRVTITCKASQDVIFAVAWYQQKPGKAPKLLIYW

ASTRHTGVPSRFSGSGSGTDYTLTISSLQPEDFATYYCQQHYSTPWTFGG

GTKVEIKRTVAAPSVFIFPPSDEQLKSGTASVVCLLNNFYPREAKVQWKV

DNALQSGNSQESVTEQDSKDSTYSLSNTLTLSKADYEKHKVYACEVTHQG

LSSPVTKSFNRGEC h89M5-H2L2 Heavy chain variable region nucleotide sequence
(SEQ ID NO: 62)
CAGGTCCAGCTCGTGCAGTCTGGGGCTGAGGTGAAGAAGCCTGGGGCCTC

TGTGAAGGTTTCCTGCAAGACTTCTGGATACACCTTCACTGGATACACCA

TGCACTGGGTTAGACAGGCCCCCGGACAAAGGCTGGAGTGGATGGGAGGT

ATTAATCCTAACAATGGTGGTACTACTTACAACCAGAACTTCAAGGGCAG

AGTCACCATTACCAGGGACACATCCGCAAGCACAGCCTACATGGAGCTGT

CCAGCCTGAGATCTGAAGACACAGCTGTGTATTACTGTGCAAGAAAGGAG

TTCTCTGATGGATACTACTTTTTTGCTTACTGGGGCCAAGGGACCCTGGT

CACCGTCAGCTCA h89M5-H2L2 Light chain variable region nucleotide sequence
(SEQ ID NO: 63)
GACATCCAGATGACCCAGTCTCCATCCTCCCTGTCTGCATCTGTCGGAGA

CAGAGTCACCATCACTTGCAAGGCCTCCCAGGATGTGATTTTTGCTGTTG

CCTGGTATCAGCAGAAACCAGGGAAAGCCCCTAAGCTCCTGATCTATTGG

GCATCCACCCGGCACACTGGGGTCCCATCAAGGTTCAGTGGCAGTGGATC

TGGGACAGATTACACTCTCACCATCAGCAGTCTGCAACCTGAAGATTTTG

CAACTTACTACTGTCAGCAACATTATAGCACTCCTTGGACTTTCGGCGGA

GGGACCAAGGTGGAGATCAAA h89M5-H2L2 Heavy chain nucleotide sequence
(SEQ ID NO: 64)
ATGGACTGGACCTGGAGGATACTCTTTCTCGTGGCAGCAGCCACAGGAGC

CCACTCCCAGGTCCAGCTCGTGCAGTCTGGGGCTGAGGTGAAGAAGCCTG

GGGCCTCTGTGAAGGTTTCCTGCAAGACTTCTGGATACACCTTCACTGGA

TACACCATGCACTGGGTTAGACAGGCCCCCGGACAAAGGCTGGAGTGGAT

GGGAGGTATTAATCCTAACAATGGTGGTACTACTTACAACCAGAACTTCA

AGGGCAGAGTCACCATTACCAGGGACACATCCGCAAGCACAGCCTACATG

GAGCTGTCCAGCCTGAGATCTGAAGACACAGCTGTGTATTACTGTGCAAG

AAAGGAGTTCTCTGATGGATACTACTTTTTTGCTTACTGGGGCCAAGGGA

CCCTGGTCACCGTCAGCTCAGCCAGCACAAAGGGCCCTAGCGTCTTCCCT

CTGGCTCCCTGCAGCAGGAGCACCAGCGAGAGCACAGCCGCCCTGGGCTG

CCTGGTCAAGGACTACTTCCCCGAACCGGTGACGGTGTCGTGGAACTCAG

GCGCTCTGACCAGCGGCGTGCACACCTTCCCAGCTGTCCTACAGTCCTCA

GGACTCTACTCCCTCAGCAGCGTGGTGACCGTGCCCTCCAGCAACTTCGG

-continued
CACCCAGACCTACACCTGCAACGTAGATCACAAGCCCAGCAACACCAAGG

TGGACAAGACAGTTGAGCGCAAATGTTGTGTCGAGTGCCCACCGTGCCCA

GCACCACCTGTGGCAGGACCGTCAGTCTTCCTCTTCCCCCCAAAACCCAA

GGACACCCTCATGATCTCCCGGACCCCTGAGGTCACGTGCGTGGTGGTGG

ACGTGAGCCACGAAGACCCCGAGGTCCAGTTCAACTGGTACGTGGACGGC

GTGGAGGTGCATAATGCCAAGACAAAGCCACGGGAGGAGCAGTTCAACAG

CACGTTCCGTGTGGTCAGCGTCCTCACCGTTGTGCACCAGGACTGGCTGA

ACGGCAAGGAGTACAAGTGCAAGGTCTCCAACAAAGGCCTCCCAGCCCCC

ATCGAGAAAACCATCTCCAAAACCAAAGGGCAGCCCCGAGAACCACAGGT

GTACACCCTGCCCCCATCCCGGGAGGAGATGACCAAGAACCAGGTCAGCC

TGACCTGCCTGGTCAAAGGCTTCTACCCCAGCGACATCGCCGTGGAGTGG

GAGAGCAATGGGCAGCCGGAGAACAACTACAAGACCACACCTCCCATGCT

GGACTCCGACGGCTCCTTCTTCCTCTACAGCAAGCTCACCGTGGACAAGA

GCAGGTGGCAGCAGGGGAACGTCTTCTCATGCTCCGTGATGCATGAGGCT

CTGCACAACCACTACACGCAGAAGAGCCTCTCCCTGTCTCCGGGTAAATG

A h89M5-H2L2 Light chain nucleotide sequence
(SEQ ID NO: 65)
ATGGACATGAGGGTCCCCGCACAGCTCCTGGGGCTCCTGCTCCTCTGGCT

CCGGGGTGCCAGATGTGACATCCAGATGACCCAGTCTCCATCCTCCCTGT

CTGCATCTGTCGGAGACAGAGTCACCATCACTTGCAAGGCCTCCCAGGAT

GTGATTTTTGCTGTTGCCTGGTATCAGCAGAAACCAGGGAAAGCCCCTAA

GCTCCTGATCTATTGGGCATCCACCCGGCACACTGGGGTCCCATCAAGGT

TCAGTGGCAGTGGATCTGGGACAGATTACACTCTCACCATCAGCAGTCTG

CAACCTGAAGATTTTGCAACTTACTACTGTCAGCAACATTATAGCACTCC

TTGGACTTTCGGCGGAGGGACCAAGGTGGAGATCAAACGGACTGTGGCTG

CACCATCTGTCTTCATCTTCCCTCCATCTGATGAGCAGTTGAAATCTGGA

ACTGCCTCTGTTGTGTGCCTGCTGAATAACTTCTATCCCAGAGAGGCCAA

AGTCCAGTGGAAGGTGGATAACGCCCTCCAATCGGGTAACTCCCAGGAGA

GTGTCACAGAGCAGGACAGCAAGGACAGCACCTACAGCCTCAGCAACACC

CTGACACTGAGCAAAGCAGACTACGAGAAACACAAAGTCTACGCCTGCGA

AGTCACCCATCAGGGCCTGAGCTCCCCCGTCACAAAGAGCTTCAACAGGG

GAGAGTGCTAA h130M23-H1L2 Light chain variable region amino
acid sequence
(SEQ ID NO: 66)
DIQMTQSPSSLSASVGDRVTITCKASQDVSSAVAWYQQKPGKAPKLLIYW

ASTRHTGVPSRFSGSGSGTDFTLTISSVQAEDFATYYCQQHYSTPWTFGQ

GTKVEIK h130M23-H1L2 Light chain amino acid sequence with
predicted signal sequence underlined
(SEQ ID NO: 67)
<u>MKYLLPTAAAGLLLLAAQPAMA</u>DIQMTQSPSSLSASVGDRVTITCKASQD

VSSAVAWYQQKPGKAPKLLIYWASTRHTGVPSRFSGSGSGTDFTLTISSV

QAEDFATYYCQQHYSTPWTFGQGTKVEIKRTVAAPSVFIFPPSDEQLKSG

TASVVCLLNNFYPREAKVQWKVDNALQSGNSQESVTEQDSKDSTYSLSNT

LTLSKADYEKHKVYACEVTHQGLSSPVTKSFNRGEC h130M23-H1L2 Light chain amino acid sequence
without predicted signal sequence underlined
(SEQ ID NO: 68)
DIQMTQSPSSLSASVGDRVTITCKASQDVSSAVAWYQQKPGKAPKLLIYW

ASTRHTGVPSRFSGSGSGTDFTLTISSVQAEDFATYYCQQHYSTPWTFGQ

GTKVEIKRTVAAPSVFIFPPSDEQLKSGTASVVCLLNNFYPREAKVQWKV

DNALQSGNSQESVTEQDSKDSTYSLSNTLTLSKADYEKHKVYACEVTHQG

LSSPVTKSFNRGEC h130M23-H1L2 Light chain variable region nucleo-
tide sequence
(SEQ ID NO: 69)
GACATCCAGATGACCCAGTCCCCTTCCTCCCTGTCTGCTTCCGTCGGAGA

CAGAGTCACCATCACTTGCAAGGCCTCCCAGGATGTGTCCTCTGCTGTCG

CTTGGTATCAGCAGAAACCAGGAAAAGCTCCTAAGCTCCTGATCTATTGG

GCATCCACCAGGCACACAGGAGTCCCTTCCAGGTTCTCCGGCTCTGGATC

TGGGACAGATTTCACTCTCACCATCAGCTCCGTGCAAGCTGAAGATTTTG

CAACTTACTACTGTCAGCAACATTATAGCACTCCTTGGACATTCGGACAA

GGGACCAAGGTGGAAATCAAA h130M23-H1L2 Light chain nucleotide sequence
(SEQ ID NO: 70)
ATGAAATACCTCCTCCCTACAGCTGCCGCTGGACTCCTCCTCCTCGCTGC

CCAGCCTGCCATGGCCGACATCCAGATGACCCAGTCCCCTTCCTCCCTGT

CTGCTTCCGTCGGAGACAGAGTCACCATCACTTGCAAGGCCTCCCAGGAT

GTGTCCTCTGCTGTCGCTTGGTATCAGCAGAAACCAGGAAAAGCTCCTAA

GCTCCTGATCTATTGGGCATCCACCAGGCACACAGGAGTCCCTTCCAGGT

TCTCCGGCTCTGGATCTGGGACAGATTTCACTCTCACCATCAGCTCCGTG

CAAGCTGAAGATTTTGCAACTTACTACTGTCAGCAACATTATAGCACTCC

TTGGACATTCGGACAAGGGACCAAGGTGGAAATCAAAAGAACTGTGGCTG

CACCTTCTGTCTTCATCTTCCCTCCATCTGATGAGCAGCTCAAATCTGGA

ACTGCCTCCGTTGTGTGCCTGCTGAATAACTTCTATCCTAGAGAGGCCAA

AGTCCAGTGGAAGGTGGATAACGCCCTCCAATCGGGTAACTCCCAGGAGT

CTGTCACAGAGCAGGACTCCAAGGACAGCACCTACTCCCTCAGCAACACC

CTGACACTGTCTAAAGCTGACTACGAGAAACACAAAGTCTACGCCTGCGA

AGTCACCCATCAGGGACTGAGCTCCCCCGTCACAAAATCCTTCAACAGGG

GAGAGTGCTAA

Human LGR4 protein sequence
(SEQ ID NO: 71)
MPGPLGLLCFLALGLLGSAGPSGAAPPLCAAPCSCDGDRRVDCSGKGLTA

VPEGLSAFTQALDISMNNITQLPEDAFKNFPFLEELQLAGNDLSFIHPKA

LSGLKELKVLTLQNNQLKTVPSEAIRGLSALQSLRLDANHITSVPEDSFE

GLVQLRHLWLDDNSLTEVPVHPLSNLPTLQALTLALNKISSIPDFAFTNL

SSLVVLHLHNNKIRSLSQHCFDGLDNLETLDLNYNNLGEFPQAIKALPSL

KELGFHSNSISVIPDGAFDGNPLLRTIHLYDNPLSFVGNSAFHNLSDLHS

LVIRGASMVQQFPNLTGTVHLESLTLTGTKISSIPNNLCQEQKMLRTLDL

```
SYNNIRDLPSFNGCHALEEISLQRNQIYQIKEGTFQGLISLRILDLSRNL
IHEIHSRAFATLGPITNLDVSFNELTSFPTEGLNGLNQLKLVGNFKLKEA
LAAKDFVNLRSLSVPYAYQCCAFWGCDSYANLNTEDNSLQDHSVAQEKGT
ADAANVTSTLENEEHSQIIIHCTPSTGAFKPCEYLLGSWMIRLTVWFIFL
VALFFNLLVILTTFASCTSLPSSKLFIGLISVSNLFMGIYTGILTFLDAV
SWGRFAEFGIWWETGSGCKVAGFLAVFSSESAIFLLMLATVERSLSAKDI
MKNGKSNHLKQFRVAALLAFLGATVAGCFPLFHRGEYSASPLCLPFPTGE
TPSLGFTVTLVLLNSLAFLLMAVIYTKLYCNLEKEDLSENSQSSMIKHVA
WLIFTNCIFFCPVAFFSFAPLITAISISPEIMKSVTLIFFPLPACLNPVL
YVFFNPKFKEDWKLLKRRVTKKSGSVSVSISSQGGCLEQDFYYDCGMYSH
LQGNLTVCDCCESFLLTKPVSCKHLIKSHSCPALAVASCQRPEGYWSDCG
TQSAHSDYADEEDSFVSDSSDQVQACGRACFYQSRGFPLVRYAYNLPRVK
D
```

Human LGR5 protein sequence
(SEQ ID NO: 72)
```
MDTSRLGVLLSLPVLLQLATGGSSPRSGVLLRGCPTHCHCEPDGRMLLRV
DCSDLGLSELPSNLSVFTSYLDLSMNNISQLLPNPLPSLRFLEELRLAGN
ALTYIPKGAFTGLYSLKVLMLQNNQLRHVPTEALQNLRSLQSLRLDANHI
SYVPPSCFSGLHSLRHLWLDDNALTEIPVQAFRSLSALQAMTLALNKIHH
IPDYAFGNLSSLVVLHLHNNRIHSLGKKCFDGLHSLETLDLNYNNLDEFP
TAIRTLSNLKELGFHSNNIRSIPEKAFVGNPSLITIHFYDNPIQFVGRSA
FQHLPELRTLTLNGASQITEFPDLTGTANLESLTLTGAQISSLPQTVCNQ
LPNLQVLDLSYNLLEDLPSFSVCQKLQKIDLRHNEIYEIKVDTFQQLLSL
RSLNLAWNKIAIIHPNAFSTLPSLIKDLSSNLLSSFPITGLHGLTHLKL
TGNHALQSLISSENFPELKVIEMPYAYQCCAFGVCENAYKISNQWNKGDN
SSMDDLHKKDAGMFQAQDERDLEDFLLDFEEDLKALHSVQCSPSPGPFKP
CEHLLDGWLIRIGVWTIAVLALTCNALVTSTVFRSPLYISPIKLLIGVIA
AVNMLTGVSSAVLAGVDAFTFGSFARHGAWWENGVGCHVIGFLSIFASES
SVFLLTLAALERGFSVKYSAKFETKAPFSSLKVIILLCALLALTMAAVPL
LGGSKYGASPLCLPLPFGEPSTMGYMVALILLNSLCFLMMTIAYTKLYCN
LDKGDLENIWDCSMVKHIALLLFTNCILNCPVAFLSFSSLINLTFISPEV
IKFILLVVVPLPACLNPLLYILFNPHFKEDLVSLRKQTYVWTRSKHPSLM
SINSDDVEKQSCDSTQALVTFTSSSITYDLPPSSVPSPAYPVTESCHLSS
VAFVPCL
```

Human LGR6 protein sequence
(SEQ ID NO: 73)
```
MGRPRLTLVCQVSIIISARDLSMNNLTELQPGLFHHLRFLEELRLSGNHL
SHIPGQAFSGLYSLKILMLQNNQLGGIPAEALWELPSLQSRLRLDANLISL
VPERSFEGLSSLRHLWLDDNALTEIPVRALNNLPALQAMTLALNRISHIP
DYAFQNLTSLVVLHLHNNRIQHLGTHSFEGLHNLETLDLNYNKLQEFPVA
IRTLGRLQELGFHNNNIKAIPEKAFMGNPLLQTIHFYDNPIQFVGRSAFQ
YLPKLHTLSLNGAMDIQEFPDLKGTTSLEILTLTRAGIRLLPSGMCQQLP
RLRVLELSHNQIEELPSLHRCQKLEEIGLQHNRIWEIGADTFSQLSSLQA
LDLSWNAIRSIHPEAFSTLHSLVKLDLTDNQLTTLPLAGLGGLMHLKLKG
NLALSQAFSKDSFPKLRILEVPYAYQCCPYGMCASFFKASGQWEAEDLHL
DDEESSKRPLGLLARQAENHYDQDLDELQLEMEDSKPHPSVQCSPTPGPF
KPCEYLFESWGIRLAVVWAIVLLSVLCNGLVLLTVFAGGPVPLPPVKFVVG
AIAGANTLTGISCGLLASVDALTFGQFSEYGARWETGLGCRATGFLAVLG
SEASVLLLTLAAVQCSVSVSCVRAYGKSPSLGSVRAGVLGCLALAGLAAA
LPLASVGEYGASPLCLPYAPPEGQPAALGFTVALVMMNSFCFLVVAGAYI
KLYCDLPRGDFEAVWDCAMVRHVAWLIFADGLLYCPVAFLSFASMLGLFP
VTPEAVKSVLLVVLPLPACLNPLLYLLFNPHFRDDLRRLRPRAGDSGPLA
YAAAGELEKSSCDSTQALVAFSDVDLILEASEAGRPPGLETYGFPSVTLI
SCQQPGAPRLEGSHCVEPEGNHFGNPQPSMDGELLLRAEGSTPAGGGLSG
GGGFQPSGLAFASHV
```

LGR5 ECD amino acids 22-564
(SEQ ID NO: 74)
```
GSSPRSGVLLRGCPTHCHCEPDGRMLLRVDCSDLGLSELPSNLSVFTSYL
DLSMNNISQLLPNPLPSLRFLEELRLAGNALTYIPKGAFTGLYSLKVLML
QNNQLRHVPTEALQNLRSLQSLRLDANHISYVPPSCFSGLHSLRHLWLDD
NALTEIPVQAFRSLSALQAMTLALNKIHHIPDYAFGNLSSLVVLHLHNNR
IHSLGKKCFDGLHSLETLDLNYNNLDEFPTAIRTLSNLKELGFHSNNIRS
IPEKAFVGNPSLITIHFYDNPIQFVGRSAFQHLPELRTLTLNGASQITEF
PDLTGTANLESLTLTGAQISSLPQTVCNQLPNLQVLDLSYNLLEDLPSFS
VCQKLQKIDLRHNEIYEIKVDTFQQLLSLRSLNLAWNKIAIIHPNAFSTL
PSLIKDLSSNLLSSFPITGLHGLTHLKLTGNHALQSLISSENFPELKVI
EMPYAYQCCAFGVCENAYKISNQWNKGDNSSMDDLHKKDAGMFQAQDERD
LEDFLLDFEEDLKALHSVQCSPSPGPFKPCEHLLDGWLIRIGV
```

LGR5-Fc protein sequence
(SEQ ID NO: 75)
```
MDTSRLGVLLSLPVLLQLATGGSSPRSGVLLRGCPTHCHCEPDGRMLLRV
DCSDLGLSELPSNLSVFTSYLDLSMNNISQLLPNPLPSLRFLEELRLAGN
ALTYIPKGAFTGLYSLKVLMLQNNQLRHVPTEALQNLRSLQSLRLDANHI
SYVPPSCFSGLHSLRHLWLDDNALTEIPVQAFRSLSALQAMTLALNKIHH
IPDYAFGNLSSLVVLHLHNNRIHSLGKKCFDGLHSLETLDLNYNNLDEFP
TAIRTLSNLKELGFHSNNIRSIPEKAFVGNPSLITIHFYDNPIQFVGRSA
FQHLPELRTLTLNGASQITEFPDLTGTANLESLTLTGAQISSLPQTVCNQ
LPNLQVLDLSYNLLEDLPSFSVCQKLQKIDLRHNEIYEIKVDTFQQLLSL
RSLNLAWNKIAIIHPNAFSTLPSLIKDLSSNLLSSFPITGLHGLTHLKL
TGNHALQSLISSENFPELKVIEMPYAYQCCAFGVCENAYKISNQWNKGDN
SSMDDLHKKDAGMFQAQDERDLEDFLLDFEEDLKALHSVQCSPSPGPFKP
CEHLLDGWLIRIGVGRADKTHTCPPCPAPELLGGPSVFLFPPKPKDTLMI
SRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPP
SRDELTKNQVSLTCLVKGFYPSDIAVEWESNGQPENNYKTTPPVLDSDGS
FFLYSKLTVDKSRWQQGNVFSCSVMHEALHNHYTQKSLSLSPGK
```

Human IgG₁ Fc region (SEQ ID NO: 76)

DKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVK
GFYPSDIAVEWESNGQPENNYKTTPPVLDSDGSFFLYSKLTVDKSRWQQG
NVFSCSVMHEALHNHYTQKSLSLSPGK

Human IgG₁ Fc region (SEQ ID NO: 77)

DKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYK
CKVSNKALPAPIEKTISKAKGQPREPQVYTLPPSREEMTKNQVSLTCLVK
GFYPSDIAVEWESNGQPENNYKTTPPVLDSDGSFFLYSKLTVDKSRWQQG
NVFSCSVMHEALHNHYTQKSLSLSPGK

Human IgG₁ Fc region (SEQ ID NO: 78)

KSSDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSRW
QQGNVFSCSVMHEALHNHYTQKSLSLSPGK

Human IgG₁ Fc region (SEQ ID NO: 79)

EPKSSDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLN
GKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKS
RWQQGNVFSCSVMHEALHNHYTQKSLSLSPGK

Human IgG₂ Fc region (SEQ ID NO: 80)

CVECPPCPAPPVAGPSVFLFPPKPKDTLMISRTPEVTCVVVDVSHEDPEV
QFNWYVDGVEVHNAKTKPREEQFNSTFRVVSVLTVVHQDWLNGKEYKCKV
SNKGLPAPIEKTISKTKGQPREPQVYTLPPSREEMTKNQVSLTCLVKGFY
PSDIAVEWESNGQPENNYKTTPPMLDSDGSFFLYSKLTVDKSRWQQGNVF
SCSVMHEALHNHYTQKSLSLSPGK

---

What is claimed is:

1. A method of treating dermal fibrosis in a subject, comprising administering to the subject a therapeutically effective amount of a human R-spondin 3 (RSPO3) antagonist antibody that specifically binds human RSPO3, wherein the antibody comprises:
   (a) a heavy chain CDR1 comprising DYSIH (SEQ ID NO:37), a heavy chain CDR2 comprising YIYPSNGDSGYNQKFK (SEQ ID NO:38), and a heavy chain CDR3 comprising TYFANNFD (SEQ ID NO:39), and a light chain CDR1 comprising KASQSVDYDGDSYMN (SEQ ID NO:41), a light chain CDR2 comprising AASNLES (SEQ ID NO:42), and a light chain CDR3 comprising QQSNEDPLT (SEQ ID NO:44); or
   (b) a heavy chain variable region having at least 97% sequence identity to SEQ ID NO: 46 and a light chain variable region having at least 97% sequence identity to SEQ ID NO: 47, wherein the heavy chain variable region comprises a heavy chain CDR3 comprising TYFANNFD (SEQ ID NO: 39) and the light chain variable region comprises a light chain CDR3 comprising QQSNEDPLT (SEQ ID NO: 44).

2. The method of claim 1, wherein the antibody of (a) comprises a heavy chain variable region having at least 97% sequence identity to SEQ ID NO: 46 and a light chain variable region having at least 97% sequence identity to SEQ ID NO: 47.

3. The method of claim 2, wherein the antibody comprises a heavy chain variable region of SEQ ID NO: 46 and a light chain variable region of SEQ ID NO: 47.

4. The method of claim 1, wherein the antibody is a recombinant antibody, a monoclonal antibody, a chimeric antibody, a monospecific antibody, a bispecific antibody, a humanized antibody, a human antibody, an IgG1 antibody, an IgG2 antibody, or an antibody fragment comprising an antigen binding site.

5. The method of claim 1, comprising administration of at least one additional therapeutic agent.

6. The method of claim 5, wherein the additional therapeutic agent is a second antibody.

7. The method of claim 6, wherein the second antibody is an antibody which specifically binds a second RSPO protein.

8. The method of claim 5, wherein the additional therapeutic agent is an anti-inflammatory agent.

9. The method of claim 1, wherein the dermal fibrosis is scleroderma, systemic sclerosis, scleroderma-like disease, sine scleroderma, keloid formation, or hypertrophic scarring.

10. The method of claim 1 further comprising determining the expression level of RSPO1, RSPO2, RSPO3, and/or RSPO4 in a sample from the subject.

11. A method of treating dermal fibrosis in a human subject, comprising:
 (a) selecting a subject for treatment based, at least in part, on the subject having a tissue sample that has an elevated level of RSPO3 expression compared to a pre-determined level of RSPO3 expression in normal tissue, and
 (b) administering to the subject a therapeutically effective amount of a human R-spondin 3 (RSPO3) antagonist antibody that specifically binds human RSPO3, wherein the antibody comprises:
 (i) a heavy chain CDR1 comprising DYSIH (SEQ ID NO:37), a heavy chain CDR2 comprising YIYPSNGDSGYNQKFK (SEQ ID NO:38), and a heavy chain CDR3 comprising TYFANNFD (SEQ ID NO:39), and a light chain CDR1 comprising KASQSVDYDGDSYMN (SEQ ID NO:41), a light chain CDR2 comprising AASNLES (SEQ ID NO:42), and a light chain CDR3 comprising QQSNEDPLT (SEQ ID NO:44); or
 (ii) a heavy chain variable region having at least 97% sequence identity to SEQ ID NO: 46 and a light chain variable region having at least 97% sequence identity to SEQ ID NO: 47, wherein the heavy chain variable region comprises a heavy chain CDR3 comprising TYFANNFD (SEQ ID NO: 39) and the light chain variable region comprises a light chain CDR comprising QQSNEDPLT (SEQ ID NO: 44).

12. The method of claim 11, wherein the antibody of (i) comprises a heavy chain variable region having at least 97% sequence identity to SEQ ID NO: 46 and a light chain variable region having at least 97% sequence identity to SEQ ID NO: 47.

13. The method of claim 12, wherein the antibody comprises a heavy chain variable region of SEQ ID NO: 46 and a light chain variable region of SEQ ID NO: 47.

* * * * *